(12) United States Patent
Nocera et al.

(10) Patent No.: US 6,863,781 B2
(45) Date of Patent: Mar. 8, 2005

(54) PROCESS FOR PHOTOCATALYSIS AND TWO-ELECTRON MIXED-VALENCE COMPLEXES

(75) Inventors: Daniel G. Nocera, Winchester, MA (US); Alan F. Heyduk, Pasadena, CA (US)

(73) Assignee: Massachusetts Institute of Technology, Cambridge, MA (US)

( * ) Notice: Subject to any disclaimer, the term of this patent is extended or adjusted under 35 U.S.C. 154(b) by 124 days.

(21) Appl. No.: 10/083,200

(22) Filed: Feb. 26, 2002

(65) Prior Publication Data

US 2003/0201161 A1 Oct. 30, 2003

(51) Int. Cl.[7] .............................. C07C 1/00; C01B 3/00
(52) U.S. Cl. .............................. 204/157.52; 204/157.15
(58) Field of Search ......................... 204/157.15, 157.52

(56) References Cited

U.S. PATENT DOCUMENTS 5,223,634 A * 6/1993 Gratzel et al. .............. 556/137

OTHER PUBLICATIONS

MacQueen et al., "Competitive Hydrogen Production and Emission Through the Photochemistry of Mixed–Metal Bimetallic Complexes", Inorganic Chemistry (no month, 1990), vol. 29, No. 12, pp. 2313–2320.*

Heyduk, A.F., Nocera D.G.: "Hydrogen produced from hydrohalic acid solutions by a two–electron mixed valence photocatalyst" Science, American Association for the Advancement of Science, US., vol. 293, Aug. 31, 2001, pp. 1639–1641, XP002217879.

Heyduk, A.F., Nocera D.G.: "Hydrido, halo, hydrido–halo complexes of two–electron mixed valence diiridium cores" Journal of the American Chemical Society American Chemical Society, Washington, D.C., US, vol. 122, 2000, pp. 9415–9426 Xp002217880, no month.

Heyduk, A.F., Nocera D.G.: "A novel two–electron mixed–valence Ir(II)–Ir(O) complex" Chemical Communications, Royal Society of Chemistry, GB, 1999, pp. 1519–1520, XP002217881, no month.

* cited by examiner

*Primary Examiner*—Edna Wong
(74) *Attorney, Agent, or Firm*—Kirkpatrick & Lockhart; Nicholson Graham LLP

(57) ABSTRACT

Embodiments for the invention include a process for the production of hydrogen comprising a protic solution, a photocatalyst capable of a two-electron reduction of hydrogen ions; and a coproduct trap. The embodiment includes exposing the reaction medium to radiation capable of photoexciting the photocatalyst to produce hydrogen. The protic solution may comprise at least one of hydrohalic acid, a silane, and water, and the hydrohalic acid may be hydrochloric acid, hydrogen bromide, hydrogen fluoride or hydrogen iodide. The present application also describes novel transition metal compounds. Embodiments of the compounds include a compound comprising two transition metal atoms, wherein the transition metal atoms are in a two-electron mixed valence state and at least one transition metal is not rhodium; and at least one ligand capable of stabilizing the transition metal atom in a two-electron mixed valence state.

43 Claims, 40 Drawing Sheets

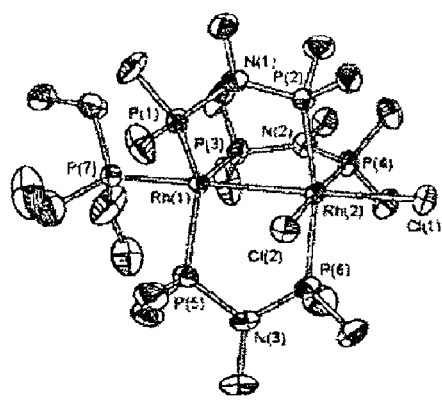
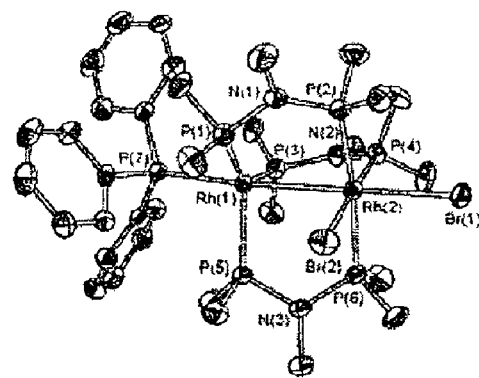
FIGURE 1(a)  FIGURE 1(b)

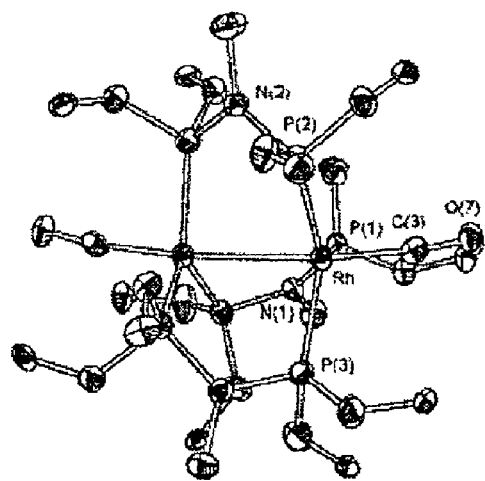
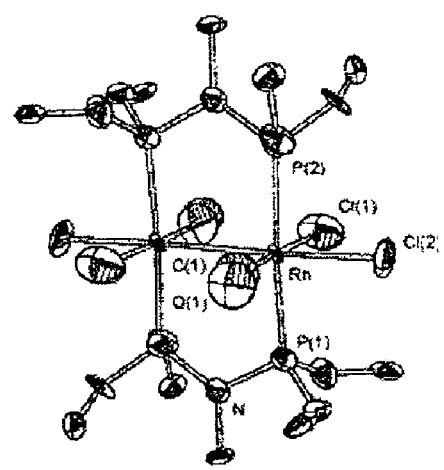
FIGURE 5(a)                FIGURE 5(b)

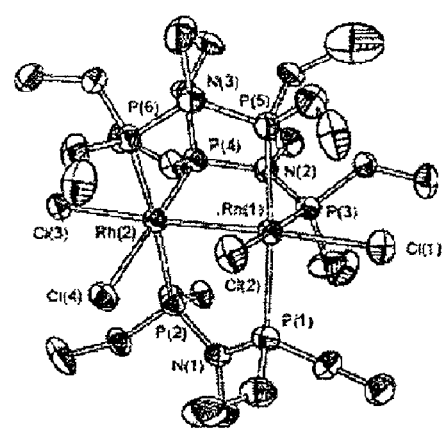 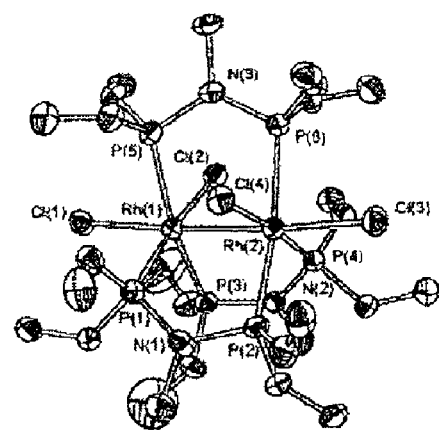
FIGURE 7(a)  FIGURE 7(b)

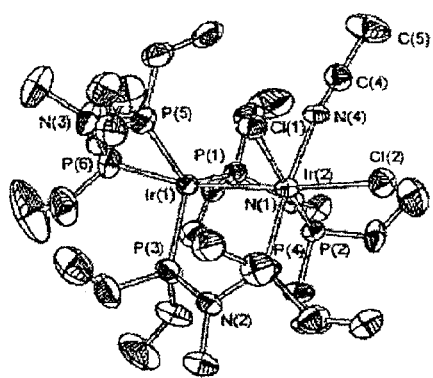
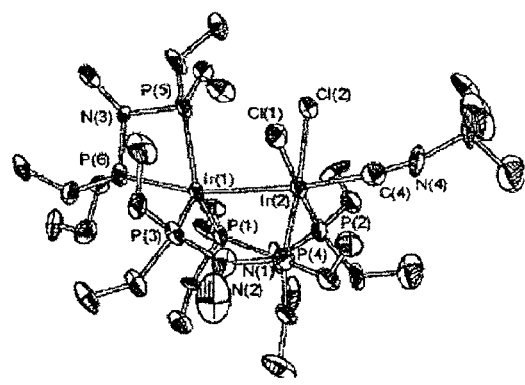
FIGURE 16(a)  FIGURE 16(b)

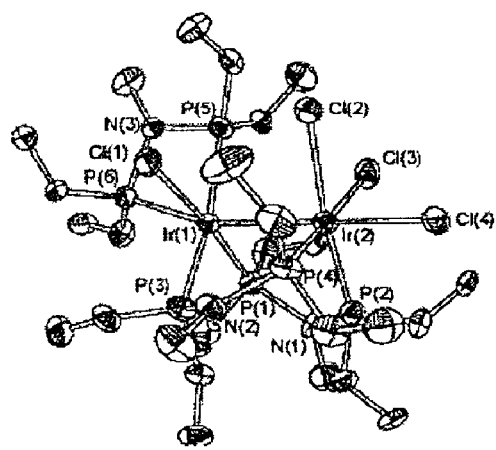 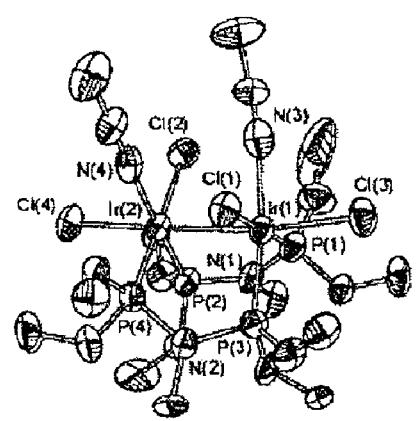
FIGURE 18(a)  FIGURE 18(b)

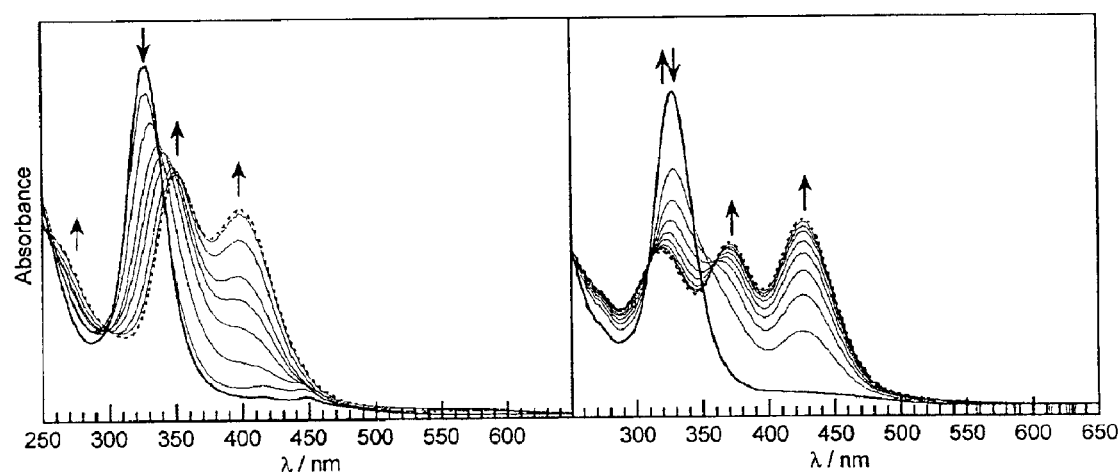
FIGURE 34(a) FIGURE 34(b)

PROCESS FOR PHOTOCATALYSIS AND TWO-ELECTRON MIXED-VALENCE COMPLEXES

FEDERALLY SPONSORED RESEARCH

This invention was made with government support under Grant Number CHE-9817851 awarded by the National Science Foundation. The government has certain rights in the invention.

TECHNICAL FIELD

Embodiments of the present invention relate to photocatalytic chemical processes. Embodiments of the present invention relate to the production of hydrogen from a hydrohalic acid solution using a homogenous photocatalyst. Embodiments of the present invention also include novel two-electron mixed-valence complexes.

DESCRIPTION

Photocatalytic production of chemical products offers an inexpensive method of driving a chemical reaction toward the production of molecules comprising more energy than the raw materials. Photocatalysts having excitation energies that fall within the spectrum of solar radiation at the surface of earth are of particular interest. The potential of solar chemistry in the generation of energy-rich molecules from inexpensive energy-poor raw materials has been extensively researched. Embodiments of the present invention comprise transition metal complexes capable of mediating multielectron transformations. These multielectron transformations allow activation of small molecules. Embodiments of the present invention comprise catalysts with a multinuclear core transition metal complex in a two electron mixed valence state. The two-electron mixed-valence state may mediate chemical processes, such as atom transfer, bond activation, and substrate functionalization, for example.

The multicore transition metal complexes may be stabilized by the chemical composition of the ligands coordinated with the multinuclear transition metal core. For example, the electronic and steric properties of bridging bis(phosphine) amine ligands favor disproportionation of valence-symmetric binuclear cores. Such properties in the bis(difluorophosphine)methyl amine ("dfpma") ligand stabilizes $Rh^0$—$Rh^{II}$ cores. The disproportionation of embodiments of the present invention include new ligands to stabilize two-electron mixed-valence complexes were developed by manipulation of the stereo-electronic effects engendered by phosphine and nitrogen functionalization.

An embodiment of the present invention is a process having a reaction medium comprising a protic solution, a photocatalyst capable of a two-electron reduction of hydrogen ions, and a coproduct trap. The reaction medium may be exposed to radiation capable of photoexciting the photocatalyst to produce hydrogen. The reaction medium may comprise any protic solution, such as a hydrohalic acid of hydrochloric acid, hydrogen bromide, hydrogen fluoride, and hydrogen iodide. A coproduct is any compound or atom produced other than the desired product, for example, the desired product may be hydrogen. A coproduct trap is any material, such as an atom or chemical compound, which may attach, react or bind with the coproduct to prevent the coproduct from interfering with the desired reaction. For example, the coproduct trap may be a compound capable of bonding with a halogen atom, such as, for example, tetrahydrofuran, dihydroanthracene, a silane, isopropanal and 2,3 dimethylbutadiene.

The photocatalyst of the present invention may be any photocatalyst capable of a two electron reduction of hydrogen ions and comprises a multinuclear transition metal core. An embodiment of the photocatalyst of the present invention is a multinuclear transition metal core which is capable of a two electron reduction of hydrogen atoms. The photocatalyst may also comprise a ligand that is capable of stabilizing a two-electron mixed-valence state of the binuclear transition metal core.

A further embodiment of the present invention includes a reaction medium comprising a protic solution; a photocatalyst comprising a binuclear transition metal complex and a ligand capable of supporting the photocatalyst in a two-electron mixed-valence state; and a coproduct trap. The photocatalyst may then be photoexcited to produce hydrogen from the reaction medium. The ligand may be, for example, a diphosphazane ligand or a ligand having a strongly Π-acidic phosphine group.

Another embodiment of the present invention comprises a process involving exciting at least two photocatalysts to an active state wherein the photocatalysts comprise two rhodium atoms; contacting the photocatalysts with hydrogen ions and halogen ions of a hydrohalic acid solution, thereby producing hydrogen and a photocatalyst in a mixed valence state comprising halogen atoms; and irradiating the photocatalyst in a mixed valence state to eliminate at least a portion of the halogen atoms. The embodiment may include a hydrogen ion and a halogen ion binding to the photocatalysts prior to reacting to produce hydrogen and an unidentified photocatalytic intermediate. It is theorized that the photocataltic intermediate reacts with additional hydrogen ions and halogen ions to form a photocatalyst comprising four halogen atoms and additional hydrogen. The process may then be continued by further radiation of the photocatalyst to eliminate the halogen atoms and absorbing the halogen atoms in a halogen-atom trap. Preferably, the photocatalyst is excited by irradiation with sunlight.

An additional embodiment of the present invention includes a compound comprising two iridium atoms, wherein the iridium atoms are in a two-electron mixed-valence state, and at least one ligand. The iridium compound may be stabilized by at least one ligand, such as, for example, a diphosphazane ligand.

BRIEF DESCRIPTION OF THE DRAWINGS

The features and advantages of embodiments of the present invention may be better understood by reference to the accompanying figures, in which:

FIG. 1(a) is a thermal ellipsoid plot (50% probability) for $Rh_2^{0,II}(dfpma)_3Cl_2(PEt_3)$ (1-$PEt_3$) and FIG. 1(b) is a thermal ellipsoid plot (50% probability) for $Rh_2^{0,II}(dfpma)_3Br_2(PPh_3)$ (2-$PPh_3$), and wherein the hydrogen atoms and solvent molecules have been omitted for clarity;

FIG. 2(a) is the $^{19}F$ NMR of $Rh_2^{II,II}(dfpma)_3Cl_4$ (4) in $CDCl_3$; FIG. 2(b) is the $^{19}F\{^{31}P\}$ NMR spectra of $Rh_2^{II,II}(dfpma)_3Cl_4$ (4) in $CDCl_3$; FIG. 2(c) is the $^{19}F$ NMR of $Rh_2^{0,II}(dfpma)_3Cl_2(PPh_3)$ ("1-$PPh_3$") in $CDCL_3$; and FIG 2(d) $^{19}F\{^{31}P\}$ NMR spectra of $Rh_2^{0,II}(dfpma)_3Cl_2(PPh_3)$ (1-$PPh_3$) in $CDCl_3$ (wherein the signals at −74 and −68 ppm in spectra 2(b) and 2(d) are artifacts due to the $^{31}P$ decoupling pulse, and the insets in FIG. 2(a) and FIG. 2(c) show the Neumann Projection structures of 4 and 1-$PPh_3$, respectively);

FIG. 5(a) is the thermal ellipsoid plot (50% probability) for Rh$_2$(dppma)$_3$(CO)$_2$ (12) and FIG. 5(b) is the thermal ellipsoid plot (50% probability) for Rh$_2$(dppma)$_2$Cl$_4$(CO)$_2$ (13) wherein the hydrogen atoms and solvent molecules have been omitted and only the ipso carbons of the phenyl ring are shown for clarity;

FIG. 7(a) is a thermal ellipsoid plot (50% probability) for syn-Rh$_2^{II,II}$(tfepma)$_3$Cl$_4$ (19) and FIG. 17(b) is a thermal ellipsoid plot (50% probability) for anti-Rh$_2^{II,II}$(tfepma)$_3$Cl$_4$ (20), wherein the hydrogen atoms and solvent molecules have been omitted for clarity;

FIG. 15 includes $^{31}$P and partial $^1$H NMR spectra of Ir$_2^{0,II}$(tfepma)$_2$Cl$_2$ (3) in d$^8$-THF at wherein FIG. 15(a) is at 20° C. and FIG. 15(b) is at −80° C.;

FIG. 16(a) is a thermal ellipsoid plot (50% probability) of Ir$_2^{0,II}$(tfepma)$_3$Cl$_2$(MeCN) (4) and FIG. 16(b) is the thermal ellipsoid plot (50% probability) of Ir$_2^{0,II}$(tfepma)$_3$Cl$_2$(CN$^t$Bu) (5-CN$^t$Bu) wherein for clarity, hydrogen atoms have been omitted and only the methylene carbons of the trifluoroethyl groups are shown;

FIG. 18(a) is a thermal ellipsoid plot (50% probability) of Ir$_2^{I,III}$(tfepma)$_3$Cl$_4$ (7), and FIG. 18(b) is a thermal ellipsoid plot (50% probability) of Ir$_2^{II,II}$(tfepma)$_2$Cl$_4$(MeCN)$_2$ (8), wherein for clarity, hydrogen atoms have been omitted and only the methylene carbons of the trifluoroethyl groups are shown;

FIG. 24 depicts molecular structures of the homologous series of binuclear rhodium complexes wherein

FIG. 34(a) is a graph of UV-Vis absorption changes associated with the photolysis ($\lambda_{exc}$≧335 nm) of Rh₂$^{0,0}$(dfpma)₃(CO)(PPh₃) in CH₂Cl₂ solution containing 0.1 M HCl, and FIG. 34(b) is a graph of UV-Vis absorption changes associated with the photolysis ($\lambda_{exc}$≧335 nm) of Rh₂$^{0,0}$(dfpma)₃(CO)(PPh₃) in CH₂Cl₂ solution containing 0.1 M HBr, wherein the spectra of FIG. 34(a) were acquired at $t_{irr}$=0, 2, 5, 7, 10, 15, 20 and 25 min. and the spectra of FIG. 34(b) were acquired at $t_{irr}$=0, 2, 5, 7, 10, 12, 15, 20, 25 and 30 min.;

CHARACTERIZATION OF LIGAND EFFECTS ON BINUCLEAR CORES

Figure 2:
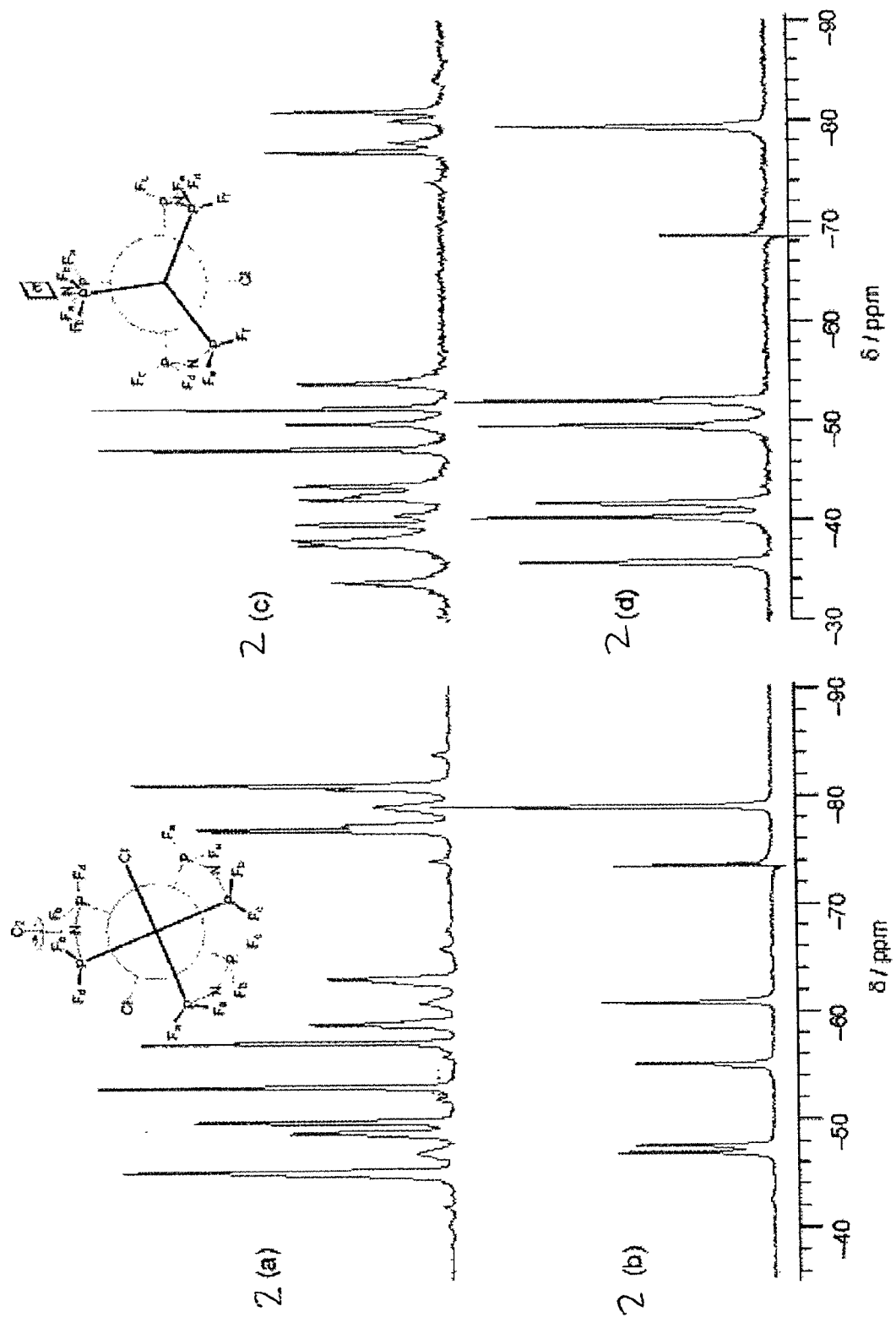
FIG. 2(a)–(d) are the following NMR spectra of dirhodium dfpma complexes.

Research in inorganic chemistry includes preparation of new molecules to mediate multi-electron transformations. Such transformations assist in the activation of small molecules and allow more controlled reactivity of small molecules. Excited-state valence disproportionation of symmetric quadruply-bonded dimers may be observed by transient spectroscopic techniques. The present inventors developed complexes in which two-electron mixed valency could be incorporated into ground state configurations of the transition metal complexes.

Preparation of two-electron mixed-valence compounds is accomplished through the internal disproportionation of valence symmetric metal complexes. The inventors envisioned three different approaches to internal disproportionation, depicted in Scheme 1, were envisioned to effect this reaction and determine ligands which are capable of stabilizing a two electron mixed valence state of a multinuclear transition metal core, and more specifically a binuclear transition metal core. In Case I of Scheme 1, an asymmetric ligand is constructed from disparate electron withdrawing and electron donating fragments. In such a case, the electron-withdrawing group may stabilize low-valent metal centers whereas the electron-donating group may stabilize high-valent metal centers such as an oxypyridinate ligand. Synthetically, disporoportionation by the method of Case I is challenging for at least two reasons. General strategies for the preparation of simple asymmetric bridging ligands utilize a complex multi-step procedure. Secondly, it is difficult to control the linkage isomerism of ligands that possess inherent asymmetry such as oxypyridinate ligands. Typically, two asymmetric ligands add to a binuclear metal core in a head-to-tail fashion,

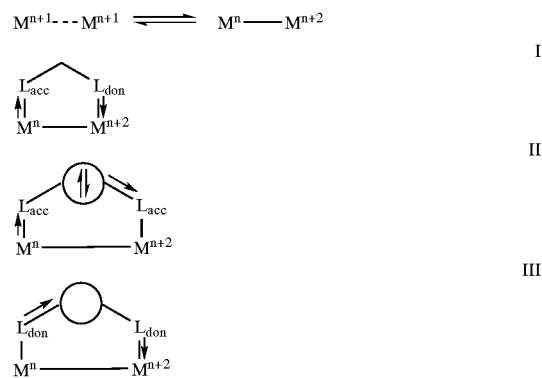

Scheme 1 yielding a net symmetric electronic environment.

Preparation of two-electron mixed-valence complexes may also be accomplished by induced asymmetry of the bridging ligand framework. See Cases II and III in Scheme 1. A bridging ligand between the metal centers may be used to create an induced asymmetric environment suitable for late transition metals. For example, a three atom bridging ligand, with π-acid groups to coordinate the metal centers and a Lewis-basic bridgehead atom, may induce an asymmetric environment via directional lone pair donation from the bridgehead atom to one π-acid group. In another embodiment, a ligand composed of hard π-donating coordination groups and a Lewis π-acidic bridgehead atom may lead to valence disproportionation in high-valent early transition metal complexes. Embodiments of the present invention may comprise any ligand capable of stabilizing a mixed valence state in the binuclear transition metal core. An embodiment of the present invention of a Case II ligand may be a ligand of the formula, RN(PY₂)₂, wherein the ligand comprises a phosphazane group, P—N—P. The Y groups may be independently selected and may be any combination of groups which give at least one phosphorous atom of the phosphazane group strong π-acid characteristics, preferably both phosphorous atoms have strong π-acid characteristics. The Y groups may not all be identical atoms or groups and all the Y's need not contribute to the π-acidity of the coordinating atoms. The Y group may be, for example, but not limited to, at least one of halogen, fluorine, chlorine, halogenated alkanes, halogenated alkenes, aryl substituted with electron withdrawing groups, and alcohols. The ligands have strong π-acid characteristics, if at least a portion of the transition metal complexes are present in the two electron mixed valence state. As the strength of the π-acidity of the attached ligands of binuclear transition metal complexes increase, the complexes will form an equilibrium wherein at least a portion of the complexes will exist in the two electron mixed valence state. These complexes will be photocatalytically active in the present invention. As the pi-acidity of the ligands increases the equilibrium of the complexes will shift toward a state in which all of the complexes are in the two electron mixed valence state. Additionally, the Figures and the Examples use three ligands to stabilize the mixed valence state of the photocatalyst, however, it is contemplated that a single ligand may be prepared comprising the characteristics necessary to stabilize the mixed valence state. The single ligand may be, for example, a multidentate ligand which comprises the electronic and steric properties described above. Such as, for example, the ligands described herein connected through the R group.

The R attached to a nitrogen atom of the phosphazane group may be any atom or group which allows participation of a lone pair of electrons to participate in π-bonding with the phosporus atoms. The R attached to a nitrogen atom may be, for example, but not limited to, a substituted or unsubstituted $C_1$–$C_{10}$ alkyl groups, methyl, ethyl, propyl, butyl, pentyl, hydrogen and a substituted phenyl, wherein the alkyl group may be a branched or an unbranched alkyl group.

A Case II ligand may be prepared by the reaction of $PCl_3$ with primary amines which leads to the formation of a bis(dichlorophosphine)amine fragment as shown in Scheme 2. This reaction has been observed for a variety of starting materials, Scheme 2

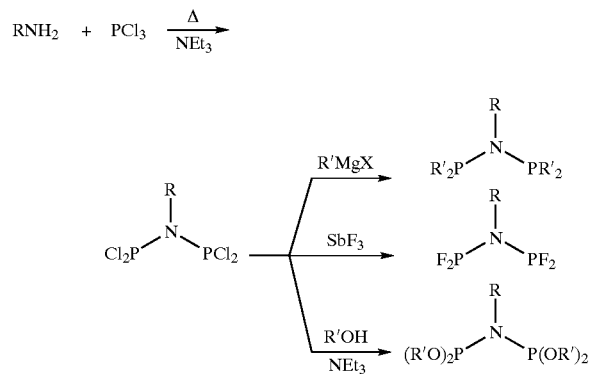

including simple alkyl amines and substituted aniline derivatives. Reaction with Grignard and alkyl lithium reagents affords alkyl phosphines; rapid reaction with alcohols in the presence of tertiary amine bases gives the corresponding phosphite derivatives. Finally, metathesis with antimony trifluoride provides a high-yield route to the bis(difluorophosphine)amine derivative, which possess more π-acidic phosphines of the PNP-type ligands. These synthetic routes are versatile. Electronic and steric parameters of the ligand can be finely manipulated by functionalization at both the nitrogen and phosphorus centers.

The ligands as described above may be used to stabilize internal disproportionation on any binuclear transition metal transition metal complex. The core may comprise different transition metals. The transition metals comprising the binuclear core may be independently selected from, for example, Rh, Ir, Cu, Fe, Ru, Cr, Mo, W, Co, Re, No, Mn, V, Nb, Ta, Zn, Au, Pd, Pt and Ag.

The chemistry of dfpma with Group VI metals was determined shortly after its preparation. Three ligands were observed to span $d^9$—$d^9$ metal cores, as observed for $Co_2^{0,0}$(dfpma)$_3$(CO)$_2$. UV-irradiation of this complex in alkane solutions containing phosphine ligands leads to carbonyl loss and coordination of the phosphine in the axial site. An extensive redox chemistry was explored for $Co_2^{0,0}$(dfpma)$_3$(CO)$_2$. For example, oxidation with $Br_2$ gave a four electron oxidized species, $Co_2^{II,II}$(dfpma)$_3Br_4$, whereas electrochemical reduction gave a two-electron reduced anionic complex, $[Co_2^{-I,-I}$(dfpma)$_3$(CO)$_2]$.

An embodiment of the present invention may also comprise a Case III ligand. A nonlimiting example of a Case III ligand is one of the formula, $RN(BY_1)$, wherein the R is as described above and the $Y_1$ may be independently selected and may be any atom or group which contributes to hard π-donating characteristic of the coordination groups. Embodiments of the present invention may comprise any ligand capable of causing internal disproportionation of the multinuclear core and capable of stabilizing a mixed valence state.

Unless otherwise indicated, all numbers expressing quantities of ingredients, time, temperatures, and so forth used in the present specification and claims are to be understood as being modified in all instances by the term "about." Accordingly, unless indicated to the contrary, the numerical parameters set forth in the following specification and claims are approximations that may vary depending upon the desired properties sought to be obtained by the present invention. At the very least, and not as an attempt to limit the application of the doctrine of equivalents to the scope Scheme 3

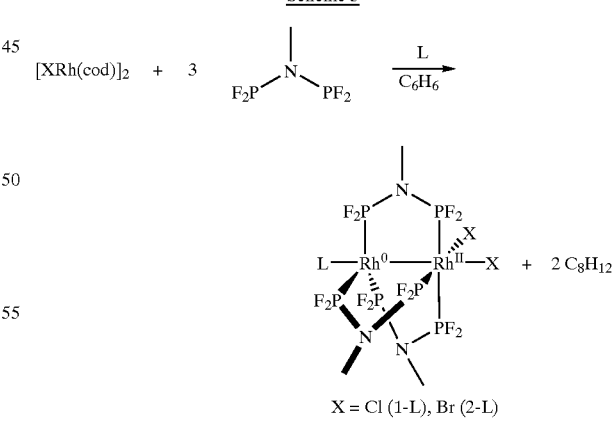

of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, may inherently contain certain errors necessarily resulting from the standard deviation found in their respective testing measurements.

To extend the two-electron mixed-valence chemistry of these ligands, the steric and electronic characteristics of the PNP ligands framework that favor the valence disproportionation of symmetric binuclear cores was explored. Embodiments described herein suggest that the induced asymmetry of Case II in Scheme 1 is effective in promoting the formation of two-electron mixed-valence complexes. The electronic and the steric parameters of the bridging PNP ligand may be controlled to favor valence disproportionation resulting in two-electron mixed-valence species.

The reaction of dfpma with the rhodium(I) dimers, such as, [XRh$^I$(PF$_3$)$_2$]$_2$ or XRhP$_4$, for example, where X=Cl, Br, I, alkyl, triflates, hydrides, and other monodentate anionic ligands, produces two-electron mixed-valence complexes Rh$_2^{0,II}$(dfpma)$_3$X$_2$(L), in which L may be, for example, PF$_3$ or a monodentate dfpma ligand, depending on reaction stoichiometry, with yields of ca. 25%. A more reliable and general path into the rhodium complexes was sought from [XRh$^I$(cyclooctadiene)]$_2$ ("[XRh$^I$(cod)]$_2$") starting materials. Rh$_2^{0,II}$(dfpma)$_3$X$_2$(L) was therefore prepared by the addition of three equivalents of dfpma and one equivalent of a two electron donor ligand (for example, P(OR)$_3$, PR$_3$, and CNR) to benzene solutions of [XRh$^I$(cod)]$_2$, as depicted in Scheme 3. Stirring at room temperature resulted in precipitation of most of the product over the span of 24 hr. Concentration by solvent distillation followed by the addition of pentane typically provided high yields of Rh$_2^{0,II}$(dfpma)$_3$X$_2$(L) (X=Cl ("1-L" in Scheme 3), Br ("2-L" in Scheme 3); L=P(OR)$_3$, PR$_3$, CNR). In the case of the carbonyl adduct, Rh$_2^{0,II}$(dfpma)$_3$Cl$_2$(CO) ("1-CO"), dfpma was reacted with the carbonyl dimer [ClRh(CO)$_2$]$_2$ in CH$_2$Cl$_2$ rather than benzene. The CH$_2$Cl$_2$ was then removed and the residue washed with 1:5 benzene/pentane to afford an orange powder that was dried briefly in vacuo. 1-CO left under vacuum for extended periods of time (a few hours) changed color from orange to green-blue. This color change was accompanied by disappearance of the carbonyl resonance in the IR spectrum, indicating loss of an axial CO ligand.

The solid-state structures for several of the two-electron mixed-valence complexes have been determined from single crystal X-ray diffraction data. Thermal ellipsoid plots for two derivatives, Rh$_2^{0,II}$(dfpma)$_3$Cl$_2$(PEt$_3$) ("1-PEt$_3$") and Rh$_2^{0,II}$(dfpma)$_3$Br$_2$(PPh$_3$) ("2-PPh$_3$"), are shown in FIGS. 1(a) and (b). Thermal ellipsoid plots are ball and stick type illustrations of structures of chemical compounds. The 50% probability thermal motion ellipsoids of the atomic sites are derived from anisotropic temperature factor parameters to indicate the thermal motion of the atom 50% of the time. Tables 1 and 2 list a few metrical parameters of complexes comprising the dirhodium cores. The dfpma bond distances of these derivatives indicates stabilization of the two-electron mixed-valence dirhodium core. For example, contraction of the N—P bond distance is observed for the phosphorus atoms coordinated to the high-valent Rh$^{II}$ (avg N—P$^{Rh(II)}$=1.634(4) Å for 1-PEt$_3$ and 1.633(6Å for 2-PPh$_3$) center, suggesting, but not meant to limit the present invention, that the nitrogen lone pair moderates the electronic properties of the π-acid PF$_2$ groups. A longer N—P bond distance is observed for the phosphorus coordinated to the Rh$^0$ (avg N—P$^{Rh(O)}$=1.659(4) Å for 1-PEt$_3$ and 1.684(5) Å for 2-PPh$_3$), consistent with a mechanism theory that there is little donation of the nitrogen lone pair to the PF$_2$ group coordinated to the low-valent Rh$^0$ center of the complex.

TABLE 1

N—P bond lengths (Å) of the bridging dfpma ligands of Rh$_2^{0,II}$(dfpma)$_3$Cl$_2$(PEt$_3$) (1-PEt$_3$) and Rh$_2^{0,II}$(dfpma)$_3$Br$_2$(PPh$_3$) (2-PPh$_3$).

| N—P Bond Distances in 1-PEt$_3$ (Å) | | | |
|---|---|---|---|
| P(1)-N(1) | 1.663(4) | P(2)-N(1) | 1.633(4) |
| P(3)-N(2) | 1.670(4) | P(4)-N(2) | 1.633(4) |
| P(5)-N(3) | 1.675(4) | P(6)-N(3) | 1.636(5) |
| N—P Bond Distances in 2-PPh$_3$ (Å) | | | |
| P(1)-N(1) | 1.684(5) | P(2)-N(1) | 1.630(6) |
| P(3)-N(2) | 1.684(5) | P(4)-N(2) | 1.634(6) |
| P(5)-N(3) | 1.685(6) | P(6)-N(3) | 1.636(6) |

Other metrical parameters of interest include the bond distances of the dirhodium core for various Rh$_2^{0,II}$(dfpma)$_3$X$_2$(L) derivatives. Lengthening of the dirhodium core bond length indicates stability in the mixed-valence structure. Several factors lead to structural perturbations along the Rh$^0$—Rh$^{II}$ axis, including, but not limited to, axial ligand coordination to the Rh$^0$ center and halogen coordination to the Rh$^{II}$ center. The metrical data in Table 2 for selected Rh$_2^{0,II}$ complexes gives insight into the effects of each of these substitutions. A lengthening of the Rh$^0$—Rh$^{II}$ bond distance occurs upon phosphine substitution. Exchange of an axial PF$_3$ in Rh$^{0,II}$ (dfpma)$_3$(Cl$_2$)(PF$_3$)("1-PF$_3$") for PEt$_3$ to form Rh$^{0,II}$(dfpma)$_3$(Cl$_2$) (PEt$_3$)("1-PEt$_3$") results in a 0.0405 Å increase in the Rh$^0$—Rh$^{II}$ separation; similarly, exchange of an axial η$^1$-dfpma for PPh$_3$ in Rh$_2^{0,II}$(dfpma)$_3$Br$_2$(η$^1$-dfpma) ("2-(η$^1$-dfpma)") and 2-PPh$_3$ results in a 0.0403 Å increase in the Rh$^0$—Rh$^{II}$ separation. Spectroscopic studies presented herein indicate that PF$_3$ and η$^1$-dfpma exert similar stereo-electronic influence on the dirhodium core, permitting a comparison of the ligand effect of 1-PF$_3$ with 2-(η$^1$-dfpma). Substitution of bromide for chloride in complexes with these π-acidic axial phosphines results in a lengthening of the Rh$^0$—Rh$^{II}$ bond by 0.013 Å. The magnitude of the perturbation exerted by halogen and phosphine substitution on the Rh$^0$—Rh$^{II}$ bond distance follows directly from the relative donor abilities of each axial ligand. Whereas exchange of bromide for chloride at the axial Rh$^{II}$ position results in only a small change in σ donor ability, PEt$_3$ and PPh$_3$ are significantly better σ donors than PF$_3$ and dfpma, and accordingly weaken the metal-metal interaction to a greater extent.

TABLE 2

Rh$^0$—Rh$^{II}$ bond lengths (Å) for Rh$_2^{0,II}$(dfpma)$_3$X$_2$(L) (X = Cl (1-L), X = Br (2-L)).
Bond Distances (Å)

| | 1-PF3a | 2-(η1-dfpma)b | 1-PEt3 | 2-PPh3 |
|---|---|---|---|---|
| Rh(1)-Rh(2) | 2.785(1) | 2.798(2) | 2.8255(5) | 2.8383(9) |
| Rh(1)-P(1) | 2.254(2) | 2.246(7) | 2.2342(13) | 2.238(2) |
| Rh(1)-P(3) | 2.209(2) | 2.229(7) | 2.1906(13) | 2.202(2) |
| Rh(1)-P(5) | 2.248(2) | 2.243(6) | 2.2228(13) | 2.259(2) |
| Rh(1)-P(7) | 2.168(2) | 2.203(6) | 3.3277(13) | 2.335(2) |
| Rh(2)-X(1) | 2.431(2) | 2.579(3) | 2.4530(12) | 2.6066(10) |
| Rh(2)-X(2) | 2.385(2) | 2.524(4) | 2.3905(12) | 2.5020(11) |
| Rh(2)-P(2) | 2.251(2) | 2.241(7) | 2.2434(13) | 2.254(2) |
| Rh(2)-P(4) | 2.183(2) | 2.185(7) | 2.1610(13) | 2.184(2) |
| Rh(2)-P(6) | 2.258(2) | 2.247(7) | 2.2420(14) | 2.249(2) |

The preparation of two-electron reduced binuclear rhodium complexes was achieved from [XRh(cod)]$_2$ starting materials. Treatment of [ClRh(cod)]$_2$ with three equivalents of dfpma, followed by two equivalents each of cobaltocene and a two-electron donor ligand resulted in the formation of binuclear rhodium complexes of the general formulation $Rh_2^{0,0}(dfpma)_3(L)_2$ (3-L where L may be $PR_3$, $P(OR)_3$, CNR for example), which are structurally analogous to $Co_2(dfpma)_3(L)_2$ (Scheme 4). The coordination environment is characterized by trigonal bipyramidal $Rh^0$ centers. A formal metal-metal bond is supported by three bridging dfpma ligands; the $PF_2$ groups of these bridging ligands define the equatorial plane of each $Rh^0$ center. The axial position, trans to the metal-metal bond is capped by a donor ligand, electron accepting axial ligands such as, for example, $PF_3$, phosphites or isonitriles impart substantial stability, and aryl and alkyl phosphines continuing complexes have been prepared as well. The stability of the reduced species is illustrated by sublimation of $Rh_2^{0,0}(dfpma)_3(PF_3)_2$ ("3-$PF_3$") and $Rh_2^{0,0}(dfpma)_3(\eta^1\text{-dfpma})_2$ ("3-($\eta^1$-dfpma)") under vacuum at 110° C.

The two-electron oxidized rhodium dimers may be prepared from $[XRh(cod)]_2$ by the addition of three equivalents of dfpma and five equivalents of $PhICl_2$ or $Br_2$ (Scheme 5). The excess oxidant may be required to drive the reaction to completion, since coordination of the dfpma resulted in the production of free 1,5-cyclooctadiene,

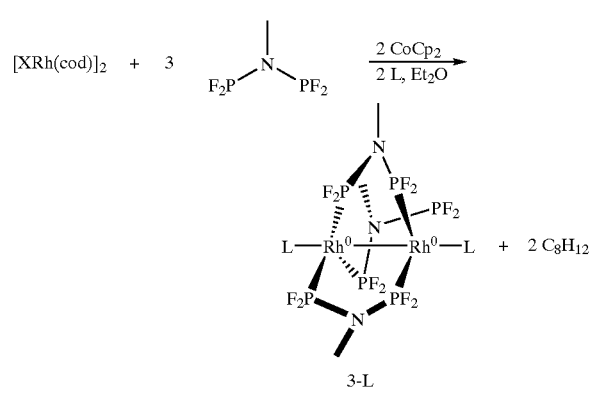

Scheme 4

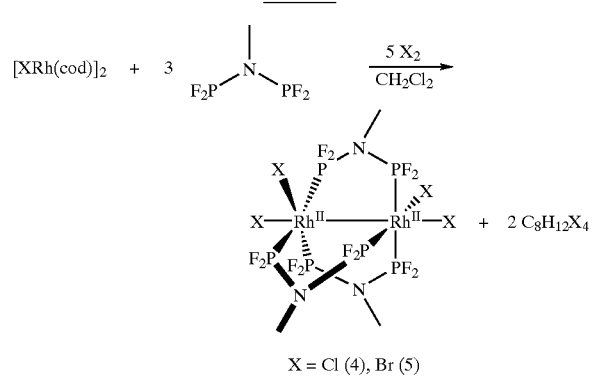

Scheme 5

X = Cl (4), Br (5)

which in turn consumed the halogen oxidant. Use of excess oxidant afforded pure $Rh_2^{II,II}(dfpma)_3X_4$ (X=Cl (4), Br (5)) in yields of greater then 90%. The oxidized $Rh_2^{II,II}(dfpma)_3X_4$ species comprises octahedral $Rh^{II}$ centers connected by a metal-metal bond. Three dfpma ligands maintain a bridging coordination mode, and halogen ligands occupy axial and equatorial portions on each metal center.

In general, the $^1H$ and $^{19}F$ NMR spectra are useful for characterizing the complexes, however due to excessively broad peaks in the output, $^{31}P$ NMR cannot be used to probe the dfpma backbone. The dfpma complexes were not fluxional on the NMR time scale. The reduced complexes, $Rh_2^{0,0}(dfpma)_3L_2$ (3-L), which display $D_{3d}$ symmetry in solution, show the simplest NMR patterns; $^1H$ and $^{19}F$ NMR data for 3-CO, 3-$PPh_3$, 3-$CN^tBu$, 3-$PF_3$ and 3-($\eta^1$-dfpma) are presented in Table 3. In addition to resonances for the axial L ligands, a singlet, the electronic state in which the total spin angular momentum is zero, is observed for the methyl groups of the bridging dfpma ligands in the 2–3 ppm region. One resonance is observed for the dfpma ligands near −40 ppm in the $^{19}F$ NMR spectrum, and is easily identified by a strong $|^1J_{PF}+^3J_{PF}|$ of 1110–1120 Hz.

TABLE 3

$^1H$ and $^{19}F$ NMR data for $Rh_2^{0,0}(dfpma)_3L_2$
(3-L; L = CO, $PPh_3$, $CN^tBu$, $PF_3$ and $\eta^1$-dfpma).
Spectra were acquired in $C_6D_6$ except as noted.

| Compound | $^1H$ (δ/ppm) | $^{19}F$ (δ/ppm)[a] |
|---|---|---|
| 3-CO | 2.17(s) | −40.31(d, 1116Hz) |
| 3-$PPh_3$[b] | 2.68(s, 9H) | −43.18(d, 1113Hz) |
| | 7.45(m, 30H) | |
| 3-$CN^tBu$ | 0.956(s, 18H) | −40.53(d, 1083Hz) |
| | 2.58(s, 9H) | |
| 3-$PF_3$ | 2.12(s) | −7.16(d, 1359Hz, 6F) |
| | | −40.74(d, 1109Hz, 12F) |
| 3-($\eta^1$-dfpma) | 2.29(s, 9H) | −29.73(d, 1175Hz, 4F) |
| | 2.34(d, 7Hz, 6H) | −40.94(d, 1116Hz, 12F) |
| | | −76.28(d, 1252Hz, 4F) |

[a]Listed coupling constant is $|^1J_{PF}+^3J_{PF}|$,
[b]Spectra acquired in $CDCl_3$.

TABLE 4

$^{19}F$ NMR (δ and $|^1J_{PF}+^3J_{PF}|$) data for
$Rh_2^{II,II}(dfpma)_3X_4$ (X = Cl (4), Br (5)), the
designations $F_{a-e}$ refer to the Neumann Projections
in FIG. 1.2. Spectra were acquired in $CDCl_3$.

| Assignment | 4 (δ/ppm) | | 5 (δ/ppm) |
|---|---|---|---|
| $F_a$ | −78.7(1164Hz) | 5 | −73.9(1101Hz) |
| $F_c$ | −46.6(1128Hz) | 2 | −44.5(1128Hz) |
| $F_d$ | −47.3(1295Hz) | 0 | −47.6(1320Hz) |
| $F_e$ | −54.9(1160Hz) | 6 | −48.9(1150Hz) |
| $F_b$ | −60.6(1200Hz) | 2 | −59.3(1185Hz) |

TABLE 5

$^{19}F$ NMR (δ and $|^1J_{PF}+^3J_{PF}|$) data for
$Rh_2^{0,II}(dfpma)_3X_2(L)$ (X = Cl (1-L), Br (2-L)), the
designations $F_{a-e}$ refer to the Neumann
Projections in FIG. 1.2. Spectra were acquired in $CDCl_3$.

| Assignment | 1-$PPh_3$ (δ/ppm) | | 2-$PPh_3$ (δ/ppm) | | 2-$P(O^iPr)_3$ (δ/ppm) |
|---|---|---|---|---|---|
| $F_c$ | −35.7(1047Hz) | 0 | −35.7(1067Hz) | 4 | −39.6(1089Hz) |
| $F_e$ | −40.6(1181Hz) | 0 | −40.4(1122Hz) | 0 | −40.9(1155Hz) |
| $F_f$ | −41.8(1106Hz) | 0 | −41.5(1187Hz) | 0 | −41.8(1115Hz) |
| $F_b$ | −49.5(1166Hz) | 3 | −46.8(1174Hz) | 0 | −46.5(1174Hz) |
| $F_d$ | −52.0(1121Hz) | 0 | −52.0(1118Hz) | 1 | −51.3(1117Hz) |
| $F_a$ | −79.1(1121Hz) | 5 | −74.1(1132Hz) | 1 | −73.0(1120Hz) |

The $^1H$ NMR spectra of the $Rh_2^{II,II}(dfpma)_3X_4$ (X=Cl (4), Br (5)) complexes show the resonances for the methyl groups of the bridging dfpma ligands as a multiplet at 3.2 ppm. The $^{19}$F NMR spectrum contains several first- and second-order spin systems, but simplifies to a five-line pattern upon $^{31}$P decoupling, consistent with a C$_2$ symmetric structure for 4 and 5 in solution. For illustrative purposes the $^{19}$F and $^{19}$F{$^{31}$P} NMR spectra of 4 are displayed in FIGS. 2(a) and (b), respectively (Table 4 contains the chemical shift values and $|^1J_{PF}+^3J_{PF}|$ coupling constants for both 4 and 5). Notably, the fluorine atoms of the PF$_2$ groups located trans to the halide ligands (F$_a$ in the Neumann Projection of FIG. 2(a)) are shifted to low frequency at −78.7 ppm. Four AB sub-spectra observed inside and outside of the $|^1J_{PF}+^3J_{PF}|$ doublet is indicative of direct ($^1J_{PF}$) and indirect ($^3J_{PF}$) phosphorus coupling constants of opposite sign. Similar XX'AA'X"X'" coupling patterns in the resonances at −60.6 and −46.6 ppm identify these resonances as the fluorine atoms F$_b$ and F$_c$, respectively, coupled to F$_a$ through the nitrogen bridgehead. The remaining resonances at −47.3 and −54.9 ppm are assigned as F$_d$ and F$_e$, respectively, each displaying only a doublet with a coupling constant given by $|^1J_{PF}+^3J_{PF}|$.

Interpretation of the NMR spectra for the Rh$_2^{0,II}$(dfpma)$_3$X$_2$(L) (X=Cl (1-L), Br (2-L)) complexes follows along similar lines. The coordination of a PF$_2$ of one dfpma ligand trans to a halogen on the octahedral Rh$^{II}$ center gives rise to two $^1$H NMR methyl resonances at 2.8 and 2.9 ppm for the bridging dfpma ligands, integrating in a 1:2 ratio, respectively. Additionally, the $^1$H NMR displays resonances diagnostic of the axial ligand, L, capping the Rh$^0$ center. The $^{19}$F and $^{19}$F{$^{31}$P} NMR spectra of 1-PPh$_3$ are presented in FIGS. 2(c) and 2(d) (representative $^{19}$F NMR data for 1-L can be found in Table 5). Several complex spin systems are observed in the $^{19}$F NMR absorption spectrum, but simplify to a six-line pattern for the dfpma ligands upon 31P decoupling. The structure of 1-PPh$_3$ is C$_s$ symmetric in solution, as can be seen in the Neumann Projection inset into FIG. 2(c); the mirror plane is defined by the two rhodium centers and the equatorial halogen ligand. By analogy to the spectra of 4, the low frequency resonance at −79.3 ppm is indicative of a PF$_2$ group coordinated trans to the halide ligand, thus assigned to F$_a$; the fluorine atoms of the Rh$^0$-coordinated PF$_2$ group (F$_b$) of this dfpma ligand are resolved at −49.5 ppm. The two Rh$^0$-coordinated PF$_2$ groups (F$_e$ and F$_f$) are observed as $|^1J_{PF}+^3J_{PF}|$ doublets at −40.6 and −41.8 by analogy to the Rh$_2^{0,0}$ complexes, 3-L. The remaining resonances at −35.7 and −52.0 ppm are assigned to the fluorine atoms of the remaining Rh$^{II}$ PF$_2$ groups, F$_c$ and F$_c$.

Bis(dimethylphosphite)methyl amine

The preparation of bis(dimethylphosphite)methyl amine (dmpma) and bis(diphenylphosphite)methyl amine (dppma) is straightforward. Treatment of MeN(PCl$_2$)$_2$ with four equivalents of methanol or phenol and four equivalents of a tertiary amine base in ether or pentane gave the ligand and HCl salt. The dmpma and dppma ligands were purified by distillation and recrystallization, respectively.

Addition of dmpma to CH$_2$Cl$_2$ solutions of [ClRh(CO)$_2$]$_2$ resulted in an immediate color change, affording an intense red solution. Precipitation yielded the product as an orange powder, which analyzed as Rh$_2$(dmpma)$_2$Cl$_2$(CO)$_2$ (6). This compound has been characterized by X-ray diffraction and has the structure depicted in Scheme 6. Infrared spectroscopy showed two CO frequencies, at 1989 and 1808 cm$^{-1}$, for both terminal and bridging CO ligands. However, $^{31}$P NMR spectroscopy showed a single resonance at 132.81 ppm with a $|^1J_{PRh}+^nJ_{PRh}|$ of 142 Hz. VT NMR studies suggested a fluxional dirhodium core. Cooling of CD$_2$Cl$_2$ solutions of 6, led to broadening of the $^{31}$P NMR resonance and a decrease in the observed phosphorus-rhodium

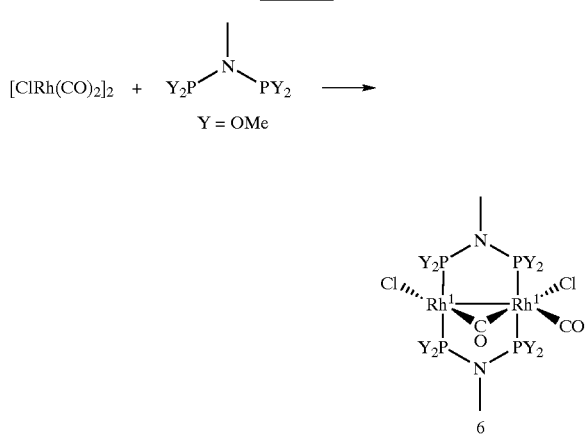

Scheme 6 coupling constant; however, the exchange process could not be arrested within the accessible temperature range. The solution NMR data is nevertheless consistent with the solid-state structure of 6 reported in the literature, in which a single CO ligand bridges the binuclear Rh$^I$ core.

Figure 3:
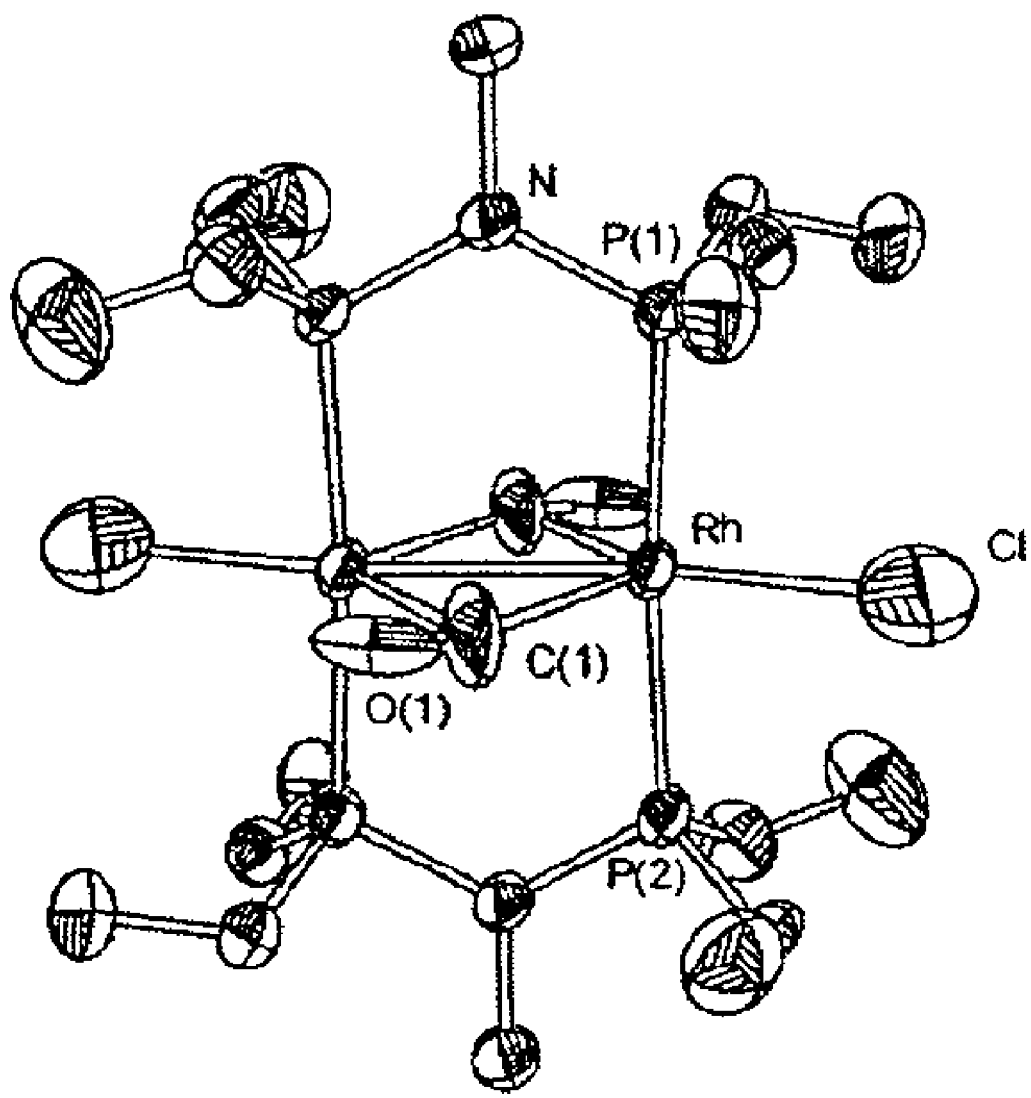
FIG. 3 is a thermal ellipsoid plot (50% probability) for $Rh_2(dmpma)_2Cl_2(\mu\text{-}CO)_2$ (6) wherein the hydrogen atoms have been omitted for clarity.

Single crystals of 6 were obtained from CH$_2$Cl$_2$/heptane solution. Here the X-ray diffraction study gave an isomeric structure with two bridging CO groups (FIG. 3). Two dmpma ligands bridge a valence-symmetric binuclear rhodium core possessing terminal chloride ligands. A Rh—Rh separation of 2.7155(10) Å and an intra-ligand P . . . P separation of 2.913(3) Å indicate the presence of a formal metal-metal bond. Other parameters of note are an average Rh—P distance of 2.2867(19) Å and an average P—N distance of 1.666(6) Å. The Rh(1)'-Rh(1)-Cl(1) angle is 159.73(12)°, and the Rh(1)-Cl(1) distance is normal at 2.418(4) Å.

Bis(diphenylphosphite)methyl amine (dppma)

Similar RhI2 products were obtained for the reaction of dppma with [ClRh(CO)$_2$]$_2$ in CH$_2$Cl$_2$ solution, as shown in Scheme 7. Ligand addition resulted in an immediate color change from pale yellow-orange to very dark purple. Addition of cold pentane caused precipitation of a purple powder in moderate yields; elemental analysis suggested the formulation Rh$_2$(dppma)$_2$Cl$_2$(CO)$_2$ (7). Infrared spectra obtained for KBr pellets of the product showed only a terminal carbonyl frequency at 2009 cm$^{-1}$. This, taken with the intense purple color of the complex suggested a structure containing face-to-face square planar rhodium(I) centers as shown for 7 in Scheme 7. However, solutions of the complex showed both bridging and terminal carbonyl resonances, and VT NMR studies suggested an equilibrium between the face-to-face structure and a structure with one bridging carbonyl (8), as observed for 6.

In solution, 7 slowly rearranged to give a new isomer with two bridging CO ligands and two terminal halides, Rh$_2$(dppma)$_2$Cl$_2$(µ-CO)$_2$ (9), characterized by a single ν$_{CO}$ at 1828 cm$^1$. The $^1$H and $^{31}$P NMR spectra of 9 revealed that this isomer is not fluxional in solution. The $^1$H NMR spectrum displayed a single methyl resonance for the bridging dppma ligands at 2.86 ppm; the protons of the phenyl rings are observed in Scheme 7

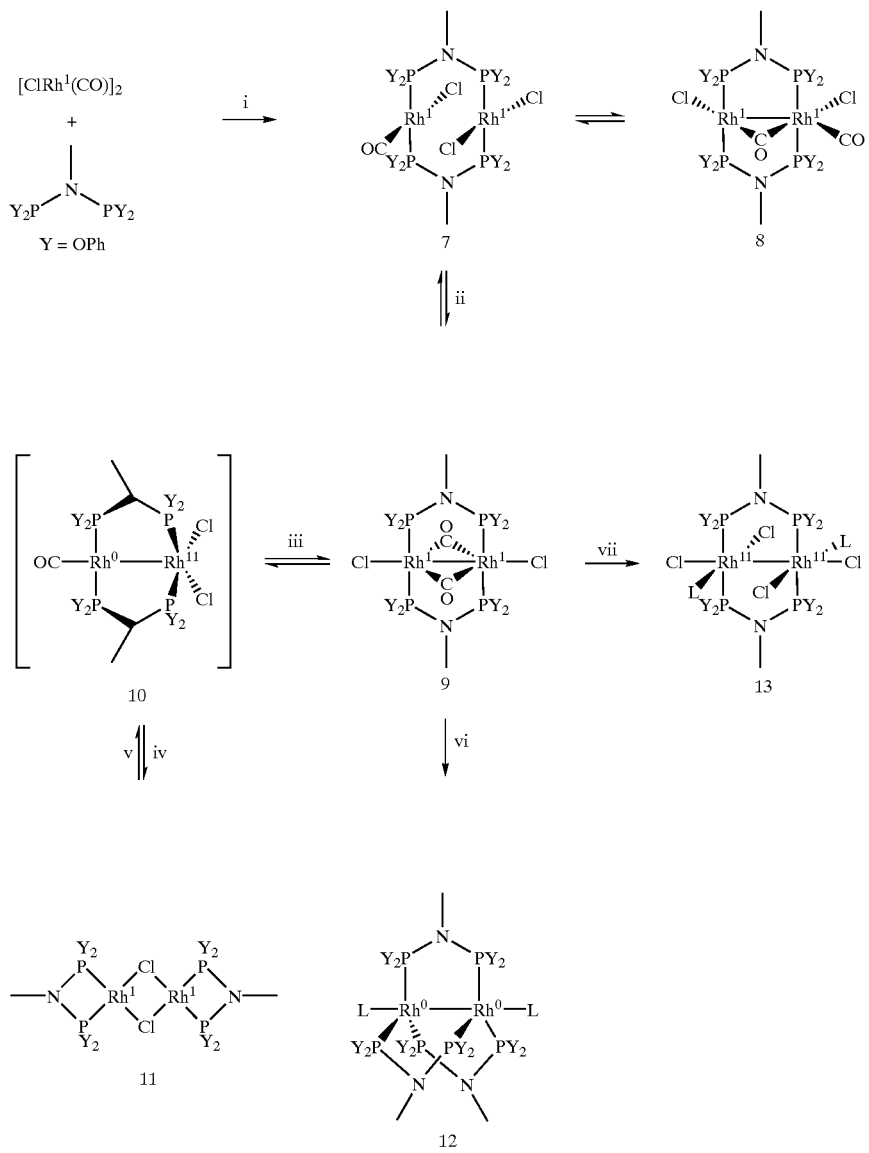

(i) two equiv dppma in THF, -78° C.,
(ii) Δ;
(iii) —CO, precip. from CHCl₃;
(iv) Δ, —CO;
(v) +CO;
(vi) one equiv dppma and two equiv CoCp₂ in CO atmosphere;
(vii) one equiv PhCl₂ and two equiv CN$^t$Bu or CO in CH₂Cl₂.

the 6.8–7.5 ppm region. A single phosphorus resonance was observed in the $^{31}$P NMR spectrum of 9 at 122.61 ppm ($|^{1}J_{PRh}+{}^{n}J_{PRh}|$=170 Hz)

Figure 4:
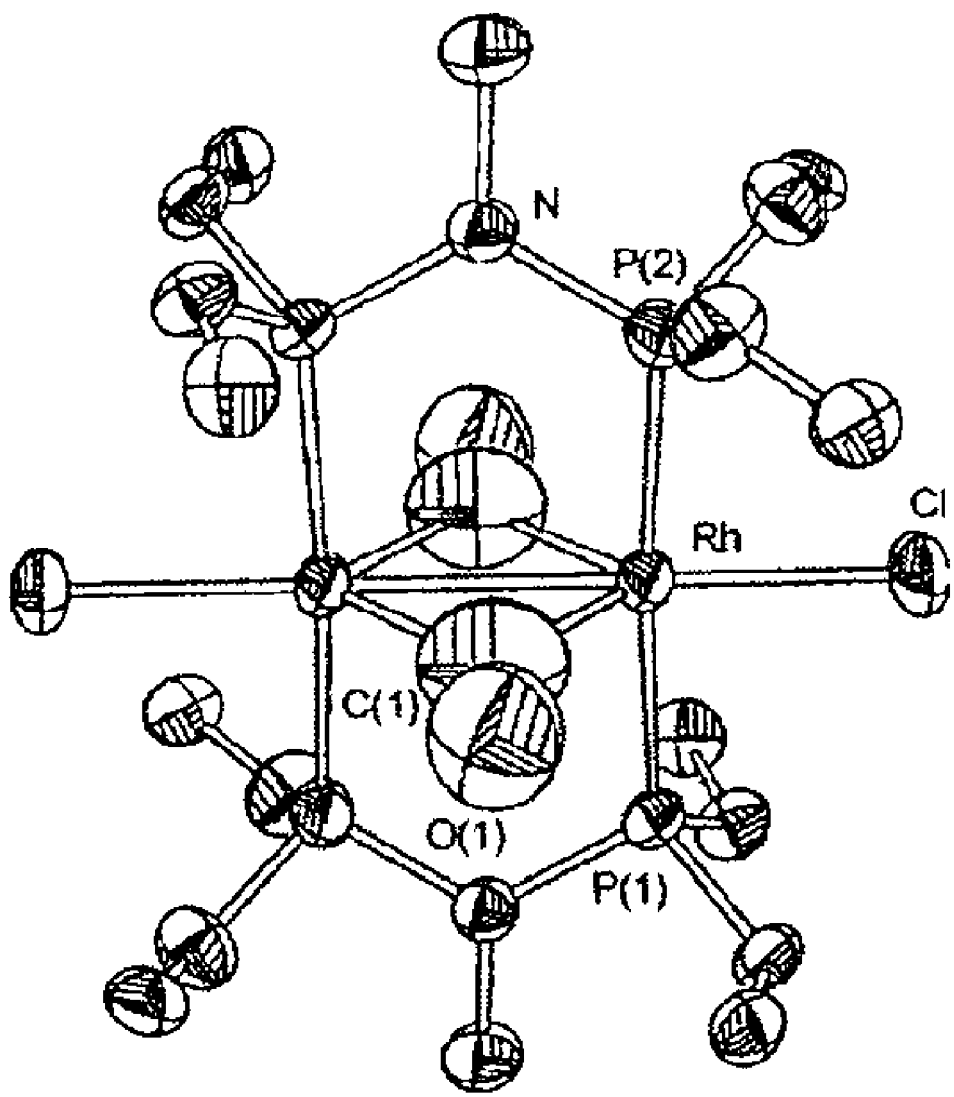
FIG. 4 is the thermal ellipsoid plot (50% probability) for Rh$_2$(dppma)$_2$Cl$_2$($\mu$-CO)$_2$ (9) wherein the hydrogen atoms and a CH$_2$Cl$_2$ solvent molecule have been omitted and only the ipso carbons of the phenyl ring are shown for clarity.

Single crystals suitable for X-ray diffraction studies were obtained for 9 and the data confirmed the solution structure assignments. FIG. 4 shows a structure with two dppma ligands and two CO ligands spanning a short metal-metal separation of 2.7076(8) Å. The carbonyl ligands bridge the dirhodium core in a symmetric fashion with Rh—C(1) and Rh'—C(1) distances of 1.990(13) and 2.010(13) Å, respectively; the Rh—C(1)-Rh' angle is 85.2(4)°. The axial halogen has a normal Rh—X distance of 2.3379(15) Å, and the Cl—Rh—Rh' angle is nearly linear at 175.64(6). The PNP backbone is symmetric with N—P distances of 1.661(5) and 1.676(5) Å, and the intra-ligand P . . . P separation is 2.886(3) Å.

Solutions of 9 decomposed slowly by loss of the carbonyl ligands. The final product observed was the chelated dimer, [ClRh(tfepma)]₂ (11), which was characterized by a single resonance in the $^{31}$P NMR spectrum at 91.13 ppm and an apparent $J_{RhP}$ coupling constant of 280 Hz. Purging solutions of 11 with carbon monoxide regenerated rhodium dimer 7. CO loss from 9 is proposed to proceed through a two-electron mixed-valence complex based on a literature report of a monocarbonyl derivative of the related bis (diphenylphosphite)ethyl amine (dppea) ligand. Single crystals of $Rh_2^{0,II}(dppea)_2Cl_2(CO)$ reportedly were obtained from $CHCl_3$ solutions of $Rh_2^{I,I}(dppea)_2Cl_2(CO)_2$ and provided the coordination environment depicted for 10 in Scheme 7. However, 10 was not explicitly isolated nor characterized as an intermediate in the conversion of 9 to 11.

The dppma ligand supported two-electron oxidation and reduction of the binuclear rhodium core, yielding $Rh_2^{0,0}$ and $Rh_2^{II,II}$ products. 9 was reduced with two equivalents of cobaltocene in the presence of dppma, affording $Rh_2(dppma)_3(CO)_2$ (12) as a yellow microcrystalline solid. Alternatively, 12 was directly prepared from the reaction of $[ClRh(CO)_2]_2$ with three equivalents of dppma and cobaltocene. Single crystals of 12 were obtained by cooling $CH_2Cl_2$/pentane solutions to −35° C. The molecular structure is presented in FIG. 5(a) and pertinent metrical parameters are listed in Table 6. The metal-metal separation in 12 is long at 2.8687(8)Å, however, it is within the range expected for a single Rh—Rh bond. The equatorial coordination planes are staggered with respect to one another, adopting a torsion angle of 35.2°. A C(3)-O(7) bond distance of 1.138(6) Å is relatively long, reflecting a decrease in bond order of the carbonyl ligand due to coordination to the electron-rich $Rh^0$ center. As expected, the PNP backbone of the bridging dppma ligands is symmetric with an average P—N distance of 1.681(4) Å.

Oxidation of 9 with dichloroiodobenzene afforded the valence-symmetric $Rh_2^{II,II}$ dimer $Rh_2(dppma)_2Cl_4(CO)_2$ (13), presented as a thermal ellipsoid plot in FIG. 5(b). Alternatively, the reaction of $[ClRh(cod)]_2$ with $PhICl_2$ and dppma yielded 13 directly. In 13, only two dppma ligands coordinate to the bimetallic core, and small donor ligands such as CO or isonitrile must be incorporated to yield the six-coordinate octahedral geometry at each rhodium center. The metal-metal separation is significantly contracted relative to the reduced complex, 12. A Rh—Rh' distance of 2.705(3) Å in 13 is complimented by a torsion angle for the equatorial planes of only 0.9°. The dppma ligands coordinate trans to one another, with average Rh—P distances of 2.300(6) Å. The Rh—Cl(2) distance of 2.382(7) Å is in the typical range for halogens coordinated trans to a Rh—Rh bond. The equatorial chloride and carbonyl ligands are coordinated in an anti conformation, with Rh—Cl(1) and Rh—C(1) distances of 2.365(8) and 1.95(4) Å, respectively. A short C(1)-O(1) bond distance of 1.09(4) reflects little decrease in the CO bond order.

TABLE 6

Selected bond lengths (Å) for $Rh_2(dppma)_3(CO)_2$ (12) and $Rh_2(dppma)_2Cl_4(CO)_2$ (13).
Selected Bond Lengths (Å)

| $Rh_2(dppma)_3(CO)_2$ | | $Rh_2(dppma)_2Cl_4(CO)_2$ | |
|---|---|---|---|
| Rh-Rh' | 2.8687(8) | Rh-Rh' | 2.705(3) |
| Rh-P(1) | 2.2911(15) | Rh-Cl(1) | 2.365(8) |
| Rh-P(2) | 2.2615(15) | Rh-Cl(2) | 2.382(7) |
| Rh-P(3) | 2.2987(15) | Rh-P(1) | 2.293(6) |
| Rh-C(3) | 1.886(6) | Rh-P(2) | 2.307(6) |
| C(3)-O(7) | 1.138(6) | Rh-C(1) | 1.95(4) |
| P(1)-N(1) | 1.686(4) | C(1)-O(1) | 1.09(4) |
| P(2)-N(2) | 1.678(3) | P(1)-N(1) | 1.680(17) |
| P(3)-N(1)' | 1.678(4) | P(2)-N(1)' | 1.674(17) |

The oxidized and reduced complexes, 12 and 13, of dppma were prepared with isonitrile ligands replacing the carbonyl groups. An X-ray structure obtained on single crystals of $Rh_2(dppma)_2Cl_4(CN^tBu)_2$ confirmed that it is isostructural with the carbonyl derivative, including the eclipsed geometry of the rhodium coordination spheres.

Bis(bis(trifluoroethyl)phosphite)methyl amine ("tfepma")

Based on the results of the methoxy- and phenoxy-substituted PNP ligands, a phosphorus substituent was sought with stronger π-acid properties and a steric parameter larger than fluorine. Tolman's steric and electronic map for tertiary phosphine ligands shows that functionalization with halogenated alkanes and alcohols result in strong π-acid characteristics. Tris(2,2,2-trichloroethyl)phosphite has a cone angle comparable to other primary alcohol derivatives, yet is a stronger π-acid. Therefore, it was surmised that the 2,2,2-trifluoroethanol derivative would give a PNP ligand with enhanced π-acid character while maintaining steric characteristics similar to those of dmpma.

The reaction of 2,2,2-trifluoroethanol with $MeN(PCl_2)_2$ in ether/pentane mixtures at dry-ice/acetone temperatures proceeded smoothly to afford $MeN[P(OCH_2CF_3)_2]_2$ (tfepma) in moderate yield after distillation. The viscous liquid was characterized by $^1H$ NMR spectroscopy, which showed a triplet-of-doublets pattern at 2.51 ppm for the methyl protons of the methylamine bridgehead and a doublet-of-pentets pattern at 3.55 ppm for the methylene protons of the trifluoroethyl substituents. The $^{31}P\{^1H\}$ NMR spectrum showed a singlet at 148.6 ppm and the $^{19}F$ NMR spectrum showed a multiplet centered at −76.90 ppm.

Complexes with Bridging tfepma Ligands

The pale orange color of $[ClRh(CO)_2]_2$ in methylene chloride immediately changed to dark red upon dropwise addition of tfepma. Concentration by vacuum distillation followed by addition of pentane afforded a yellow-orange powder in moderate yield. Elemental analysis suggested the formulation $Rh_2(tfepma)_2Cl_2(CO)_2$ (14), and infrared spectra obtained on KBr pellets of this product showed a carbonyl stretch at 2007 $cm^{-1}$. As with the dmpma and dppma complexes, 14 is fluxional in solution. At room temperature, time-averaged NMR spectra were obtained: a single methyl resonance was observed at 2.94 ppm in the $^1H$ NMR spectrum and a symmetric $^{31}P$ resonance was observed at 131.16 ppm ($|^1J_{PRh}+^nJ_{PRh}|$=149 Hz) in the $^{31}P$ NMR spectrum. Based on the observed $|^1J_{PRh}+^nJ_{PRh}|$ coupling constant, a structure with two tfepma ligands spanning a $Rh^I_2$ core, axial Cl ligands, and bridging and terminal carbonyl ligands is assigned for 14 as shown in Scheme 8.

Modified forcing reaction conditions afforded a doubly CO-bridged isomer. Refluxing $[ClRh(CO)_2]_2$ with two equivalents of tfepma in toluene gave $Rh_2(tfepma)_2Cl_2(\mu\text{-}CO)_2$ (15) in quantitative yield. Infrared spectroscopy showed only a bridging carbonyl stretch at 1824 $cm^{-1}$. $^{31}P$ NMR spectroscopy again revealed a symmetric complex, with a single resonance at 128.4 ppm ($|^1J_{PRh}+^nJ_{PRh}|$=164 Hz). The IR and NMR data are consistent with rearrangement of the metal core to give a structure analogous to 9. However, unlike the dppma compound, 15 is thermally robust and is not subject to further rearrangements of the metal core in the absence of other reagents: even at reflux in toluene, CO was not lost from the complex.

Scheme 8

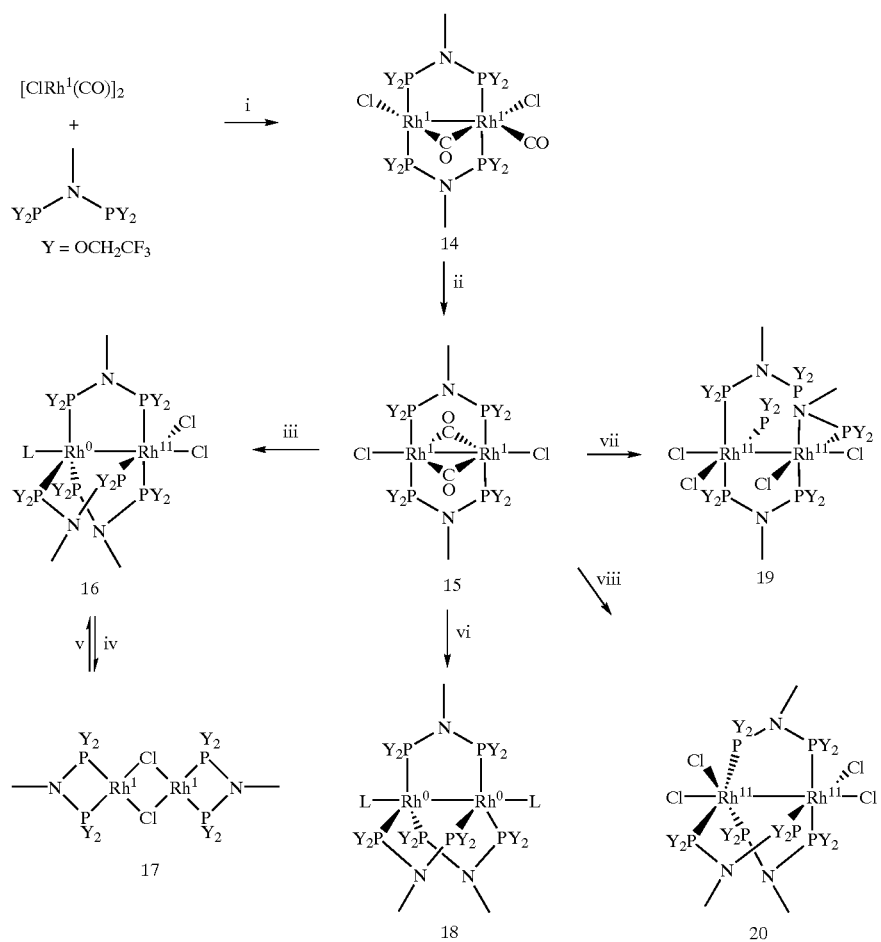

(i) two equiv tfepma in CH$_2$Cl$_2$;
(ii) Δ;
(iii) one equiv tfepman, L = CO, slow precip. from CH$_2$Cl$_2$;
(iv) Δ, ——L;
(v) one equiv tfepma and one equiv L = CN$^t$Bu, slow precip. from CH$_2$Cl$_2$;
(vi) one equiv tfepma and two equiv CoCp$_2$ in a CO atmosphere;
(vii) one equiv tfepma and one equiv PhICl$_2$ in CH$_2$Cl$_2$;
(viii) one equiv tfepma, one equiv PhICl$_2$, Δ in C$_6$H$_6$.

Figure 6:
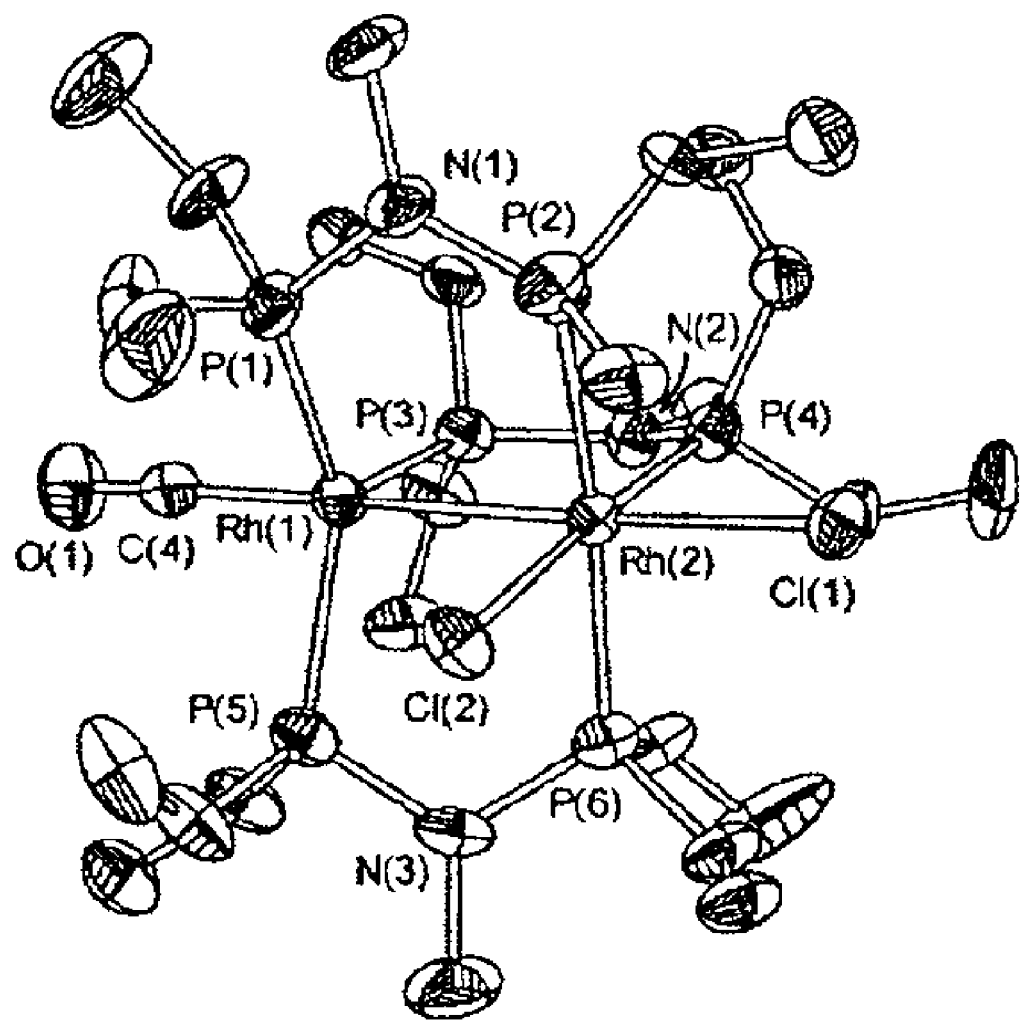
FIG. 6 is a thermal ellipsoid plot (50% probability) for Rh$_2^{0,II}$(tfepma)$_3$Cl$_2$(CO) (16) wherein for clarity, only the methylene carbons of the CH$_2$CF$_3$ groups are shown.

Treatment of solutions of 14 or 15 with one equivalent of tfepma gave a dark red solution from which maroon crystals were deposited upon prolonged standing. The crystals proved suitable for X-ray diffraction studies and yielded the molecular structure presented in FIG. 6 for Rh$_2$$^{0,II}$(tfepma)$_3$Cl$_2$(CO) (16). As observed for the dfpma chemistry of rhodium, three tfepma ligands span the bimetallic core of 16. The two-electron mixed-valence complex comprises octahedral Rh$^{II}$ and trigonal bipyramidal Rh$^0$ centers. The axial site of the Rh$^0$ is coordinated by a CO ligand, and two chloride ligands occupy axial and equatorial sites of the Rh$^{II}$. The metal-metal separation is normal at 2.7662(11) Å. Rh—P bond distances are longer by an average of 0.037 Å than those observed for the dfpma complexes due to the greater steric demand of the P(OCH$_2$CF$_3$)$_2$ groups. Other metrical parameters for 16 are listed in Table 7, and in general suggest an expanded core coordination environment for the dirhodium center.

In solution, the two-electron mixed-valence complex was unstable with respect to loss of the axial CO ligand. The principal species observed by NMR spectroscopy was in fact the halogen-bridged Rh$^I$$_2$ dimer with two chelating tfepma ligands, [ClRh(tfepma)]$_2$ (17). This complex was prepared independently by the addition of two equivalents of tfepma to [ClRh(cod)]$_2$. The symmetric dimer was treated with one equiv of tfepma and one equiv of CN$^t$Bu to reform the two-electron mixed-valence complex, Rh$_2$$^{0,II}$(tfepma)$_3$Cl$_2$(CN$^t$Bu), with an axial isonitrile ligand; however, the product was always contaminated with 17.

TABLE 7

Bond lengths (Å) and angles (deg) for Rh$_2$$^{0,II}$(tfepma)$_3$Cl$_2$(CO) (16).

Selected Bond Lengths (Å)

| | | | |
|---|---|---|---|
| Rh(1)-Rh(2) | 2.7662(11) | Rh(2)-Cl(1) | 2.513(3) |
| Rh(1)-P(1) | 2.284(3) | Rh(2)-Cl(2) | 2.399(3) |
| Rh(1)-P(3) | 2.255(3) | Rh(2)-P(2) | 2.308(3) |
| Rh(1)-P(5) | 2.287(3) | Rh(2)-P(4) | 2.214(3) |
| Rh(1)-C(4) | 1.895(12) | Rh(2)-P(6) | 2.281(3) |

TABLE 7-continued

Bond lengths (Å) and angles
(deg) for $Rh_2^{0,II}(tfepma)_3Cl_2(CO)$ (16).

| P(1)-N(1) | 1.685(10) | P(2)-N(1) | 1.670(10) |
|---|---|---|---|
| P(3)-N(2) | 1.686(9) | P(4)-N(2) | 1.667(9) |
| P(5)-N(3) | 1.673(10) | P(6)-N(3) | 1.658(10) |
| Selected Bond Angles (deg) | | | |
| Rh(2)-Rh(1)-C(4) | 176.9(4) | Cl(1)-Rh(2)-Cl(2) | 91.51(10) |
| Rh(1)-Rh(2)-Cl(1) | 176.54(7) | Cl(1)-Rh(2)-P(2) | 82.86(10) |
| Rh(1)-Rh(2)-Cl(2) | 87.97(7) | Cl(1)-Rh(2)-P(4) | 87.23(10) |
| Cl(2)-Rh(2)-P(2) | 87.34(11) | Cl(1)-Rh(2)-P(6) | 98.51(10) |
| Cl(2)-Rh(2)-P(4) | 175.59(11) | P(7)-Rh(1)-P(1) | 90.0(3) |
| Cl(2)-Rh(2)-P(6) | 85.20(11) | C(4)-Rh(1)-P(3) | 94.5(4) |
| P(1)-Rh(2)-P(3) | 110.68(12) | C(4)-Rh(1)-P(5) | 90.0(3) |
| P(1)-Rh(2)-P(5) | 130.87(12) | Rh(1)-C(4)-O(1) | 177.8(11) |

The tfepma ligand supports two-electron reduced species, $Rh_2^{0,0}(tfepma)_3L_2$, (18-L) upon reduction of $[ClRh(CO)_2]_2$ with cobaltocene in the presence of three equiv tfepma and two equiv of L (L=CO, CN$^t$Bu). Alternatively, cobaltocene reduced 15 to 18-L in the presence of L and one equivalent of tfepma. Spectroscopic data is consistent with a binuclear Rh$^0$ core bridged by three tfepma ligands. The $^{31}$P NMR of 18-CN$^t$Bu showed a single resonance at 142.08 ppm displaying a 216 Hz coupling constant. Similarly, the $^1$H NMR showed one methyl and one methylene resonance for the bridging tfepma ligands at 2.44 and 4.18 ppm, respectively, and a resonance for the CN$^t$Bu ligands at 1.05 ppm.

Oxidation of the dirhodium core proceeded smoothly but yielded different structural isomers depending on reaction conditions. The reaction of tfepma and PhICl$_2$ with [ClRh(CO)$_2$]$_2$ at room temperature in CH$_2$Cl$_2$ afforded a bright yellow powder with the formula $Rh_2^{II,II}(tfepma)_3Cl_4$ in moderate yields. X-ray diffraction studies on single crystals of this product yielded the molecular structure depicted in FIG. 7(a), identifying the complex as the syn isomer, syn-$Rh_2^{II,II}(tfepma)_3Cl_4$ (19). If the reaction instead was conducted at reflux in toluene, an orange product was obtained, the solid-state structure as determined by X-ray diffraction identified this product as the anti isomer, anti-$Rh_2^{II,II}$(tfepma)$_3$Cl$_4$ (20). The molecular structure for 20 is presented in FIG. 7(b). Selected bond distances and angles for each complex are presented in Table 8. Comparison of the two isomers reveals a significant contraction of the metal core for 19. The Rh(1)-Rh(2) separation in the syn isomer is 2.6688(8) Å, whereas the metal-metal distance in 20 is 2.7152(10) Å. Similarly, the metal-phosphorus and metal-halogen distances are markedly different: the Rh—P distances in 20 are longer by 0.045 Å and the axial and equatorial Rh—Cl distances are elongated by 0.062 and 0.061 Å, respectively. The syn isomer also shows a much smaller twist about the Rh—Rh axis, with an average torsion angle of 26.8° as compared to that of the anti isomer at 40.4°, which is almost perfectly eclipsed.

TABLE 8

Bond lengths (Å) for syn-$Rh_2^{II,II}(tfepma)_3Cl_4$ (19)
and anti-$Rh_2^{II,II}(tfepma)_3Cl_4$ (20).
Selected Bond Lengths (Å)

| syn-$Rh_2^{II,II}(tfepma)_3Cl_4$ | | anti-$Rh_2^{II,II}(tfepma)_3Cl_4$ | |
|---|---|---|---|
| Rh(1)-Rh(2) | 2.6688(8) | Rh(1)-Rh(2) | 2.7152(10) |
| Rh(1)-Cl(1) | 2.401(2) | Rh(1)-Cl(1) | 2.456(2) |
| Rh(1)-Cl(2) | 2.334(2) | Rh(1)-Cl(2) | 2.398(2) |
| Rh(2)-Cl(3) | 2.385(2) | Rh(2)-Cl(3) | 2.455(2) |
| Rh(2)-Cl(4) | 2.342(2) | Rh(2)-Cl(4) | 2.399(2) |
| Rh(1)-P(1) | 2.281(2) | Rh(1)-P(1) | 2.223(2) |
| Rh(1)-P(3) | 2.152(2) | Rh(1)-P(3) | 2.271(2) |
| Rh(1)-P(5) | 2.248(2) | Rh(1)-P(5) | 2.329(2) |
| Rh(2)-P(2) | 2.258(2) | Rh(2)-P(2) | 2.275(2) |
| Rh(2)-P(4) | 2.154(2) | Rh(2)-P(4) | 2.216(2) |
| Rh(2)-P(6) | 2.271(2) | Rh(2)-P(6) | 2.319(2) |

Figure 8:
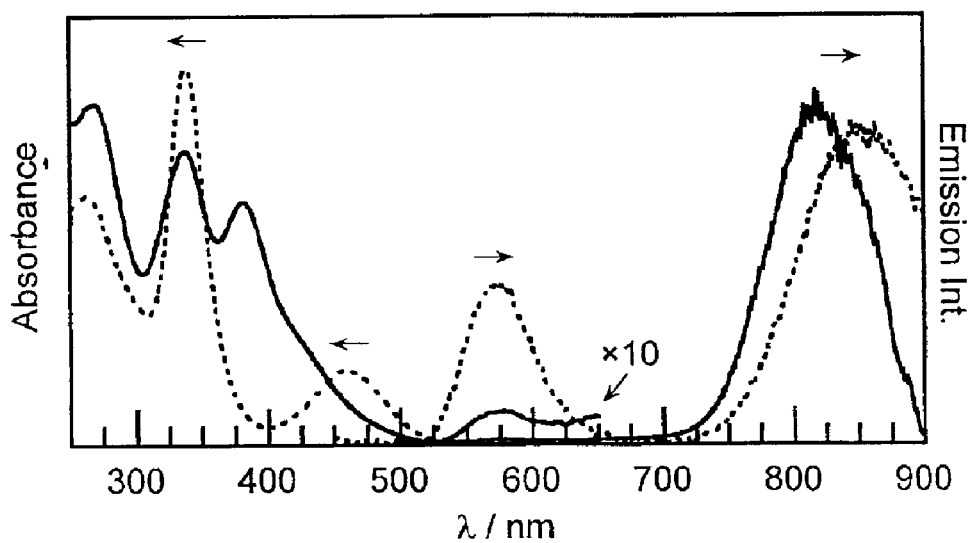
FIG. 8 includes the solution absorption and solid-state emission spectra of syn-Rh$_2^{II,II}$(tfepma)$_3$Cl$_4$ (19) and anti-Rh$_2^{II,II}$(tfepma)$_3$Cl$_4$ (20)

The structural differences between the syn and anti isomers of $Rh_2^{II,II}(tfepma)_3Cl_4$ are manifested in the absorption and emission spectra of each complex, presented in FIG. 8. The absorption spectra of 19 and 20 are dominated by three bands in the near-UV and visible regions. Two high-energy bands, assigned to transitions from the configurationally mixed Cl($\sigma$)/$d_{z^2}\sigma$ to the $d_{z^2}\sigma$* LUMO, shift little between the two isomeric forms. However, the lowest energy transition shows a pronounced dependence on the geometry of the dirhodium core: the transition, of $d\pi$*→$d_{z^2}\sigma$* parentage, shifts from 352 nm in 19 to 458 nm in 20. This red shift of over 6500 cm$^{-1}$ is accompanied by a decrease in the extinction coefficient of the band from 11,000 M$^{-1}$ cm$^{-1}$ to 4700 M$^{-1}$ cm$^{-1}$ for the syn and anti isomers, respectively. Excitation of solid samples of both 19 and 20 cooled to 77 K results in visible luminescence. The emission spectrum of 19 is dominated by bright, long-lived phosphorescence observed at 819 nm ($\tau$=350 $\mu$s). A high-energy band is also observed at 578 nm ($\tau$<8 ns), but has only $\frac{1}{100}^{th}$ of the intensity of the phosphorescent peak, suggesting facile deactivation of the $^1d_{z^2}\sigma$* excited state. Conversely, both fluorescence and phosphorescence are strong for 20. A high-energy emission band at 573 nm ($\tau$<8 ns) and a low-energy emission band at 857 nm ($\tau$=150 $\mu$s) are observed with an intensity ratio of 1:2 (the relative intensities of 19 to 20 were not determined).

The influence of structure on electronic character is further emphasized by the similarity between the electronic features of 20 and the dfpma congener, $Rh_2^{II,II}(dfpma)_3Cl_4$ (4). The absorption maxima of the two high-energy transitions are essentially identical and the low energy $d\pi$*→$d_{z^2}\sigma$* transition of 20 is red-shifted by only 640 cm$^{-1}$ relative to the same transition in 4. Though negligible differences are observed in the fluorescence emission maxima, the phosphorescence of 20 is red shifted by 511 cm$^{-1}$. This small low-energy shift is diagnostic of a weaker metal-metal interaction in 20, and correlates well with the observed difference in metal-metal separation for 4 and 20 ($\Delta$Rh(1)-Rh(2)=0.008(1) Å).

A Chelating tfepma Ligand

Figure 9:
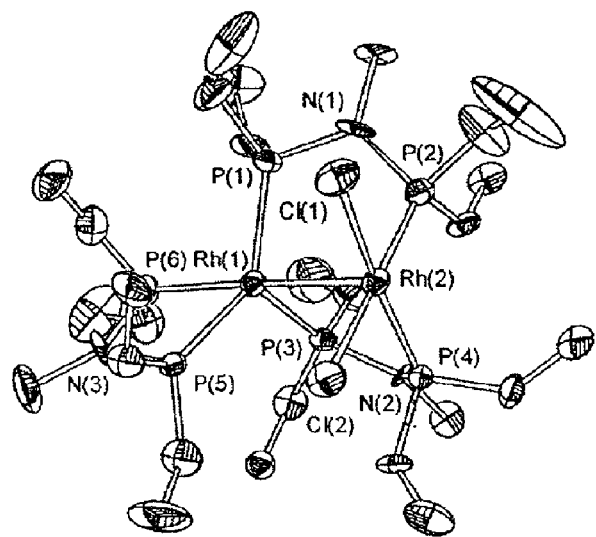
FIG. 9 is a thermal ellipsoid plot for Rh$_2^{0,II}$(tfepma)$_3$Cl$_2$ (21) from preliminary X-ray data wherein for clarity, only the methylene carbons of the CH$_2$CF$_3$ groups are shown.

The tfepma ligand may be used to stabilize a new two-electron mixed-valence rhodium platform in the absence of an axial donor ligand. [ClRh(cod)]$_2$ reacted with three equivalents of tfepma in CH$_2$Cl$_2$, affording $Rh_2^{0,II}(tfepma)_3Cl_2$ (21). Dark green single crystals of 21 were obtained by diffusing pentane into a CH$_2$Cl$_2$ solution of the complex. The structure presented in FIG. 9 was obtained from X-ray diffraction studies; selected bond distances and angles are presented in Table 9. The molecular structure of 21 reveals a departure from the coordination geometry observed for other diphosphazane complexes of rhodium. In the absence of a suitable donor ligand for the Rh$^0$ center, a tfepma ligand binds in a chelating mode leaving only two tfepma ligands to bridge the bimetallic core. A consequence of this chelating ligand is the vacant axial coordination site at the $Rh^{II}$ center. Two phosphorus of the bridging tfepma ligands and one phosphorus of the chelating tfepma ligand define the equatorial plane of a distorted trigonal bipyramidal $Rh^0$ center. The axial positions are capped by the other phosphorus of the chelate and the proximate $Rh^{II}$ center, bound at a metal-metal separation of 2.7529(19) ∈. The $Rh^0$ center defines the apex of a square pyramid about the $Rh^{II}$ center. Two phosphorus of the bridging tfepma ligands and two chloride ligands occupy cis positions of the basal plane, with P(2)-Rh(2)-P(4) and Cl(1)-Rh(2)-Cl(2) angles of 95.65(18)° and 86.52(18)°, respectively.

TABLE 9

Bond lengths (Å) and angles (deg) for $Rh_2^{0,II}(tfepma)_3Cl_2$ (21) from preliminary X-ray data.

Selected Bond Lengths (Å)

| | | | |
|---|---|---|---|
| Rh(1)-Rh(2) | 2.7529(19) | Rh(2)-Cl(1) | 2.359(5) |
| Rh(1)-P(1) | 2.240(5) | Rh(2)-Cl(2) | 2.361(5) |
| Rh(1)-P(3) | 2.295(5) | Rh(2)-P(2) | 2.188(5) |
| Rh(1)-P(5) | 2.285(5) | Rh(2)-P(4) | 2.190(5) |
| Rh(1)-P(6) | 2.176(5) | | |
| P(1)-N(1) | 1.689(16) | P(2)-N(1) | 1.692(17) |
| P(3)-N(2) | 1.668(13) | P(4)-N(2) | 1.677(14) |

Selected Bond Angles (deg)

| | | | |
|---|---|---|---|
| P(5)-Rh(1)-P(1) | 137.48(18) | Cl(1)-Rh(2)-Cl(2) | 86.52(18) |
| P(5)-Rh(1)-P(3) | 114.79(17) | Cl(1)-Rh(2)-P(2) | 88.15(18) |
| P(5)-Rh(1)-P(6) | 70.07(18) | Cl(1)-Rh(2)-P(4) | 171.09(18) |
| P(6)-Rh(1)-Rh(2) | 164.31(15) | | |

Aniline-Derived Diphosphazanes

As a preliminary investigation of the electronic factors associated with exchanging the methyl group on the nitrogen bridgehead, 3,5-xylidene was refluxed in $PCl_3$ to afford bis(dichlorophosphine)-3,5-xylidene (dcpx). This precursor can be further functionalized as shown in Scheme 2, yielding the same variety of phosphorus groups for metal coordination. Fluorination with $SbF_3$ provided bis(difluorophosphine)xylidene (dfpx) in good yields after recrystallization from pentane and sublimation. Similarly, 2,2,2-trifluoroethanol reacted with dcpx to yield the corresponding trifluoroethyl derivative bis(bis(trifluoroethyl)phosphite)-3,5-xylidene (tfepx) as a crystalline solid from pentane.

Bis(difluorophosphine)-3,5-xylidene (dfpx)

Figure 10:
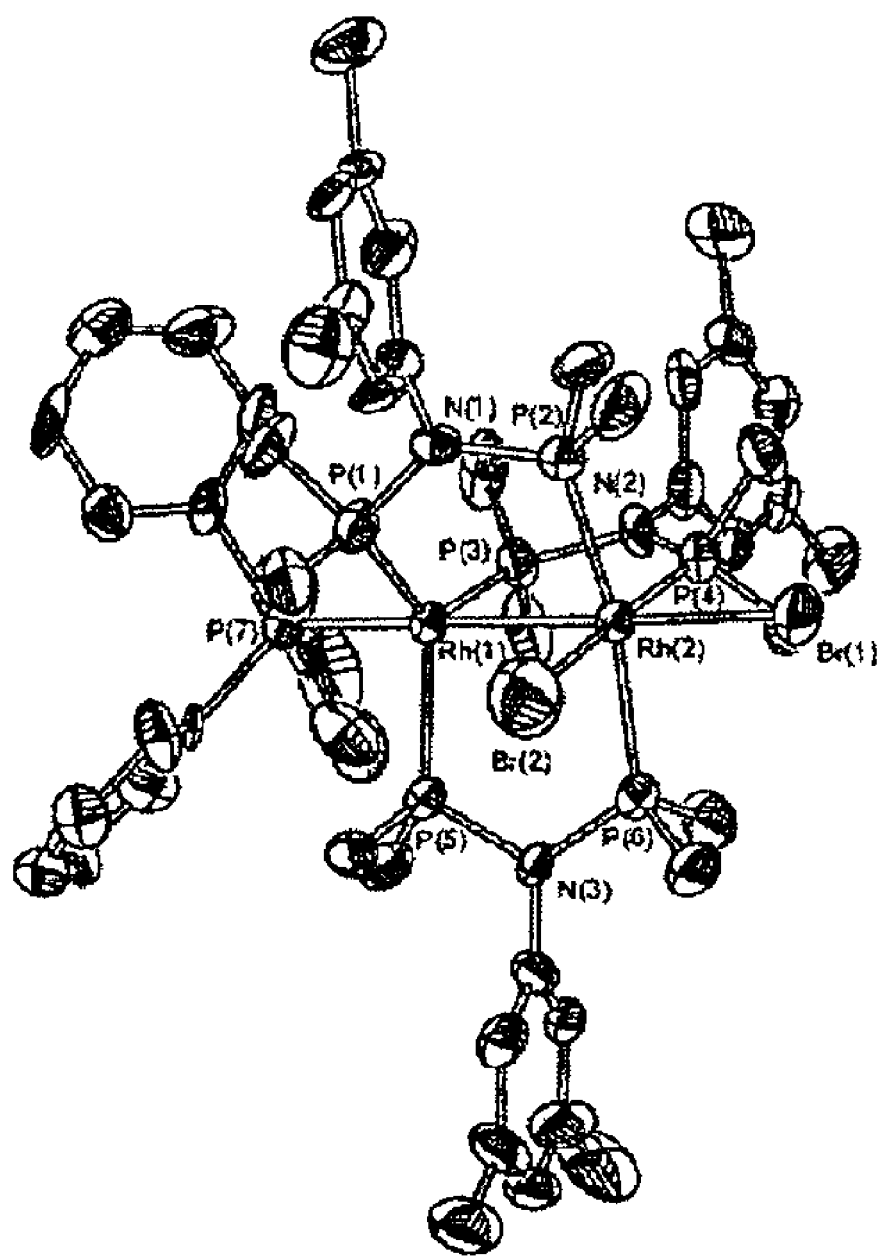
FIG. 10 is the thermal ellipsoid plot (50% probability) for Rh$_2^{0,II}$(dfpx)$_3$Br$_2$(PPh$_3$) (22) wherein the solvent molecules and hydrogen atoms have been omitted for clarity.

Two-electron mixed-valence complexes of dfpx were prepared by the strategy presented in Scheme 3. A dirhodium core isostructural to 1 and 2 is presented in FIG. 10 for $Rh_2^{0,II}(dfpx)_3Br_2(PPh_3)$ (22). The metrical parameters for the metal core of 22 are presented in Table 10, and are similar to those of the corresponding dfpma-bridged dirhodium complexes (Table 2); the N—P distances for the bridging dfpx ligands are 1.611(18) and 1.679(16) Å for the phosphines coordinated to the $Rh^{II}$ and $Rh^0$ centers, respectively. The aryl rings on the nitrogen bridgehead align perpendicularly to the P—N—P plane, with an average dihedral angle of 90.4°. At 2.819(3) Å, the metal-metal separation is slightly shorter than that of the dfpma derivative; Rh—Br distances of 2.570(3) and 2.463(5) are contracted as well. Other ligand distances are undistinguished from the dfpma analog.

The absorption spectra of the homologous dfpma and dfpx complexes provided further evidence for the complete decoupling of the aryl π system of dfpx from the core of the dirhodium complex. Aside from subtle changes in the peak intensities, absorption features are identical, displaying the expected three band pattern: for comparison, $\lambda_{abs\ max}$=309, 366 and 410 nm for 2-$PPh_3$ and $\lambda_{abs\ max}$=314, 370 and 411 nm for 22-$PPh_3$.

TABLE 10

Bond lengths (Å) and angles (deg) for $Rh_2^{0,II}(dfpx)_3Br_2(PPh_3)$ (22).

Selected Bond Lengths (Å)

| | | | |
|---|---|---|---|
| Rh(1)-Rh(2) | 2.819(3) | Rh(2)-Br(1) | 2.570(3) |
| Rh(1)-P(1) | 2.227(6) | Rh(2)-Br(2) | 2.463(5) |
| Rh(1)-P(3) | 2.220(7) | Rh(2)-P(2) | 2.219(6) |
| Rh(1)-P(5) | 2.242(6) | Rh(2)-P(4) | 2.184(7) |
| Rh(1)-P(7) | 2.330(6) | Rh(2)-P(6) | 2.262(6) |
| P(1)-N(1) | 1.658(16) | P(2)-N(1) | 1.641(17) |
| P(3)-N(2) | 1.689(17) | P(4)-N(2) | 1.571(19) |
| P(5)-N(3) | 1.690(15) | P(6)-N(3) | 1.620(16) |

Selected Bond Angles (deg)

| | | | |
|---|---|---|---|
| Rh(2)-Rh(1)-P(7) | 179.07(17) | Br(1)-Rh(2)-Br(2) | 90.79(13) |
| Rh(1)-Rh(2)-Br(1) | 178.13(9) | Br(1)-Rh(2)-P(2) | 95.35(17) |
| Rh(1)-Rh(2)-Br(2) | 90.68(12) | Br(1)-Rh(2)-P(4) | 85.61(18) |
| Br(2)-Rh(2)-P(2) | 87.7(2) | Br(1)-Rh(2)-P(6) | 91.98(17) |
| Br(2)-Rh(2)-P(4) | 176.35(18) | P(7)-Rh(1)-P(1) | 93.8(2) |
| Br(2)-Rh(2)-P(6) | 84.0(2) | P(7)-Rh(1)-P(3) | 92.3(2) |
| P(1)-Rh(2)-P(3) | 126.2(2) | P(7)-Rh(1)-P(5) | 93.1(2) |
| P(1)-Rh(2)-P(5) | 114.2(2) | | |

Bis(bis(trifluoroethyl)phosphite)-3,5-xylidene (tfepx)

Figure 11:
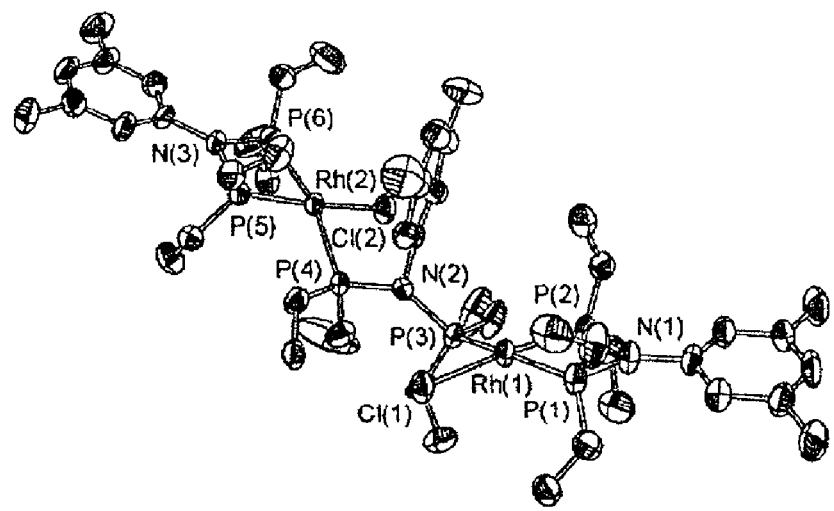
FIG. 11 is a thermal ellipsoid plot (50% probability) for [ClRh(tfepx)]$_2$($\mu$-tfepx) (23) wherein for clarity, only the methylene carbons of the CH$_2$CF$_3$ groups are shown.

The reaction of tfepx with [ClRh(cod)]$_2$ did not provide direct access to a two-electron mixed-valence complex. Rather, a bright yellow microcrystalline product precipitated from the green solution afforded by 1:3 mixtures of the rhodium starting material and ligand in $CH_2Cl_2$. Elemental analysis suggested the empirical formulation $Rh_2(tfepx)_3Cl_2$, consistent with the formulation of 21. However, X-ray diffraction studies revealed a divergent binuclear RhI structure, [ClRh(tfepx)]$_2$($\mu$-tfepx) (23), shown as a thermal ellipsoid plot in FIG. 11. Here, two four-coordinate RhI fragments are tethered by a bridging tfepx ligand. A single chloride and a chelating tfepx ligand complete the distorted square planar coordination environment about each rhodium center. An average intra-ligand P—Rh—P angle of 70.38(8)° is acute for a square-planar metal complex, suggesting a significant degree of strain in the four-membered chelate ring. All tfepx ligands show symmetric PNP backbones, with an average N—P distance of 1.694(6) Å. As observed in the structure of 22, the aryl ring of the bridging tfepx ligand is nearly orthogonal to the P(2)-N(2)-P(3) plane, adopting a torsion angle of 81.4°. Conversely, the aryl rings of the chelating tfepx ligands of 23 are rotated to be coplanar with the P—N—P triad, displaying torsion angles of 14.30 and 9.10 for the tfepx ligands of the Rh(1) and Rh(2) centers, respectively. Rotation of the aryl rings into the P—N—P plane delocalizes the nitrogen lone pair into the aromatic system, shortening the N—C bond. In accord with this suggestion, the average N—C bond length for the chelating tfepx ligands is 1.446(9) Å versus 1.485(9) Å for the N—C bond of the bridging tfepx ligand.

Isolation of discrete two-electron mixed-valence complexes of rhodium relies on a delicate balance of stereoelectronic properties within the diphosphazane ligand framework. The results suggest that in addition to the coordination of three ligands to the binuclear core, the strong π-acid phosphine groups and a polarizable lone pair on the nitrogen bridgehead atom help induce valence-symmetric cores to disproportionate.

The fluorinated diphosphazane, dfpma, rapidly reacts with $Rh^I$ starting materials to afford two-electron mixed-valence complexes in nearly quantitative yields. The strong π-acid character of the difluorophosphine groups coupled with the small steric parameter facilitates coordination of three ligands to the bimetallic core. Crystal structures of various derivatives of 1 provide evidence for induced polarization of the PNP backbone as proposed in Scheme 1. A contracted N—P bond for the phosphines coordinated to the Rh$^{II}$ center is indicative of significant N→P donation, serving to stabilize the π-acid phosphines coordinated to the oxidized metal center. With the N lone pair electron density channeled away from the PF$_2$ groups bonded to the Rh$^0$, the strong π accepting properties of this phosphine are maintained and hence the reduced rhodium center is stabilized.

In complexes with only two bridging diphosphazane ligands, valence disproportion of the binuclear rhodium core is circumvented. The dmpma and dppma ligands exclusively form 2:1 complexes with divalent rhodium cores. In these cases, valence disproportionation is not observed, and only symmetric Rh$^I_2$ cores are obtained. Within the framework outlined in Scheme 1, coordination of two diphosphazane ligands defeats induced polarization of the ligand backbone. Scheme 9 shows that coordination of two diphosphazane ligands to a binuclear complex provides the system a facile comproportionation pathway to produce symmetric cores. Polarization of one PNP ligand via donation of the nitrogen lone pair to one phosphine group is countered by lone pair donation in the opposite direction for the other bridging ligand. N—P bond lengths for the Rh$^I$ complexes of dmpma and dppma support this contention: 6 shows N—P bond distances of 1.670(6) Å and 1.661(6) Å and 9 shows N—P distances of 1.661(5) Å and 1.676(5) Å. The literature report of Rh$_2^0$ l(dppea)$_2$Cl$_2$(CO) indicates that two diphosphazanes may be able to stabilize a two-electron mixed-valence species transiently, but results presented here suggest that such a complex rapidly rearranges in solution to give symmetric species.

The driving force for valence disproportionation engendered by coordination of a third PNP ligand is illustrated by the conversion of 15 to 16 as shown in Scheme 8. In the absence of a third tfepma ligand, the Rh$^I$...Rh$^I$ core of 15 is robust, withstanding refluxing toluene without rearrangement or ligand loss. However, addition Scheme 9

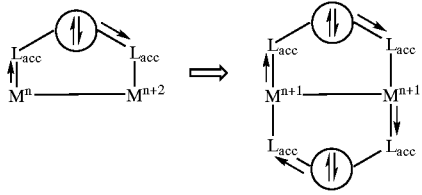

of one equivalent of tfepma to room temperature solutions of 15 induces valence disproportionation to the Rh$_2^{0,II}$ species, 16. It is suggested that although the symmetrization mechanism of Scheme 9 is operative in 15, introduction of a third tfepma ligand "frustrates" the binuclear core, thus forcing the system to polarize and form the two-electron mixed-valence complex.

Interplay of the π-acid phosphine with the nitrogen lone pair defines the ligands' ability to polarize the binuclear core. Diphosphazane functionalization at phosphorus and nitrogen may be used to probe these mediating effects of the nitrogen atom. The methyl amine bridgehead provides maximum participation of the nitrogen lone pair in π bonding with the proximate phosphine groups. Conversely, competition for the nitrogen lone pair is possible in diphosphazanes with aniline bridgeheads. Participation of the bridgehead nitrogen lone pair in the π system of an aryl group might drastically influence the ability of a diphosphazanes to stabilize two-electron mixed valence cores. Isolation of 22 in high yields suggests that the strong π-accepting properties of the difluorophosphine group override the electron accepting properties of the dfpx aryl group. Rotation of the aryl group perpendicular to the P—N—P plane completely decouples the 1 system from the PNP backbone and indicates complete utilization of the nitrogen lone pair by the PF$_2$ groups. Comparison of the absorption spectrum of 22 to the analogous dfpma complex 2-PPh$_3$ lends further support to the electronic homology between the dfpx and dfpma ligands. The low energy dπ*→dσ* transition, which should be most sensitive to changes in the electronic properties of the bridging diphosphazane, blue-shifts by only 59 cm$^1$ upon substitution of dfpx for dfpma in 22 and 2-PPh$_3$, respectively. Conversely, the aryl π system competes effectively with the weaker π-acid group bis(trifluoroethyl) phosphite for the nitrogen lone pair of tfepx. This competition forces the tfepx system to adopt a valence-symmetric configuration. Whereas the coordination of three tfepma ligands to a Rh$_2$ core produces the two-electron mixed-valence complex 21, tfepx provides a structure for 23 with two non-interacting Rh$^I$ centers. Rotation of the aryl ring of the chelating tfepx ligands into the P—N—P plane indicates a significant degree of N→aryl lone pair donation. Contracted N—C bond lengths for the chelating ligands further support this contention. Apparently, in the tfepx case, interaction of the nitrogen bridgehead with the aryl π system reduces the polarizability of the lone pair and thus valence disproportionation is not observed.

Manipulation of the steric and electronic properties of the phosphorus substituents of the PNP ligand set leads to varied chemical reactivity. The juxtaposition of strong π-acid phosphines with the nitrogen lone pair in dfpma leads to a polarization of the PNP backbone to stabilize the two-electron mixed-valence species. Furthermore, incorporation of sequentially more π-acidic phosphines revealed a step-by-step rearrangement of the binuclear Rh$^I$ core culminating with valence disproportionation and formation of a two-electron mixed-valence core. Diphosphazane ligands with small steric requirements, in addition to the requisite π-acidity, incorporate a third bridging ligand into the binuclear core. At least three ligands may be required to stabilize the two-electron mixed-valence complex and overcome the thermodynamic driving force for valence-symmetric binuclear cores.

Reactivity Studies of the Two-Electron Mixed-Valence Complex Ir$_2^{0,II}$(tfepma)$_3$Cl$_2$ The chemistry of two-electron mixed valency was generalized to transition metals other than rhodium. Ongoing interest in hydrogen photocatalysis, suggested investigation of the two-electron mixed-valence chemistry of iridium to acquire an understanding of the hydrido and hydrido-halo chemistry of this new class of compounds. Ir$_2^{0,II}$(tfepma)$_3$ Cl$_2$, was used for consideration of the stability of third-row metal-hydride bonds, to systematically investigate the reaction chemistry of H$_2$, HX and X$_2$ with M$_2^{0,II}$ cores.

Homogeneous metal complexes provide a useful tool for probing small molecule reactivity with spectroscopic techniques available for thermodynamic and kinetic studies. Significant advances have been made in understanding the operation of industrial catalysts through the reactivity studies of mononuclear inorganic and organometallic complexes. This insight has led to the discovery of homogeneous molecular catalysts that rival their heterogeneous brethren in both activity and long-term stability. Furthermore, the advantage of "molecular tuning," provides substrate and product selectivities unprecedented in heterogeneous catalysis.

Notwithstanding, an advantage of the heterogeneous catalyst is the cooperative reactivity afforded by adjacent metal centers available at the catalyst surface. Many industrial processes from olefin polymerization to nitrogen fixation and carbon monoxide functionalization rely on such cooperativity for efficient operation. Though interest in multimetallic homogenous catalysts is longstanding, the chemistry of transition metal clusters is less advanced than that of mononuclear compounds. Whereas the same palette of reactions, such as oxidative-addition, reductive-elimination and atom transfer, is available to mononuclear and multinuclear metal complexes, cluster compounds are distinguished by reactivity patterns arising from cooperative effects. For example, β-hydrogen elimination is a well-known reaction observed for late transition metal alkyl complexes leading to the formation of a metal-hydride-olefin complex. Conversely, alkyl cluster complexes have been observed to react by α-hydrogen abstraction pathways; the proximity of the second metal center can interact in a cooperative fashion to activate the nearest C—H bond.

The logical starting point for the development of multimetallic catalysts is with the simplest type of cluster compounds. The chemistry of bimetallic transition metal complexes largely parallels that of analogous mononuclear complexes, since their construction is often predicated on the assembly of mononuclear metal fragments. As an example, in Scheme 10, the chemistry of square planar $d^8$ metal fragments tethered with one or more bridging ligands, typified by pyrazolate-bridged $Rh^I$ and $Ir^I$ dimers, is dominated by oxidative addition and reductive elimination. Addition occurs either across the bimetallic core to yield a $d^9$—$d^9$ dimer, or is localized at one metal of the complex to yield a $d^8 \rightarrow d^{10}$ complex. Subsequent functionalization of substrates has been achieved, but coupling of the two metal centers impedes further reactivity, which obviates the development of an efficient catalytic cycle. Binuclear complexes that avoid the alternate making and breaking of a metal-metal bond show enhanced potential for catalyst development. For example, the A-frame derived complexes, [MM'(dppm)$_2$(CO)$_3$] (M=M'=Rh, Ir; M=Ir, M'=Rh), possess a formal metal-metal bond by virtue of coordinative unsaturation that is maintained upon substrate addition. As a result, further substrate addition and functionalization reactivity is observed after the initial activation step.

The diphosphazane ligand framework provides an excellent opportunity to develop new systems for small molecule activation and transformation reactions. The coordination chemistry of dfpma, dppma and tfepma with rhodium elucidates a ligand framework capable of stabilizing a variety of metal geometries and oxidation states while preserving a metal-metal interaction. A foray into the chemistry of these ligands with iridium, has led to the preparation of a two-electron mixed-valence complex, Ir$_2^{0,II}$(tfepma)$_3$Cl$_2$. The unique electronic and coordinative structure of this compound provides a novel platform for the detailed study of small molecule activation reactions en route to catalytic functionalization schemes. The inventors conducted structure and reactivity studies of Ir$_2^{0,II}$(tfepma)$_3$Cl$_2$ with H$_2$, HX and X$_2$ substrates, revealing a binuclear metal complex that maintains the facile addition pathways of mononuclear complexes with the caveat of a neighboring metal center to promote cooperative activation of small molecule substrates.

Iridium Chemistry of dfpma and dppma

Building upon studies of bis(phosphine)amine ligands with rhodium, the chemistry of these ligands with iridium was developed. The reaction of dfpma (dfpma =bis(difluorophosphine)methylamine) with monomeric iridium (I) starting materials such as ClIr(CO)(PPh$_3$)$_2$ leads to the formation of monomeric materials, ClIr(L)(dfpma) (L=CO, Scheme 10

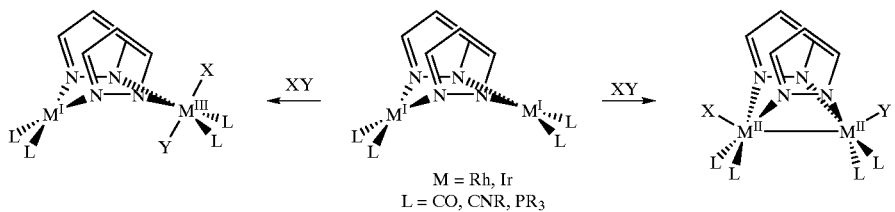

M = Rh, Ir
L = CO, CNR, PR$_3$

PPh$_3$). Similarly, in the absence of a suitable ligand, addition of two equivalents of dfpma leads to the formation of the dfpma-chelated dimer, [ClIr(dfpma)]$_2$. Synthetic methodologies that typically provided high-yields of two-electron mixed-valence dirhodium products, invariably gave intractable oils with iridium, as illustrated by the reaction of three equivalents of dfpma and one equivalent of L (L=P(OR)$_3$, PR$_3$, CNR) with [ClIr(cod)]$_2$, which affords orange to red oils that elude crystallization.

Figure 12:
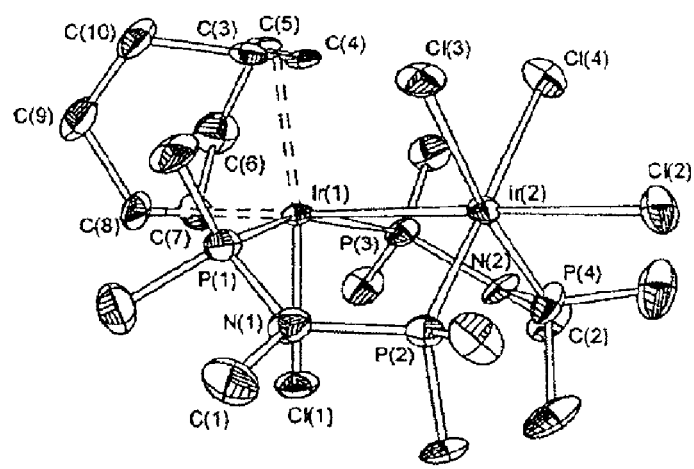
FIG. 12 is a thermal ellipsoid plot (50% probability) of Ir$_2^{I,III}$(dfpma)$_2$Cl$_4$(cod) (1) wherein hydrogen atoms have been omitted for clarity.

A two-electron mixed-valence iridium complex was obtained when dfpma was added to [ClIr(cod)]$_2$ in the presence of excess PhICl$_2$. A yellow microcrystalline powder was obtained in moderate yield. X-ray diffraction studies on single crystals yielded the results presented in FIG. 12 and Table 11. Ir$_2^{I,III}$(dfpma)$_2$Cl$_4$(cod) (31) is structurally divergent from the observed rhodium dfpma chemistry: two dfpma ligands span a binuclear iridium core composed of octahedral Ir$^I$ and Ir$^{III}$ centers rotated by 47.1°. The metal-metal separation in 31 is long at 2.8657(6) Å, but still within the range observed for other diiridium complexes with a formal metal-metal bond. A single 1,5-cyclooctadiene ligand remains coordinated to the Ir$^I$ center, occupying an axial site and an equatorial site trans to one chloride ligand. Three chloride ligands coordinate to the iridium(III) center, adopting a facial geometry, with surprisingly similar Ir$^{III}$—Cl bond distances of 2.407(3) and 2.417(3) Å for the two equatorial and axial chloride ligands, respectively. The similarity in Ir$^{III}$—Cl distances further indicates a weakened metal-metal bond; normally a significant trans influence is observed in the M-X distances for halogens coordinated opposite to a strong metal-metal bond. The octahedral Ir$^{III}$ is completed by two cis disposed PF$_2$ groups, bonded at an average Ir—P distance of 2.170(3) Å. The dfpma ligands display an induced asymmetry across the binuclear core, with an average N—P bond distance of 1.639(10) Å to the Ir$^{III}$-coordinated phosphorus and an average N—P bond distance of 1.660(9) Å to the Ir$^I$-coordinated phosphorus. The PF$_2$ groups coordinated to the Ir$^I$ center adopt a transoid arrangement (P(1)-Ir(1)-P(3)=155.56(10)°), resulting in significantly longer Ir$^I$—P distances of 2.281(3) Å. Metal-olefin distances to the C═C centroid of the chelating 1,5-cyclooctadiene ligand are distinguished for the axial and equatorial coordination sites at 2.222(11) and 2.182(11) Å, respectively. In accord with these different metal-olefin distances, C(3)-C(4) and C(7)-C(8) distances of 1.381(16) and 1.356(17) Å, respectively, reflect a slight decrease in C—C bond order for the more tightly bound equatorial olefin.

TABLE 11

Bond lengths (Å) for $Ir_2^{I,III}(dfpma)_2Cl_4(cod)$ (31).
Selected Bond Lengths (Å)

| | | | |
|---|---|---|---|
| Ir(1)-Cl(1) | 2.385(3) | Ir(1)-Ir(2) | 2.8657(6) |
| Ir(1)-P(1) | 2.281(3) | Ir(2)-Cl(2) | 2.417(3) |
| Ir(1)-P(3) | 2.281(3) | Ir(2)-Cl(3) | 2.407(3) |
| Ir(1)-C(3) | 2.294(11) | Ir(2)-Cl(4) | 2.407(3) |
| Ir(1)-C(4) | 2.283(11) | Ir(2)-P(2) | 2.169(3) |
| Ir(1)-C(7) | 2.314(11) | Ir(2)-P(4) | 2.171(3) |
| Ir(1)-C(8) | 2.332(10) | | |
| P(1)-N(1) | 1.667(9) | P(2)-N(1) | 1.642(10) |
| P(3)-N(2) | 1.652(9) | P(4)-N(2) | 1.636(9) |
| C(3)-C(4) | 1.381(16) | C(7)-C(8) | 1.356(17) |

Figure 13:
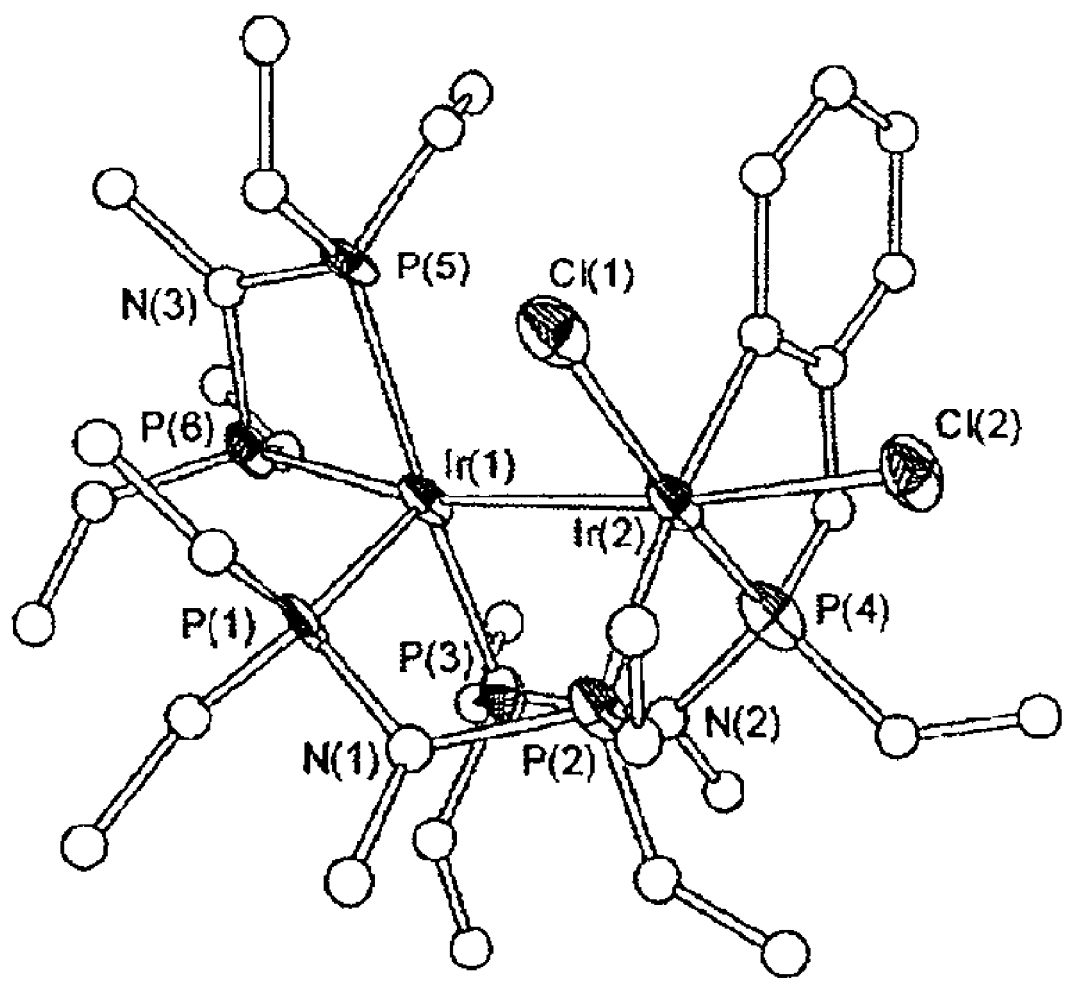
FIG. 13 depicts the molecular structure of Ir$_2^{I,III}$(dppma)$_3$Cl$_2$ (2), taken from preliminary X-ray crystal structure data wherein for clarity, hydrogen atoms have been omitted and only the ipso carbons of the phenyl rings are shown.

To investigate whether a stronger donating, more sterically demanding ligand might displace the 1,5-cyclooctadiene ligand, [ClIr(cod)]$_2$ was treated with three equivalents of the dppma ligand (dppma=MeN[P(OPh)$_2$]$_2$) in the absence of excess oxidant. Insoluble molecular compounds precipitate from reactions conducted in benzene, yielding a salmon-colored powder. Analysis suggests the formulation Ir$_2$(dppma)$_3$Cl$_2$ (2), indicating complete removal of 1,5-cyclooctadiene by the three dppma ligands. X-ray quality crystals of 32 were obtained from methylene chloride solution cooled to −35° C., and yielded the molecular structure depicted in FIG. 13. As observed in the structure of 31, two PNP ligands bridge the binuclear metal core, with a third chelating dppma ligand replacing the chelating 1,5-cyclooctadiene ligand of 31. Notably, in the absence of an external oxidant, the divalent Ir$_2$ core activates a C—H bond at an ortho position of the phenyl ring of one of the bridging dppma ligands. A metal-metal distance of 2.7919 (15) Å is consistent with an Ir$^I$→Ir$^{II}$dative bond. A vacant coordination site at the Ir$^I$ metal center (P(3)-Ir(1)-P(5)= 160.7(3)° and P(6)-Ir(1)-Ir(2)=167.57(18)°) is presumably occupied by the abstracted hydrogen atom from the orthometallated phenyl group. $^1$H NMR spectroscopy of 32 confirms the presence of a hydride ligand by the presence of a single low frequency resonance observed at −17.08 ppm. Coordination to the hydride to the Ir$^I$ center is established by an apparent doublet-of-triplet-of-doublets pattern with a $^2J_{HP}$ coupling constant of 218 Hz to the trans phosphorus atoms and $^2J_{HP}$ couplings of 17 and 12 Hz to the cis phosphorus atoms.

Preparation of Ir$_2^{0,II}$(tfepma)$_3$Cl$_2$

Figure 14:
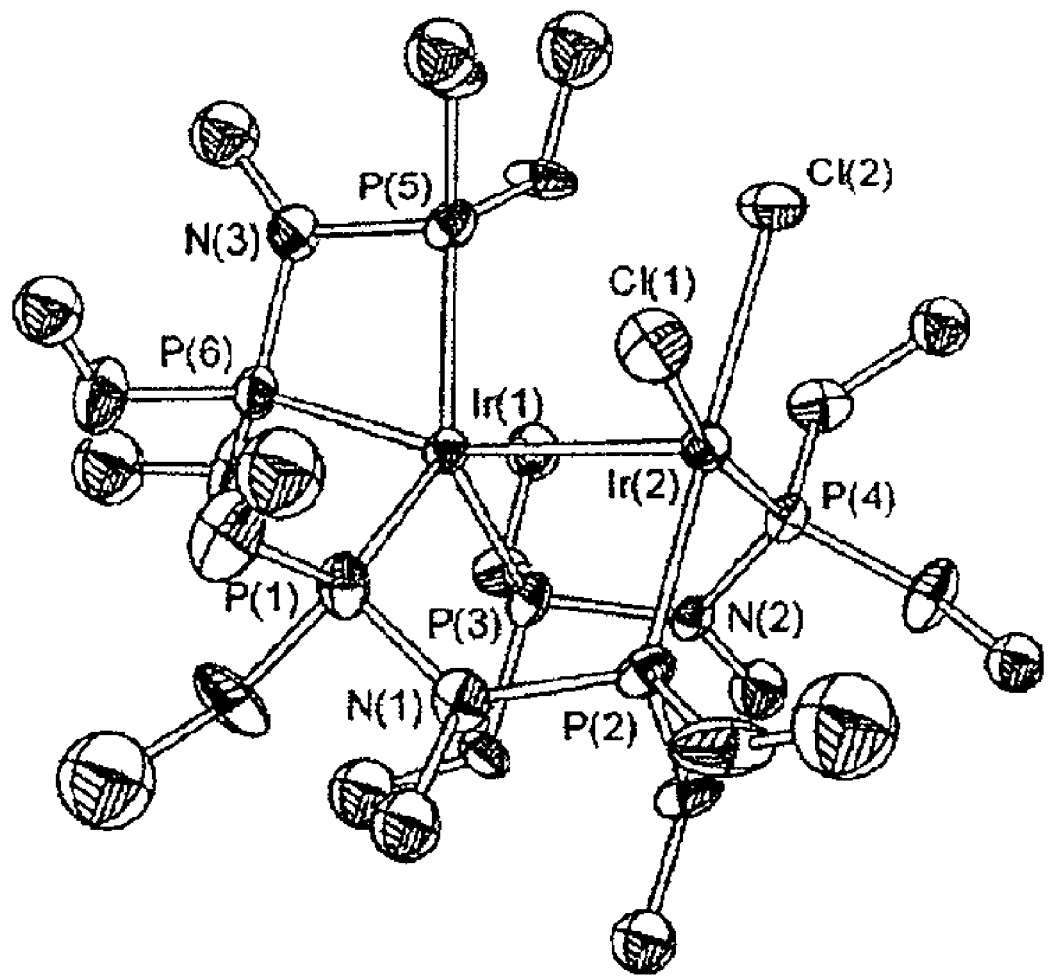
FIG. 14 is a thermal ellipsoid plot (50% probability) of Ir$_2^{0,II}$(tfepma)$_3$Cl$_2$ (3) wherein for clarity, hydrogen atoms have been omitted and only the methylene carbons of the trifluoroethyl groups are shown.

In an effort to avoid orthometallation of the bridging PNP ligands, the reaction chemistry of tfepma with [ClIr(cod)]$_2$ was investigated. Initial attempts to add the tfepma ligand to iridium followed the synthetic methodology used to prepare the dppm-bridged binuclear iridium complex Ir$_2$(dppm)$_2$Cl$_2$ (CO)$_2$: the dropwise addition of a CH$_2$Cl$_2$ solution of [ClIr(cod)]$_2$ to a CH$_2$Cl$_2$ solution of tfepma under an atmosphere of CO resulted in the formation of an orange solution. After 48 hours, dark green, X-ray quality crystals precipitated from solution. FIG. 14 presents the molecular structure of Ir$_2^{0,II}$(tfepma)$_3$Cl$_2$ (33) as determined from the X-ray diffraction data, Table 12 presents selected bond distances and angles of the bimetallic iridium core. As observed in the structure of 32, two of the three bidentate ligands bridge the binuclear core of 33 with the third ligand binding as a chelate. The Ir$^0$ center possesses distorted trigonal bipyramidal geometry that is typical for d$^9$ metals. Two equatorial sites of the Ir$^0$ center are coordinated by phosphites from the bridging tfepma ligands with the third equatorial site occupied by one end of a chelating tfepma ligand. The other end of the chelating ligand caps the axial position of the Ir$^0$ center at a short Ir—P distance of 2.201(5) Å, and a metal-metal bond distance of 2.7871(8) Å joins the two metal centers. The square pyramidal Ir$^{II}$center is characterized by a regular basal plane tilted by 8° from normal to the Ir(1)-Ir(2) vector. Two cis equatorial sites are occupied by phosphites from the bridging tfepma ligands at an average Ir—P distance of 2.192(5) Å, while the other two equatorial sites are occupied by chloride ligands at an average Ir—Cl distance of 2.372(5) Å.

TABLE 12

Bond lengths (Å) and angles (deg) for $Ir_2^{0,II}(tfepma)_3Cl_2$ (33).

Selected Bond Lengths (Å)

| | | | |
|---|---|---|---|
| Ir(1)-Ir(2) | 2.7876(10) | Ir(2)-Cl(1) | 2.379(5) |
| Ir(1)-P(1) | 2.235(6) | Ir(2)-Cl(2) | 2.365(5) |
| Ir(1)-P(3) | 2.274(5) | Ir(2)-P(2) | 2.198(5) |
| Ir(1)-P(5) | 2.268(5) | Ir(2)-P(4) | 2.186(5) |
| Ir(1)-P(6) | 2.201(5) | | |
| P(1)-N(1) | 1.667(17) | P(2)-N(1) | 1.693(17) |
| P(3)-N(2) | 1.649(16) | P(4)-N(2) | 1.686(16) |

Selected Bond Angles (deg)

| | | | |
|---|---|---|---|
| P(5)-Ir(1)-P(1) | 136.7(2) | Cl(1)-Ir(2)-Cl(2) | 85.3(2) |
| P(5)-Ir(1)-P(3) | 115.7(2) | Cl(1)-Ir(2)-P(2) | 88.0(2) |
| P(5)-Ir(1)-P(6) | 69.4(2) | Cl(1)-Ir(2)-P(4) | 169.50(19) |
| P(6)-Ir(1)-Ir(2) | 164.04(15) | | |

The synthesis of 33 shown in FIG. 14 can be targeted directly by reacting [ClIr(cod)]$_2$ with three equivalents of tfepma in CH$_2$Cl$_2$. Dark green crystalline 33 precipitates from the dark red solution of tfepma and the iridium starting material. Alternatively, slightly higher yields are obtained if the reaction is carried out in refluxing benzene, but the necessity to recrystallize the product reduces the value of this preparative method. The reactivity of 33 is outlined in Scheme 11.

Ligand Exchange Reactions of Ir$_2$0$^{II}$(tfepma)$_3$Cl$_2$

Solvent Exchange Reactions of 33 (I of Scheme 11)

Figure 15:
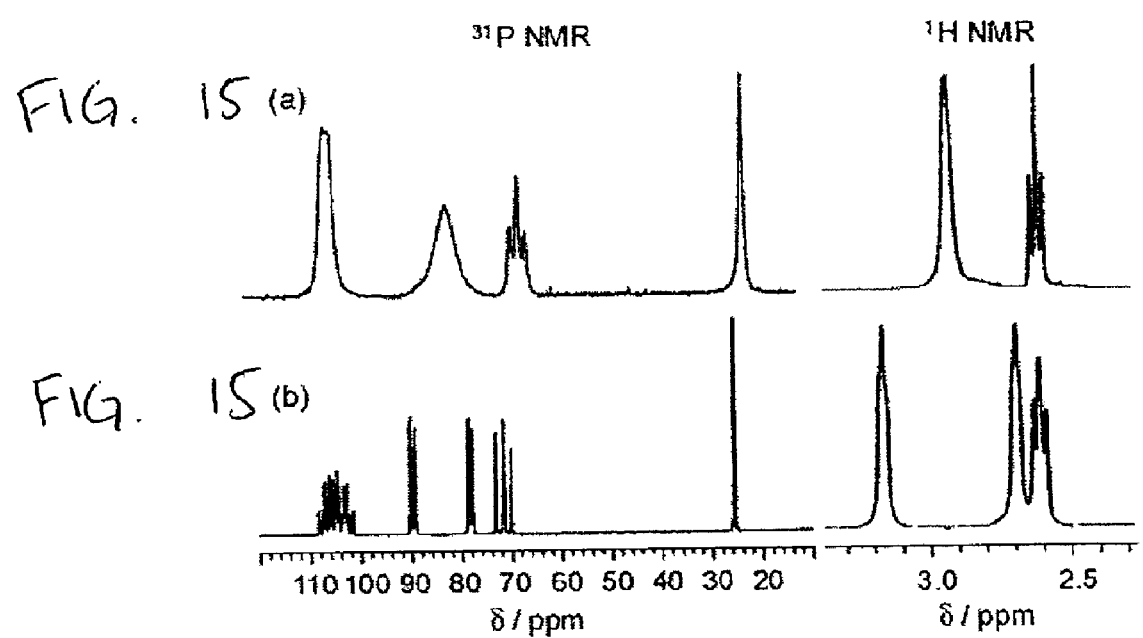

$^1$H NMR and $^{31}$P NMR spectroscopy reveal a fluxional coordination environment for 33 in which the diiridium complex is under dynamic solvent exchange. At room temperature, d$^8$-THF solutions of 33 show a $^{31}$P NMR spectrum of four distinct resonances, albeit with significant line broadening, consistent with a C$_s$ symmetric structure for 33 in solution (FIG. 15(a)). A low frequency singlet at 20.91 ppm is assigned to the axial phosphorus coordinated to the Ir$^0$ center; the apparent triplet at 65.59 ppm is the equatorial phosphorus of the chelating tfepma ligand. The excessively broad singlet at 80.19 ppm is assigned to the Ir$^{II}$-coordinated phosphites leaving the high-frequency resonance to the Ir$^0$-coordinated phosphites of the bridging tfepma ligands. The $^1$H NMR spectrum at 20° C. is consistent with a symmetric complex as well, only two methyl resonances at 2.93 and 2.62 ppm are observed for the tfepma ligands, integrating in a 2:1 ration for the bridging and chelating ligands, respectively. Upon cooling to −80° C., the fluxional behavior of 33 is arrested, giving the NMR spectra of FIG. 15(b). The resonance for the chelating tfepma ligand is largely unchanged in the $^1$H NMR spectrum, however, the resonance for the bridging tfepma ligand is split into distinct signals at 3.17 and 2.70 ppm (Δ=238 Hz), indicating an inequivalence of the bridging tfepma ligand. Even more dramatic changes are observed in the $^{31}$P NMR spectrum. In addition to a significant improvement in line shape for the resonances of the chelating tfepma ligand, two distinct signals can be resolved in the 100–110 ppm region for the equatorial phosphites of the bridging tfepma ligands. The most striking feature is the separation of two very different $Ir^{II}$-phosphite resonances, at 78.31 and 89.77 ppm ($\Delta$=2321 Hz), immediately suggesting the coordination of different ligands across the metal center from the phosphorus atoms.

Rate constants for the fluxional process equilibrating the $Ir^{II}$-phosphites were determined by monitoring the $^1H$ methyl resonances of the bridging tfepma ligands in $d^8$-THF over the temperature range of –70° C. to +30° C.; analysis of the Eyring plot yields activation parameters of $\Delta H^\ddagger = 13 \pm 1$ kcal $mol^{-1}$ and $\Delta S^\ddagger = 6.6 \pm 2$ cal $mole^{-1}$ $K^{-1}$. A similar exchange process is observed in $CD_3CN$, and evaluation of the corresponding kinetic data reveals a strongly solvent dependent process: over a temperature range of –5° C. to +30° C., $\Delta H^\ddagger$ and $\Delta S^\ddagger$ were determined to be 25±4 kcal $mol^{-1}$ and 38±5cal $mol^{-1}$ $K^{-1}$, respectively. The positive activation entropies in both solvent systems comply with a dissociative process. This, taken with the differences in chemical shift for the $Ir^{II}$-phosphites suggests the equilibrium depicted by reaction (i) of Scheme 11, in which a THF or MeCN ligand reversibly binds to an equatorial $Ir^{II}$ site with concomitant shift of a halide to the position opposite the metal-metal bond.

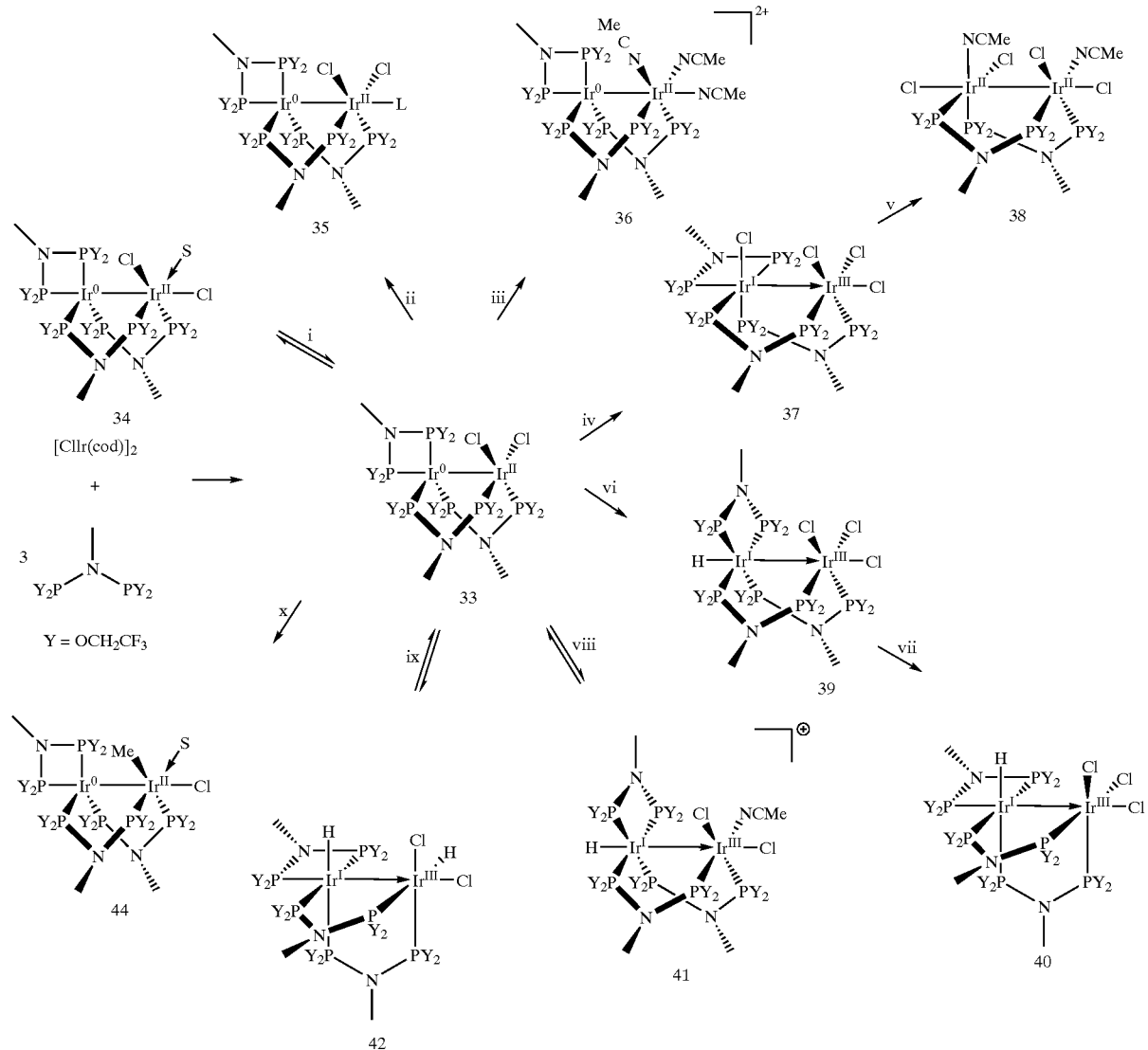

Scheme 11

(i) dissolution in THF or MeCN (S = THF, MeCN);
(ii) one equiv L in $CH_2Cl_2$ (L = $PR_3$, CNR, $X^-$);
(iii) two equiv Ag($PF_6$) or Tl($PF_6$) in MeCN;
(iv) $PhICl_2$ in $CH_2Cl_2$;
(v) excess $PhICl_2$ at reflux in MeCN;
(vi) HCl gas in $CH_2Cl_2$;
(vii) room temperature in $CH_2Cl_2$;
(viii) $HOSO_2CF_3$ in $CH_2Cl_2$ containing MeCN;
(ix) $H_2$ gas;
(x) MeMgBr in THF The solvent adduct 34, see FIG. 16 has been isolated and structurally characterized; FIG. 16(a) shows a thermal ellipsoid plot for $Ir_2^{0,II}(tfepma)_3Cl_2(MeCN)$ (4-MeCN). As deduced from NMR studies, the coordination core of the parent complex, 33 in Scheme 11, is mostly unchanged, with two chelating tfepma ligands and a third tfepma ligand chelated to the $Ir^0$ center; a slight elongation of the metal-metal separation accompanies coordination of the acetonitrile ligand. Table 13 presents other pertinent metrical parameters of the $Ir^0$—$Ir^{II}$ core of 34.

Addition of Strong σ-Donors to 33 (ii of Scheme 11)

Figure 17:
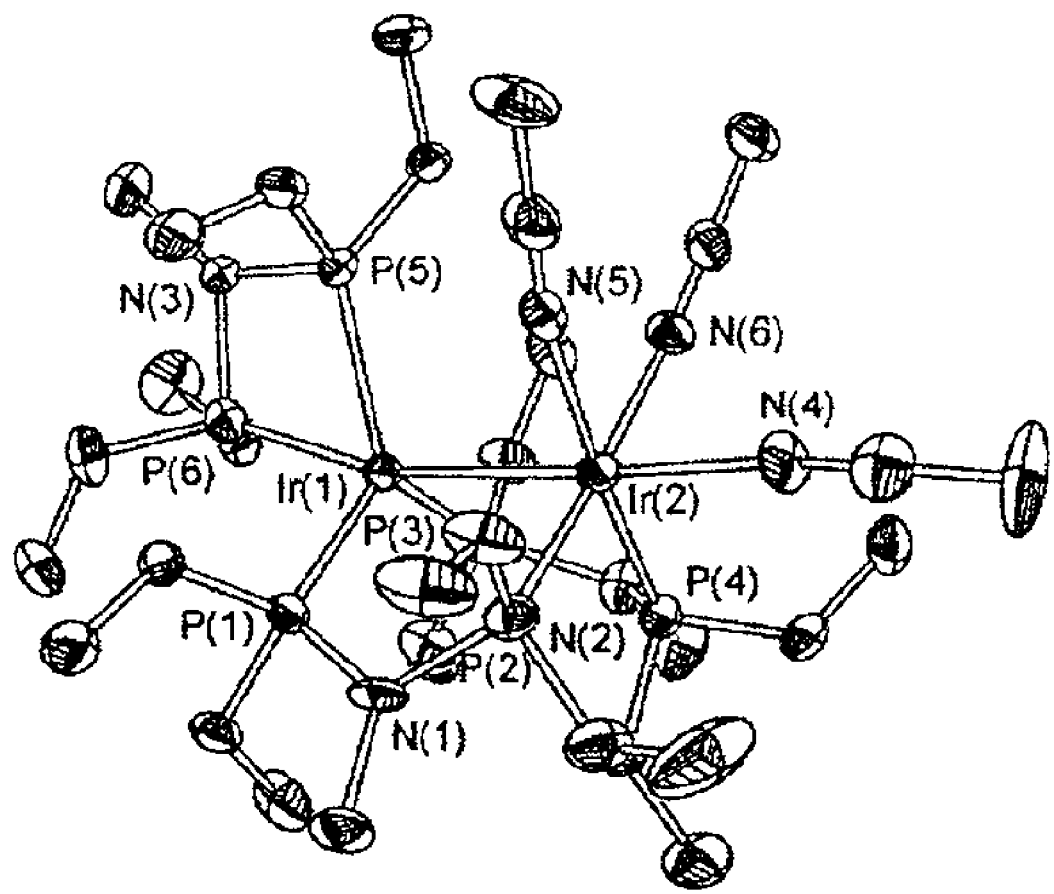
FIG. 17 is a thermal ellipsoid plot (50% probability) of the Ir$_2^{0,II}$(tfepma)$_3$(MeCN)$_3^{2+}$ (6) cation wherein for clarity, hydrogen atoms and two PF$_6^-$ anions have been omitted and only the methylene carbons of the trifluoroethyl groups are shown.

In contrast to the solution behavior of 33, σ-donating ligands such as isonitriles, phosphines and even halides, coordinate the $Ir^{II}$ center at the axial position, trans to the metal-metal bond yielding species of the formulation $Ir_2^{0,II}$ $(tfepma)_3Cl_2(L)$ (35-L, L=CNR, $PR_3$, X⁻). As is apparent in the thermal ellipsoid plot of the CN$^t$Bu derivative, $Ir_2^{0,II}$ $(tfepma)_3Cl_2(CN^tBu)$ (35-CN$^t$Bu) shown in FIG. 16(b), the $Ir_2^{0,II}$ mixed-valence core is preserved upon addition of the donor ligand. Apart from the differing coordination positions of the MeCN and CN$^t$Bu ligands, the X-ray crystal structure of 35-CN$^t$Bu is largely undistinguished from that of 34. Metrical parameters of the bimetallic core are presented for comparison in Table 13. In agreement with the solid-state results, the integration ratios for the proton resonances of the axial ligands of 35-L to those of the tfepma ligands establish that only one donor ligand is incorporated into the diiridium coordination sphere. Moreover, room temperature NMR spectra of the addition products with strong σ-donor ligands reveal static solution structures that are consistent with the results of X-ray crystallography. Notably, the $Ir^{II}$-coordinated phosphites of the 35-L species give rise to sharp, apparent triplets in the $^{31}P\{^1H\}$ NMR spectrum between 66 and 73 ppm. The absence of fluxional behavior is also in evidence from the sharp high frequency doublet resonances at about 95 ppm for the $Ir^0$-coordinated phosphites of the bridging ligands. The $^{31}P$ resonance for the axial $Ir^0$-phosphite is sensitive to the coordination of an axial ligand at $Ir^{II}$, shifting to progressively higher frequency (δ=35.0, 52.5 and 53.3 ppm along the series L=Br⁻, $PEt_3$, CN$^t$Bu) with increasing L σ-donor strength.

a four-line pattern analogous to that observed for the $C_s$ symmetric complexes 35-L. The axial phosphorus of the chelating tfepma ligand is observed as a singlet at 28 ppm, whereas the equatorial phosphorus is observed at 50 ppm as a triplet displaying a $^2J_{PP}$ coupling constant of 273 Hz to the doublet at 89 ppm for the $Ir^0$ phosphorus atoms of the bridging tfepma ligands. Finally, the $Ir^{II}$ phosphorus atoms give a single resonance at 57 ppm. Similarly, the $^1H$ NMR spectrum of 36 displays two resonances for the tfepma methyl groups at 2.83 and 2.70 ppm, the 2:1 integration ratio is consistent with the expected bridging/chelating coordination mode. Complete exchange of the MeCN ligands occurs upon dissolution of the solid as evidenced by a singlet at 1.96 ppm for uncoordinated MeCN. Single crystals diffraction analysis of the product confirm the preservation of the $Ir_2^{0,II}$ core as depicted in FIG. 17. For comparison purposes, the metric parameters for the core of 36 are presented in Table 13 alongside those of $Ir_2^{0,II}$ complexes 34 and 35-L. Removal of the halogen ligands results in a contracted metal-metal separation of 2.7805(7) Å, as well as a shorter axial $Ir^0$—P bond. Conversely, whereas the equatorial $Ir^0$—P bond distances are similar in 34–36, the $Ir^{II}$—P distances are elongated by nearly 0.02 Å in 36.

Oxidative Addition Reactions of $Ir_2^{0,II}(tfepma)_3Cl_2$

Chlorine Addition to 3 (iv and v of Scheme 11)

Chlorine, in the form of its iodobenzene adduct, facilely adds to 33 to give the two-electron mixed-valence complex $Ir_2I,III$ $(tfepma)_3Cl4$ (37) as shown in reaction (iv) of Scheme 11. X-ray crystallographic studies on single crystals of 37 yielded the molecular structure depicted in FIG. 18(a). Halogen addition occurs across the metal-metal bond of 33. The Ir—Ir distance of 2.7765(8) Å (Table 14) is well within the range for a metal-metal bond. Simple electron counting arguments are consistent with the formulation of an $Ir^I \rightarrow Ir^{III}$ dative bond where both metals assume octahedral coordination geometry. The octahedral metal centers of 37 are rotated with respect to one another by an average value of 32°. The $Ir^{III}$—Cl bonds are noticeably longer than those for the reduced $Ir_2^{0,II}$ complexes, at an average value of 2.446 (4) Å. This result is peculiar in light of the anticipated contraction of the iridium radius upon oxidation of $Ir^{II}$ to

TABLE 13

Selected bond lengths (Å) for $Ir_2^{0,II}(tfepma)_3Cl_2(MeCN)$ (4), $Ir_2^{0,II}(tfepma)_3Cl_2(CN^tBu)$ (35-CN$^t$Bu) and $[Ir_2^{0,II}(tfepma)_3(MeCN)_3][PF_6]_2$ (6[PF$_6$]$_2$).

| $Ir_2^{0,II}(tfepma)_3Cl_2(MeCN)$ | | $Ir_2^{0,II}(tfepma)_3Cl_2(CN^tBU)$ | | $[Ir_2^{0,II}(tfepma)_3(MecN)_3]^{2+}$ | |
|---|---|---|---|---|---|
| Ir(1)-Ir(2) | 2.7964(11) | Ir(1)-Ir(2) | 2.8088(1) | Ir(1)-Ir(2) | 2.7805(7) |
| Ir(1)-P(1) | 2.216(2) | Ir(1)-P(1) | 2.215(5) | Ir(1)-P(1) | 2.230(3) |
| Ir(1)-P(3) | 2.225(2) | Ir(1)-P(3) | 2.225(6) | Ir(1)-P(3) | 2.231(3) |
| Ir(1)-P(5) | 2.272(2) | Ir(1)-P(5) | 2.317(6) | Ir(1)-P(5) | 2.280(3) |
| Ir(1)-P(6) | 2.227(2) | Ir(1)-P(6) | 2.233(6) | Ir(1)-P(6) | 2.216(4) |
| Ir(2)-P(2) | 2.186(2) | Ir(2)-P(2) | 2.206(6) | Ir(2)-P(2) | 2.220(4) |
| Ir(2)-P(4) | 2.176(2) | Ir(2)-P(4) | 2.188(6) | Ir(2)-P(4) | 2.194(3) |
| Ir(2)-Cl(1) | 2.427(2) | Ir(2)-Cl(1) | 2.452(5) | Ir(2)-N(5) | 2.079(12) |
| Ir(2)-N(4) | 2.122(7) | Ir(2)-Cl(2) | 2.429(6) | Ir(2)-N(6) | 2.089(12) |
| Ir(2)-Cl(2) | 2.512(2) | Ir(2)-C(4) | 2.03(2) | Ir(2)-N(4) | 2.183(12) |

Halogen Removal from 33 (iii of Scheme 11)

Halogen removal from 33 can be effected with silver or thallium hexafluorophosphate in acetonitrile solution. A highly crystalline product analyzing as $[Ir_2^{0,II}(tfepma)_3(MeCN)_3][PF_6]_2$ (6[PF$_6$]$_2$) is recovered in quantitative yield. Solution NMR spectroscopy suggests preservation of the $Ir_2^{0,II}$ core. Excepting the resonance for the $PF_6$ anions at –143 ppm, the 31P NMR spectrum of 36 in FIG. 17 shows $Ir^{III}$. The coordination of the bridging tfepma ligands is unchanged from 33; however, the Ir—P distances associated with the chelating ligand elongate by ~0.1 Å.

NMR spectra of 37 are consistent with the octahedral coordination geometry of the oxidized metal core. The distinct environments of a chelating and two bridging ligands are signified by ligand methyl resonances in the $^1H$ NMR spectrum at 2.71 ppm and 2.88 and 2.93 ppm, respectively. The $^{31}P\{^1H\}$ NMR spectrum of 37 consists of six separate resonances, one for each of the unique phosphites under $C_1$ symmetry. Referring to the numbering scheme of FIG. 18(a), P(3) and P(5) are expected to be strongly coupled owing to their trans arrangement. In this context, signals at 13.14 and 74.31 ppm are ascribed to P(5) and P(3), respectively, based on a $^2J_{PP}$ coupling constant of 901 Hz. As in the reduced $Ir_2^{0,II}$ complexes, a low frequency resonance at 9.24 ppm is attributed to the P(6) phosphite trans to the Ir—Ir bond. Based on the $^{31}P$ COSY spectrum of 37, the 66.46-ppm resonance is ascribed to the $Ir^I$-bound P(1) phosphite of the bridging ligand, while the signals at 54.98 and 57.11 ppm are assigned to $Ir^{III}$-bound P(2) and P(4) phosphites of the bridging ligands, respectively.

ligand indicating that the bound solvent molecule is exchanged immediately upon dissolution of solid samples of the compound. The $^{31}P$ NMR spectrum of 38 exhibits two resonances at 54.97 and 57.87 ppm with a simple AA'BB' coupling pattern. These NMR results point towards a symmetric complex, which is verified by X-ray diffraction studies (FIG. 18(b)). Two bridging cis-diphosphazane ligands span a valence-symmetric $Ir_2^{II,II}$ core supporting octahedral coordination geometries that are related to each other by a 30° twist about the Ir—Ir axis. A metal-metal bond distance of 2.7525(9) Å signifies a formal bonding interaction that is characteristic of a $d^7$—$d^7$ complexes. Each metal center is coordinated by one equatorial and one axial chloride ligand, leaving acetonitrile to complete the octahe-

TABLE 14

Selected bond lengths (Å) and angles (deg) for $Ir_2^{I,III}(tfepma)_3Cl_4$ (37),[a] equatorial $Ir_2^{I,III}(tfepma)_3HCl_3$ (40) and $Ir_2^{I,III}(tfepma)_3H_2Cl_2$ (42).

|  | $Ir_2^{I,III}(tfepma)_3Cl_4$[b] | $Ir_2^{I,III}(tfepma)_3HCl_3$[c] | $Ir_2^{I,III}(tfepma)_3H_2Cl_2$[d] |
|---|---|---|---|
| Selected Bond Lengths (Å) | | | |
| Ir(1)-Ir(2) | 2.7765(8) | 2.7775(11) | 2.7561(7) |
| Ir(1)-X(1) | 2.435(4) | — | — |
| Ir(2)-Cl(2) | 2.405(4) | 2.450(2) | 2.465(3) |
| Ir(2)-X(3) | 2.428(4) | 2.418(2) | — |
| Ir(2)-Cl(4) | 2.504(4) | 2.487(2) | 2.511(3) |
| Ir(1)-P(1) | 2.223(4) | 2.314(2) | 2.300(3) |
| Ir(1)-P(3) | 2.282(4) | 2.241(2) | 2.259(3) |
| Ir(1)-P(5) | 2.375(4) | 2.322(2) | 2.271(3) |
| Ir(1)-P(6) | 2.350(4) | 2.269(2) | 2.278(3) |
| Ir(2)-P(2) | 2.198(4) | 2.188(2) | 2.160(3) |
| Ir(2)-P(4) | 2.191(4) | 2.175(2) | 2.277(3) |
| Selected Bond Angles (deg) | | | |
| P(1)-Ir(1)-X(1) | 173.3(2) | — | — |
| P(1)-Ir(1)-P(3) | 93.4(2) | 100.60(8) | 96.70(11) |
| P(1)-Ir(1)-P(5) | 99.9(2) | 103.61(7) | 93.99(11) |
| P(2)-Ir(2)-P(4) | 96.0(2) | 94.05(8) | 103.61(12) |
| P(2)-Ir(2)-Cl(2) | 170.7(2) | 175.14(7) | 169.33(12) |
| P(2)-Ir(2)-X(3) | 86.2(2) | 89.13(8) | — |
| P(6)-Ir(1)-Ir(2) | 165.20(11) | 167.41(6) | 158.45(10) |
| Cl(4)-Ir(2)-Ir(1) | 178.07(10) | 171.62(5) | 176.34(8) |
| Selected Torsion Angles (deg) | | | |
| X(1)-Ir(1)-Ir(2)-Cl(2) | 39.4 | 19.2 | 7.2 |
| P(1)-Ir(1)-Ir(2)-P(2) | 24.4 | 15.2 | 18.5 |
| P(3)-Ir(1)-Ir(2)-P(4) | 27.0 | 21.9 | 11.5 |
| P(5)-Ir(1)-Ir(2)-X(3) | 37.9 | 0.7 | 1.6 |

[a]The bond lengths and distances presented for 37 are the average values for two crystallographically distinct but chemically equivalent molecules within the unit cell.
[b]X(1) = X(3) = Cl.
[c]X(1) = H, X(3) = Cl.
[d]X(1) = X(3) = H Upon treatment with excess oxidant, 37 loses the chelating tfepma ligand according to reaction (v) of Scheme 11. The liberated tfepma is in turn oxidized, preventing its incorporation back into the coordination sphere of the binuclear core. A bright yellow solid analyzing as $Ir_2(tfepma)_2Cl_4(MeCN)_2$ (38), and possessing relatively simple NMR spectra, is obtained. The $^1H$ NMR spectrum comprises a single methyl resonance at 2.80 ppm and four methylene resonances between 4.48 and 5.46 ppm for the tfepma ligands. The $^1H$ NMR signal of $CH_3CN$ is that of free dral coordination spheres of the metal centers. The Ir—P bond distances average 2.206(5) Å, and the Ir—Cl bond distances are 2.432(5) and 2.476(5) Å for the equatorial and axial halogens, respectively.

The lability of the acetonitrile ligands suggested that their displacement by a tfepma ligand would provide access to a symmetric $Ir_2^{II,II} Cl_4$ complex spanned by three bridging ligands, similar to that observed for the chemistry of rhodium with dfpma and tfepma. Addition of one equivalent of tfepma to solutions of 38 in $CH_2Cl_2$, however, leads to nearly quantitative (>90%) conversion to the $Ir_2^{I,III}$ complex, 37, as determined with NMR spectroscopy.

Acid Addition to 33 (vi–viii of Scheme 11)

Figure 19:
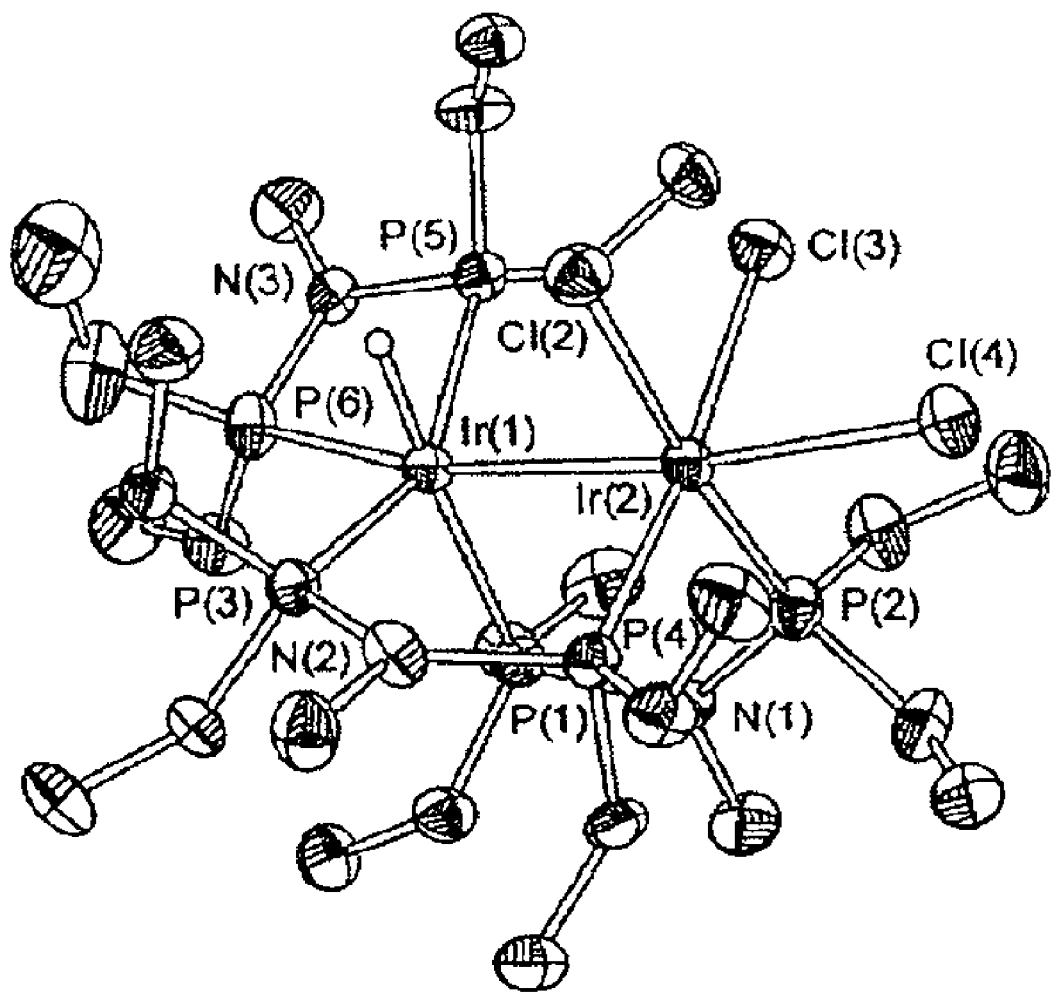
FIG. 19 is a thermal ellipsoid plot (50% probability) of Ir$_2^{I,III}$(tfepma)$_2$HCl$_3$ (10) wherein for clarity, hydrogen atoms have been omitted and only the methylene carbons of the trifluoroethyl groups are shown.

Suspensions of 33 in $CH_2Cl_2$ readily react with anhydrous HCl gas. Analysis of the final product provides the formulation $Ir_2(tfepma)_3HCl_3$ (40), indicating oxidative addition of HCl has occurred. An Ir—H stretch in the IR spectrum at 2115 cm$^{-1}$ is consistent with the presence of a terminal hydride ligand situated trans to a phosphorus atom. FIG. 19 displays the results of single crystal X-ray data analysis of 40 as a thermal ellipsoid plot; selected bond distances and angles are listed in Table 14. As observed in the halogen addition reaction, a metal-metal separation of 2.7775(11) Å is consistent with an $Ir^I \rightarrow Ir^{III}$ formulation containing a dative bond. Interestingly, the octahedral metal centers are nearly eclipsed with an average torsion angle of only 14°. A conspicuously vacant site in the X-ray crystal structure of 40 confirms the location of the hydride in the equatorial plane of the $Ir^I$ center (P(3)-Ir(1)-P(5)=153.90(7)° and P(6)-Ir(1)-Ir(2)=167.41(6)°). Moreover, subsequent to the location of all non-hydrogen atoms, the Fourier difference map showed a single peak in the vacant iridium coordination site of appropriate intensity for a hydride ligand though the proximity of the hydride to a heavy nucleus precludes the determination of an accurate Ir—H distance. Further evidence for the hydride location comes from the elongated Ir(1)-P(1) bond distance, resulting from the strong trans influence of the hydride ligand. The Ir(1)-P(1) bond distance of 2.314(2) Å is 0.091(3) Å longer than that observed in the chloride analog 37. Excluding Ir(1)-P(1), all other metal-ligand bond distances of 40 are similar to those observed in 37.

The results of NMR spectroscopy are consistent with the X-ray structural studies. A single hydride resonance is observed in the $^1$H NMR spectrum of 40 (FIG. 20(a)) at −10.24 ppm. A 178 Hz $^2J_{PH}$ coupling constant confirms the coordination of a phosphorus trans to the hydride is maintained in solution. The three different tfepma ligand environments are distinguished in the $^1$H NMR spectrum by unique methyl resonances at 2.65, 2.77 and 2.89 ppm. $^{31}$P-$^1$H HMQC experiments were used to assign a $^{31}$P NMR resonance at 86.4 ppm as the $Ir^I$ phosphite coordinated trans to the hydride ligand. The high frequency shift of this resonance follows from the strong trans influence of the hydride ligand observed in the solid-state structure. Two resonances at 64.4 and 67.8 ppm in the $^{31}$P NMR spectrum are assigned to $Ir^{III}$ phosphites, whereas the low frequency singlet at 21.6 ppm is assigned to the axially coordinated phosphite of the chelating ligand. As in 37, a strong $^2J_{PP}$ of 761 Hz observed in resonances at 26.6 and 82.2 ppm points to their assignment as the trans disposed $Ir^I$-phosphites of the chelating and bridging tfepma ligands, respectively.

Figure 20:
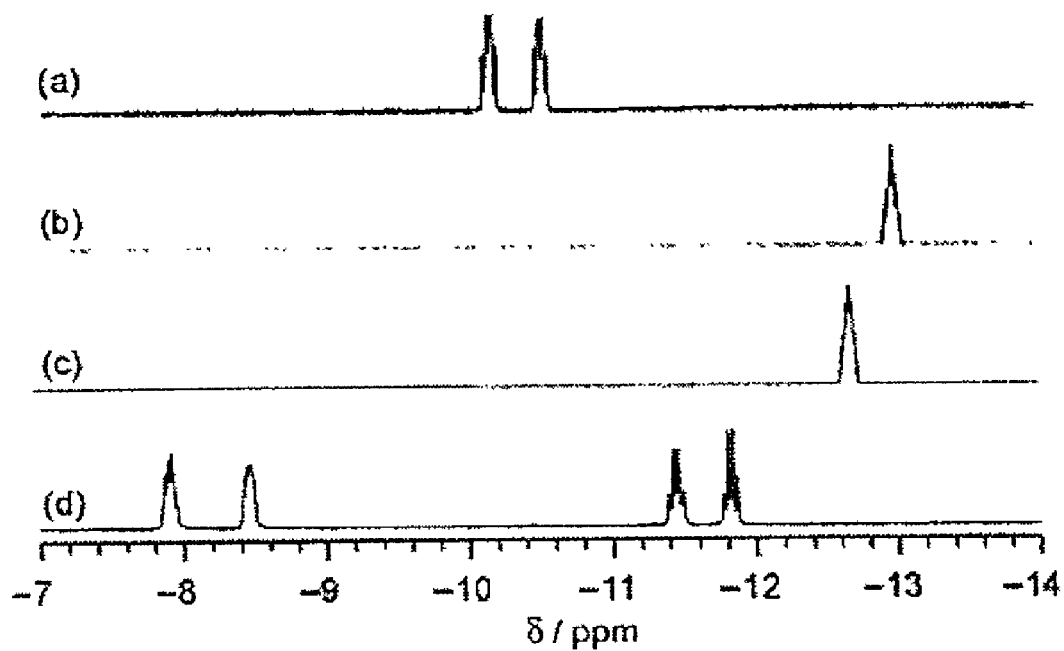
FIG. 20 shows $^1$H NMR spectra of (a) the equatorial isomer of Ir$_2^{I,III}$(tfepma)$_3$HCl$_3$ (10), (b) the axial isomer of Ir$_2^{I,III}$(tfepma)$_3$HCl$_3$ (9), (c Ir$_2^{I,III}$(tfepma)$_3$HCl$_2$(MeCN)] [PF$_6$]$_2$ (11), and (d) Ir$_2^{I,III}$(tfepma)$_3$H$_2$Cl$_2$ (12), wherein the spectra were acquired at room temperature in CD$_3$CN.

At early reaction times, another isomer of $Ir_2(tfepma)_3HCl_3$ with an axial hydride ligand is observed (39 in Scheme 11). As indicated by reactions (vi) and (vii) of Scheme 11, 39 converts to 40 upon stirring in $CH_2Cl_2$. Examination of the Ir—H stretching region of the IR spectrum gives a single stretch at 2037 cm$^{-1}$, and the $^1$H NMR spectrum of 39 shown in FIG. 20(b) shows a single hydride resonance at −13.0 ppm. The absence of a large $^2J_{PH}$ coupling in the low frequency resonance suggests only cis H,P interactions, requiring protonation to occur at the axial coordination site of either the $Ir^0$ or $Ir^{II}$ center. The $^{31}$P NMR spectrum of 39 shows strong $^2J_{PP}$ couplings of 795 and 752 Hz in both the 35.7 and 47.9-ppm resonances of the chelating phosphite, respectively. Moreover, the resonances for the other $Ir^I$ phosphites at 80.9 and 88.7 ppm show the same 795 and 752 Hz coupling constants. Finally, the chemical shifts and coupling patterns of the $Ir^{III}$-coordinated phosphites at 63.8 and 66.3 ppm suggest an $Ir^{III}$ center equivalent to that observed in the final product 40. These NMR data suggest the reaction sequence shown in Scheme 11.

In order to elucidate further the initial steps of acid addition to 33, the protonation reaction was studied with the acids of non-coordinating anions. Addition of neat triflic acid to suspensions of 33 in $CH_2Cl_2$ yields no appreciable reaction, even after 24 h, in stark contrast to the instantaneous addition of HCl to suspensions of 33. However, if the triflic acid is added as a solution in MeCN, rapid dissolution of the solid occurs to give a pale yellow, almost colorless solution from which a pale yellow solid precipitates. Spectroscopic studies suggest the formulation $Ir_2^{I,III}(tfepma)_3HCl_2(MeCN)$ (41) with a structure analogous to 39 as shown in reaction viii of Scheme 11. The presence of a hydride ligand is indicated by an Ir—H stretching mode at 2042 cm$^{-1}$ in the infrared spectrum of the product as well as a single low frequency hydride resonance at −12.67 ppm (FIG. 20(c)) in the $^1$H NMR spectrum. The $^{31}$P NMR spectrum of 41 shows other similarities to 39. Two pairs of strongly coupled phosphite signals are observed: resonances at 43.0 and 48.4 ppm can be assigned to the chelating tfepma ligand coordinated to $Ir^I$ with $^2J_{PP}$ coupling constants of 740 and 720 Hz, respectively, reflected in the resonances for the other $Ir^I$ phosphites at 75.9 and 85.0 ppm. Two remaining peaks at 53.6 and 66.9 ppm are in the range for phosphites at the $Ir^{III}$ center. In this case the low frequency shift of the former resonance results from coordination of an acetonitrile molecule across the $Ir^{III}$ center as observed for 33 in solution.

As observed for 33, the MeCN ligand of 41 undergoes exchange in $CD_3CN$ solvent. The disappearance of the coordinated MeCN signal is complemented by the appearance of a signal for free MeCN at 1.96 ppm. The exchange process is sufficiently slow such that the loss in intensity of the $^1$H resonance of the $Ir^{III}$-coordinated MeCN may be easily monitored over the course of a day. A plot of ln I vs t is linear ($R^2$=0.9984), yielding a first-order decay rate constant of $k_H$=1.25×10$^{-4}$ s$^{-1}$. Interestingly, the MeCN exchange process is significantly accelerated ($k_D$=1.90×10$^{-4}$ sec$^{-1}$, $R^2$=0.9985) when 33 is deuterated by DOTf, yielding an inverse kinetic isotope effect of 0.66.

Reversible $H_2$ Addition to 33 (ix of Scheme 11)

Hydrogen adds to 3 with equal facility to the $X_2$ and HX. Suspensions of 3 in $CH_2Cl_2$ rapidly afford a pale yellow solution upon bubbling with hydrogen gas at room temperature to yield $Ir_2^{I,III}(tfepma)_3H_2Cl_2$ (42) as shown in reaction (ix) of Scheme 11. The reaction can be reversed with $N_2$ purging. Two iridium-hydride resonances appear in the low frequency region of the $^1$H NMR spectrum at −11.51 and −8.32 ppm signaling $H_2$ addition to the $Ir_2^{0,II}$ core. FIG. 20(d) reveals large $^2J_{PH}$ coupling constants in both hydride resonances of 42. A coupling constant of 172 Hz in the low frequency doublet is commensurate with the 178 Hz coupling constant observed for the $Ir^I$ hydride in the equatorial isomer of 40. An even larger $^2J_{PH}$ coupling constant of 270 Hz observed in the −8.32 ppm resonance points toward an equatorial hydride ligand at the $Ir^{III}$ center, where the contracted radius of the oxidized metal center leads to an even larger coupling constant to a trans phosphorus. The $^{31}$P NMR spectrum of 42 shows a six-resonance pattern similar to those observed for complexes 37 and 40, supporting the $Ir_2^{I,III}(tfepma)_3H_2Cl_2$ formulation. The chelating ligand resonances appear shifted to low frequency as a doublet-of-triplets at 17.8 ppm and a strongly coupled doublet at 45.3 ppm ($2J_{PP}$=750 Hz). This 750-Hz coupling constant is mirrored in a resonance at 95.5 ppm, easily identifying this resonance as an Ir1-phosphite from a bridging tfepma ligand. $^{31}$P-$^1$H HMQC experiments provided coupling-correlation of the $^{31}$P NMR resonances at 86.8 ppm and 99.4 ppm to the Ir$^{III}$ and Ir$^I$-coordinated hydrides, respectively. A peak at 71.3 ppm is assigned to the remaining Ir$^{III}$ phosphite, located trans to a chloride ligand.

Figure 21:
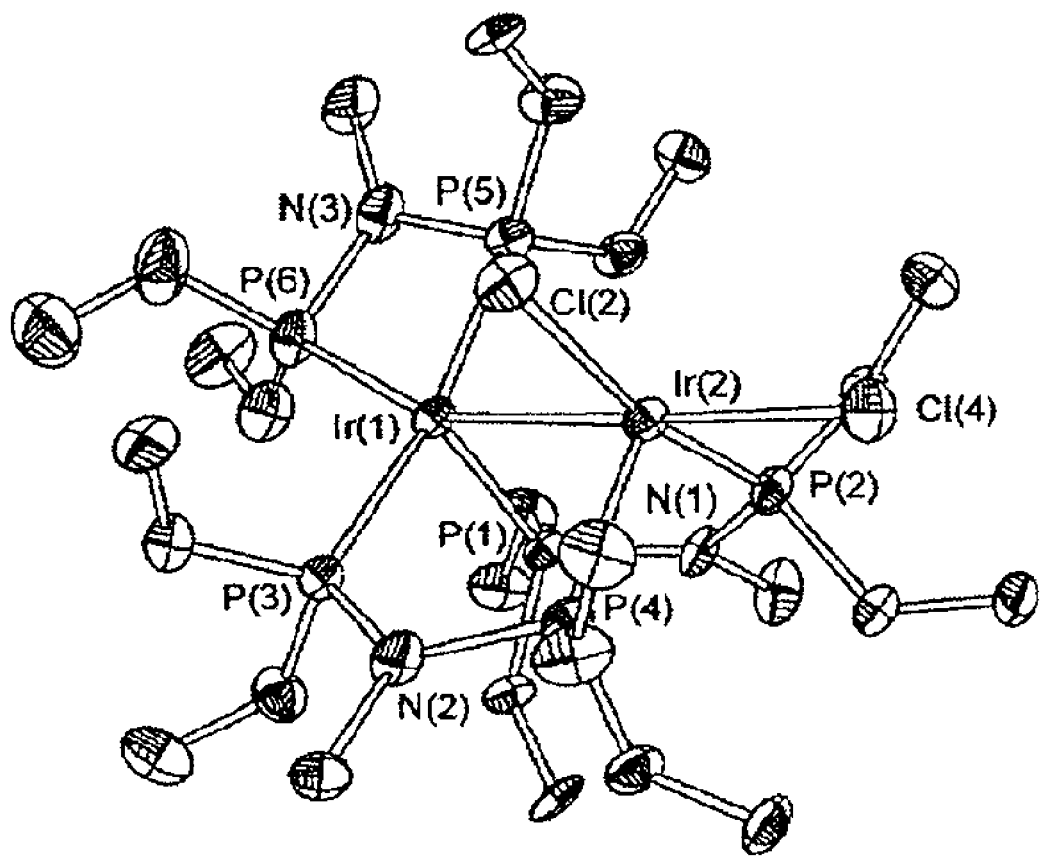
FIG. 21 is a thermal ellipsoid plot (50% probability) of Ir$_2^{I,III}$(tfepma)$_2$H$_2$Cl$_2$ (12) wherein for clarity, hydrogen atoms have been omitted and only the methylene carbons of the trifluoroethyl groups are shown.

Oxidative addition of hydrogen across the diiridium bond to give a HIr$^I$→Ir$^{III}$Cl$_2$H core is confirmed by the X-ray crystal structure of Ir$_2$$^{I,III}$(tfepma)$_3$H$_2$Cl$_2$ shown in FIG. 21; selected bond distances and angles are presented in Table 14. Though the Ir$^{III}$-coordinated hydride could not reliably be located (the Ir$^I$-coordinated hydride was located in the difference Fourier map), the vacant coordination sites of each octahedral ligand sphere establishes the location of the hydride ligands (P(5)-Ir(1)-P(3)=168.72(12), P(6)-Ir(1)-Ir(2)=158.46(10) and P(2)-Ir(2)-Cl(2)=169.35(12) Cl(4)-Ir(2)-Ir(1)=176.35(8)). Furthermore, the Ir(1)-P(1) and Ir(2)-P(4) bond distances of 2.300(3) and 2.277(3) Å are significantly longer than the same distances in Ir$_2$$^{I,III}$(tfepma)$_3$Cl$_4$, in accord with the trans influence associated with the terminal hydride ligands. The average twist angle about the Ir—Ir bond axis is only 10°; the H(1)-Ir(1)-Ir(2)-H(2) dihedral angle in the solid state is 88°. The diiridium bond distance is significantly shorter at 2.7561(7) Å than those observed in Ir$_2$$^{I,III}$ complexes Ir$_2$$^{I,III}$(tfepma)$_3$Cl$_4$ and Ir$_2$$^{I,III}$(tfepma)$_3$HCl$_3$, and in fact is more comparable to the bond distance observed in the Ir$_2$$^{II,II}$ complex, Ir$_2$$^{II,II}$(tfepma)$_2$Cl$_2$(MeCN)$_2$. Other metrical parameters of Ir$_2$$^{I,III}$(tfepma)$_3$H$_2$Cl$_2$ are largely unchanged from the other Ir$_2$$^{I,III}$ complexes.

The equilibrium isotope effect may be evaluated for hydrogen addition to 33 according to reaction (ix) of Scheme 11. Addition of 1 atm of an equimolar mixture of H$_2$ and D$_2$ to an NMR tube containing 33 in d$^8$-THF results in the rapid color change to yellow associated with hydrogen addition. Integration of the $^1$H NMR spectrum after ~30 min yielded a ratio of 42 to 42-d$_2$ of 0.90±0.05. The ratio remained constant for several hours, until significant H/D exchange prevented further measurements.

The $^1$H NMR spectrum of 42 in d$^8$-THF was observed to evolve slowly for several days. Heating accelerates this reaction; d$^8$-THF solutions of 42 heated to 80° C. under an H$_2$ atmosphere are converted to new products as evidenced by $^1$H and $^{31}$P NMR spectroscopy. An integration ratio of nine methyl protons of three tfepma ligands to two hydride ligands suggests that no subsequent H$_2$ addition has occurred. Assignment of the reaction products is preliminary, but $^1$H and $^{31}$P NMR suggest the formation of a 1:1 ratio of two major iridium hydride products, 43a and 43b depicted in Scheme 12, with the same empirical formula as 42. Several overlapping resonances in the tfepma methyl and methylene regions precludes their utility in making structural assignments. However, the hydride region shows four distinct signals at −11.23, −12.63, −13.71 and −14.07 ppm that account for 90% of 42 (additional smaller peaks are observed at −12.85 and −13.78 ppm). The three high frequency hydride resonances show $^2J_{HP}$ coupling constants diagnostic of hydride coordination trans to a phosphorus ligand: $^2J_{HP}$=184, 177 and 181 Hz, respectively. The low frequency, −14.07-ppm

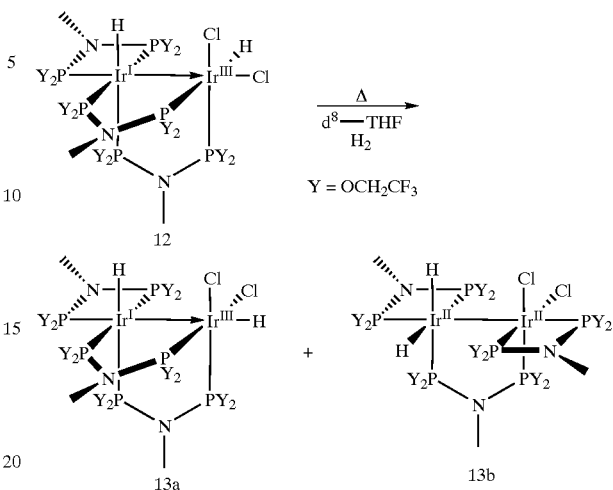

Scheme 12

Y = OCH$_2$CF$_3$ resonance is an apparent quartet with only C is $^2J_{HP}$ couplings. The $^{31}$P{$^1$H} NMR spectrum confirms the presence of two principal reaction products by the appearance of twelve distinct phosphorus resonances (as discussed above, the Ir$_2$$^{I,III}$ complexes 37 and 39–42 typically show six unique phosphorus environments).

Assignment of the structure for 43a begins with the diagnostic pair of resonances observed in the 31P NMR spectrum for a chelating tfepma ligand at 41.7 and 59.0 ppm, with the former displaying a 692 Hz coupling constant. This $^2J_{PP}$ coupling is reflected in a high frequency resonance at 99.9 ppm, confirming a trans phosphite arrangement on an Ir$^I$ center. The chemical shift of the −11.23-ppm hydride resonance is consistent with the chemical shift of the equivalent Ir$^I$ hydride of 32. Selective decoupling experiments show strong correlation between this and a $^{31}$P resonance at 85.8 ppm; a $^2J_{HP}$-coupling constant of 184 Hz is also congruent with the coupling constant for the same hydride-phosphite pair in 42. $^2J_{PP}$ couplings observed in the 99.9 and 85.8-ppm 31p resonances are reflected in resonances at 72.5 and 63.6 ppm, respectively, and are characteristic of phosphorus-phosphorus couplings through the nitrogen bridgehead of the tfepma ligand. Finally, equatorial chlorides and an axial hydride (−14.07 ppm) complete the Ir$^{III}$ coordination sphere; the axial assignment of the hydride is based on the observed high frequency shift of the axial Ir$^I$ phosphite singlet to 59.0 ppm.

Of the twelve phosphorus resonances the remaining six and two hydride resonances characterize 13b. Notably, none of the $^{31}$P resonances display a large $^2J_{PP}$ coupling constants, indicating a lack of trans disposed phosphite groups, furthermore, both hydride resonances show signature $^2J_{HP}$ couplings distinctive for a hydride coordinated trans to a phosphorus. Based on this evidence, as shown in Scheme 2.3, valence disproportionation to yield an Ir$_2$$^{II,II}$ species is tentatively suggested for 43b. In support of this assignment, the chemical shifts and the observed phosphorus-hydrogen coupling constants of the hydride ligands are not consistent with those observed for the Ir$^{III}$-hydride ligand of 42 (δ=−8.32 ppm, $^2J_{HP}$=270 Hz). Furthermore, no low-frequency $^{31}$P resonances, characteristic of phosphite coordination to an Ir$^I$ center, are observed.

Organometallic Aspects of Two-Electron Mixed-Valence Reactivity

The reactivity of $Ir_2^{0,II}(tfepma)_3Cl_2$ with dihydrogen provided the impetus for investigating the organometallic chemistry of the two-electron mixed-valence platform. Preliminary experiments indicate that alkyl derivatives of 33 can be prepared, and that the $Ir_2^{0,II}$ core is maintained. Treatment of 33 with one equiv of methide source MeMgBr or MeLi at low temperature in THF results in a color change from brown to yellow. Upon warming to room temperature the color returns to brown. Solvent removal followed by trituration with $CH_2Cl_2$ affords a gray-green powder in moderate yield. The 31P NMR reveals six different phosphorus environments consistent with the solution structure shown in reaction (x) of Scheme 11 for $Ir_2^{0,II}(tfepma)_3(Me)Cl(MeCN)$ (44). A singlet is observed at 29.5 ppm for the axial $Ir^0$ phosphite, with the typical pseudo-triplet at 44.8 ppm for the equatorial $Ir^0$ phosphite of the chelating tfepma ligand. The equatorial $Ir^0$ phosphites of the bridging tfepma ligands appear as two doublets-of-multiplets at 93.8 and 95.5 ppm. One $Ir^{II}$ phosphite is observed at 72.5 ppm with the second shifted to high frequency at 109.3 ppm. The $^1H$ NMR in $CD_3CN$ reveals a doublet-of-doublets resonance at 1.11 ppm that integrates to three protons. Selective $^{31}P$ decoupling gives a $^3J_{HP}$ coupling constant of 8.1 Hz to the high frequency, 109.3 ppm, phosphite resonance and a $^3J_{HP}$ coupling constant of 2.8 Hz to the 72.5 ppm phosphite resonance, establishing the equatorial coordination of a methyl group on the $Ir^{II}$ center. Coordination of a solvent molecule is confirmed by the presence of precisely one equivalent of free THF or MeCN in the $^1H$ NMR spectrum of thoroughly dried compound.

The preparation of two-electron mixed-valence complexes of iridium would seem to follow directly from studies of the $Rh_2^{0,II}$ platform. However, the stronger metal-ligand bonds of iridium starting materials do not permit methodologies used in the rhodium chemistry described above to translate to iridium. In order to isolate binuclear complexes of the dfpma ligand with iridium, excess oxidant must be employed to react with 1,5-cyclooctadiene liberated during the reaction. Nevertheless, the $Ir^I$ center of 31 maintains a chelated 1,5-cyclooctadiene ligand, presumably because the poor σ-donor ligand dfpma cannot displace it from the iridium coordination sphere. Dppma proved to displace 1,5-cyclooctadiene more efficiently, however, in this case the metal core inserts into an aryl C—H bond subsequent to the addition of three dppma ligands. Only the low solubility of $Ir_2^{0,II}(tfepma)_3Cl_2$ (33) in methylene chloride permits its isolation in moderate yields, free of the 1,5-cyclooctadiene byproduct that plagues isolation of other diphosphazane derivatives of iridium. Indeed, attempts to directly prepare $Ir_2^{0,II}$ species with an axial ligand coordinated to the $Ir^{II}$ center results in the formation of oils that preclude isolation of the metal-containing complex.

The preparation and reactivity of 33 suggests that the preferred coordination geometry for iridium maintains a π-acid ligand chelated to the low-valent metal center. Though steric constraints imposed by the tfepma ligand are initially appealing reasons for this structural departure from the three bridging ligand motif, the preparation of the homologous rhodium series based on the tfepma ligand, $Rh_2^{0,0}(tfepma)_3(L)_2$, $Rh_2^{0,II}(tfepma)_3Cl_2(L)$, $Rh_2^{II,II}(tfepma)_3Cl_4$, suggests that three bridging tfepma ligands can be accommodated by a binuclear core. Furthermore, coordination of tfepma in a chelating mode to the valence symmetric 38 suggests a thermodynamic preference for a mixed-valence system with tfepma chelating the low-valent metal center.

Figure 22:
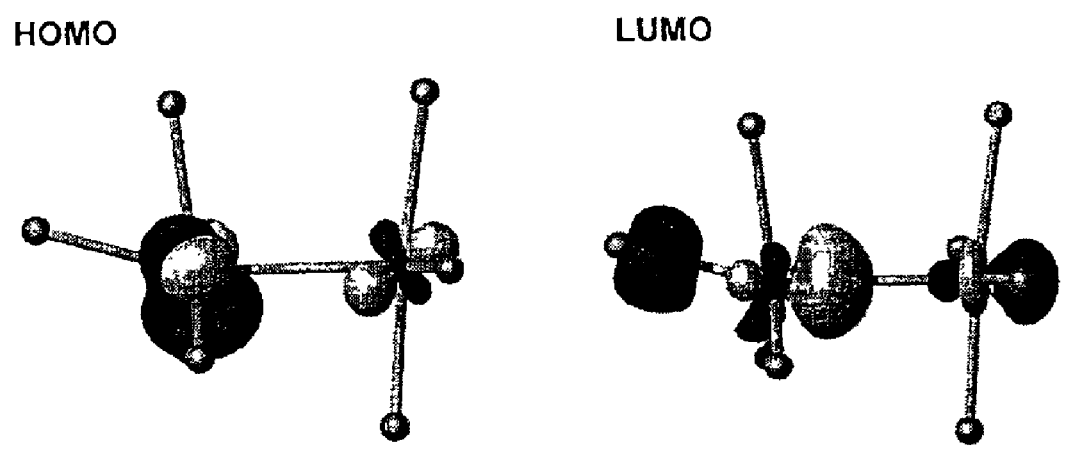
FIG. 22 is a pictorial representation of the HOMO and LUMO of Ir$_2$(PH$_3$)$_6$Cl$_2$ as calculated by the extended Hückel program YAeHMOP.

The reactivity patterns of 33 reveal a complex with considerable Lewis acid character. In particular, addition of reducible small molecule substrates $Cl_2$ and HCl proceeds with facility. In contrast, MeI, HOTf and MeOTf do not add to 33 in the absence of suitable donor ligands, suggesting an XY addition mechanism in which $X^-$ coordination precedes attack by $Y^+$. The metal-centered frontier molecular orbitals for 33, presented in FIG. 22, support this contention. A HOMO of mixed dπ*/dδ* character is complemented by a low-energy LUMO of dσ* parentage. Coordination of a ligand to the vacant axial site of 33, as in the reaction of 33 to 34 or 33 to 35, results in the formation of a stable octahedral iridium center, with the destabilization of the LUMO providing the required energy compensation for bond formation. Similarly, oxidative addition of small molecule substrates to 33 leads to occupation of the vacant axial site by $X^-$. Again, destabilization of the LUMO attends the formation of the ligand-centered bonding orbital.

The preference of strong σ-donor ligands for the axial position of the $Ir^{II}$ center provides further evidence for the Lewis acid character of the bimetallic core. Ligands with σ-donor properties stronger than chloride coordinate to the $Ir^{II}$ center opposite the M-M bond whereas the weaker donor ligands are forced into equatorial positions with concomitant chloride migration to the axial site. No spectroscopic evidence for equatorial coordination was observed among the series CNR, $PR_3$, $Br^-$. Conversely, THF and MeCN were observed to coordinate only in the equatorial position. These results are in contradistinction to other studies on binuclear metal complexes that preferentially coordinate the weakest σ-donor opposite the metal-metal bond. In the present case, the Lewis acid character of the dσ* orbital apparently dominates the trans influence normally associated with metal-metal bonds.

The oxidative addition reactivity of 33 is notable in light of previous studies of two-electron mixed-valence complexes. The ability of the tfepma ligand to be sufficiently flexible to support the variant coordination geometries and correspondent electronic structures of the two-electron mixed-valence cores is crucial to the reactivity of Scheme 11. In one-electron mixed-valence compounds, a single electron change can be accommodated with an inflexible coordination sphere; however, this is unlikely to be the case for two-electron mixed-valence species. Significant changes in the reorganization of the primary coordination environment typically accompany the addition or removal of more than one electron from a metal center. As Bosnich postulates in his studies of 6-4 binucleating complexes, this ligand reorganization or "mechanical coupling" between metal centers is manifested in arrested multi-electron redox reactivity of mixed-valence complexes. In 33, adverse energetics associated with mechanical coupling are circumvented by the flexible coordination environment offered by the tfepma ligands. The three atom diphosphazane backbone can support twist angles from 0 to 45°, thus permitting the preferred trigonal bipyramidal and octahedral coordination geometries of $d^9$ and $d^7$ metal centers, respectively, to be adopted with

Scheme 13

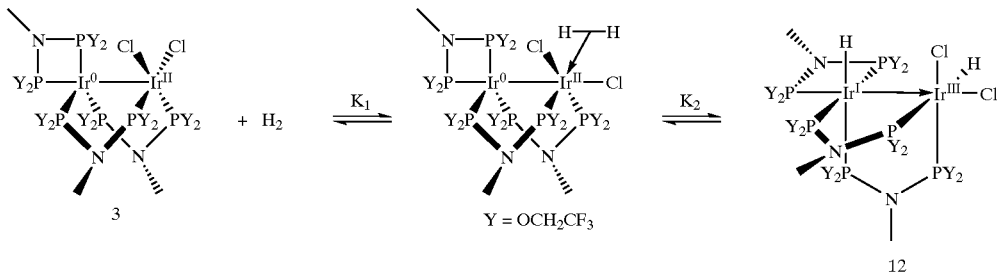

Y = OCH$_2$CF$_3$ facility upon oxidative-addition to the Ir$_2^{0,II}$ bimetallic core.

The addition of H$_2$ to 33 and its elimination from 42 is an unusual and intriguing observation. There are relatively few examples of reversible H$_2$ addition across metal-metal bonds, and in no case, has such a reaction been observed to occur reversibly across a preserved metal-metal single bond. Variable temperature NMR studies of 33 provide insight into the H$_2$ addition mechanism. The addition of weak 2e$^-$ donors to an equatorial Ir$^{II}$ site of 33, suggests that this coordinatively unsaturated metal center is a logical site for initial H$_2$ attack as depicted in Scheme 13. The addition of hydrogen to a single metal center of a binuclear metal core is consistent with conventional oxidative-addition mechanisms; furthermore, Poilblanc and Cowie previously have observed single-site H$_2$ addition followed by hydride migration to produce the 1,2-dihydride. Conversely, a concerted 1,2 addition of H$_2$ across a metal-metal bond is forbidden by orbital symmetry considerations, as is the reverse, reductive elimination. Pre-coordination of dihydrogen at Ir$^{II}$ is further supported by the empirical observation that the rate of H$_2$ addition to 38 decreases with donor ability of the solvent, i.e., CH$_2$Cl$_2$>THF>MeCN. Presumably, CH$_2$Cl$_2$ cannot compete with H$_2$ as a sufficient donor ligand, whereas THF and MeCN show progressively higher Ir-solvent bond dissociation energies, slowing the H$_2$ addition.

Evaluation of equilibrium isotope effects for the reversible addition of H$_2$ to 33 provides mechanistic support for the addition mechanism of Scheme 13. Recent studies suggest that inverse EIEs, defined as follows:

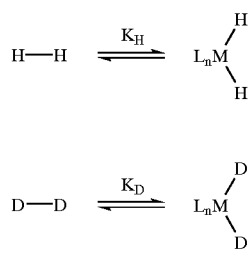

$$EIE = K_H/K_D, \quad (1)$$

may be characteristic for the concerted addition of H$_2$ to a single metal center. For example, an inverse EIE of 0.70±0.06 was obtained for the coordination of H$_2$ versus D$_2$ in tungsten dihydrogen complexes and an EIE of 0.63±0.05 was obtained for dihydride/dideuteride formation from W(PMe$_3$)$_4$I$_2$. A more thorough experimental and theoretical treatment of equilibrium isotope effects for the oxidative addition of H$_2$ to Vaska's complex has been reported as well (EIE=0.55±0.06). In order to model accurately both the direction and the magnitude of the equilibrium isotope effects in the Vaska system, it was necessary to use a full statistical mechanics treatment of the isotope equilibrium, as given by:

$$EIE = SYM \times MMI \times EXC \times ZPE, \quad (2)$$

where SYM is the symmetry number ratio factored from the rotational partition function, MMI is EIE component of the mass moment of inertia, EXC is the vibrational excitation constant and ZPE is the zero point energy term. The first three factors describe the entropic element of the equilibrium. SYM (1.0), MMI (5.66) and EXC (0.84) components for the Vaska system resulted in a normal contribution to the isotope effect (i.e., $\Delta S°_H - \Delta S°_D > 0$), leaving the inverse nature of the EIE to be enthalpic (i.e., $\Delta H°_H - \Delta H°_D > 0$), as reflected by a zero point energy term of 0.10. The inverse ZPE term turns out to be a special case for hydrogen addition. Though consideration of the H—H/D-D bond strength difference ($\Delta$BDE=1.8 kcal mol$^{-1}$) would suggest a strong normal ZPE contribution, this single isotopically sensitive vibrational mode in the reactant is dominated by five new isotopically sensitive modes in the isotope-containing product (i.e., MH$_2$/MD$_2$). In all other equilibrium isotope studies, the number of isotopically sensitive modes is essentially the same in reactant and product, and as such the value of the equilibrium isotope effect is directly determined by the relative strengths of the bonds being made and broken.

A minor inverse equilibrium isotope effect (EIE) of 0.9±0.05 is observed for the addition of hydrogen versus deuterium to 33. This is an interesting result in light of the equilibrium isotope effect reported for the reversible addition of H$_2$ to fulvalene dimers of chromium (EIE= 1.45±0.10). In this latter case, ready access to the diradical as shown in Scheme 14 suggests a symmetric addition of H$_2$ across the metal-metal bond, as observed for rhodium porphyrin dimers. The pre-equilibrium step to form the diradical is not isotope sensitive, thus the EIE reflects only the thermodynamic characteristics of the second equilibrium step, namely the relative Scheme 14

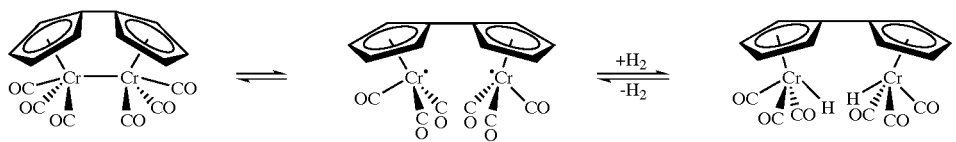

stability of H-M ... M-H/D-M ... M-D versus $H_2/D_2$. Conversely, the proposed two-step hydrogen addition of 33 as depicted in Scheme 13, is characterized by two isotope sensitive equilibria: $K_1$, which is the equilibrium for binding and forming the putative dihydrogen complex (eq 3), and $K_2$, which is the equilibrium for 1,2-hydride migration (eq 4). Substitution of eq 4 into eq 3 gives $K_1 \times K_2$ in terms of measurable species, i.e., the reactants and the final products (eq 5), which gives the relation in eq 6 for the EIE experiment ($[H_2]=[D_2]$).

$K_1 = [Ir_2-(H_2)]/[Ir_2][H_2]$  Equation (3)

$K_2 = [H-Ir-Ir-H]/[Ir_2-(H_2)]$  Equation (4)

$K_1K_2 = [H-Ir-Ir-H]/[Ir_2][H_2]$  Equation (5)

$(K1H/K1D)(K_2H/K_2D) = [H-Ir-Ir-H]/[D-Ir-Ir-D]$  Equation (6)

It has been proposed that EIEs for hydrogen addition to transition metal complexes are general for a given type of equilibrium. Thus, referring to eq 4 and 6, the value of $K_1{}^H/K_1{}^D$ can be approximated by Kubas' EIE of 0.70±0.06 for the formation of $W(CO)_3(PCy_3)_2(\eta^2-H_2)$ vs $W(CO)_3(PCy_3)_2(\eta^2-D_2)$. Similarly it would be a reasonable approximation to use Volhardt's EIE of 1.45±0.10 for the formation of the 1,2-dihydride/dideuteride of Scheme 14 ($K_2{}^H/K_2{}^D$). Though crude, this estimation provides a value for ($K_1{}^H/K_1{}^D$)($K_2{}^H/K_2{}^D$) of 1.02, which is in reasonable agreement with the measured EIE of 0.9±0.05 for hydrogen/deuterium addition to 33, supporting the intermediacy of a dihydrogen adduct in the addition mechanism of Scheme 13.

Figure 23:
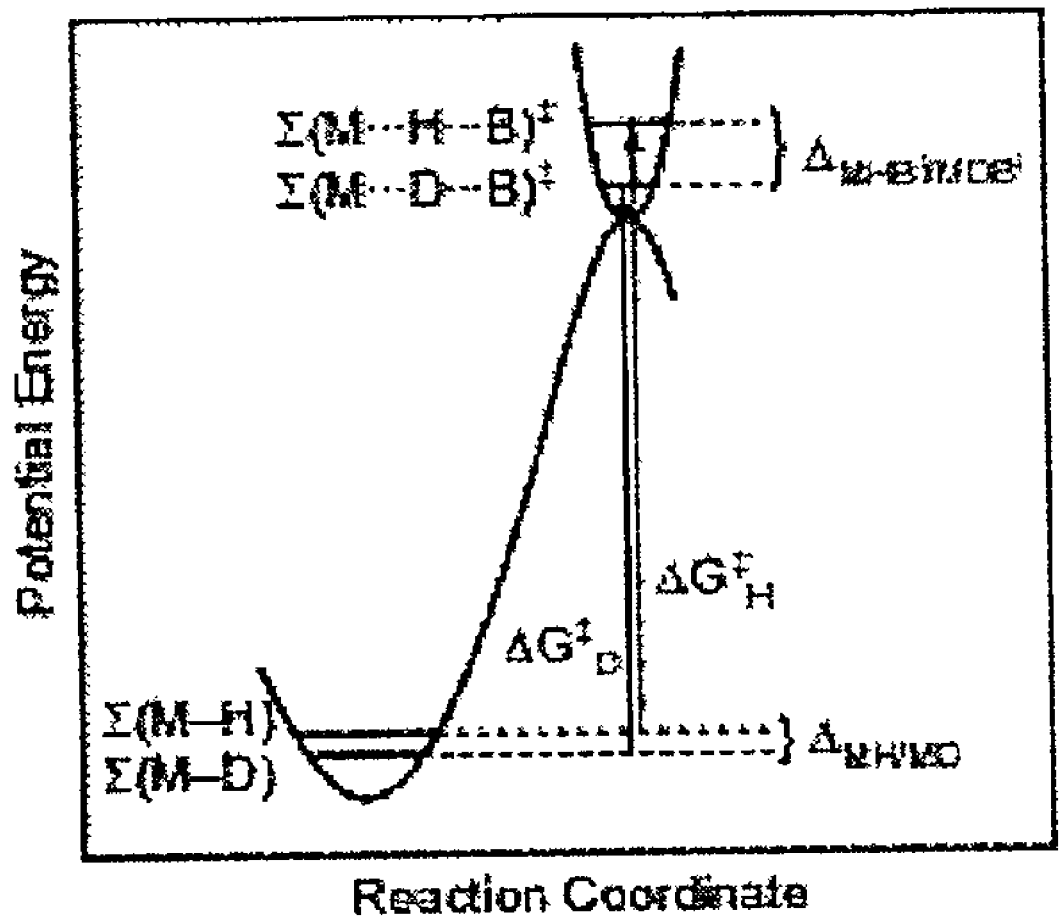
FIG. 23 is a qualitative potential energy diagram for MeCN exchange from [Ir$_2^{I,III}$(tfepma)$_3$HCl$_2$(MeCN)]$^{2+}$ (11), illustrating the origin of the inverse isotope effect.

Isotope effects are also useful in elucidating the solvent exchange mechanism of 41. Solutions of 41 in $CD_3CN$ slowly exchange the coordinated acetonitrile ligand, as evidenced by decay of the $^1H$ NMR resonance for the coordinated ligand with concomitant growth of free MeCN. At 20° C. an inverse kinetic isotope effect (KIE) of 0.66 was measured for this process. Such isotope dependencies have been rationalized by invoking product-like transition states with higher force constants for isotope-sensitive stretching and bending modes. As shown qualitatively in FIG. 23, a "tighter" transition state results in a greater difference in zero point energy in the transition state relative to the ground state, thus $\Delta G^{\ddagger}_H$ is greater than $\Delta G^{\ddagger}_D$. Loss of the coordinating MeCN ligand followed by rearrangement of the $Ir^{III}$ center to square pyramidal in the transition state is expected to strengthen the remaining interactions along the metal-metal axis in the transition state. This assumption is supported by the contracted Ir(1)-Ir(2) and Ir(1)-P(6) bond distances in 33 relative to those of 37 and 40. Thus, a one-step solvent exchange process could reasonably give rise to an inverse KIE via strengthening of the Ir—H bond in the transition state. However, the magnitude of the KIE is suspiciously large for a secondary isotope effect.

Alternatively, the observed inverse KIE could be the result of an equilibrium step, prior to actual solvent exchange, which exhibits an inverse isotope effect. Consider the proposed reaction sequence presented in Scheme 15. Proton abstraction from 41 by the weakly basic solvent, in this case $CD_3CN$ ($pK_a \approx -10$), would (in effect) give 34 and $CD_3CN$ ... $H^+$. The iridium complex could then rapidly exchange the coordinated MeCN ligand as established by studies of the solution NMR spectra of 33. For this situation, the primary isotope effect (the Ir—H bond is being broken) arises from the higher force constants associated with N—H/$D^+$ species as opposed to M-H/$D^+$ species, resulting in a lower activation barrier for deuterium transfer; that is, Scheme 15

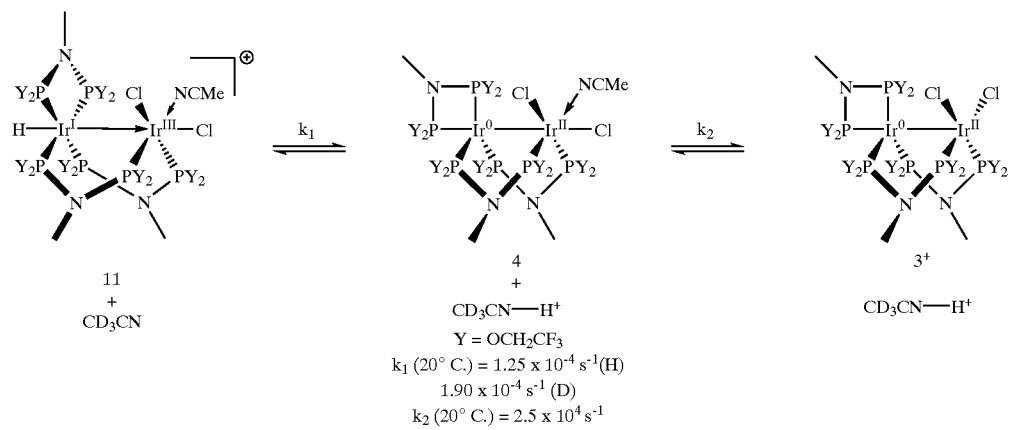

$Y = OCH_2CF_3$
$k_1 (20° C.) = 1.25 \times 10^{-4} s^{-1} (H)$
$1.90 \times 10^{-4} s^{-1} (D)$
$k_2 (20° C.) = 2.5 \times 10^4 s^{-1}$ isotopic labeling of the iridium complex favors proton transfer to the $CD_3CN$ solvent. This model is in agreement with the arrested reactivity of HOTf with 33 in the absence of MeCN; initial coordination of MeCN to 33 to yield 34 is apparently prerequisite to the protonation yielding 41, microscopic reversibility would then require deprotonation of 41 to occur prior to MeCN exchange.

Summary

The tfepma ligand presents a novel platform for binuclear iridium chemistry, providing a flexible electronic environment and coordination sphere. A two-electron mixed-valence core is stabilized by three tfepma ligands in a coordinatively unsaturated framework providing easy access to multi-electron reactivity. Oxidative addition of small molecule substrates is complemented by facile reductive elimination in the case of hydrogen, suggesting the binuclear framework to be an excellent model complex for the study of stoichiometric and catalytic small molecule activation and functionalization.

TABLE 15

Crystal data and structure refinement parameters for $Ir_2^{I,III}(dfpma)_2Cl_2(cod)$ (1), $Ir_2^{I,III}(dppma)_3Cl_2$ (2) and $Ir_2^{0,II}(tfepma)_3Cl_2$ (3).

|  | 1 | 2 | 3 |
|---|---|---|---|
| Empirical formula | $C_{10}H_{18}Cl_4F_8Ir_2N_2P_4$ | $C_{76}H_{70}Cl_4Ir_2N_3O_{12}P_6$ | $C_{275}H_{33}Cl_3F_{36}Ir_2N_3O_{12}P_6$ |
| Formula weight | 968.34 | 1929.37 | 1958.14 |
| Crystal system | Monoclinic | Monoclinic | Monoclinic |
| Space group | $P2_1/n$ | $P2_1/n$ | $C2/c$ |
| Unit cell dimensions | a = 15.8546(10) Å | a = 14.427(2) Å | a = 22.6597(5) Å |
|  | b = 9.9373(6) Å | b = 24.780(4) Å | b = 12.8038(2) Å |
|  | c = 16.3834(10) Å | c = 26.389(4) Å | c = 40.1310(6) Å |
|  | α = 90° | α = 90° | α = 90° |
|  | β = 115.4270(10)° | β = 94.870(3)° | β = 92.4210(10)° |
|  | γ = 90° | γ = 90° | γ = 90° |
| Volume | 2331.2(2) Å³ | 9400(3) Å³ | 11632.8(4) Å³ |
| Z | 4 | 4 | 4 |
| Density (calculated) | 2.759 Mg/m³ | 1.363 Mg/m³ | 2.236 Mg/m³ |
| Absorption coefficient | 12.205 mm⁻¹ | 3.095 mm⁻¹ | 5.043 mm⁻¹ |
| F(000) | 1784 | 3820 | 7472 |
| Crystal size (mm) | 0.33 × 0.21 × 0.19 | 0.40 × 0.21 × 0.08 | 0.30 × 0.30 × 0.12 |
| θ min for data collection | 2.37° | 1.13° | 1.02° |
| θ max for data collection | 23.27° | 20.00° | 23.24° |
| Index ranges | −10 ≤ h ≤ 17 | −13 ≤ h ≤ 12 | −20 ≤ h ≤ 25 |
|  | −11 ≤ k ≤ 11 | −23 ≤ k ≤ 23 | −14 ≤ k ≤ 13 |
|  | −18 ≤ l ≤ 15 | −25 ≤ l ≤ 21 | −44 ≤ l ≤ 44 |
| Reflections collected | 8646 | 28006 | 23134 |
| Independent reflections | 3336 [$R_{int}$ = 0.0542] | 8762 [$R_{int}$ = 0.1012] | 8322 [$R_{int}$ = 0.0696] |
| Absorption correction | Empirical | Empirical | psi-scans |
| Max. Transmission | 1.0000 | 1.000000 | 0.9876 |
| Min. Transmission | 0.3788 | 0.625348 | 0.4679 |
| Data/restraints/parameters | 3336/0/272 | 8762/0/474 | 8312/1/783 |
| Goodness-of-fit on F2 | 1.168 | 1.175 | 1.054 |
| Final R indices [l > 2σ(l)] | R1 = 0.0444 | R1 = 0.1153 | R1 = 0.0593 |
|  | wR2 = 0.1131 | wR2 = 0.2904 | wR2 = 0.1253 |
| R indices (all data) | R1 = 0.0469 | R1 = 0.1387 | R1 = 0.0882 |
|  | wR2 = 0.1147 | wR2 = 0.3087 | wR2 = 0.1476 |
| Extinction coefficient | 0.00037(8) | 0.0214(8) | 0.000015(11) |
| Largest diff. peak | 1.984 eÅ⁻³ | 4.736 eÅ⁻³ | 2.785 eÅ⁻³ |
| Largest diff. hole | −3.084 eÅ⁻³ | −2.038 eÅ⁻³ | −1.386 eÅ⁻³ |

TABLE 16

Crystal data and structure refinement parameters for $Ir_2^{0,II}(tfepma)_3Cl_2(MeCN)$ (4), $Ir_2^{0,II}(tfepma)_3Cl_2(CN^tBu)$ (5-$CN^tBu$) and $[Ir_2^{0,II}(tfepma)_3(MeCN)_3][PF_6]_2$ (6 $[PF_6]_2$).

|  | 4 | 5-$CN^tBu$ | 6 $[PF_6]_2$ |
|---|---|---|---|
| Empirical formula | $C_{31}H_{39}Cl_2F_{36}Ir_2N_5O_{12}P_6$ | $C_{32.5}H_{42}Cl_3F_{36}Ir_2N_4O_{12}P_6$ | $C_{35}H_{45}F_{48}Ir_2N_7O_{12}P_8$ |
| Formula weight | 1998.79 | 2041.27 | 2299.94 |
| Crystal system | Orthorhombic | Monoclinic | Triclinic |
| Space group | $P2_12_12_1$ | $P2_1/n$ | $P\bar{1}$ |
| Unit cell dimensions | a = 13.078(6) Å | a = 13.0879(2) Å | a = 13.1419(3) Å |
|  | b = 17.505(9) Å | b = 54.4519(9) Å | b = 13.3846(4) Å |
|  | c = 27.837(14) Å | c = 18.4318(3) Å | c = 24.1808(6) Å |
|  | α = 90° | α = 90° | α = 86.3020(10)° |
|  | β = 90° | β = 101.1890(10)° | β = 84.5500(10)° |
|  | γ = 90° | γ = 90° | γ = 62.6840(10)° |

TABLE 16-continued

Crystal data and structure refinement parameters for $Ir_2^{0,II}(tfepma)_3Cl_2(MeCN)$ (4), $Ir_2^{0,II}(tfepma)_3Cl_2(CN^tBu)$ (5-CN$^t$Bu) and $[Ir_2^{0,II}(tfepma)_3(MeCN)_3][PF_6]_2$ (6 [PF$_6$]$_2$).

| | 4 | 5-CN$^t$Bu | 6 [PF$_6$]$_2$ |
|---|---|---|---|
| Volume | 6373(5) Å$^3$ | 12885.9(4) Å$^3$ | 3760.95(17) Å$^3$ |
| Z | 4 | 8 | 2 |
| Density (calculated) | 2.083 Mg/m$^3$ | 2.104 Mg/m$^3$ | 2.031 Mg/m$^3$ |
| Absorption coefficient | 4.566 mm$^{-1}$ | 4.558 mm$^{-1}$ | 3.877 mm$^{-1}$ |
| F(000) | 3832 | 7840 | 2212 |
| Crystal size (mm) | 0.24 × 0.32 × 0.32 | 0.42 × 0.19 × 0.14 | 0.05 × 0.50 × 0.75 |
| θ min for data collection | 2.43° | 1.35° | 1.69° |
| θ max for data collection | 23.31° | 23.27° | 23.27° |
| Index ranges | −11 ≤ h ≤ 14 | −13 ≤ h ≤ 14 | −14 ≤ h ≤ 13 |
| | −19 ≤ k ≤ 18 | −51 ≤ k ≤ 60 | −12 ≤ k ≤ 14 |
| | −30 ≤ l ≤ 30 | −20 ≤ l ≤ 20 | −26 ≤ l ≤ 24 |
| Reflections collected | 25467 | 52085 | 15572 |
| Independent reflections | 9155 [$R_{int}$ = 0.0335] | 18440 [$R_{int}$ = 0.1427] | 10588 [$R_{int}$ = 0.0675] |
| Absorption correction | Empirical | psi-scans | psi-scans |
| Max. Transmission | 0.427270 | 1.000 | 0.3463 |
| Min. Transmission | 0.314766 | 0.3175 | 0.2421 |
| Data/restraints/parameters | 9155/0/848 | 18405/0/1696 | 10588/0/1017 |
| Goodness-of-fit on F2 | 1.056 | 1.171 | 1.152 |
| Final R indices [I > 2σ(I)] | R1 = 0.0290 | R1 = 0.0891 | R1 = 0.0743 |
| | wR2 = 0.0699 | wR2 = 0.1701 | wR2 = 0.1977 |
| R indices (all data) | R1 = 0.0335 | R1 = 0.1525 | R1 = 0.0790 |
| | wR2 = 0.0721 | wR2 = 0.2113 | wR2 = 0.2029 |
| Extinction coefficient | 0.00021(5) | 0.000000(12) | 0.0025(2) |
| Largest diff. peak | 0.913 eÅ$^{-3}$ | 2.995 eÅ$^{-3}$ | 4.706 eÅ$^{-3}$ |
| Largest diff. hole | −0.464 eÅ$^{-3}$ | −2.759 eÅ$^{-3}$ | −2.438 eÅ$^{-3}$ |

TABLE 17

Crystal data and structure refinement parameters for $Ir_2^{I,III}(tfepma)_3Cl_4$ (7) and $Ir_2^{I,III}(tfepma)_3Cl_4(MeCN)_2$ (8).

| | 7 | 8 |
|---|---|---|
| Empirical formula | C$_{55}$H$_{68}$Cl$_{10}$F$_{72}$Ir$_4$N$_6$O$_{24}$P$_{12}$ | C$_{225}$H$_{29}$Cl$_5$F$_{24}$Ir$_2$N$_4$O$_8$P$_4$ |
| Formula weight | 4060.09 | 1625.03 |
| Crystal system | Monoclinic | Triclinic |
| Space group | P2$_1$/c | P$\bar{1}$ |
| Unit cell dimensions | a = 23.6253(3) Å | a = 16.5448(11) Å |
| | b = 24.3565(4) Å | b = 16.5925(11) Å |
| | c = 24.93500(10) Å | c = 19.2595(13) Å |
| | 90° | 96.1220(10)° |
| | 116.5400(10)° | 90.0930(10)° |
| | 90° | 104.0800(10)° |
| Volume | 12836.3(3) Å$^3$ | 5096.9(6) Å$^3$ |
| Z | 8 | 4 |
| Density (calculated) | 4.202 Mg/m$^3$ | 2.118 Mg/m$^3$ |
| Absorption coefficient | 9.310 mm$^{-1}$ | 5.735 mm$^{-1}$ |
| F(000) | 15504 | 3084 |
| Crystal size (mm) | | 0.50 × 0.20 × 0.08 |
| θ min for data collection | 1.28° | 1.27° |
| θ max for data collection | 23.25° | 23.26° |
| Index ranges | −26 ≤ h ≤ 22 | −18 ≤ h ≤ 12 |
| | −27 ≤ k ≤ 23 | −16 ≤ k ≤ 18 |
| | −27 ≤ l ≤ 27 | −21 ≤ l ≤ 20 |
| Reflections collected | 51161 | 20933 |
| Independent reflections | 18247 [$R_{int}$ = 0.0955] | 14281 [$R_{int}$ = 0.0419] |
| Absorption correction | Empirical | Empirical |
| Max. Transmission | 0.9884 | 0.8939 |
| Min. Transmission | 0.5789 | 0.3785 |
| Data/restraints/parameters | 18247/0/1646 | 14280/1/1250 |
| Goodness-of-fit on F$^2$ | 1.144 | 1.144 |
| Final R indices [I > 2σ(I)] | R1 = 0.0803 | R1 = 0.0749 |
| | wR2 = 0.1363 | wR2 = 0.1598 |
| R indices (all data) | R1 = 0.1207 | R1 = 0.1074 |
| | wR2 = 0.1504 | wR2 = 0.1789 |
| Extinction coefficient | 0.000188(13) | 0.00054(5) |
| Largest diff. peak | 1.456 eÅ$^{-3}$ | 1.484 eÅ$^{-3}$ |
| Largest diff. hole | −1.221 eÅ$^{-3}$ | −1.235 eÅ$^{-3}$ |

TABLE 18

Crystal data and structure refinement
parameters for $Ir_2^{I,III}(tfepma)_3HCl_3$ (10)
and $Ir_2^{I,III}(tfepma)_3H_2Cl_2$ (12).

| | 10 | 12 |
|---|---|---|
| Empirical formula | $C_{28}H_{36}Cl_5F_{36}Ir_2N_3O_{12}P_6$ | $C_{28}H_{37}Cl_4F_{36}Ir_2N_3O_{12}P_6$ |
| Formula weight | 2038.07 | 2003.63 |
| Crystal system | Monoclinic | Monoclinic |
| Space group | $P2_1/c$ | $P2_1/c$ |
| Unit cell dimensions | a = 12.807(8) Å | a = 10.9265(3) Å |
| | b = 17.012(9) Å | b = 24.1981(7) Å |
| | c = 28.463(14) Å | c = 22.6237(7) Å |
| | 90° | 90° |
| | 99.200(13)° | 97.1070(10)° |
| | 90° | 90° |
| Volume | 6121.6(57) Å³ | 5935.8(3) Å³ |
| Z | 4 | 4 |
| Density (calculated) | 2.211 Mg/m³ | 2.242 Mg/m³ |
| Absorption coefficient | 4.881 mm⁻¹ | 4.988 mm⁻¹ |
| F(000) | 3896 | 3832 |
| Crystal size (mm) | 0.50 × 0.32 × 0.10 | 0.20 × 0.15 × 0.06 |
| θ min for data collection | 1.40° | 1.24° |
| θ max for data collection | 23.29° | 23.27° |
| Index ranges | −14 ≤ h ≤ 13 | −12 ≤ h ≤ 4 |
| | −18 ≤ k ≤ 13 | −26 ≤ k ≤ 26 |
| | −31 ≤ l ≤ 24 | −25 ≤ l ≤ 24 |
| Reflections collected | 21797 | 19042 |
| Independent reflections | 8704 [$R_{int}$ = 0.0442] | 8475 [$R_{int}$ = 0.0717] |
| Absorption correction | Empirical | Empirical |
| Max. Transmission | 0.9279 | 0.2661 |
| Min. Transmission | 0.4311 | 0.1216 |
| Data/restraints/parameters | 8701/0/834 | 8475/3/829 |
| Goodness-of-fit on $F^2$ | 1.140 | 1.263 |
| Final R indices [I > 2σ(I)] | R1 = 0.0422 wR2 = 0.1002 | R1 = 0.0549 wR2 = 0.1491 |
| R indices (all data) | R1 = 0.0487 wR2 = 0.1146 | R1 = 0.0672 wR2 = 0.1550 |
| Extinction coefficient | 0.00046(5) | 0.00143(10) |
| Largest diff. peak | 1.643 eÅ⁻³ | 2.034 eÅ⁻³ |
| Largest diff. hole | −1.667 eÅ⁻³ | −1.569 eÅ⁻³ |

Reductive Elimination Photochemistry of Rhodium Diphosphazanes

Extending the development of two-electron mixed-valence complexes, the viability of promoting multi-electron transformations from the excited state of $M_2^{0,II}$ cores was investigated. Excepting $H_2$ and RH eliminations that result in the formation of strong H—H and C—H bonds, scant precedent exists for such multi-electron reactivity among molecular species. Coupling of individual two-electron photoreactions with a $Rh_2^{0,II}$ complex provides the first example of a four-electron photoreaction among discrete molecular species.

Oxidation-reduction reactions of electronically excited transition metal complexes customarily proceed by one electron. By itself, single electron transfer is confining inasmuch as most activation reactions involve multi-electron processes. Primary one-electron photoredox events must therefore be coupled to oxidation-reduction processes remote to the excited state to effect overall multi-electron reactivity. Such conformity in multi-electron design finds its origins in the nature of the excited state, which at the most general level is the same despite the many different types of transition metal photoreagents. As instructive examples, consider the three systems schematically represented in Scheme 16. The photochemistry of mononuclear $d^6$ metals, for which tris(bipyridyl)ruthenium(II) is the archetype, originates from a metal-to-ligand Scheme 16

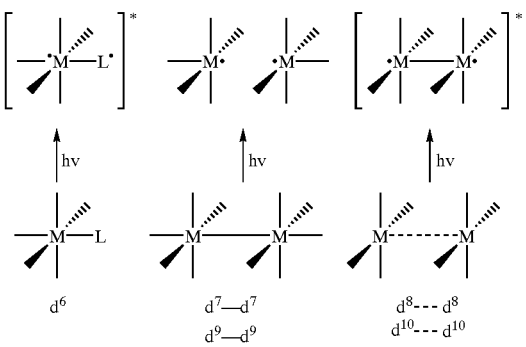

charge transfer (MLCT) excited state in which electrons localized on the metal and ligand are triplet-paired. A relay catalyst must convey single electron equivalents from the metal photosensitizer to a homogeneous or heterogeneous site capable of storing multiple redox equivalents. A biradical model is also pertinent to the excited state chemistry of binuclear $d^{7(9)}$ and $d^{8(10)}$ metal complexes, but in different guises. The dσ(or dπ*)dσ* excited states of $d^{7(9)}$—$d^{7(9)}$ complexes are short-lived and dissociative, producing an .M,M. biradical pair. Because the photogenerated radicals are uncoupled, selective multi-electron activation of substrates is difficult to control and therefore free radical reactions are typically observed Conversely, a stable and long-lived biradical tethered by a metal-metal bond, .M-M., is produced upon $d_{z^2}\sigma^* \rightarrow p_z\sigma$ (excitation of $d^{8(10)} \ldots d^{8(10)}$ complexes The proximity of the radical metal centers permits coupling of their single electron reactions to effect selective multi-electron transformations.

Whereas the general formalism of biradical excited states naturally leads to two-electron processes one electron at a time, approaches to explore photoredox reactions in excess of two electrons are not at hand. In the absence of a well-defined framework, it is not surprising to find scant precedence for three- and four-electron photoreactions. Photoinduced decomposition of $Pt^{IV}$ salts to metal colloids along ill-defined mechanistic pathways is the only documented photoredox reaction involving more than two electrons. In no case has a four-electron photoreaction along a controlled reaction pathway been achieved.

The challenges confronting the design of multi-electron photoreactions are formidable. Reorganization of the primary coordination environment typically accompanies the addition or removal of more than one electron from a metal center. If ligand reorganization does not occur, the thermodynamic barrier associated with the transfer of redox equivalents to or from the metal center becomes insurmountable at chemically relevant redox potentials. This is a particularly germane problem for excited state redox schemes because reactivity is usually confined to the lowest energy excited state, constraining the overall internal energy of the system. As an example, again consider the oxidation-reduction chemistry of $d^6$ $Ru^{II}$ polypyridyl systems. The one-electron oxidation and reduction potentials of the $Ru^{II}$ metal, octahedrally coordinated by a conventional polypyridyl ligand set, are ~1.0 to 1.5 V. By virtue of its inflexibility, the polypyridine coordination sphere imposes thermodynamic remuneration of an additional 1.5 V and 3.3 V for the metal-based reduction and oxidation, respectively, of a second electron equivalent. An excited state energy of only ~2 eV therefore confines reaction to single electron transfer. When the coordination environment of the metal is able to adopt a geometry to accommodate a two-electron photoconversion, the electronic structure responsible for excited state reactivity is invariably lost. A lowest energy, reactive excited state maintains a fragile existence among the multitude of energy-dissipating excited states of a metal complex. Changes in coordination geometry will re-order state parentages with any one of the neighboring, non-reactive states ready to assume the lowest energy position. In this case, an excited state pathway encompassing redox reactivity beyond two electrons will be circumvented. With these considerations in mind, further advances in multi-electron photoredox chemistry must require novel molecular structures that would preserve the same lowest energy, reactive excited state across a multi-electron series of complexes.

As single-electron mixed-valence compounds react in one-electron steps from their excited states, electronically excited $M^n$-$M^{n+2}$ complexes may react in two-electron steps at the bimetallic core. Although the occurrence of authentic $M^n$-$M^{n+2}$ compounds is unusual bis(difluorophosphine) methylamine (dfpma) stabilizes a four-electron series of $Rh_2$ complexes based upon the two-electron mixed-valence complex $Rh_2^{0,II}(dfpma)_3X_2(L)$ (L=$PR_3$, CNR or CO; X=Cl or Br). Electronic absorption and luminescence spectra of the $Rh_2^{0,0}$, $Rh_2^{0,II}$ and $Rh_2^{II,II}$ dfpma complexes are consistent with each possessing a lowest energy excited state of $d\sigma^*$ parentage. The results presented herein show that the $d\sigma^*$ excited state permits interconversion among $Rh_2^{0,0}$, $Rh_2^{0,II}$ and $Rh_2^{II,II}$ cores, enabling the rational design of a system to support four-electron photochemistry among discrete molecular species.

Structure and Electronic Spectroscopy of $Rh_2$-dfpma Complexes

Figures 24A, 24B, 24C:
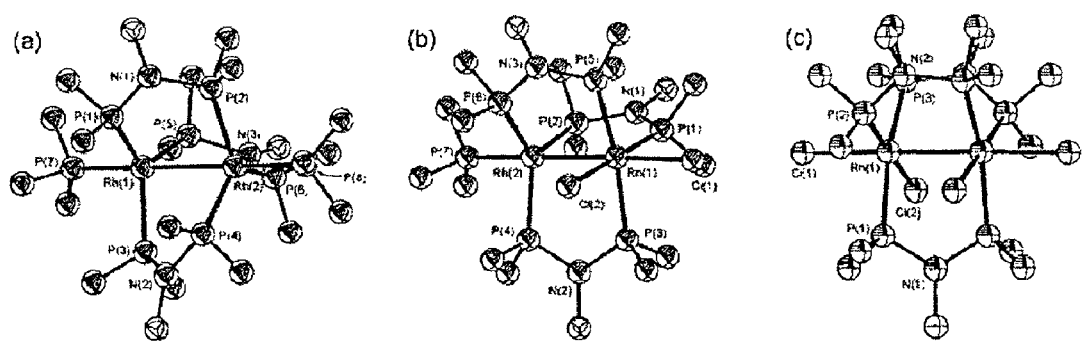
FIG. 24(a) depicts Rh$_2^{0,0}$(dfpma)$_3$(PF$_3$)$_2$.
FIG. 24(b) depicts Rh$_2^{0,II}$(dfpma)$_3$Cl$_2$(PF$_3$)
FIG. 24(c) depicts Rh$_2^{II,II}$(dfpma)$_3$Cl$_4$.

The ability of the dfpma ligand to stabilize trigonal bipyramidal $Rh^0$ and octahedral $Rh^{II}$ centers provides a homologous series of complexes with singly bonded $Rh^0$—$Rh^0$, $Rh^0$—$Rh^{II}$ and $Rh^{II}$—$Rh^{II}$ cores. For reference, representative structures of the $Rh_2^{0,0}(dfpma)_3(L)_2$, $Rh_2^{0,II}(dfpma)_3X_2(L)$ and $Rh_2^{II,II}(dfpma)_3X_4$ presented in FIG. 24.

Figures 25, 25A, 25B, 25C:
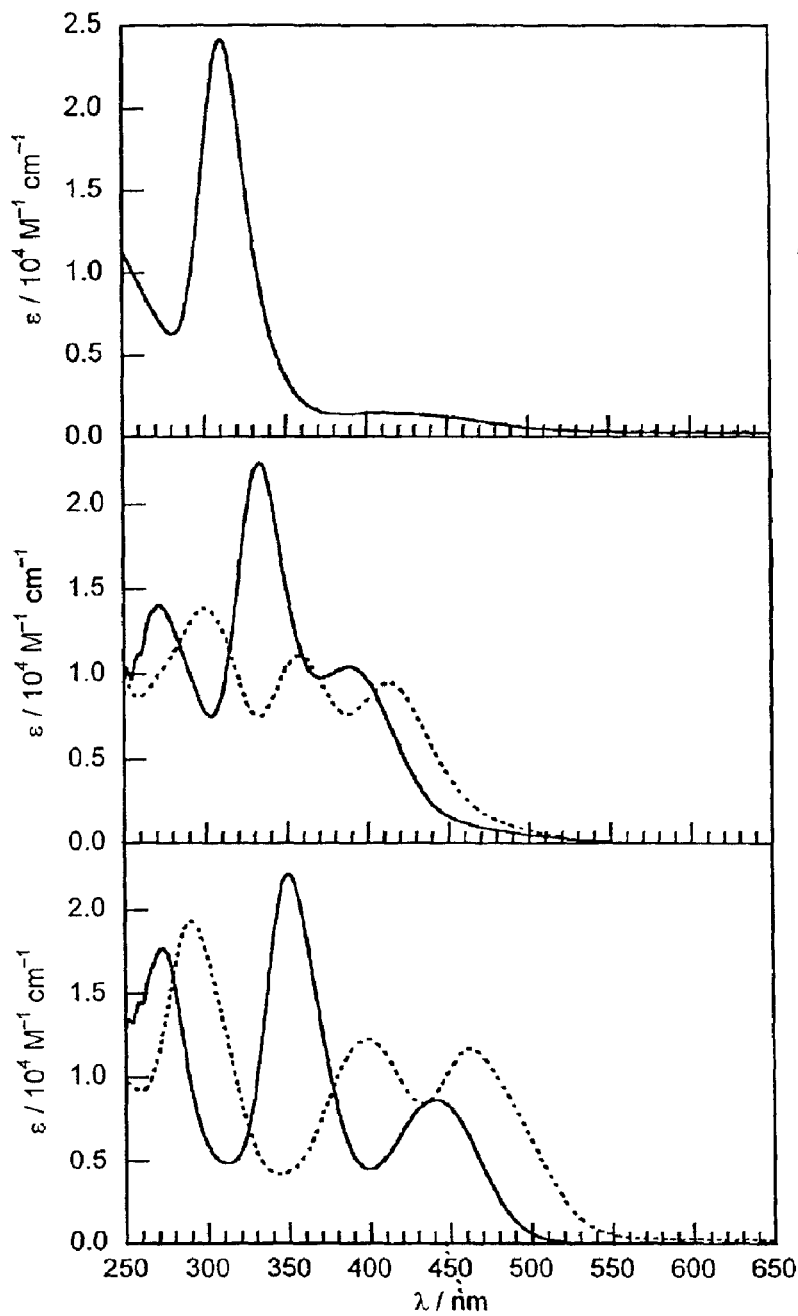
FIG. 25(a) is an electronic absorption spectrum of Rh$_2^{0,0}$(dfpma)$_3$($\eta^1$-dfpma)$_2$.
FIG. 25(b) is electronic absorption spectra of Rh$_2^{0,II}$(dfpma)$_3$Cl$_2$($\eta^1$-dfpma) and Rh$_2^{0,II}$(dfpma)$_3$Br$_2$($\eta^1$-dfpma)
FIG. 25(c) is electronic absorption spectra of Rh$_2^{II,II}$(dfpma)$_3$Cl$_4$ and Rh$_2^{II,II}$(dfpma)$_3$Br$_4$ in THF at room temperature.

The electronic absorption and emission spectra clearly distinguish members of the $Rh_2^{0,0}$, $Rh_2^{0,II}$ and $Rh_2^{II,II}$ series. FIG. 25 displays representative spectra for each compound; Table 19 summarizes both absorption and emission data for several $Rh_2$ congeners. The high optical electronegativity of the terminal fluorophosphine ligand reduces configurational mixing of the $d\sigma$ and $L\sigma$ orbitals, thus a relatively straightforward absorption spectrum, typical of $d^9$—$d^9$ compounds, is observed for $Rh_2^{0,0}(dfpma)_3(L)_2$. An intense 305-nm band, attributable to the allowed $d\sigma \to d\sigma^*$ transition, is flanked to lower energy by the less intense $d\pi^* \to d\sigma^*$ absorption band for the L=$PF_3$ derivative. The absorption spectra of $Rh_2^{II,II}(dfpma)_3X_4$ and $Rh_2^{0,II}(dfpma)_3X_2(L)$ complexes exhibit more congested profiles in the near-UV as a result of configurational mixing between the metal-$d_{z^2}$ and X-$p_z$ $\sigma$ orbitals. Significant LMCT character is revealed in the highest energy absorption band of both $Rh_2^{II,II}(dfpma)_3X_4$ and $Rh_2^{0,II}(dfpma)_3X_2(L)$, red-shifting by 3861 cm$^{-1}$ upon substitution of bromide for chloride. The mid-spectrum band of the $Rh_2^{II,II}$ complex also shows a dramatic 4851 cm$^{-1}$ red-shift upon halogen substitution, however, in the $Rh_2^{0,II}$ complexes this transition appears to be equally influenced by the nature of the halogen and the axial $Rh^0$ donor ligand. The low energy absorption band red-shifts to a lesser extent upon halogen substitution (~1254 cm$^{-1}$ for Br$^-$/Cl$^-$) in both $Rh_2^{II,II}$ and $Rh_2^{0,II}$, consistent with greater metal-based character of a $d\pi^* \to d\sigma^*$ transition.

TABLE 19

Absorption and emission spectral data for various $Rh_2^{0,0}(dfpma)_3(L)_2$, $Rh_2^{0,II}(dfpma)_3X_2(L)$ and $Rh_2^{II,II}(dfpma)_3X_4$ complexes.

| Compound | $\lambda_{max}$ Absorbance (nm) | | |
|---|---|---|---|
| | X($\sigma$)/d$\sigma \to$ d$\sigma^*$ (1) | X($\sigma$)/d$\sigma \to$ d$\sigma^*$ (2) | d$\pi^* \to$ d$\sigma^*$ |
| $Rh_2^{0,0}(dfpma)_3(PF_3)_2$[a] | 305 | — | 440 |
| $Rh_2^{0,0}(dfpma)3(\eta^1$-dfpma$)_2$[a] | 310 | — | 411 |
| $Rh_2^{0,II}(dfpma)_3Cl_2(PF_3)$ | 270 | 330 | 385 |
| $Rh_2^{0,II}(dfpma)_3Br_2(\eta^1$-dfpma) | 299 | 358 | 411 |
| $Rh_2^{0,II}(dfpma)_3Cl_2(PPh_3)$ | 275 | 353 | 402 |
| $Rh_2^{0,II}(dfpma)_3Br_2(PPh_3)$ | 315 | 371 | 424 |
| $Rh_2^{II,II}(dfpma)_3Cl_4$ | 265 | 335 | 445 |
| $Rh_2^{II,II}(dfpma)_3Br_4$ | 291 | 400 | 462 |

Figure 26:
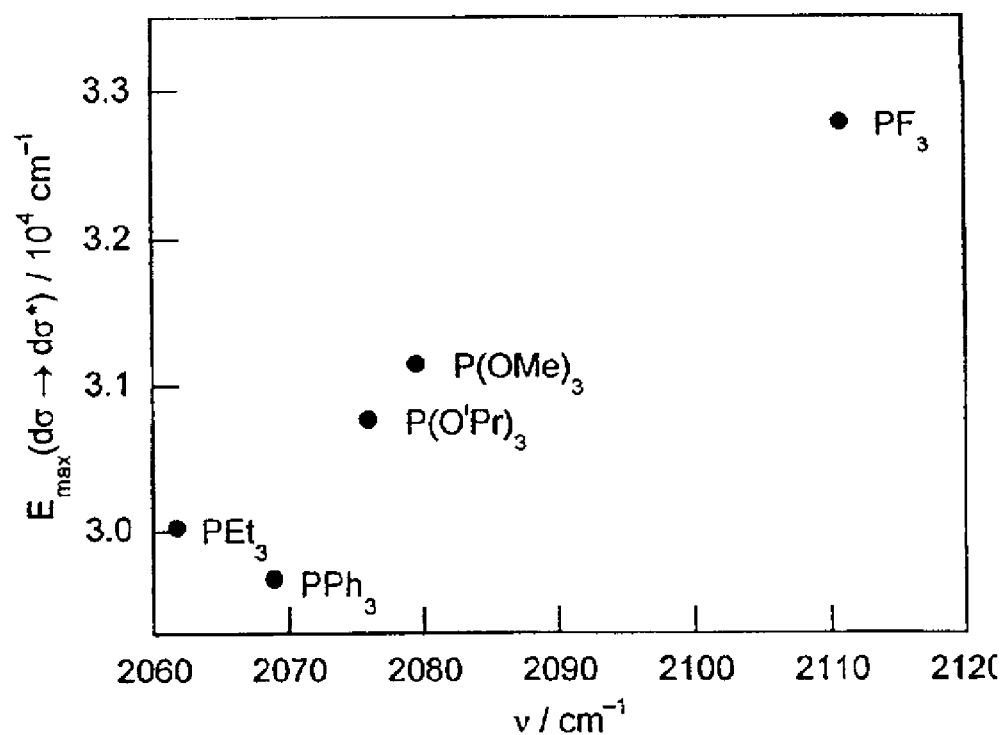
FIG. 26 is a plot of the energy maximum of the d$\sigma \rightarrow$d$\sigma$* transition of Rh$_2^{0,0}$(dfpma)$_3$(L)$_2$ (L=PEt$_3$, P(OMe)$_3$, P(O$^i$Pr)$_3$, PPh$_3$, and PF$_3$) vs. Tolman electronic parameter.

[a]Only one d$\sigma \to$ d$\sigma^*$ transition is observed for the $Rh_2^{0,0}$ complexes Whereas substitution of PF3 by $\eta^1$-dfpma barely perturbs the electronic structure of the dirhodium core, coordination of the more basic $PR_3$ ligands to the $Rh^0$ center of the $Rh_2$ dfpma series notably disrupts the electronic structure of the system. Consistent with the perturbation of the Rh—Rh bond distances of the $Rh_2^{0,II}(dfpma)_3X_2(L)$ complexes absorption maxima of complexes with basic phosphines are red-shifted by >20 nm relative to those with $\pi$-accepting fluorophosphines as the axial ligand. The effect is even more pronounced in the absorption spectra of the fully reduced $Rh_2^{0,0}(dfpma)_3L_2$ compounds containing two axially donor ligands. FIG. 26 plots the absorption maximum of the d$\sigma \to$ d$\sigma^*$ transition of $Rh_2^{0,0}(dfpma)_3L_2$ for L=$PEt_3$, $P(OMe)_3$, $P(O^iPr)_3$, $PPh_3$ and $PF_3$ vs the Tolman electronic parameterization of phosphine ligands. The observed trend of the d$\sigma \to$ d$\sigma^*$ transition towards lower energy with an increase in the basicity of the phosphine logically follows from considerations of P$\sigma$ orbital mixing into the metal-metal $\sigma$ framework. Although linear combinations of P$\sigma$ orbitals have the appropriate symmetries to mix with both d$\sigma$ and d$\sigma^*$, destabilization of the energetically proximate do orbital will be greater, resulting in the observed red shift. With the exception of $PPh_3$, the size of the phosphine is of little consequence in the overall correlation since the cone angles of the phosphines are relatively constricted (<135°). The anomalously small d$\sigma \to$ d$\sigma^*$ transition energy of $PPh_3$ is attributed to structural distortions of the ligand and metal framework. Steric-induced lengthening of the Rh—Rh bond by PPh$_3$ augments the ligand's electronic effect, leading to a smaller d$\sigma$/d$\sigma$* splitting and consequently lower observed transition energy than that predicted by the Tolman electronic parameter.

Excitation into the absorption manifold of crystalline solids of the Rh$_2$ dfpma compounds produces a long-lived red luminescence with spectral features characteristic of a d$\sigma$* excited state parentage. Luminescence is not detected from solutions at temperatures equivalent to those at which the crystalline solids emit. Moreover, the loss of luminescence from solutions of the Rh$_2$ dfpma complexes immediately above solvent glassing transition temperatures suggested a prevalence for bond cleavage chemistry as a dominant nonradiative decay pathway of the d$\sigma$* excited state. These photophysical observations provided the impetus to undertake investigations of the solution photochemistry of this series of complexes.

Rh$_2$-dfpma Reductive Elimination Photochemistry

Figure 27:
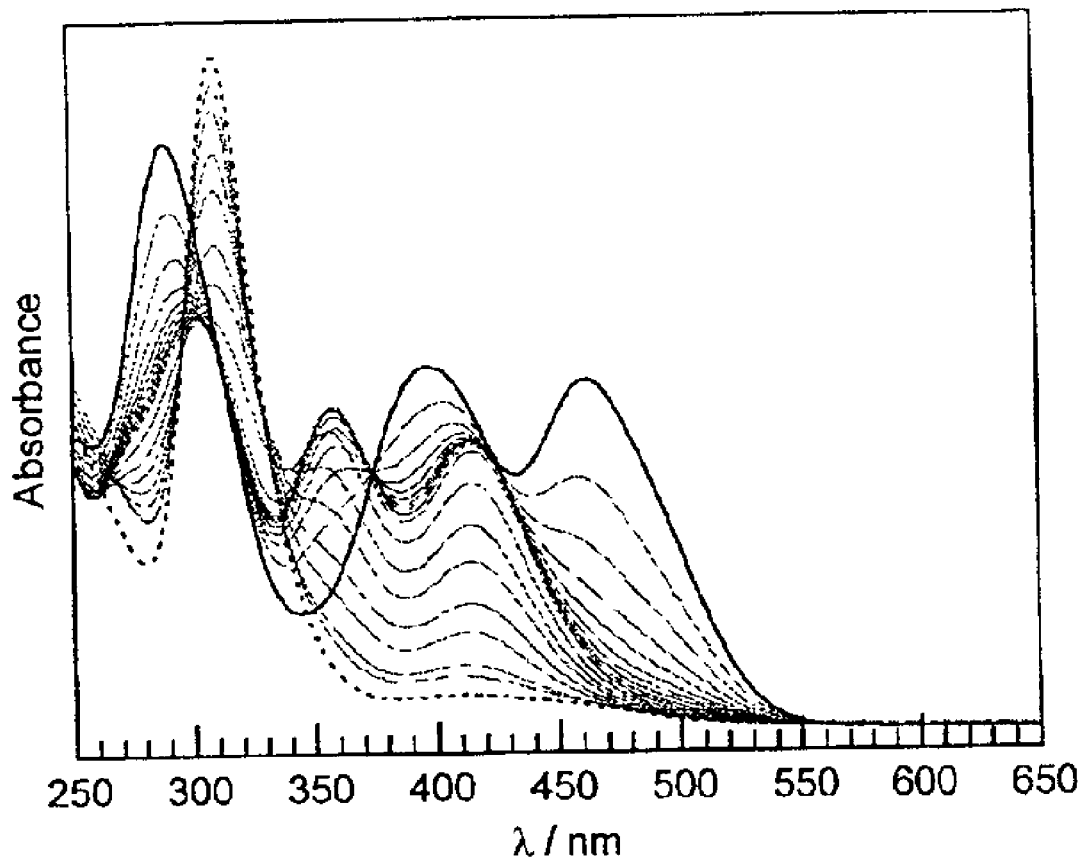
FIG. 27 is a graph depicting spectral changes in the electronic absorption spectrum during the photolysis ($\lambda_{exc}$>335 nm) of Rh$_2^{II,II}$(dfpma)$_3$Br$_4$ in THF and in the presence of 250 equiv. of dfpma at 0° C. wherein the spectra were recorded over the span of 2 hours.
Figure 28:
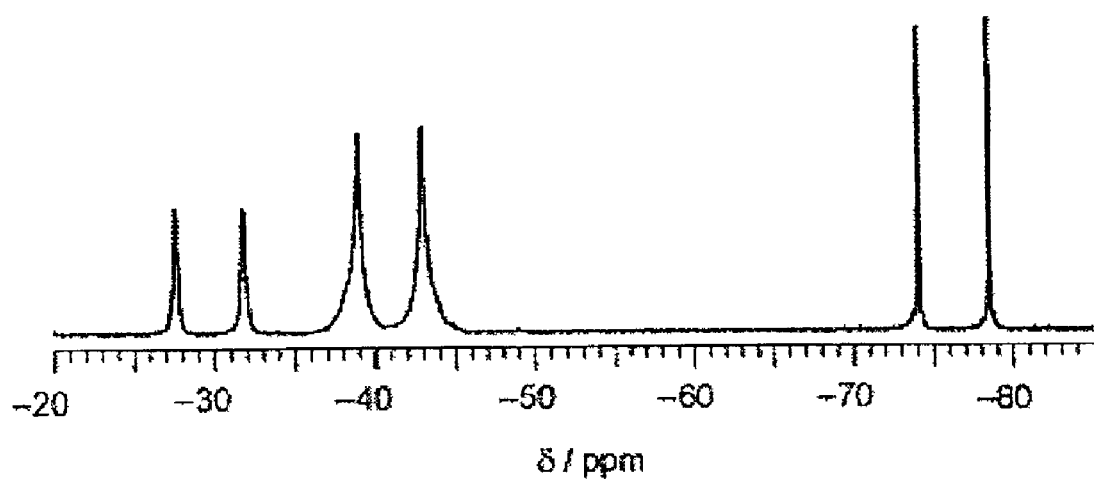
FIG. 28 is the $^{19}$F NMR (C$_6$D$_6$) spectrum of the photoproduct obtained from the irradiation ($\lambda_{exc} \geq$335 nm) of Rh$_2^{II,II}$(dfpma)$_3$Br$_4$ in the presence of excess dfpma in THF at 0° C.

Irradiation of THF solutions of Rh$_2^{II,II}$(dfpma)$_3$X$_4$ (X=Cl or Br) in THF solution containing excess L (L=PF$_3$, $\eta^1$-dfpma) with UV-Vis white light leads to rapid changes in the absorption spectrum. FIG. 27 conveys the complexity of Rh$_2^{II,II}$(dfpma)$_3$Br$_4$ photochemistry when THF solutions containing $\eta^1$-dfpma are photolyzed at $\lambda_{exc}$>335 nm. Isosbestic points at 311, 373 and 425 nm, maintained early during photolysis, are lost with continued irradiation, indicating the occurrence of a secondary reaction at longer times. Comparison of the terminating absorption profile of the photolyzed solution to the absorption spectra of FIG. 25(a) identifies the final photoproduct as Rh$_2^{0,0}$(dfpma)$_3$($\eta^1$-dfpma)$_2$. Independent verification of this assignment was afforded by bulk photolysis experiments. Irradiation of Rh$_2^{II,II}$(dfpma)$_3$Br$_4$ in the presence of $\eta^1$-dfpma in THF followed by solvent removal yielded the final product, which was extracted into pentane. Recrystallization at low temperature afforded Rh$_2^{0,0}$(dfpma)$_3$($\eta^1$-dfpma)$_2$ as determined by the $^{19}$F NMR spectrum reproduced in FIG. 28. Three $^{19}$F NMR resonances are observed in a 1:3:1 ratio. A doublet at −40.96 ppm displaying a $|^1J_{FP}+^3J_{FP}|$ coupling constant of 1117 Hz identifies the fluorines of the bridging dfpma ligands. Doublets at −29.72 ($|^1J_{FP}+^3J_{FP}|$=1252 Hz) and −76.29 ppm ($|^1J_{FP}+^3J_{FP}|$=1253 Hz) are assigned to the coordinated and free PF$_2$ groups of the $\eta^1$-dfpma ligands, respectively. Similar results are obtained if the photolysis is carried out in the presence of excess PF$_3$: the final $^{19}$F NMR spectrum of Rh$_2^{0,0}$(dfpma)$_3$(PF$_3$)$_2$ displays doublets at −37.89 ($|^1J_{FP}+^3J_{FP}|$=1110 Hz) and −4.16 ($|^1J_{FP}+^3J_{FP}|$=1359 Hz) ppm for the bridging dfpma and axial PF$_3$ ligands, respectively.

Figures 29, 29A, 29B:
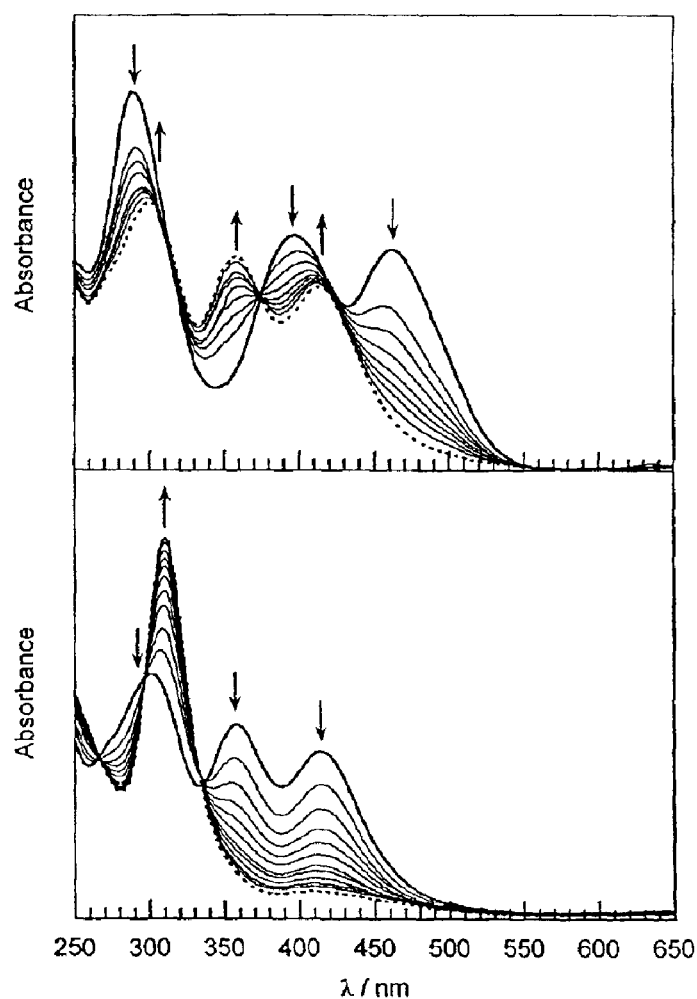
FIG. 29(a) is a graph depicting the spectral changes in the electronic absorption spectrum during the photolysis ($\lambda_{exc} \geq$436 nm) of Rh$_2^{II,II}$(dfpma)$_3$Br$_4$ in THF and in the presence of 250 equiv. of dfpma at 0° C. wherein the spectra were recorded over the span of 15 min. and the photolysis was terminated when the 358-nm absorption was maximized.
FIG. 29(b) is a graph depicting spectral changes associated with continued irradiation of the solution resulting from the photolysis depicted in FIG. 29(a) with higher energy light ($\lambda_{exc} \geq$335 nm) wherein spectra were recorded over the span of 3 hours.

Owing to the well separated spectra of the Rh$_2^{II,II}$(dfpma)$_3$Br$_4$ and Rh$_2^{0,II}$(dfpma)$_3$Br$_2$($\eta^1$-dfpma) complexes, wavelength selection of the excitation light permitted deconstruction of the overall photo transformation of FIG. 27 into a stepwise reaction sequence. Though solutions of Rh$_2^{II,II}$(dfpma)$_3$Br$_4$ in THF are stable in the absence of irradiation, FIG. 29(a) displays the changes in the absorption profile upon photolysis at $\lambda_{exc}$≧436 nm. Well-anchored isosbestic points are maintained throughout the photolysis. Comparison of the terminating absorption spectrum to those of FIG. 25(b) reveals that Rh$_2^{0,II}$(dfpma)$_3$Br$_2$($\eta^1$-dfpma) is the photoproduct. On the basis of the measured molar absorption coefficients, the photoconversion of the Rh$_2^{II,II}$ complex to the mixed-valence Rh$_2^{0,II}$ complex is quantitative. Although this photoreacted solution is stable under the low-energy excitation conditions of FIG. 29(a), further reaction is observed when the excitation wavelength is moved into the UV spectral region. As shown in FIG. 29(b), the final absorption spectrum of the solution under 335-nm irradiation is that of Rh$_2^{0,0}$(dfpma)$_3$($\eta^1$-dfpma)$_2$, which is also produced in quantitative yield. These results demonstrate that the overall photoreaction proceeds in two steps: Rh$_2^{II,II}$(dfpma)$_3$Br$_4$ is photolyzed to Rh$_2^{0,II}$(dfpma)$_3$Br$_2$($\eta^1$-dfpma) for $\lambda_{exc}$≧436 nm and subsequently Rh$_2^{0,II}$(dfpma)$_3$Br$_2$($\eta^1$-dfpma) is photolyzed to Rh$_2^{0,0}$(dfpma)$_3$($\eta^1$-dfpma)$_2$ for $\lambda_{exc}$≧335 nm.

Figure 30:
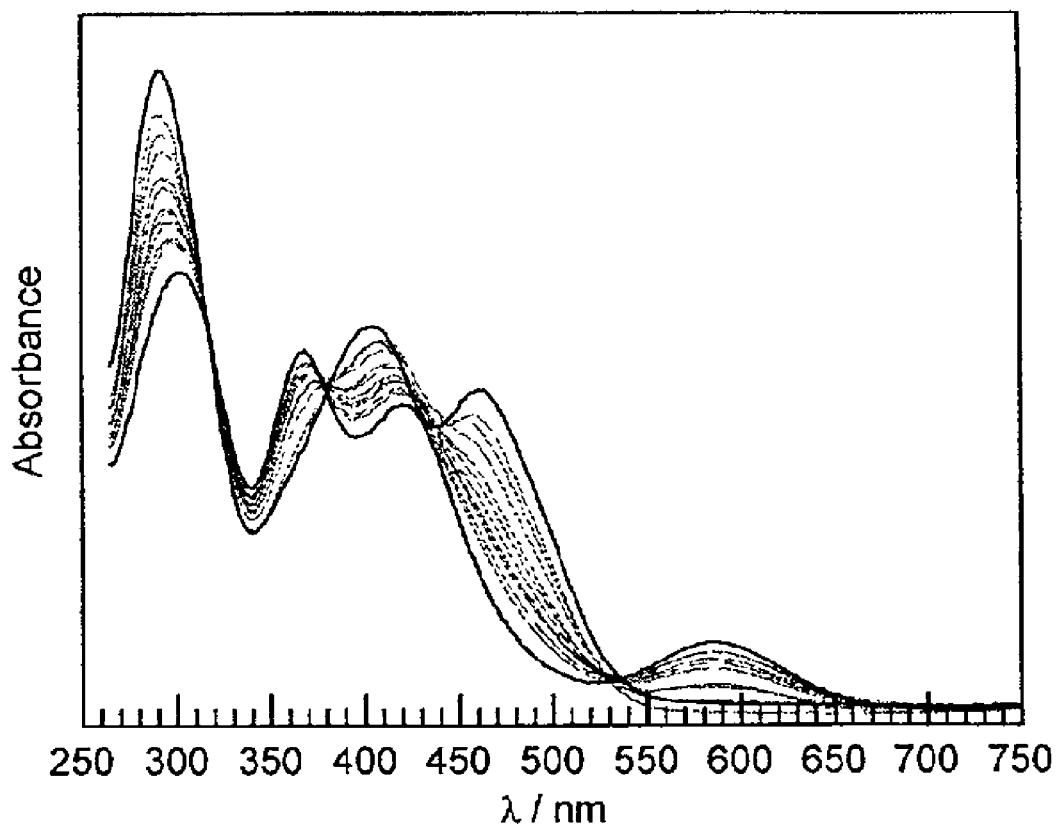
FIG. 30 is a graph depicting the spectral changes associated with the monochromatic irradiation ($\lambda_{exc}$=335 nm) of Rh$_2^{II,II}$(dfpma)$_3$Br$_4$ in THF at 0° C.

In the absence of a donor ligand to cap the reduced Rh$^0$ center during irradiation of Rh$_2^{II,II}$ complexes, an intermediate species is observed at early reaction times (FIG. 30). Photolysis of Rh$_2^{II,II}$(dfpma)$_3$Br$_4$ in THF without any donor ligand causes a rapid color change of the solution to blue. The color results from the appearance of a new absorbance in the visible region of the spectrum at 583 nm. Comparison of the maximum intensity of the 583-nm band with the absorption bands of the starting Rh$_2^{II,II}$(dfpma)$_3$Br$_4$ complex provides a crude estimate of 4000 M$^{-1}$ cm$^{-1}$ as the extinction coefficient of this 583-nm band. If the solutions are maintained in the dark, the blue color fades within minutes, and the observed absorption spectrum shows only bands in the near UV region of the spectrum attributable to the Rh$_2^{0,II}$ photoproduct.

Identification of the Halogen Photoproduct

The fate of the halogen in the overall photoreaction sequence is disclosed by undertaking the appropriate trapping experiments. Because the weak α C—H bonds of THF are susceptible to hydrogen atom abstraction, THF could participate in the photoreaction as a halogen trap. Two observations support this contention. No photoreaction is observed in benzene or CH$_2$Cl$_2$ unless a halogen trap such as 2,3-dimethyl-1,3-butadiene or 9,10-dihydroanthracene is present. The inability of these solvents to furnish a hydrogen atom appears to circumvent net photochemistry as the halogen photoproduct can simply re-oxidize the reduced metal center. Conversely, photoreactions in THF proceed with facility regardless of the concentration of auxiliary trapping reagent. Addition of 2,3-dimethyl-1,3-butadiene or 9,10-dihydroanthracene to THF solutions of Rh$_2^{II,II}$(dfpma)$_3$X$_4$ or Rh$_2^{0,II}$(dfpma)$_3$X$_2$($\eta^1$-dfpma) has little affect on the overall conversion efficiency. Considering the high concentration of neat solvent, auxiliary traps cannot effectively compete for the halogen photoproduct and thus its presence has little affect on the outcome of the photochemistry performed in THF.

If hydrogen atom abstraction from THF does occur, the ultimate fate of the Br photoproduct should be HX (X=Cl, Br). The conditions under which the above photolyses reactions were executed, however, preclude detection of hydrohalic acids. Because hydrohalic acids readily hydrolyze the N—P bond of F$_2$PNR$_2$ to form [H$_2$NR$_2$]$^+$X$^-$ (and PF$_2$X), the acid photoproducts would be scavenged by the excess dfpma present under photolytic conditions, thus preventing its stoichiometric determination. Accordingly, the dirhodium photochemistry was investigated in the presence of PPh$_3$, as this phosphine effectively coordinates reduced Rh$^0$ centers and also offers suitable hydrolytic stability.

Figure 31:
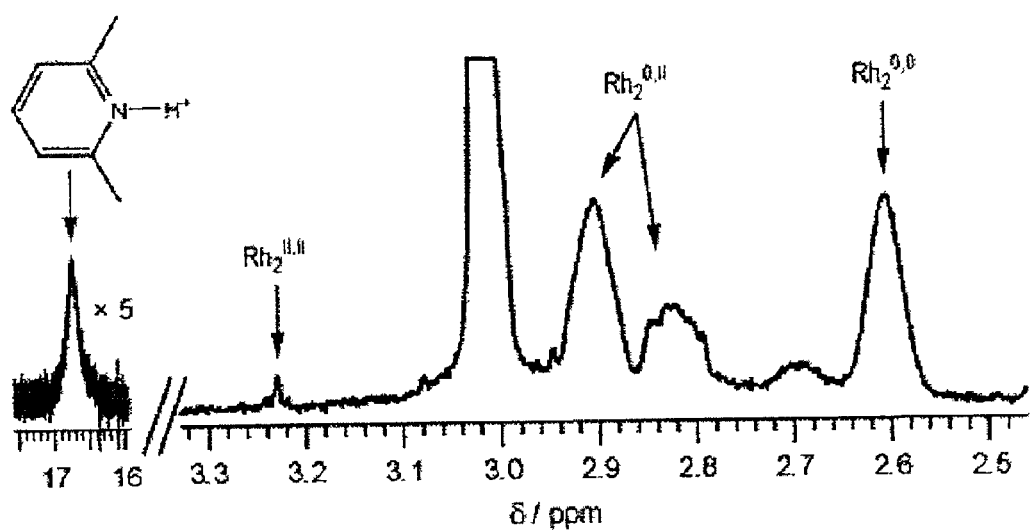
FIG. 31 is a graph of the $^1$H NMR (CDCl$_3$) spectrum of the photoproduct obtained from the irradiation ($\lambda_{exc}$>335 nm) of Rh$_2^{II,II}$(dfpma)$_3$Br$_4$ in the presence of 4.3 equiv. of 2,6-lutidine and 2.5 equiv. of PPh$_3$ in THF at 0° C., showing the methyl resonances of the Rh$_2^{0,II}$ and Rh$_2^{0,0}$ photoproducts and the high frequency resonance for protonated 2,6-lutidine.

The photochemistry of Rh$_2^{II,II}$(dfpma)$_3$Br$_4$ in the presence of excess PPh$_3$ proceeds according to the same two-step reaction sequence that was described for dfpma with the minor difficulty that Rh$_2^{0,II}$(dfpma)$_3$Br$_2$(PPh$_3$) can not be cleanly produced by wavelength selection. As listed in Table 19, the middle-energy X($\sigma$)/d$\sigma$→(d$\sigma$* transition of Rh$_2^{0,II}$(dfpma)$_3$Br$_2$(PPh$_3$) is observed at 371 nm. The red-shifted LMCT transition tails significantly into the visible spectral region such that the 436-nm excitation wavelength used to photoconvert $Rh_2^{II,II}(dfpma)_3Br_4$ to $Rh_2^{0,II}(dfpma)_3Br_2$ $(PPh_3)$ is also sufficiently energetic to slowly convert $Rh_2^{0,II}(dfpma)_3Br_2(PPh_3)$, as it is produced, to $Rh_2^{0,0}(dfpma)_3$ $(PPh_3)_2$. Despite experimental complexity, the $PPh_3$ system is ideal for quantifying the HBr produced from the overall photoreaction sequence. Quantification of HBr was indirectly determined by its reaction with a nitrogen base. The sterically encumbered 2,6-lutidine proved most useful, as the methyl groups flanking the amine prevents competitive coordination of the base to the metal center. Thus, bulk photolysis ($\lambda_{exc} \geq 335$ nm, THF, 0° C.) of $Rh_2^{II,II}(dfpma)_3$ $Br_4$ (1 equiv, 20 µmol) was performed in the presence of 2.5 equiv of $PPh_3$ and 4.3 equiv of 2,6-lutidine. After solvent removal the solid residue was taken up in $CDCl_3$, and the $^1H$ NMR spectrum was recorded (FIG. 31). Singlet resonances for the methyl groups of the bridging dfpma ligands of $Rh_2^{0,II}$ at 2.83 and 2.91 ppm and of $Rh_20,0$ at 2.60 ppm distinguish the $Rh_2$ dfpma photoproducts. A broad singlet at 16.8 ppm and sharp singlet at 3.02 ppm are signatures of the acid proton and methyl groups, respectively, of lutidinium bromide. Integration of the dfpma methyl proton signals reveal the production of 0.59 equiv of $Rh_2^{0,II}(dfpma)_3Br_2$ $(PPh_3)$ and 0.41 equiv of $Rh_2^{0,0}(dfpma)_3(PPh_3)_2$; the lutidinium bromide resonance integrates to 3.0 equiv. If two equiv of HBr are produced for each two-electron photoconversion of $Rh_2^{II,II}(dfpma)_3Br_4$ and $Rh_2^{0,II}(dfpma)_3Br_2$ $(PPh_3)$, then the production of 1.18 and 1.64 equiv of HBr, respectively, or total of 2.82 equiv of HBr is required to accompany this photolysis reaction. The good agreement between the calculated and experimental yields of lutidinium bromide establishes Scheme 17 as the overall photoreaction sequence for the $Rh_2$ dfpma system.

Scheme 17

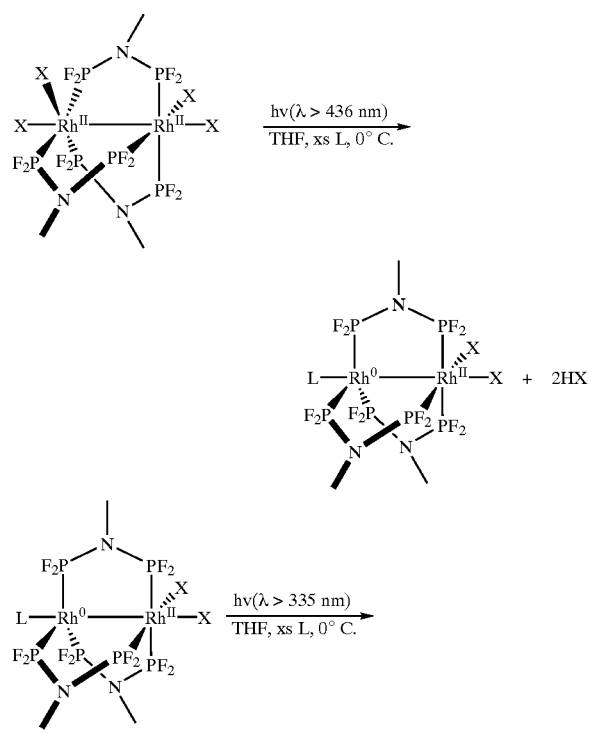

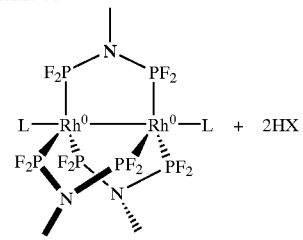

Quantum Yield Determination

Determination of the photoreaction stoichiometry permits measurement of quantum yields ($\Phi_p$) for the photoreactions of Scheme 20 at selected excitation wavelengths as in Table 20. For $Rh_2^{II,II}(dfpma)_3Br_4$ photochemistry, quantum yields are virtually constant from 313 nm to 405 nm ($\Phi_p^{313-405} = 0.022 \pm 0.003$) but then begin to decrease as $\lambda_{exc}$ is moved into the visible spectral region ($\Phi_p^{436-468} = 0.012 \pm 0.001$). Exchange of bromide for chloride results in an enhancement in the quantum yield as evidenced by the $\Phi_p^{365}$ of $0.05 \pm 0.01$ determined for $Rh_2^{II,II}(dfpma)_3Cl_4$. A similar trend is observed in the attenuated quantum yields measured for $Rh_2^{0,II}(dfpma)_3X_2(L)$ photochemistry. The onset for the decrease in quantum yield for the photoreduction of $Rh_2^{0,II}(dfpma)_3Br_2(\eta^1\text{-dfpma})$ occurs at shorter wavelengths ($\Phi_p^{313-365} = 0.0035 \pm 0.0003$, $\Phi_p^{405-436} = 0.0017 \pm 0.0003$) than in corresponding $Rh_2^{II,II}$ complex, and halogen exchange results in a slight increase in efficiency upon chloride substitution.

TABLE 20

Product quantum yields (%) for photoreduction of $Rh_2^{II,II}(dfpma)_3X_4$ and $Rh_2^{0,II}(dfpma)_3X_2(\eta^1\text{-dfpma})$ (X = Cl, Br) complexes according to the stoichiometry of Scheme 17.

| Starting Rh₂ Complex | $\lambda_{exc}$ (nm) | | | | | | |
|---|---|---|---|---|---|---|---|
| | 313 | 334 | 365 | 395 | 405 | 436 | 468 |
| $Rh_2^{II,II}(dfpma)_3Cl_4$ | — | — | 5.0 | — | — | — | — |
| $Rh_2^{II,II}(dfpma)_3Br_4$ | 2.4 | 2.5 | 2.0 | 1.7 | 2.2 | 1.2 | 1.3 |
| $Rh_2^{0,II}(dfpma)_3Cl_2$ ($\eta^1$-dfpma) | — | — | 0.60 | — | — | — | — |
| $Rh_2^{0,II}(dfpma)_3Br_2$ ($\eta^1$-dfpma) | 0.32 | — | 0.38 | — | 0.20 | 0.14 | — |

The efficacy of THF to trap the halogen photoproduct is effectively illustrated in the quantum yields determined in the presence and absence of auxiliary coproduct traps. Irradiation of $Rh_2^{0,II}(dfpma)_3Br_2(\eta^1\text{-dfpma})$ in THF containing 0.1 M 2,3-dimethyl-1,3-butadiene and excess dfpma gives a product quantum yield of $0.0048 \pm 0.0005$, confirming that the diene cannot effectively compete with H-atom abstraction from the THF solvent. Similarly, evaluation of the quantum yields in the presence and absence of excess donor ligand underscores the importance of the incoming axial ligand to the overall stability of the $Rh^0$ center. If solutions of $Rh_2^{0,II}(dfpma)_3Br_2(\eta^1\text{-dfpma})$ in THF are irradiated in the absence of dfpma, the quantum yield values drop by nearly an order of magnitude ($\Phi_p^{365}$(no dfpma) = $5.8 \times 10^{-4}$).

Electronic Structure Calculations

Figures 32A, 32B, 32C:
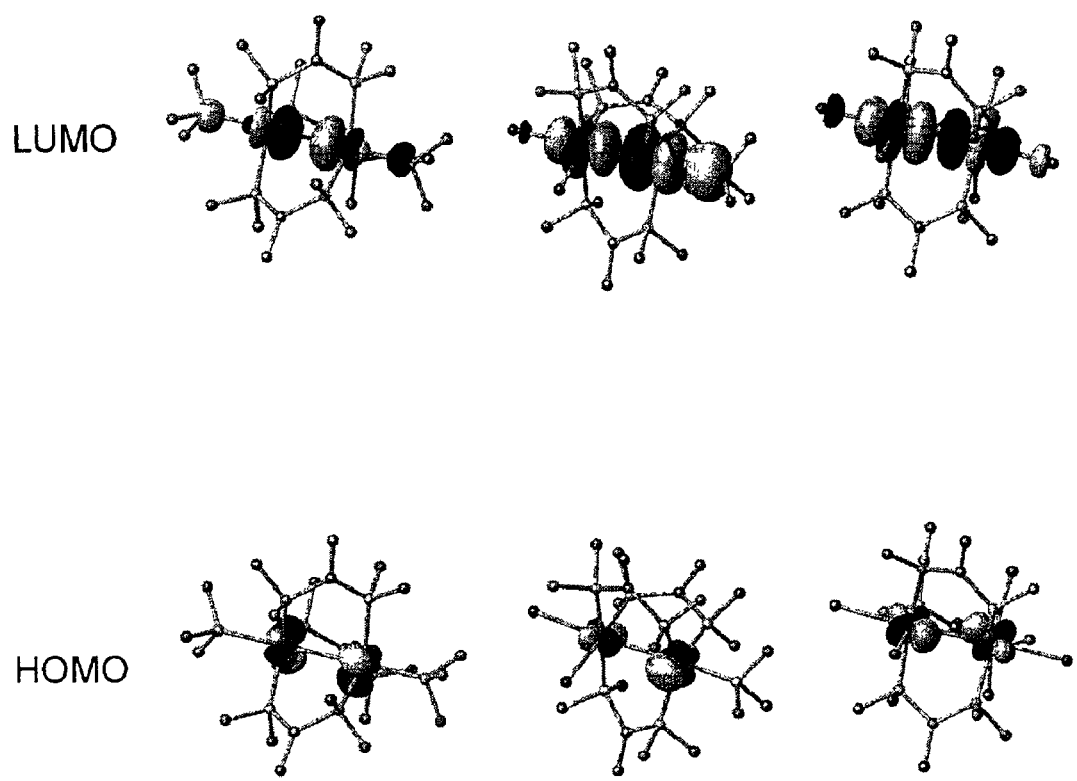
FIG. 32(a) depicts the HOMO and LUMO for Rh$_2^{0,0}$(dfpma)$_3$(PF$_3$)$_2$.
FIG. 32(b) depicts the HOMO and LUMO for Rh$_2^{0,II}$(dfpma)$_3$Br$_2$(PF$_3$)
FIG. 32(c) depicts the HOMO and LUMO for Rh$_2^{II,II}$(dfpma)$_3$Br$_4$ as determined at the extended Hückel level using YAeHMOP.

Molecular orbital calculations emphasize the electronic structure features that are crucial to promoting the four-electron photochemistry of the Rh$_2$ dfpma series. FIG. 32 shows the HOMOs and LUMOs of Rh$_2^{II,II}$(dfpma)$_3$Br$_4$, Rh$_2^{0,II}$(dfpma)$_3$Br$_2$(PF$_3$), and Rh$_2^{0,0}$(dfpma)$_3$(PF$_3$)$_2$ derived from extended Hückel calculations. For each complex, the HOMO is approximately two-fold degenerate and of metal dπ* or dδ* character, while the LUMO is primarily localized between the metal centers and of σ* character. This homology in the HOMOs and the LUMOs is striking considering the disparate metal coordination geometries and oxidation states across the Rh$_2$ dfpma series.

The frontier MOs are largely a consequence of the large one-electron splitting arising from the combination of spatially directed d$_{z^2}$ orbitals of the individual fragments composing the Rh$_2$ dfpma complexes. A qualitative molecular orbital diagram for the Rh$_2^{0,0}$, Rh$_2^{0,II}$ and Rh$_2^{II,II}$ species, adapted from the extended Hücckel calculations, is shown in Scheme 19. Consider the Rh$^0$P$_4$ (C$_{3v}$) building block of the Rh$_2^{0,0}$(dfpma)$_3$(L)$_2$ complex. The fragment has eight electrons residing in (d$_{xz}$, d$_{yz}$) and (d$_{xy}$, d$_{x^2-y^2}$) orbitals and the odd electron occupying the d$_{z^2}$ orbital. The d$_{z^2}$ orbitals combine to give rise to the dσ* LUMO and a filled dσ level, energetically stabilized relative to the dπ/dπ*(d$_{xz}$, d$_{yz}$) and dδ/dδ*(d$_{xy}$, d$_{x^2-y^2}$) manifold. Thus the HOMO is either dπ* or dδ*, with the former prevailing when two Rh$^0$P$_4$ fragments are combined, and the formal Rh—Rh single bond results from the pairing of the d$_{z^2}$ electrons within the d$_{z^2}$σ level. Similar orbital energetics are preserved for the Rh$_2^{II,II}$(dfpma)$_3$X$_4$ and Rh$_2^{0,II}$(dfpma)$_3$X$_2$(L)$_2$ complexes. The d$_{x^2-y^2}$ level of the Rh$^{II}$P$_3$X$_2$ fragment is empty and displaced to high energy owing to the destabilizing M-L$_{eq}$ σ* interactions. Consequently, as with the Rh$^0$P$_4$ fragment, the odd electron of the Rh$^{II}$P$_3$X$_2$ fragment resides in the d$_{z^2}$ orbital, with the remaining six electrons of the d$^7$ metal center occupying the lower energy (d$_{xz}$, d$_{yz}$) and d$_{xy}$ orbitals. Linear combinations of the Rh$^{II}$P$_3$X$_2$ fragment orbitals with those of another Rh$^{II}$P$_3$X$_2$ fragment to give Rh$_2^{II,II}$(dfpma)$_3$X$_4$, or with those of a Rh$^0$P$_4$ fragment to give Rh$_2^{0,II}$(dfpma)$_3$X$_2$to a dσ* LUMO. As was the situation for Rh$_2^{0,0}$(dfpma)$_3$(L)$_2$, the dσ level is stabilized significantly with respect to the energetically proximate dπ* and dδ* levels, a result of much smaller one-electron splittings engendered by π and δ overlap. The only difference for the oxidized complexes is that the dπ* orbitals (vs dδ* orbitals in FIG. 32(a)) emerge as the LUMO. Again, a single Rh—Rh bond arises from electron pairing within the d$_{z^2}$σ orbital.

Scheme 18

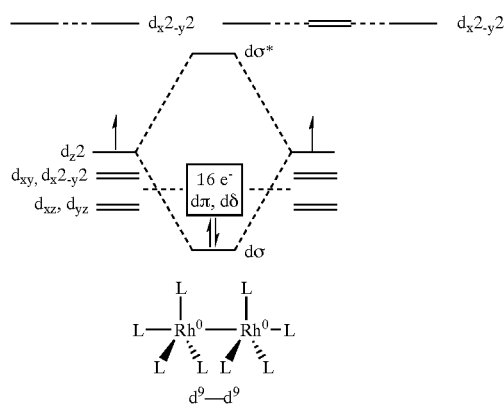

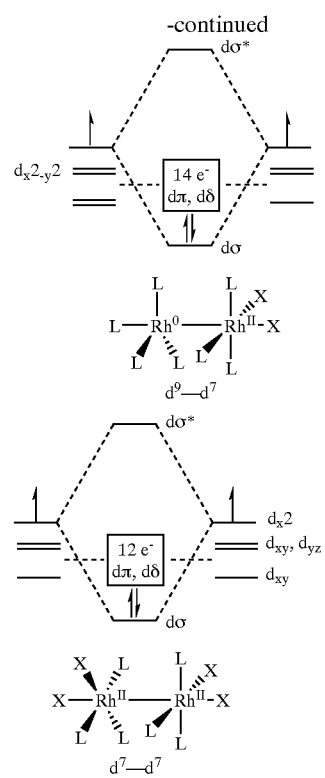

The preservation of the metal-metal bond and consequently a lowest energy dσ* excited state across the Rh$_2$ series is the key to the multi-electron photoreactivity. Scheme 19 displays a simplified orbital diagram for the sigma manifold along the metal-metal axis of the Rh$_2^{II,II}$ complex based on the extended Hückel results of FIG. 32 and Scheme 18. The oxidized Rh$_2^{II,II}$ and Rh$_2^{0,II}$ compounds are distinguished from their fully reduced Rh$_2^{0,0}$ counterpart by a charge-transfer component associated with promotion of an electron from the σ-bonding orbitals (labeled 1a$_g$ and 2a$_g$ in Scheme 19) to the σ* LUMO (2a$_u$). Here, the results of the extended Hückel calculation and the observed photochemistry converge. Population of the LUMOs of Rh$_2^{II,II}$ and Rh$_2^{0,II}$ is consistent with Rh—X bond homolysis and concomitant one-electron reduction of the Rh$^{II}$metal center. Moreover, a stepwise process for the reductive elimination of bromine is suggested by the nodal structure of the LUMOs. The localization of antibonding character along the metal-metal internuclear axis points towards the initial activation of the Rh—X$_{ax}$ bond.

Scheme 19

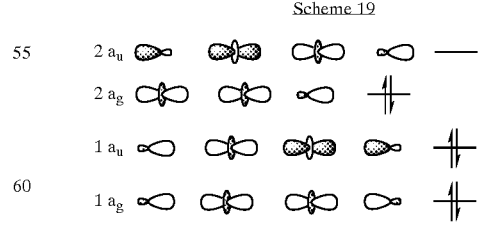

Discussion

As one-electron mixed-valence bimetallic cores promote single electron transfer reactions, the results presented here show that two-electron mixed-valence cores can support two-electron redox pathways, affording a framework in which to rationally design multi-electron reactivity. The metal-metal bonded $Rh_2^{0,II}$ complex sustains the multi-electron reactivity of the $Rh_2$ dfpma system by coupling two-electron reduced $Rh_2^{0,0}$ and two-electron oxidized $Rh_2^{II,II}$ species.

oxidative back-reaction. Similarly, the photochemical reductive elimination chemistry of $Rh_2^{0,II}(dfpma)_3X_2(L)$ appears to proceed by an initial one-electron halogen elimination. Formation of the metal-metal bond upon reduction to $Rh_2^{0,0}$ facilitates expulsion of the second halogen from the bimetallic core.

Scheme 20

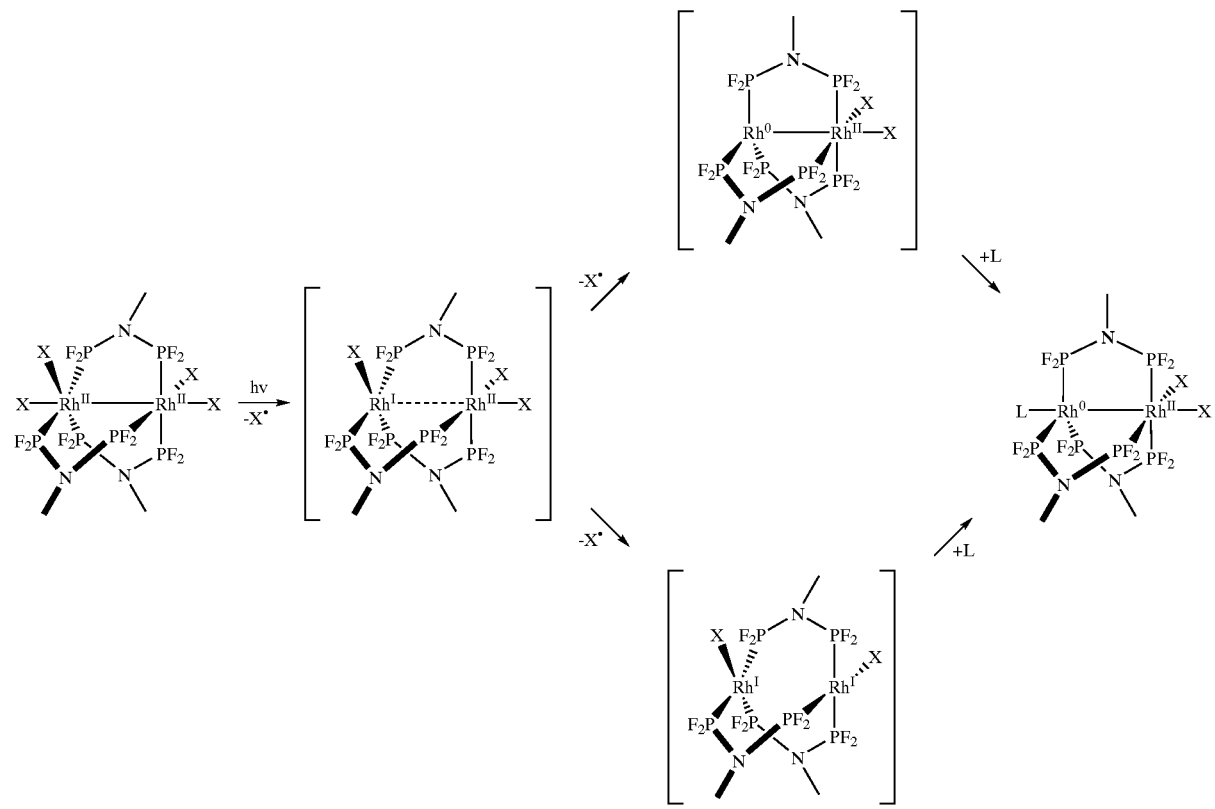

The thermodynamic driving force imparted by Rh—Rh bond formation (BDE=32±4 kcal mol$^{-1}$) precludes the stabilization of one-electron intermediates that would short-circuit multi-electron reactivity. Photon absorption into the $X(\sigma)/d\sigma \rightarrow d\sigma^*$ manifold of $Rh_2^{II,II}$ complexes prompts activation of an axial Rh—X bond leading to one-electron reduction of the bimetallic core and elimination of the halogen. Two unimolecular pathways from the one electron intermediate can afford the observed $Rh_2^{0,II}(dfpma)_3X_2(L)$ photoproduct. Reductive cleavage of the equatorial $Rh^I$—X bond of the initial photoproduct would directly yield the reduced metal center (Scheme 20, top pathway). Coordination of a donor ligand would then give the $Rh_2^{0,II}(dfpma)_3X_2(L)$ product. Alternatively, the orbital diagram of Scheme 19 implies that ejection of the remaining axial halogen might occur rapidly. As shown in the bottom pathway of Scheme 20, loss of the second axial halogen ligand would produce a dirhodium core of square planar $Rh^I$ centers, which then disproportionate to a $Rh^0$—$Rh^{II}$ species to restore the metal-metal bond. The observation of a blue intermediate upon irradiation of $Rh_2^{II,II}(dfpma)_3Br_4$ in THF solutions absent a donor ligand supports the intermediacy of $Rh^I$ centers. In either mechanism, thermodynamic remuneration afforded by re-establishing the Rh—Rh bond drives elimination of the second halogen and stabilizes the binuclear core to Sustaining the metal-metal bond of the $Rh_2$ dfpma system also circumvents problems previously associated with the utilization of two-electron mixed-valency in the design of multi-electron schemes. Previous to the studies described here, the presence of a two-electron mixed-valence intermediate has been observed to render complexes inert to further oxidation-reduction chemistry. This redox deactivation has been attributed to the inability of the ligand to electronically and conformationally support the appropriate energetics that make the bimetallic core amenable to further reaction. Along this line, the flexibility of the dfpma ligand allows for the respective octahedral and trigonal bipyramidal geometries of di- and zero-valent rhodium to be accommodated with facility. Stabilization of these disparate coordination geometries within a single bimetallic core of the $Rh_2^{0,II}$ complex maintains the reactivity of the species by avoiding metal-metal bond cleavage that typically deactivates binuclear complexes to multi-electron reactivity.

Coupled two-electron photoreactions assume a prominent position in energy conversion chemistry, especially when a metal-halide bond is involved. Consider the splitting of hydrohalic acids to $H_2$ and $X_2$. Whereas the elimination of $H_2$ from metal centers is feasible, the benchmark studies on the energy conversion chemistry of $d^8 \ldots d^8$ dimers show that the elimination of $X_2$ poses a more significant challenge owing to the high stabilities of the metal-halide bond. For instance, the HX photochemistry of $Rh^I_2$ diisocyanide complexes is stoichiometric because the cycle to regenerate the initial photoreagent terminates with the formation of the $Rh^{II}$—X bond. The incorporation of a dσ* excited state across the $Rh_2^{II,II}(dfpma)_3X_4$, $Rh_2^{0,II}(dfpma)_3X_2(L)$, $Rh_2^{0,0}(dfpma)_3(L)_2$ series surmounts the energetic barrier to halogen atom elimination, and therefore provides a means for interconversion between the series members in two electron steps.

Sequential two-electron reductive-elimination photoreactions provide for efficient interconversion among the members of the $Rh_2$-dfpma series. Photon absorption promotes activation of an axial halogen leading to reduction of the metal center and cleavage of the Rh—X bond. Preservation of the metal-metal bond across the series maintains the reactivity of the binuclear core, providing a reasonable platform for the investigation of multi-electron reactions.

HX Photochemistry of Rhodium Diphosphazanes

The photochemical activation of M-X bonds in two electron mixed-valence complexes prompted the development of a scheme to produce hydrogen photocatalytically from hydrohalic acid. Initial studies probed whether a Rh0 diphosphazane center could efficiently reduce protons to dihydrogen. Methods to couple the stoichiometric proton reduction to the reductive elimination photochemistry were then be investigated. These studies led to the construction of two HX splitting cycles using $Rh_2$ diphosphazanes as photocatalysts.

Light driven energy conversion schemes were suggested as an alternative energy source to expendable fossil fuel reserves nearly a century ago. The Scheme 21

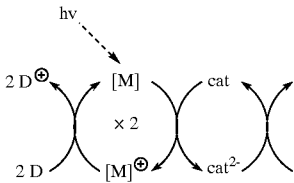

target fuel of schemes developed since this proposal has been hydrogen, generated from protic solutions. The most successful approaches to date have used a heterogeneous catalyst to couple the single electron equivalency provided by a photoexcited transition metal sensitizer (e.g. Ru(II) polypyridine complexes) to the two-electron equivalency required for hydrogen production (Scheme 21). Photoexcited electrons in the conduction bands of semiconducting electrodes and nanoparticles are especially effective in promoting the reduction of protons to hydrogen. Utilization of the attendant hole in the valence band to generate a complementary oxidation product completes a photocatalytic cycle. Hydrogen production in the absence of mediators has also been realized, but only under stoichiometric conditions. Research in the 1950's and 1960's established that the ultraviolet irradiation of acidic solutions containing reduced metal ions such as $Ce^{3+}$, $Cr^{2+}$ and $Fe^{2+}$ produced hydrogen and the one-electron oxidized metal cation. In these schemes, excitation of a charge-transfer-to-solvent (CTTS) absorption band effectively produces a solvated electron that is trapped by a proton to produce hydrogen atom radicals, which combine to produce hydrogen.

Gray and co-workers' seminal work on the photochemistry of dirhodium(I) isocyanides in hydrohalic acid solutions established the viability of using a molecular excited state to promote proton reduction in homogeneous solution (Scheme 22). Irradiation of the binuclear $Rh^I$ complex, $[Rh_2^{I,I}(bridge)_4]^{2+}$ (bridge =1,3-diisocyanopropane) in aqueous concentrated hydrohalic acid solutions resulted in the stoichiometric production of one equivalent of $H_2$ and one equivalent of the two-electron oxidized complex $[Rh_2^{II,II}(bridge)_4Cl_2]^{2+}$. This system was of great importance because it demonstrated the feasibility of driving a multi-electron reduction from a discrete molecular excited state. Whereas Ru-bipyridyl systems exemplified by Scheme 21 and single-metal CTTS systems were based on single electron transfer from a molecular excited state, the $[Rh_2^{I,I}(bridge)_4]^{2+}$ complex could directly provide both reducing equivalents for $H_2$ production. The inability to subsequently activate the $Rh^{II}$—X bond of $[Rh_2^{II,II}(bridge)_4Cl_2]^{2+}$ obviated the regeneration of the initial photoreagent, thus Scheme 22

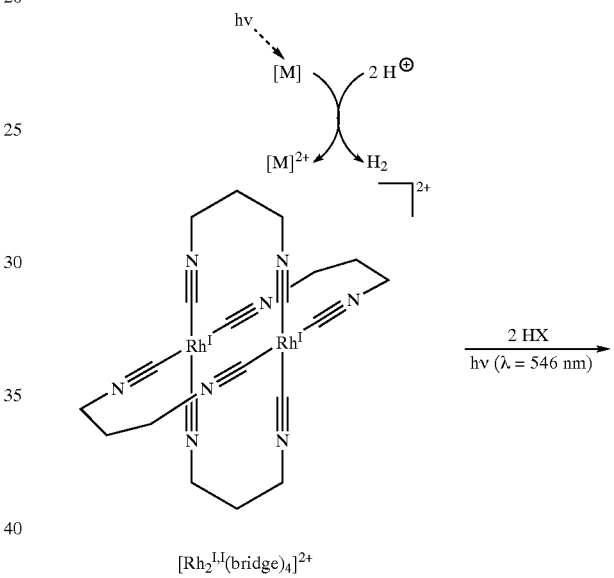

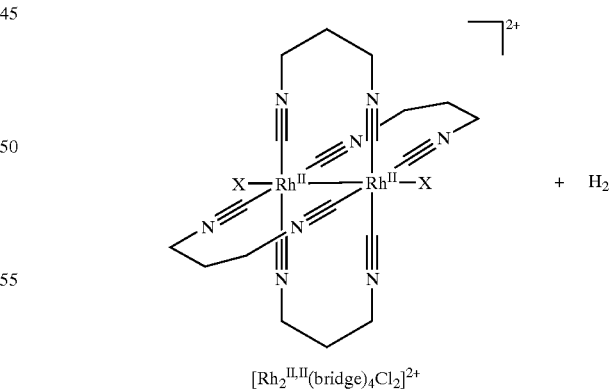

preventing catalytic turnover.

The four-electron reductive elimination photochemistry of the $Rh_2$-dfpma class of complexes. Coupling to a viable proton reduction pathway represents in light-to-chemical energy scheme for catalytic hydrogen production directly promoted by

Scheme 23

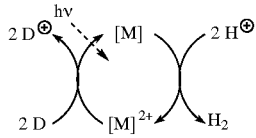

a molecular photocatalyst (Scheme 23). The M-X photoactivation from this dirhodium platform allows for the photocatalytic production of hydrogen from homogeneous solutions of hydrohalic acid.

Hydrogen Production from Rhodium Dihydrides

Initial attempts to prepare binuclear rhodium hydride species involved the treatment of $Rh_2^{0,II}$ and $Rh_2^{II,II}$ halides with hydride transfer reagents. Upon treatment of $Rh_2^{II,II}$ $(dfpma)_3X_4$ (X=Cl, Br) with reagents capable of delivering multiple hydride equivalents such as $NaBH_4$ or $LiAlH_4$, uncontrolled reduction of the rhodium complex was observed, yielding intractable product mixtures. $^{19}F$ NMR spectroscopy indicated the presence of both $Rh_2^{0,II}$ and $Rh_2^{0,0}$ products depending on reaction conditions.

The preparation of rhodium dihydrides was targeted directly by the reaction of dfpma with monomeric $Rh^I$-hydride starting materials. $Rh^I$-halides, such as

Scheme 24

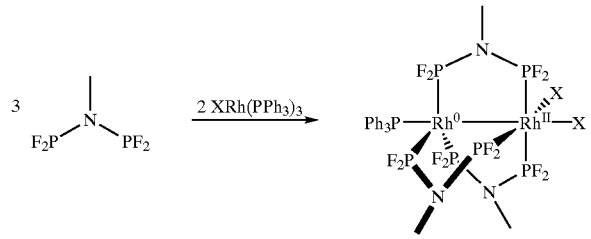

Wilkinson's catalyst, react with dfpma to afford two-electron mixed-valence complexes according to Scheme 24. By analogy, the reaction of dfpma with $HRh(L)_n$ starting materials was expected to afford species of the general formulation $Rh_2^{0,II}(dfpma)_3H_2(L)$. The addition of dfpma to $HRh(PPh_3)_4$ in benzene solution resulted in an immediate color change to red with concomitant gas evolution. The product, $Rh_2^{0,0}(dfpma)_3(PPh_3)_2$, was isolated as an orange powder from the reaction mixture in nearly quantitative yield. The product was identified by $^1H$ and $^{19}F$ NMR spectroscopy. A single methyl resonance was observed at 2.68 ppm for methylamine bridgehead of the dfpma ligands and a high frequency multiplet at 7.39–7.50 ppm was observed for the axial $PPh_3$ ligands. Appropriate integration ratios of 9:30 established the incorporation of two $PPh_3$ ligands within the dirhodium framework. A single $^{19}F$ NMR doublet observed at 43.2 ppm and a $|^1J_{PF}+^3J_{PF}|$ coupling constant of 1113 Hz are diagnostic of the formation of a $Rh_2^{0,0}$

Scheme 25

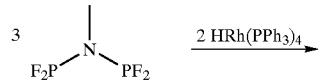

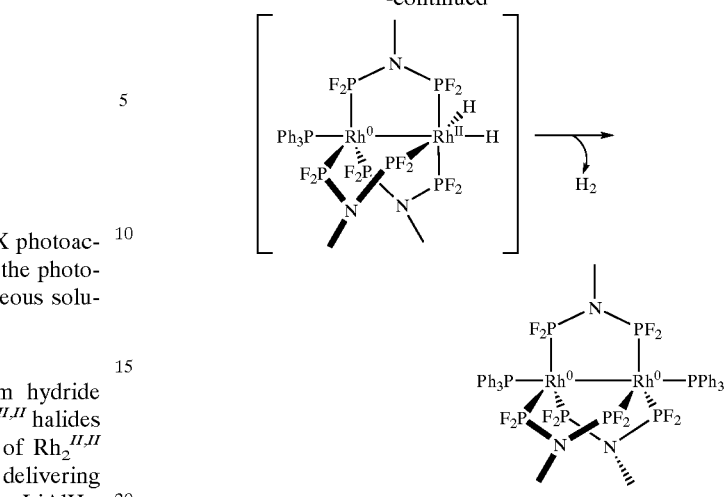

dimer possessing three bridging dfpma ligands.

The $H_2$ gas liberated from the reaction of Scheme 25 was quantified independently by its collection with a Toepler pump. Benzene was vacuum distilled from Na/benzophenone to a flask containing $HRh(PPh_3)_4$. The benzene solution was frozen and exactly 1.6 equiv of the dfpma ligand was transferred into the flask. Immediate reaction was observed upon thawing the benzene solution, as evidenced by a color change to red and by gas evolution. The solution was frozen and the $H_2$ was collected by Toepler pumping. 0.72 equiv of non-condensable gas was identified to be $H_2$ by burning over hot CuO. The $Rh_2^{0,0}(dfpma)_3(PPh_3)_2$ product was collected in 85% yield, confirming the 1:1 ratio of rhodium dimer:$H_2$ gas. A two-electron mixed-valence rhodium dihydride is presumably the intermediate species from which $H_2$ is evolved.

Stoichiometric Proton Photoreduction

The facile elimination of $H_2$ from a dihydride intermediate indicated that the binuclear rhodium core is sufficiently electron-rich to effect the reduction of protons. This potential reactivity pathway was explored by investigating the reaction of HX with the $Rh_2$ platform. However, solutions of $Rh_2^{0,0}(dfpma)_3(L)_2$ complexes in $CH_2Cl_2$ or THF did not oxidatively add hydrohalic acids in the absence of light. It is well established that oxidative addition to electronically saturated metal complexes must be preceded by dissociation of a coordinated ligand. Accordingly, the lack of reactivity observed for $Rh_2^{0,0}(dfpma)_3(L)_2$ complexes with HX is ascribed to the coordinatively saturated, 36e$^-$, $Rh_2^{0,0}$ core. One strategy for generating vacant coordination sites is the photoelimination of carbonyl or isonitrile ligands from a metal core. Thus $Rh_2^{0,0}(dfpma)_3(L)_2$ complexes containing L=CO and CN$^t$Bu were prepared.

Preparation of the symmetric complexes $Rh_2^{0,0}(dfpma)_3(CO)_2$ and $Rh_2^{0,0}(dfpma)_3(CN^tBu)_2$ followed as previously described. Treatment of $[ClRh(CO)_2]_2$ with three equivalents of dfpma under a CO atmosphere afforded the dicarbonyl complex after recrystallization from $CH_2Cl_2$/hexanes at $-80°$ C. Similarly, $[ClRh(cod)]_2$ reacted in the presence of two equivalents of CN$^t$Bu to give the isonitrile derivative after similar workup. The complexes were readily identified by $^{19}F$ NMR spectra, which display $|^1J_{PF}+^3J_{PF}|$ doublets at $-40.3$ and $-40.5$ ppm for the CO and CN$^t$Bu derivatives, respectively. Though no net reaction occurs, the rhodium dimers can be reversibly protonated with strong acids. The reaction of $Rh_2^{0,0}(dfpma)_3(CO)_2$ with HCl in $CH_2Cl_2$ afforded an off-white solid upon precipitation with pentane.

Drying under reduced pressure resulted in a color change back to yellow, and NMR spectra of the yellow solid identically match the $Rh_2^{0,0}$ dicarbonyl dimer. Similarly, treatment of $Rh_2^{0,0}(dfpma)_3(CN^tBu)_2$ with one equivalent of trifluoromethanesulfonic acid (HOTf, triflic acid) afforded [HRh$_2$(dfpma)$_3$(CN$^t$Bu)$_2$][OTf] upon precipitation, as determined by elemental analysis. In solution, the cation deprotonates to regenerate $Rh_2^{0,0}(dfpma)_3(CN^tBu)_2$ and the triflic acid.

Figure 33:
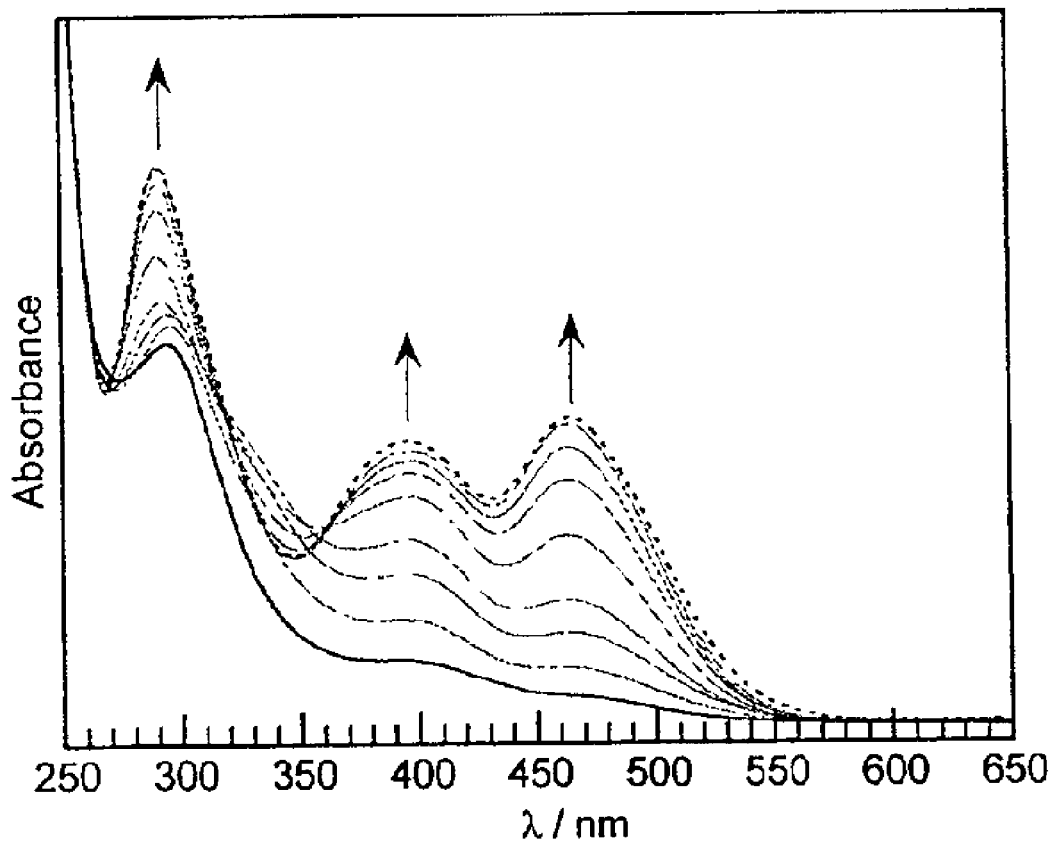
FIG. 33 is a graph of the UV-Vis spectral changes associated with the irradiation (300$\leq \lambda_{exc} \leq$400 nm) of Rh$_2^{0,}$ o(dfpma)₃(CN$^t$Bu)₂ in CH₂Cl₂ containing 0.1 M HBr wherein the spectra were acquired at $t_{irr}$=0, 10, 20, 30, 50, 70, 90, 120 and 180 min.

In the absence of light, solutions of $Rh_2^{0,0}(dfpma)_3(CN^tBu)_2$ with HBr in $CH_2Cl_2$ are stable for hours; however, FIG. 33 presents the spectral changes observed upon irradiation of a $CH_2Cl_2$ solution containing $Rh_2^{0,0}(dfpma)_3(CN^tBu)_2$ and 0.1 M HBr. The dicarbonyl compound gave similar results, as did substitution the reaction with HCl substituted for HBr. Excitation of the dσ→dσ* transition of the $Rh_2^{0,0}$ complex with $300 \leq \lambda \leq 400$ nm light resulted in loss of the axial isonitrile ligand from the metal coordination sphere followed by acid reaction. The absorption spectrum of the final rhodium-containing product corresponds to $Rh_2^{II,II}(dfpma)_3Br_4$ production. Attendant $H_2$ evolution was confirmed by Toepler pump experiments, which revealed ca. two equivalents of non-condensable gas that combusted over hot cupric oxide, establishing the overall stoichiometry of the reaction to be, Equation (11)

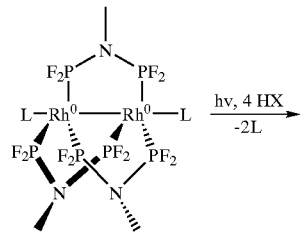

The photo-inertness of phosphine ligands allows the four-electron proton reduction of Equation 11 to be deconstructed into distinct two-electron reactions. A monocarbonyl dirhodium complex is directly available from the in situ reduction of $Rh_{2,II}(dfpma)_3Cl_2(CO)$ with cobaltocene in the presence of triphenylphosphine. The complex, $Rh_2^{0,0}(dfpma)_3(CO)(PPh_3)$, is characterized by two $|^1J_{PF}+^3J_{PF}|$ doublets in the $^{19}F$ NMR spectrum at −41.8 and −43.6 ppm. FIG. 34(a) displays the changes in the absorption profile when $Rh_2^{0,0}(dfpma)_3(CO)(PPh_3)$ is photolyzed with $\lambda_{exc} \geq 335$ nm light in $CH_2Cl_2$ solution containing 0.1 M HCl. As shown in FIG. 34(b), similar reactivity was observed with HBr. Examination of the terminating absorption spectrum revealed that $Rh_2^{0,II}(dfpma)_3Cl_2(PPh_3)$ is the photoproduct. On the basis of the measured molar absorption coefficients, the photoconversion of the $Rh_2^{0,0}$ complex to the mixed-valence $Rh_2^{0,II}$ complex was quantitative. Furthermore, collection of non-condensable gas with a Toepler pump was consistent with the formation of one equivalent of $H_2$ during the photolysis.

Figures 35A, 35B:
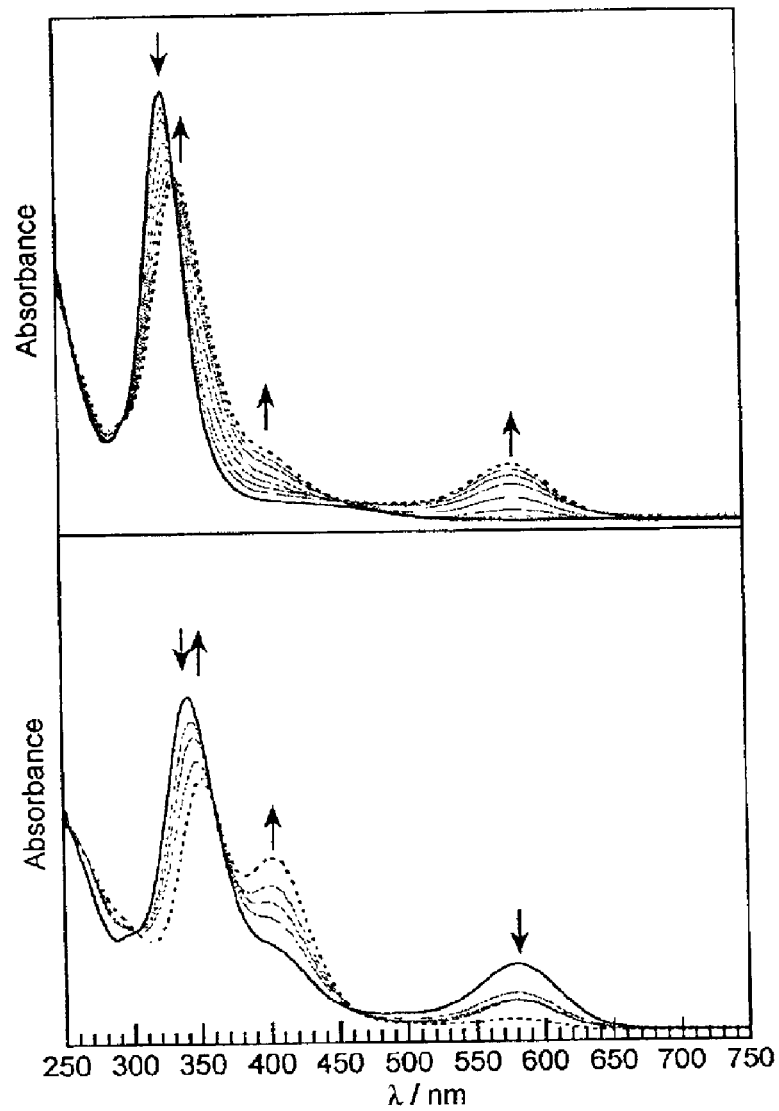
FIG. 35(a) is a graph of the changes in electronic absorption spectrum during monochromatic UV photolysis ($\lambda_{exc}$=335 nm) of Rh2(dfpma)₃(CO)(PPh₃) in 0.1 M HCl/THF solution at 20° C. wherein the spectra were collected at $t_{irr}$=0, 10, 20, 30, 40, 50, 60 and 90 min.
FIG. 35(b) is a graph of changes in the electronic absorption of the continued photolysis of the sample in FIG. 35(a) using white light ($\lambda_{exc}$≧335 nm) wherein spectra of FIG. 35(b) were acquired at $t_{irr}$=5, 10, 15 and 20 min. after the last spectrum of FIG. 35(a)

Wavelength selection of the excitation light suggests that the two-electron reduction of $H_2$ proceeds by a stepwise reaction sequence. Irradiation of $Rh_2^{0,II}(dfpma)_3Cl_2(PPh_3)$ in a 0.1 M HCl/THF solution with $\lambda_{exc}$=335 nm light caused the changes in the UV-Vis absorption spectrum shown in FIG. 35(a). Disappearance of the $Rh_2^{0,0}(dfpma)_3(PPh_3)$ (CO) absorption features were accompanied by the growth of an absorption band centered at 580 nm. After 90 min of irradiation, no further changes were observed in the 580-nm absorption band; scaled up reaction conditions provided 0.35(7) equiv of $H_2$ per mole of $Rh_2$ complex. The 580-nm absorption profile did not change with continued irradiation nor did its intensity change when solutions were stored in the dark. Though the 580-nm intermediate has not been isolated and characterized, its spectral features are characteristic of linear tetranuclear rhodium clusters possessing mixed-valence character. As observed by Gray and co-workers in their studies of $[Rh_2^{I,I}(bridge)_4]^{2+}$, a tetranuclear rhodium species can result from the bimolecular reaction of two hydrido-halo dirhodium cores to produce 0.5 equiv of $H_2$ and the tetranuclear species. Upon changing the excitation wavelength to include visible wavelength frequencies, the absorbance decreased with the concomitant appearance of the two-electron mixed-valence dihalide, $Rh_2^{0,II}(dfpma)_3Cl_2(PPh_3)$ (FIG. 35(b)). Consistent with the overall stoichiometry of eq 11, Toepler pumping of scaled-up photoreactions gave an additional 0.38(7) equiv of $H_2$.

Figure 36:
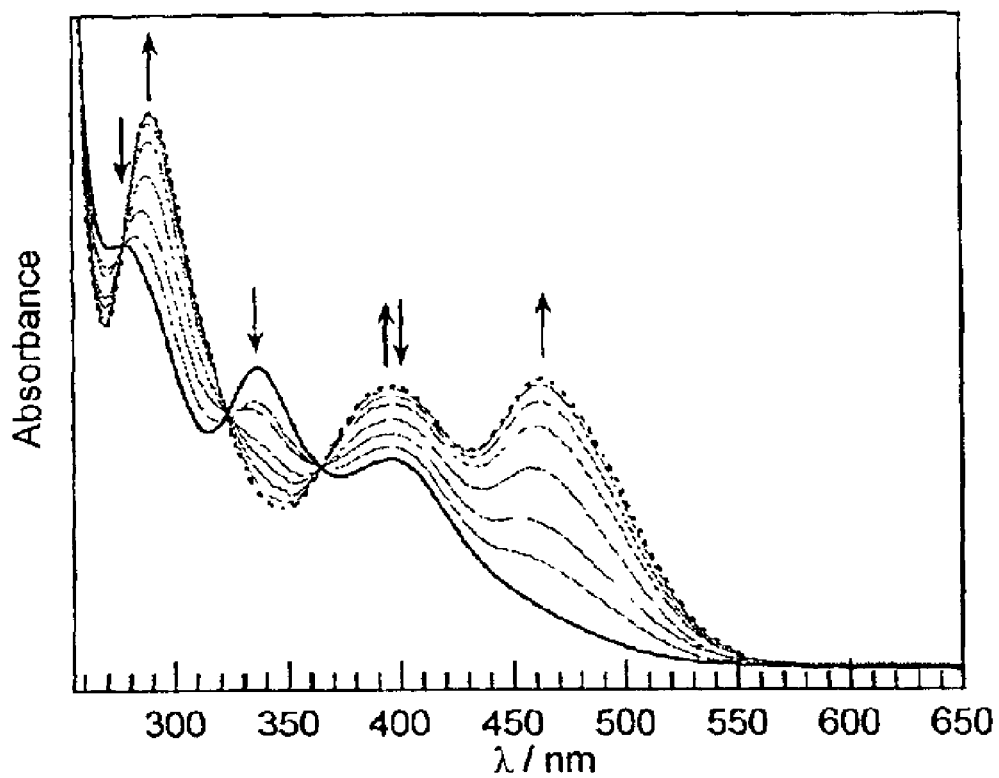
FIG. 36 is a graph of UV-Vis absorption changes associated with photolysis ($\lambda_{exc}$≧365 nm) of Rh₂$^{0,II}$(dfpma)₃Br₂(CN$^t$Bu) in CH₂Cl₂ containing 0.1 M HBr wherein the spectra were acquired at $t_{irr}$=0, 5, 10, 20, 30, 40, 50 and 60 min.

Equation 11 suggests that a second two-electron proton reduction must be possible for the $Rh_2^{0,II}$ complex. Irradiation of $Rh_2^{II}(dfpma)_3Br_2(CN^tBu)$ in $CH_2Cl_2$ solutions containing 0.1 M HBr gave rise to the absorption changes of FIG. 36. Similar results were obtained for irradiation of $Rh_2^{0,II}(dfpma)_3Cl_2(CN^tBu)$ with HCl. Again, quantitative two-electron reaction was observed, yielding $Rh_2^{II,II}(dfpma)_3Br_4$ and one equivalent of hydrogen gas. Thus, each metal center appears to react independently in two-electron steps according to the sequence, Equation (12)

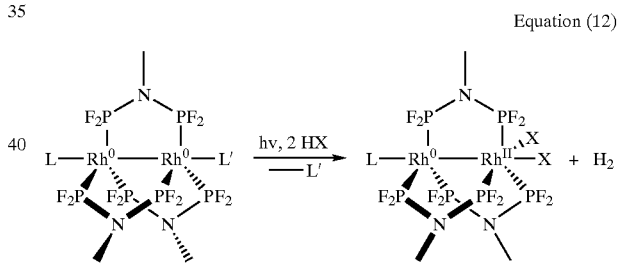

Equation (13)

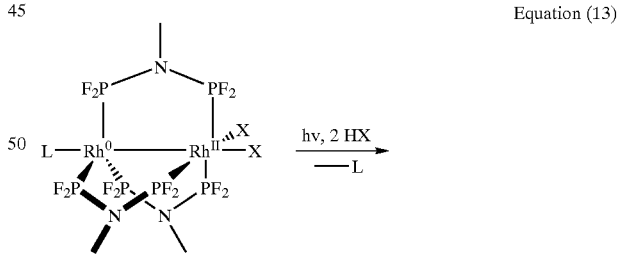

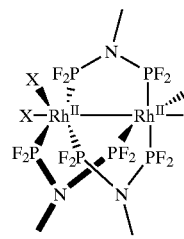

Low-Valent $H_2$ Photocatalysis

Figure 37A:
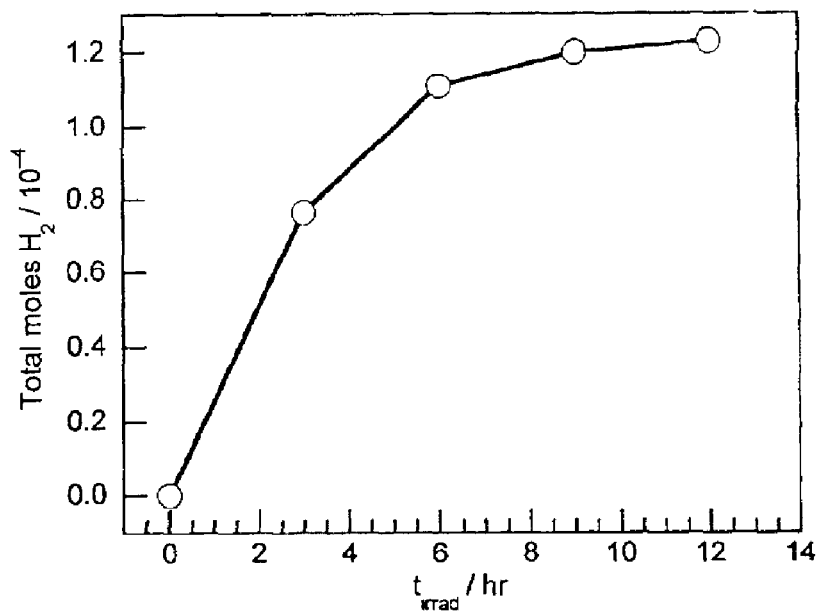
FIG. 37(a) is a plot of total hydrogen collected as a function of time for UV-Vis white light irradiation ($\lambda_{exc}$≧335 nm) of Rh₂$^{0,II}$(dfpma)₃Cl₂(PPh₃) in 0.1 M HCl/THF solution at 20° C.
Figure 37B:
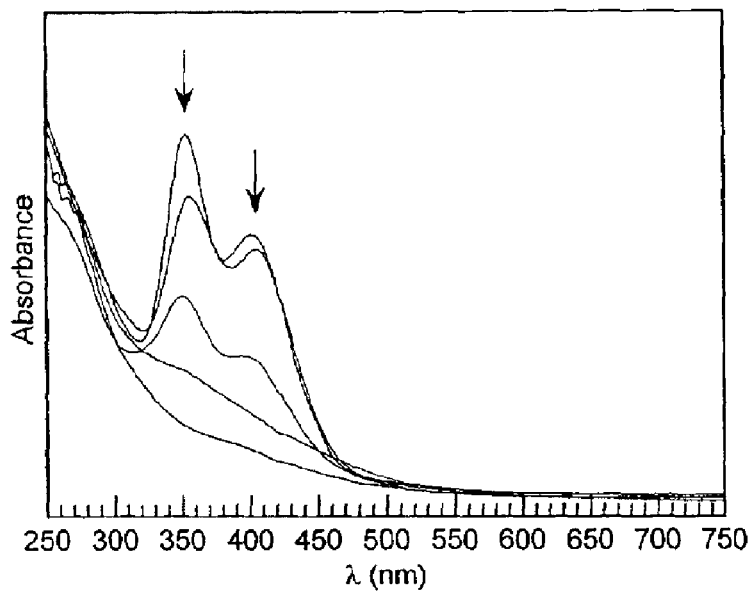
FIG. 37(b) is a graph of UV-Vis absorption spectra of the sample of FIG. 37(a) indicating the decay of the Rh₂$^{0,II}$(dfpma)₃Cl₂(PPh₃) catalyst during irradiation.
Figure 38:
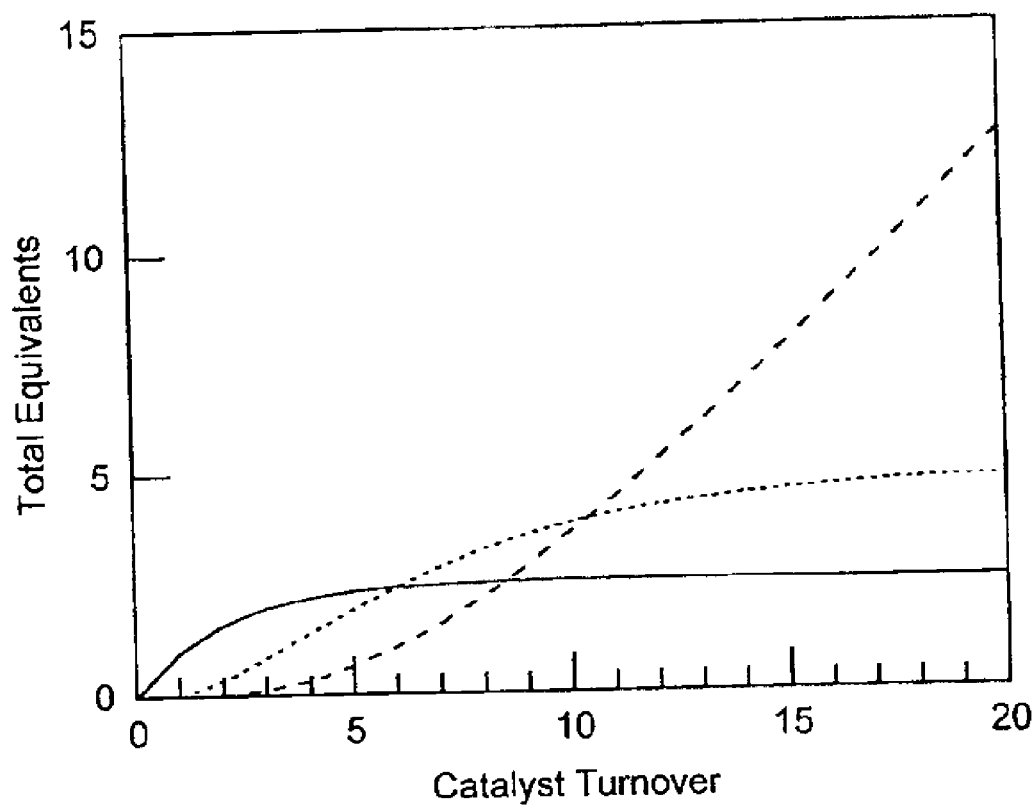
FIG. 38 is a plot of predicted H₂, D₂, and HD production based on irradiation of Rh₂$^{0,II}$(dfpma)₃Cl₂(PPh₃) in d$^8$-THF initially containing 10 equiv. of HCl.

Because a $Rh_20,0$ species can be regenerated by photolysis of $Rh_2^{0,II}(dfpma)_3X_2(PPh_3)$ in the presence of halogen atom traps, eq 12 can be turned over and $H_2$ can be generated photocatalytically. A 50-mL THF solution containing $Rh_2^{0,II}$ (dfpma)$_3$Cl$_2$(PPh$_3$) (0.95 μmol) and 0.1 M HCl was irradiated with $\square_{exc} \geq 335$ nm after which the photolysis was halted and $H_2$ was collected by Toepler pumping. This procedure was repeated at 3-hour intervals to generate the plot in FIG. 37(a), which displays total $H_2$ production vs. time. A pseudo-initial rate of 27 turnovers per hour was observed during the first 3-hour interval followed by a decreased rate of $H_2$ production with continued photolysis. An attendant decrease in the absorbance of the $Rh_2^{0,II}$ (dfpma)$_3$Cl$_2$(PPh$_3$) catalyst is shown in FIG. 37(b), indicating decomposition of the two-electron mixed-valence dimer.

Photolyses carried out with high catalyst concentrations for long irradiation times resulted in polymerization of the THF solvent. To determine if $H_2$ formation originated from the HX or from the decomposition of THF solvent, an isotope crossover experiment was conducted. A photolysis carried out using ten equivalents of HCl in d$^8$-THF was monitored by $^1$H NMR spectroscopy. Only $H_2$ was observed during the first few hours of irradiation (ca. 1–2 turnovers). Subsequently, HD was observed in the $^1$H NMR spectrum, resulting from deuterium atom abstraction by photo-eliminated halogen (Scheme 26, presumably $D_2$ was also formed, but not observed by $^1$H NMR spectroscopy). After five turnovers of the dirhodium catalyst, the ratio of $H_2$:HD was determined to be 1.4(2). The production of $H_2$, $D_2$ and HD may be modeled as a binomial distribution with the caveat that once HCl reacts to form $H_2$ or HD, it is permentantly removed from the catalytic cycle. Deuterium atom abstraction from THF gives DCl, thus the total acid concentration remains constant. Scheme 26 presents projected $H_2$, $D_2$ and HD quantities, based on the reaction chemistry of Scheme 26. After five turnovers, the projected $H_2$:HD ratio is 1.2, in good agreement with the ratio measured by NMR spectroscopy.

Scheme 26

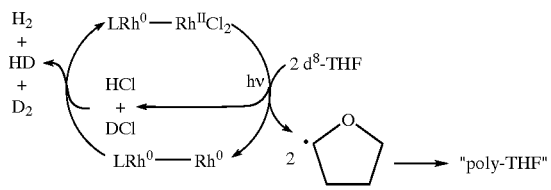

Figures 39A, 39B:
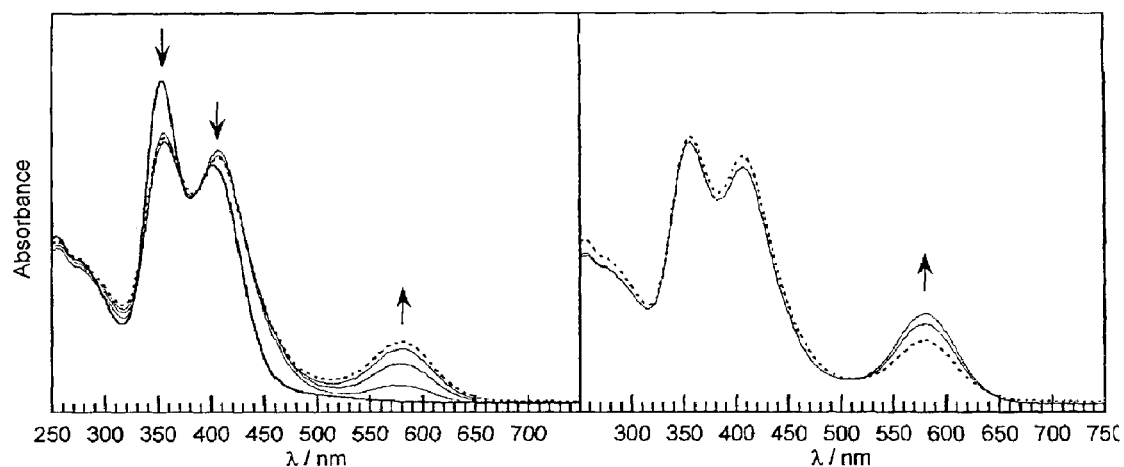
FIG. 39(a) is a graph of changes in electronic absorption spectrum during the monochromatic UV photolysis ($\lambda_{exc}$=335 nm) of Rh₂$^{0,II}$(dfpma)₃Cl₂(PPh₃) in 0.1 M HCl/THF solution at 20° C. wherein the spectra were acquired at $t_{irr}$=0, 10, 20, 30 and 40 min.
FIG. 39(b) is a graph of spectral changes for the solution in FIG. 39(a) kept in the dark for five minutes and wherein the spectra were recorded 5 and 10 minutes after the last spectrum of FIG. 39(a)

Attempts to determine the quantum yield for $H_2$ production were complicated by the appearance of the 580-nm intermediate during monochromatic UV irradiation. FIG. 39(a) shows the UV-Vis absorption changes associated with the irradiation ($\lambda_{exc}$=335 nm) of $Rh_2^{0,II}$(dfpma)$_3$Cl$_2$(PPh$_3$) in THF solution containing 0.1 M HCl. Monitoring the disappearance of the band at 350 nm provided a crude estimate of 0.005(2) for the photochemical quantum yield. As seen in FIG. 39(a), the changes in the UV region of the absorption spectrum were complete after 10 min of irradiation, yet continued growth of the 580-nm band was observed. This continued growth resulted from a slower dark reaction, evident in FIG. 39(b), which shows a slow increase in intensity for the 580-nm band in the absence of irradiation. Though inconclusive, such an observation is in accord with the dimerization of Rh$^0$- - - Rh$^I$ species to form a tetranuclear cluster, as low local concentrations of the one-electron mixed-valence species should result in slow rates of formation. Analogous to the 580-nm intermediate observed for the monochromatic irradiation of $Rh_2^{0,0}$(dfpma)$_3$(PPh$_3$)(CO), excitation of this intermediate solution within the envelope of the 580-nm absorption band led to regeneration of the $Rh_2^{0,II}$(dfpma)$_3$Cl$_2$(PPh$_3$) complex.

The above results are consistent with the catalytic cycle shown in Scheme 27. Per Toepler pump experiments, two equivalents of HX react with two unsaturated LRh$^0$—Rh$^0$ species to produce one equivalent of $H_2$ and the blue intermediate, which is tentatively ascribed to a tetranuclear rhodium complex. This intermediate species is photochemically stable in the absence of visible-light irradiation; however, absorption of a 580 nm photon prompts cleavage of the suspected tetramer followed by subsequent reaction to give two molecules of the LRh$^0$—Rh$^{II}$X$_2$ mixed-valence complex with the generation of an additional equivalent of $H_2$. The near-UV irradiation of the two-electron mixed-valence photoproduct in the presence of halogen atom trap regenerates LRh$^0$—Rh$^0$, which is available to react with HX to turn the cycle over.

High-Valent $H_2$ Photocatalysis

The rate of hydrogen production appears to track both the wavelength

Scheme 27

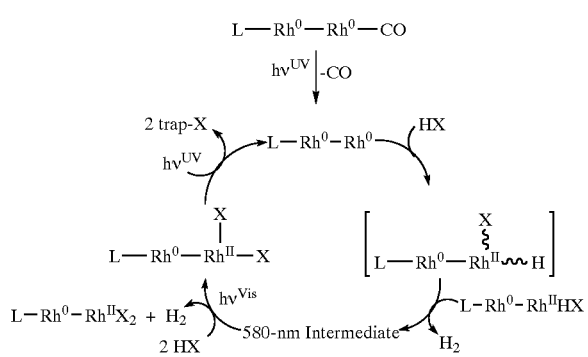

dependence (300 nm$\leq\lambda\leq$400 nm) as well as the quantum efficiency ($\Phi$~0.002–0.006) for reductive elimination from the two-electron mixed-valence species. Photochemical reductive elimination from $Rh_2^{II,II}$(dfpma)$_3$X$_4$ occursat a higher quantum yield ($\Phi$~0.01–0.05) and with lower energy light (300 nm$\leq\lambda\leq$480 nm) than from $Rh_2^{0,II}$(dfpma)$_3$X$_2$ (L). Therefore, one strategy to improve both quantum efficiency for $H_2$ production and photoreaction wavelength would be to catalytically turnover the proton reduction of eq 13.

Figure 40:
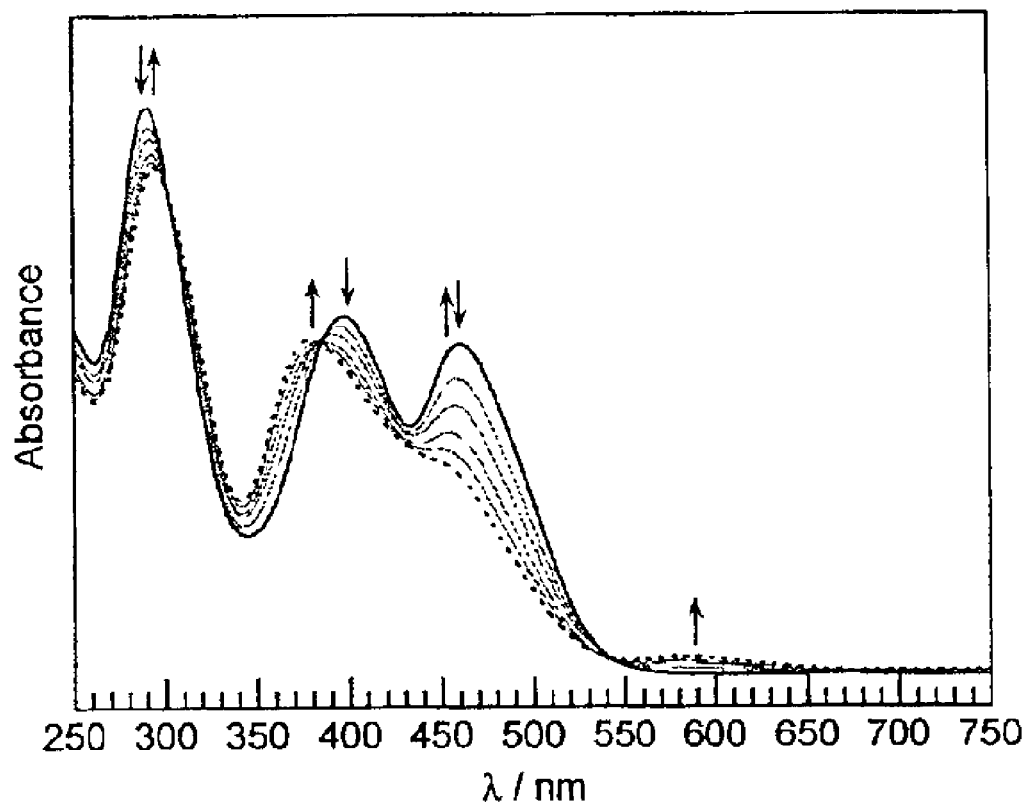
FIG. 40 is a graph of absorption spectra recorded during photolysis (300 nm≦$\lambda_{exc}$<400 nm) of Rh₂$^{II,II}$(dfpma)₃Br₄ at 20° C. in THF solution containing 0.1 M HCl wherein the spectra were acquired at $t_{irr}$=0, 1, 2, 3, 4 and 5 min.

Unlike the photochemistry of the $Rh_2^{0,II}$(dfpma)$_3$X$_2$(L) species, which only show slow catalyst decomposition during HX photolysis, irradiation of $Rh_2^{II,II}$(dfpma)$_3$X$_4$ complexes in the presence of hydrohalic acids leads to rapid UV-Vis absorption changes. The spectral changes associated with the photochemical reaction of $Rh_2^{II,II}$(dfpma)$_3$Br$_4$ with 0.1 M HCl in THF are displayed in FIG. 40. An identical final spectrum was obtained when using $Rh_2^{II,II}$(dfpma)$_3$Cl$_4$. Isosbestic points at 303, 383 and 542 nm are maintained throughout the transformation. Bands centered at 294 nm ($\epsilon$=17,700 M$^{-1}$ cm$^{-1}$) and 379 nm ($\epsilon$=11,700 M$^{-1}$ cm$^{-1}$) are suggestive of X($\sigma$)/d$\sigma\rightarrow$d$\sigma$* transitions derived from a metal-metal bonded species. A shoulder observed near 450 nm attributed to a d$\pi$*$\rightarrow$d$\sigma$* type transition and a weak band centered at 583 nm ($\epsilon$=525 M$^{-1}$ cm$^{-1}$) also grow in with photolysis. Continued irradiation of the new species led to hydrogen production, as determined by Toepler pump collection. Moderate turnover numbers varying between 20 and 50 were obtained for experiments employing $Rh_2^{II,II}$(dfpma)$_3$Cl$_4$ and $Rh_2^{II,II}$(dfpma)$_3$Br$_4$, respectively (all used HCl as the acid).

Figure 41:
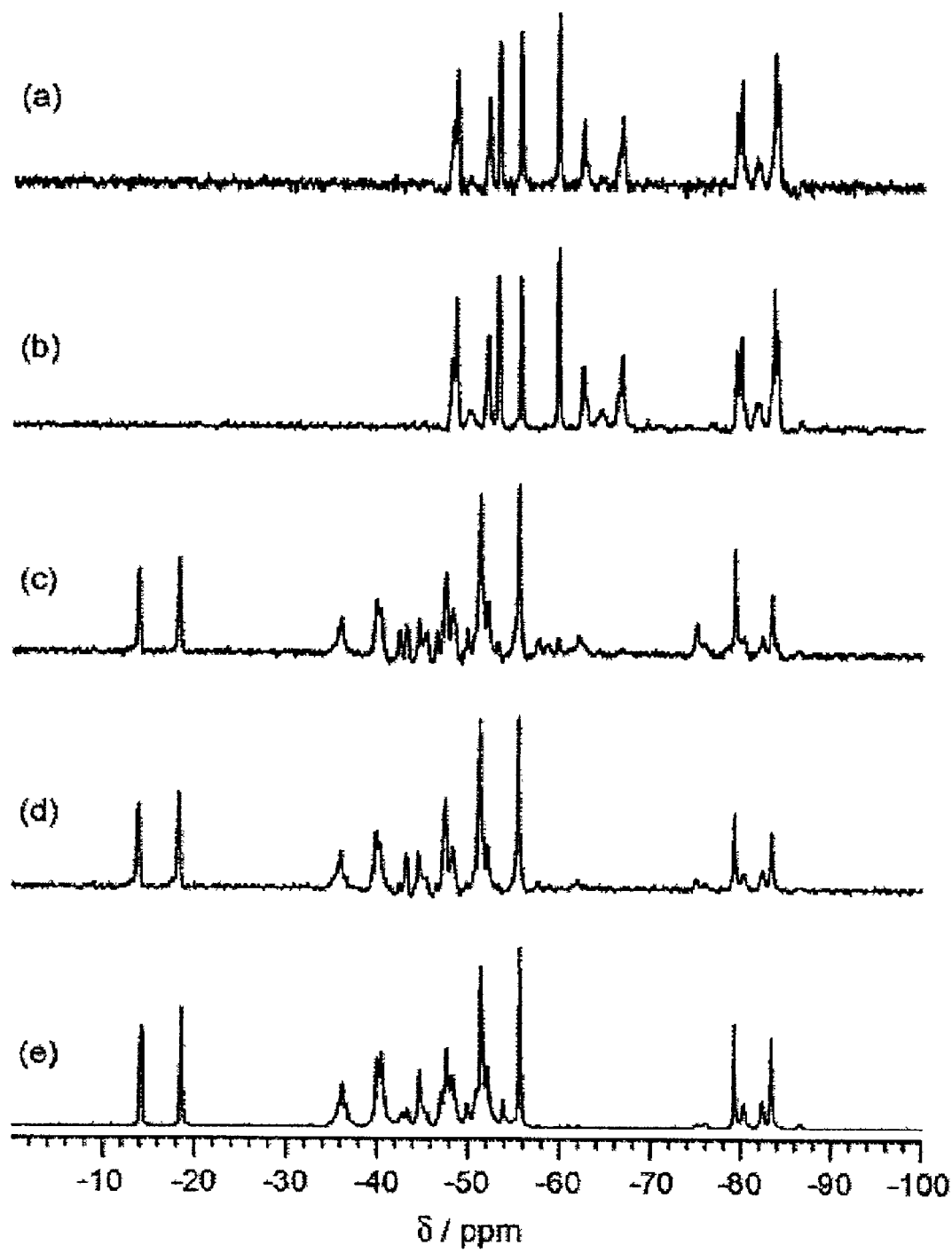
FIG. 41(a) is a $^{19}$F NMR spectrum for the photoreaction of Rh₂$^{II,II}$(dfpma)₃Cl₄ with HCl in d$^8$-THF.
FIG. 41(b) is $^{19}$F NMR spectrum for the photoreaction of Rh₂$^{II,II}$(dfpma)₃CO₄ with HCl in d$^8$-THF after the addition of 0.2 M HCl.
FIG. 41(c) is a $^{19}$F NMR spectrum for the photoreaction of Rh₂$^{II,II}$(dfpma)₃Cl₄ with HCl in d$^8$-THF after addition of 0.2 M HCl and irradiation (300 nm≦$\lambda$≦400 nm) for 3 hr.
FIG. 41(d) is a $^{19}$F NMR spectrum for the photoreaction of Rh₂$^{II,II}$(dfpma)₃Cl₄ with HCl in d$^8$-THF after addition of 0.2 M HCl and irradiation (300 nm≦$\lambda$≦400 nm) for 18 hr.
FIG. 41(e) is a $^{19}$F NMR spectrum of independently prepared Rh₂$^{0,II}$(dfpma)₃Cl₂ in d$^8$-THF.
Figure 42:
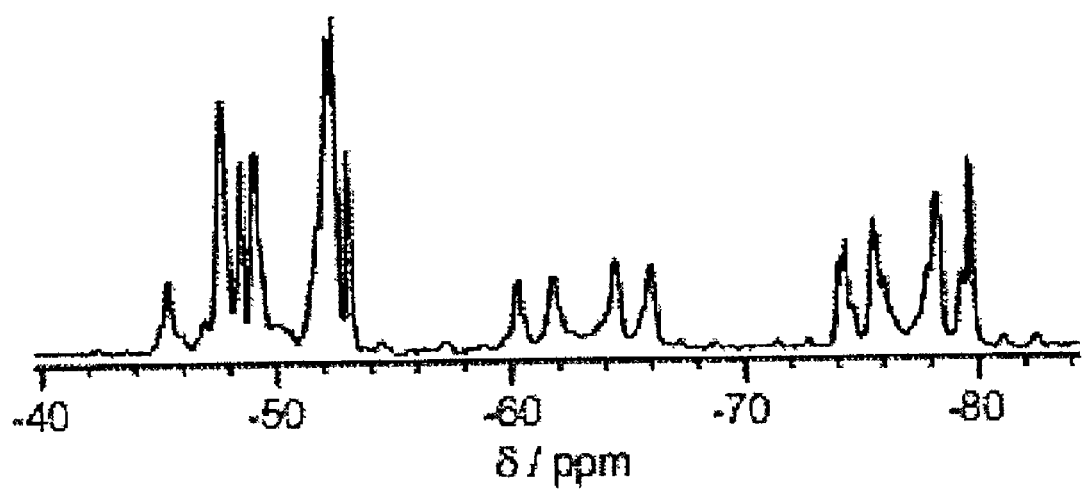
FIG. 42 is a $^{19}$F NMR spectrum of Rh₂$^{II,II}$(dfpma)₃Cl₂Br₂ in d$^8$-THF from the reaction of Rh₂$^{0,II}$(dfpma)₃Cl₂ with bromine.

To help elucidate the molecular structure of the new dirhodium species, photolyses were carried out on a scale suitable for NMR analysis. FIG. 41 presents the $^{19}$F NMR spectra obtained for the irradiation of a 0.7 mL d$^8$-THF solution of Rh$_2^{II,II}$(dfpma)$_3$Cl$_4$ containing 0.2 M HCl. The spectrum of FIG. 41(a) is the $^{19}$F NMR spectrum of Rh$_2^{II,II}$(dfpma)$_3$Cl$_4$, showing the five-resonance $|^1J_{PF}+^3J_{PF}|$ doublet pattern characteristic of the Rh$_2^{II,II}$ core. Condensation of anhydrous HCl into the NMR tube resulted in no reaction as evidenced by the $^{19}$F NMR spectrum presented in FIG. 41(b). The sample was then irradiated using a 360-nm band-pass filter (300 nm$\leq\lambda_{exc}\leq$400 nm) at 20° C. Within minutes the orange-red solution had turned intense purple. When the sample was removed from the irradiation source, the purple color rapidly faded to a dark red. After 3 hours of irradiation, the sample was removed from the light source and $^1$H and $^{19}$F NMR spectra were recorded. The $^1$H NMR spectrum showed a new dfpma methyl resonance at 3.05 ppm and a small peak at 4.53 ppm, attributed to H$_2$ gas. The $^{19}$F NMR, presented in FIG. 41(c), indicated the formation of a new dirhodium species. The conversion to the new complex was completed with continued irradiation (18 hr) as shown in the $^{19}$F NMR spectrum of FIG. 41(d). The $^1$H NMR spectrum showed evidence for H$_2$ evolution over the entire 18-hour irradiation period. Furthermore, a 1:1:1 triplet at 4.50 ppm ($^1J_{HD}$=43 Hz) indicated the production of HD. As discussed herein, halogen trapping by d$^8$-THF generates DCl, which in turn enters the photocatalytic cycle to produce HD and D$_2$.

The most notable feature of the spectra in FIG. 41(c)–(d) is the low frequency doublet –15.4 ppm, which is diagnostic of a PF$_2$ group coordinated axially to a Rh$^0$ center. Rearrangement of a single bridging dfpma ligand to a chelating coordination mode would account for this low frequency PF$_2$ resonance. One possible assignment for this new rearranged species is shown in Scheme 28. In the absence of a suitable donor ligand, a structure analogous to that observed for Ir$_2^{0,II}$ cores can be obtained by photochemical reductive elimination from the Rh$_2^{II,II}$ platform.

Scheme 28

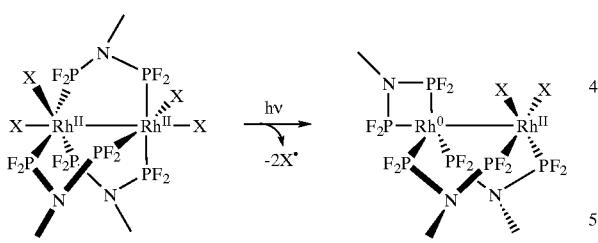

The new complex, Rh$_2^{0,II}$(dfpma)$_3$Cl$_2$, was independently prepared by treating [ClRh(CO)$_2$]$_2$ with three equivalents of dfpma in CH$_2$Cl$_2$. Gas evolution was accompanied by the formation of a deep red solution. The solvent was then removed to leave a sticky red solid that was treated with a 1:2 solution of benzene and pentane. Rh$_2^{0,II}$(dfpma)$_3$Cl$_2$(CO) was isolated as an orange-red powder. Unlike the other Rh$_2^{0,II}$(dfpma)$_3$X$_2$(L) derivatives described herein, Rh$_2^{0,II}$(dfpma)$_3$Cl$_2$(CO) is not stable in the solid state. Orange-red samples turned green if left under active vacuum overnight, with concomitant loss CO as indicated by the loss of the $v_{CO}$ stretch at 2057 cm$^{-1}$. The green solid affords deep red solutions in THF, and as shown in FIG. 41(e), the $^{19}$F NMR spectrum in d$^8$-THF solution identically matches the Rh$_2$ photoproduct. Presumably, CO loss gives the intermediate species depicted in Scheme 29, which rearranges to the final structure in solution. The most notable features in the $^{19}$F NMR spectrum of Rh$_2^{0,II}$(dfpma)$_3$Cl$_2$ product are the high frequency doublet for the axial PF$_2$ of the chelating ligand, observed at –15.4 ppm, and the low frequency $|^1J_{PF}+^3J_{PF}|$ doublet for the PF$_2$ groups located trans to the chloride ligands, observed at –80.8 ppm. A critical difference in the $^{19}$F NMR spectra of FIG. 41 is the conditions under which the data were collected. In the spectra of FIG. 41(b)–(d), the d$^8$-THF solution was 0.2 M in HCl; in the spectrum of FIG. 41(e), no acid was present. Indeed, treatment of d$^8$-THF solutions of Rh$_2^{0,II}$(dfpma)$_3$Cl$_2$ with up to 10 equiv of anhydrous HCl gas resulted in no observable change in either the $^1$H or $^{19}$F NMR spectra (excepting observation of the solvated proton in the $^1$H NMR spectrum).

Scheme 29

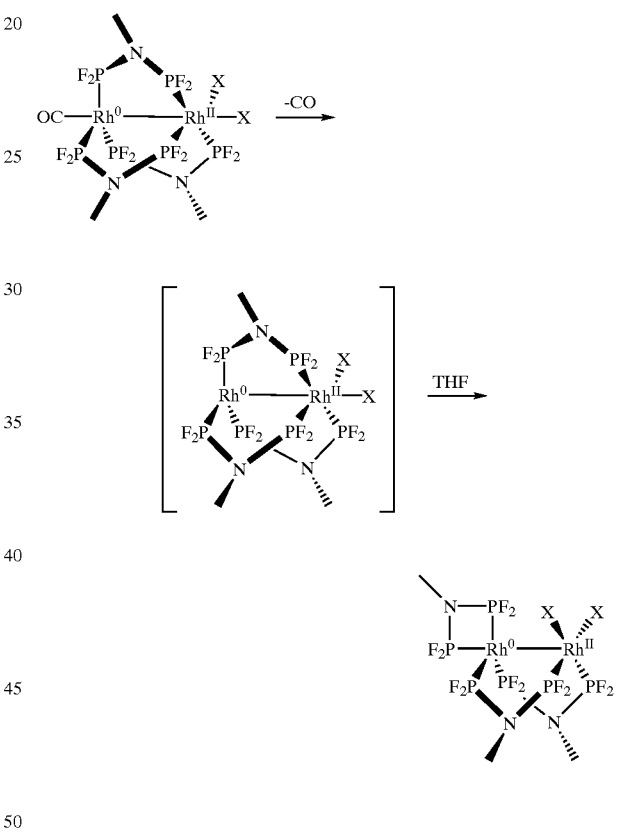

In contrast to the low reactivity of Rh$_2^{0,II}$(dfpma)$_3$Cl$_2$ with proton sources, pure σ-donor ligands add to the vacant axial site of the rhodium dimer as in Scheme 30. The $^1$H NMR of the PMe$_3$ derivative shows a doublet for the alkyl phosphine ligand at 1.78 ppm ($^2J_{PH}$=11 Hz) and two distinct methyl resonances at 2.93 and 3.10 ppm for the chelating and bridging dfpma ligands, respectively. The $^{19}$F NMR spectrum of the PMe$_3$ complex displays a low frequency pattern largely unchanged from the parent Rh$_2^{0,II}$(dfpma)$_3$Cl$_2$ complex, but the high frequency axial PF$_2$ groups shifts slightly downfield to –13.1 ppm. Similarly, the $^1$H NMR of the [Rh$_2^{0,II}$(dfpma)$_3$Cl$_3$]$^-$ anion shows resonances at 2.79 and 2.86 ppm for the dfpma ligands. The signature resonance for the axial PF$_2$ group of the [Rh$_2^{0,II}$(dfpma)$_3$Cl$_3$]$^-$ anion is shifted up to +7.4 ppm in the $^{19}$F NMR spectrum.

Scheme 30

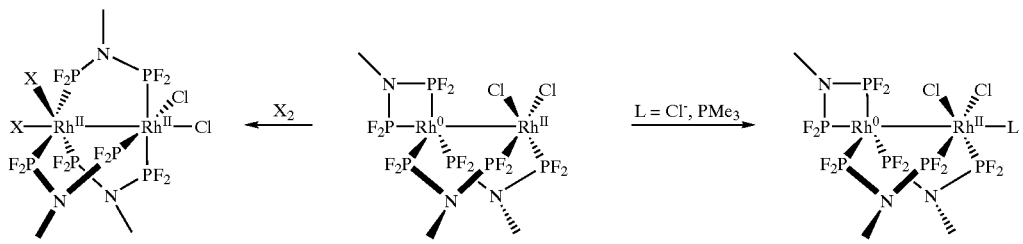

Oxidative addition of halogens to $Rh_2^{0,II}(dfpma)_3Cl_2$ proceeded smoothly, yielding valence-symmetric $Rh_2^{II,II}(dfpma)_3Cl_2X_2$ products (Scheme 30). This is a structural departure from the reactivity displayed by $Ir_2^{0,II}(tfepma)_3Cl_2$, which affords $Ir_2^{I,III}(tfepma)_3Cl_4$ upon oxidation with chlorine. Moreover, the addition of bromine to $Rh_2^{0,II}(dfpma)_3Cl_2$ proceeded at one metal center, to give a $Br_2Rh^{II}$—$Rh^{II}Cl_2$ oxidation product as indicated by the $^{19}F$ NMR spectrum of Scheme 30. The most notable indicator of coordination geometry is the low-frequency resonances at −76.1 and −77.6 ppm, assigned to $PF_2$ groups of the dfpma ligands located trans to halide ligands. The observation of two distinct resonances in this region unambiguously establishes the absence of a mirror plane in the $Rh_2^{II,II}$ product, which would be expected for a $ClBrRh^{II}$—$Rh^{II}BrCl$ complex.

Based on the observed reactivity of $Rh_2^{0,II}(dfpma)_3Cl_2$, the cycle shown in Scheme 31 is proposed for photochemical hydrogen production using the high-valent catalyst. Irradiation with UV-visible light promotes halogen elimination from the binuclear $Rh^{II}$ complex to afford $Rh_2^{0,II}(dfpma)_3Cl_2$ after rearrangement of a bridging dfpma ligand. As observed in the chemistry of $Ir_2^{0,II}(tfepma)_3Cl_2$, coordination of a halide to form the 36e⁻ anion facilitates protonation of the binuclear species before a hydrogen-evolving step to regenerate the $Rh2^{II,II}$ tetrahalide complex.

Scheme 31

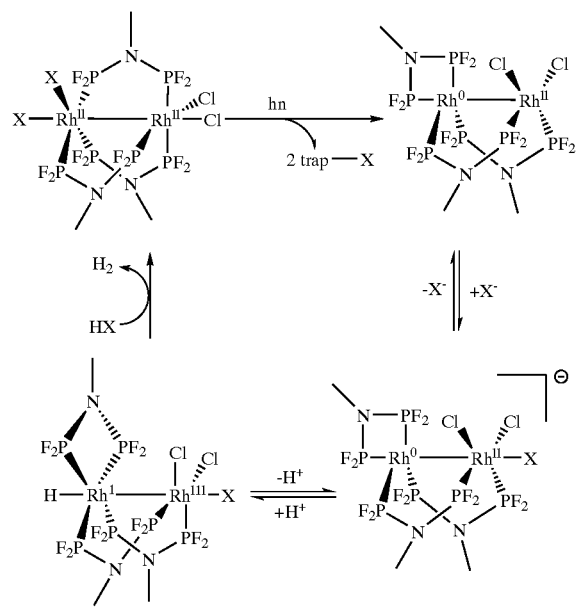

$Rh_2$-dfpma complexes have provided a novel platform for the photocatalytic production of hydrogen from hydrohalic acids. Irradiation of $Rh_2^{0,II}(dfpma)3X2(L)$ complexes in acidic THF solution resulted in hydrogen production via turnover of a $Rh_2^{0,II}/Rh_2^{0,0}$ valence couple. Similarly, a high-valent two-electron couple between $Rh_2^{II,II}$ and $Rh_2^{0,II}$ provides photocatalytic proton reduction. The unifying feature in these two systems is the preservation of a metal-metal bond across the four-electron $Rh_2^{0,0}/Rh_2^{0,II}/Rh_2^{II,II}$ series. The formation of a metal-metal bond can provide a strong driving force for reductive elimination from binuclear rhodium cores. In this manner, halogen elimination from the $Rh_2$-dfpma core is facilitated and the catalytic cycles of Schemes 27 and 31 can be successfully turned over.

This result is where the $Rh_2$-dfpma chemistry diverges from the system of Gray and co-workers shown in Scheme 22. Here formation of a metal-metal bond provides a strong driving force for oxidation of a binuclear core, facilitating the multi-electron proton reduction. However, regeneration of the $Rh^I$ hydrogen-generating species requires cleavage of the metal-metal bond in the $[Rh_2^{II,II}(bridge)_4X_2]^{2+}$ photoproduct, adding a 32±4 kcal mol⁻¹ energy disbursement to the energy required for M-X bond cleavage. By maintaining the metal-metal bond throughout the catalytic cycle the $Rh_2$-dfpma system circumvents this operational energy cost.

Halogen reduction by a sacrificial trap drives the catalytic turnover of both the high-valent and the low-valent rhodium systems. Thus, catalytic $H_2$ production is only realized in the presence of an external reductant, which in the $Rh_2$-dfpma systems reduces halogen atoms to halides. The thermodynamic driving force imparted by halogen trapping in the current scheme obviates the design of an energy storing cycle, as an authentic light-to-energy strategy requires isolation of the attendant oxidizing equivalents. As shown in Scheme 32, for cycles based on HX cleavage, the next step must be to design a system capable of delivering both $H_2$ and $X_2$ products.

Scheme 32

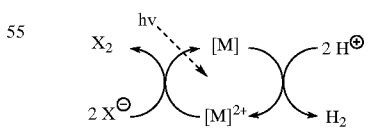

The processes described in the Examples utilize transition metal catalyst complexes as homogenous catalysts. However, the catalysts may be modified to be immobilized on solid surfaces or as solid surfaces to provide a heterogeneous catalytic process. Such solid surfaces may include, but are not limited to, ion exchange resins, silicon containing particles, solid surfaces, for example.

EXAMPLES

General Synthetic Considerations

Synthetic manipulations were conducted in the dry, anaerobic environment provided by a Schlenk-line or by a nitrogen-filled glove box. Solvents for synthesis were reagent grade or better and were dried by following standard procedures. Elemental analyses were performed at H. Kolbe Mikroanalytisches Laboratorium.

The starting materials $[ClRh(CO)_2]_2$ and $[ClRh(cod)]_2$ (Strem) were used as received. The ligands, $MeN(PF_2)_2$, (dfpma), $MeN[P(OMe)_2]_2$ (dmpma) and $MeN[P(OPh)_2]_2$ (dppma) were prepared by published procedures, $MeN[P(OCH_2CF_3)_2]_2$ (tfepma) and $ArN(PX2)_2$ (dfpx) were prepared by adaptation of these procedures.

Chlorine was delivered by means of the iodobenzene adduct, $PhICl_2$. The starting materials triethylamine (Alfa-Aesar), 2,2,2-trifluoroethanol (Aldrich), triphenylphosphine (Alfa-Aesar), trifluoromethanesulfonic acid (Alfa-Aesar), d1-trifluoromethanesulfonic acid (Aldrich) and gaseous reactants, bromine, $H_2$ (BOC Gases, UHP Grade 5), HCl, $D_2$ and DCl (Aldrich), were used as received. The ligand precursor $MeN(PCl_2)_2$ was prepared by following published procedures. The acid HCl was generated by dropping concentrated sulfuric acid (95–98%, Alfa-Aesar) onto anhydrous NaCl (Aldrich). The gas was collected under vacuum and freeze-pump-thaw degassed once before being introduced to the reaction vessel. Anhydrous HBr was used from a lecture bottle (AGA) and freeze-pump-thaw degassed at least twice before being introduced to the reaction vessel.

Spectroscopic and photochemistry experiments employed spectroscopic grade tetrahydrofuran (Burdick & Jackson) and benzene (Aldrich), which were stored over Nak-benzophenone under vaccum or in a glove box. Bis(diflurophosphine)methyl amine was prepared by literature procedures, phosphorous triflouride (Elf Atochen) and 2,6-Lutidrine (Aldrich, redistilled) were used as received. Triphenylphosphine (Strem) and 9,10-dihydroanthracene (Aldrich) were recrystallized at least once and 2,3-dimethylbutadiene (Aldrich) was distilled from $NaBH_4$ and stored under high vaccum.

Physical Methods

All NMR spectra were collected at the MIT Department of Chemistry Instrumentation Facility on a Varian Inova-Unity 500, Varian Unity 300 Spectrometer, or Varian Mercury 300 Spectrometer at 25° C. The NMR solvents, $C_6D_6$, d8-THF, $CD_3CN$ and $CDCl_3$ (Cambridge Isotope Laboratories) were dried using appropriate agents and degassed by at least three freeze-pump-thaw cycles or used as received in glass ampoules. 1H NMR spectra were referenced to TMS using the residual proteo impurities of the given solvent. 1H NMR (300 MHz), 19F and 19F{31P} NMR spectra were referenced to an internal $CFCl_3$ or TMS standard. All chemical shifts are reported using the standard $\delta$ notation in parts-per-million; positive chemical shifts are to a higher frequency from the given reference.

IR spectra were recorded on a Nicolet Impact 410 spectrometer either as KBr pellets or as $CH_2Cl_2$ solutions between NaCl plates. Absorption spectra were recorded on an OLIS-modified CARY-17 Spectrophotometer in quartz cells isolated from air by Teflon valves. Steady-state and time-resolved emission spectra were recorded on isomorphous powders contained in quartz tubes, cooled in quartz finger dewars.

Emission lifetimes were measured on a nanosecond laser instrument utilizing a Coherent Infinity XPO laser as the source. The 3rd-harmonic of a diode pumped Nd:YAG laser passed through a tunable Type I XPO cavity housing a BBO crystal. The 710 nm output, was then doubled to 355 nm ($\leq 7$ ns FWHM and average power of 1 mJ). Solid samples sealed in a quartz tube were excited orthogonal to detection. Scattered excitation light was omitted from the optical detection train by a 366-nm long pass filter. Emitted light from the sample passed through f/4 collimating and f/4 focusing lenses onto the entrance slit of an Instruments SA Triax 320 monochromator. The signal wavelengths were dispersed by a grating possessing a blaze wavelength of 500 nm and a 300 grooves/cm density. Signal was detected with a Hamamatsu R928 PMT. The output from the PMT was fed into a LeCroy 1 GHz 9384CM digital oscilloscope, which was triggered from the Q-switch sync output of the laser. Monochromator operation, data storage and data manipulation were managed by National Instruments driver software (Labview) incorporated into programs written at MIT. Communication between a Dell Optiplex GX-1 computer and the instrumentation was achieved through a IEEE-488 (GPIB) interface. Lifetime decays were obtained at 820 nm and signal averaged at 20 Hz for 1000 pulses.

Hydrogen gas was collected on a vacuum line equipped with Toepler pump and CuO burn tube. Solutions were frozen in liquid nitrogen and the non-condensable gases were passed through three U-traps maintained at liquid nitrogen temperatures. Solutions were typically thawed and re-frozen twice during gas collection to ensure complete removal of dissolved hydrogen. Gas collection was typically continued for an hour after visible signs of gas transfer ceased (i.e., no gas bubbled up past the check valve). The efficiency of the Toepler pump was determined by collecting gas from a flask containing a known volume and pressure of hydrogen, and repeatedly gave collection quantities that were 70–75% of the known quantity; nevertheless, all H2 quantities reported here are the measured values and are not adjusted for this systematic error. Confirmation that the non-condensable gas was hydrogen came from re-circulating the gas over CuO heated to 320° C. for an hour followed by collection of residual non-condensable gas. In all cases, only insignificant gas quantities remained after combustion.

Crystallographic Procedures

X-ray diffraction data were collected on a Siemens 3-circle platform diffractometer equipped with a CCD detector. Measurements were carried out at −90° C. using Mo Kα ($\lambda = 0.71073$ Å) radiation, which was wavelength selected with a single crystal graphite monochromator. Four sets of data were collected using ω scans and a −0.3° scan width. All calculations were performed on a Silicon Graphics Indigo 2 workstation. The data frames were integrated to hkl/intensity and final unit cells were calculated by using the SAINT program v.4.050 from Siemens. The structures were solved and refined with the SHELXTL v5.03 suite of programs developed by G. M. Sheldrick and Siemens Industrial Automation, Inc, 1995.

General Details of X-Ray Data Collection and Reduction

X-ray diffraction data were collected on a Siemens 3-circle platform diffractometer equipped with a CCD detector. Measurements were carried out at −90° C. using Mo Kα ($\lambda = 0.71073$ Å) radiation, which was wavelength selected with a single crystal graphite monochromator. Four sets of data were collected using ω scans and a −0.3° scan width. All calculations were performed on Windows NT workstations equipped with Intel x86 processors. The data frames were integrated to hkl/intensity and final unit cells were calculated by using the SAINT+ program v.6.01 from Bruker AXS, 1999. The structures were solved by the Patterson heavy atom method in conjunction with standard difference Fourier techniques. Fluorine atoms of the —CF3 groups were placed in ideal positions and refined as a rigid group before being allowed to refine freely in the final refinement cycles. Hydrogen atoms were placed in calculated positions using a standard riding model and they were refined isotropically. All data manipulations were conducted within the SHELXTL v5. 1 suite of programs developed by G. M. Sheldrick and Bruker AXS, 1998.

Extended Hückel Calculations

Electronic structure calculations were performed on a Silicon Graphics Indy workstation using the YAeHMOP software, v2.0.69 Valence orbitals for all atoms were used in the basis set. The molecular structure of complex 3 was approximated as the idealized molecule, $Ir2(PH3)_6Cl2$. Iridium-ligand bond lengths and angles for the complex were taken from the crystal structure of 3. Graphic representations of the metal-based HOMO and LUMO for each molecule were generated from the Viewkel output of the YAeMOP calculation and subsequently modified with the ray-tracing program Rayshade.

The extended Hückel calculations of the $Rh_2 0,0$ and $Rh_2^{II,II}$ complexes were performed by using the atomic positions taken from the crystal structures of $Rh_2 0,0$ $(dfpma)_3(PF_3)_2$ and $Rh_2^{II,II}(dfpma)_3Br4$, respectively. For the mixed-valence $Rh_2^{0,II}$ compound, an idealized molecule, $Rh_2^{0,II}(dfpma)_3Br_2(PF_3)$, was constructed with the atomic positions obtained from the crystal structure of $Rh_2^{0,II}$ $(dfpma)_3Br_2(\eta 1\text{-}dfpma)$. The axially coordinated dfpma ligand was replaced by $PF_3$ (P—F bond lengths of 1.57 Å and Rh—P—F angles of 120°); bond angles and lengths were obtained from the average values of the terminal $PF_3$ ligands in the crystal structure of $Rh_2 0,0(dfpma)_3(PF_3)_2$. An idealized conformation was adopted such that the $PF_3$ fluorines were staggered with respect to the three phosphorous atoms of the Rh0 equatorial plane.

General Photochemical Procedures

Small-scale photolysis experiments were carried out in high vacuum cells composed of a 1-cm clear-fused-quartz cuvette and 20-ml solvent reservoir isolated from each other and the atmosphere by Teflon valves. Spectroscopic grade solvent was dried and added to the cell by vacuum transfer. Hydrogen halide gases were freeze-pump-thawed once before transfer into the cell. Large-scale photolysis experiments were performed in 100-ml custom high-vacuum quartz reaction tubes with a path length of ~2.5 cm. Samples were irradiated with light from a 1000-W high pressure Oriel Hg—Xe lamp. The two-inch collimated light beam passed through a distilled water filter to remove infrared wavelengths and long wave pass filters to remove high-energy light prior to focusing and collimating to a diameter of 0.5". The high-energy cut-off filters were replaced with 10-nm bandpass mercury line interference filters (Oriel) for quantum yield experiments. The light flux used for quantum yield determination at a given wavelength was measured using the standard ferrioxalate actinometer just before and just after sample irradiation. The progress of the photoreaction was monitored with absorption spectra recorded on a Spectral Instruments CCD Array Spectrophotometer.

HX Control Reactions

The thermal reactivity of $Rh_2^{II,II}(dfpma)3X4$, $Rh_2^{0,II}$ $(dfpma)_3X\ 2(L)$ and $Rh_2 0,0(dfpma)_3(L)_2$ with HX in THF was evaluated under the conditions employed for photochemical experiments. Thus, a cuvette of a photolysis cell was charged with either a small amount of the rhodium complex. THF was distilled into the solvent reservoir of the cell under vacuum and subjected to three freeze-pump-thaw cycles. Anhydrous HX was then frozen into the reservoir after a single freeze-pump-thaw cycle. The HX/THF solution was thawed and then mixed with the rhodium complex under photographic darkroom lights. An initial absorption spectrum was recorded. The cell was wrapped in foil and maintained at 20° C. overnight. After twelve hours, another UV-Vis spectrum of the sample showed only negligible changes in the absorption profile.

Similarly, thermal hydrogen evolution by the rhodium complexes was investigated by conducting experiments on a larger scale. 50-mL THF solutions of each rhodium complex (ca. 0.1 mM) containing 0.1 M HCl were wrapped in foil and maintained at 20° C. for 12 h. Toepler pump collection of all non-condensables afforded an insignificant quantity of non-condensable gas ($\leq 3\times 10-6$ mol), which did not burn over CuO.

Hydrogen evolution in the absence of a rhodium catalyst was not observed either. A 50-mL THF solution containing 0.1 M HCl was irradiated ($\lambda exc \geq 338$ nm) for 12 h at 20° C. Subsequent Toepler pump collection of non-condensable gases afforded $<2\times 10-6$ mol gas that did not combust over CuO.

Example 1

Preparation of tfepma

Dropwise addition of $CF_3CH_2OH$ (36.8 g, 368 mmol, 4.25 equiv) to a −80° C. solution of triethylamine (36.4 g, 360 mmol, 4.16 equiv) and $MeN(PCl_2)_2$ (20.15 g, 86.56 mmol, 1 equiv) in 500 mL of diethyl ether results in a rapid and exothermic reaction, with concomitant formation of the white [$Et_3NH$]Cl salt. After warming to room temperature, the mixture was stirred for 24 h. Filtration followed by rotary evaporation to remove ether afforded impure product as a clear, viscous liquid. Distillation under reduced pressure (75–85° C., 0.5 torr) was accompanied by some decomposition of the ligand, necessitating a second filtration to give 23.6 g (58% yield) of pure ligand. 1H NMR (300 MHz, $C_6D_6$) δ/ppm: 2.506 (td, 3.898 Hz, 0.600 Hz, 3H), 3.55 (dp, 17.12 Hz, 4.4 Hz, 8H). 31P{1H} NMR (121.4 MHz, $C_6D_6$) δ/ppm: 148.614 (s). 19F NMR (282MHz, $C_6D_6$) δ/ppm: −76.90 (m).

Example 2

Preparation of Bis(dichlorophosphine)-3,5-xylidene (dcpx)

Freshly distilled 3,5-dimethyl aniline (3,5-xylidene, ~97 g, 0.8 mol) was transferred under $N_2$ with a cannula to a flask containing rapidly stirred $PCl_3$ (450 g, 3.28 mol) at −10° C. White solid began precipitating immediately with aniline addition. When addition was complete, the mixture was heated to reflux until all solid had dissolved (48 hr). The solution was then cooled to room temperature and stored at −35° C. overnight. A mass of white crystals was precipitated from solution. The solid was collected by filtration and recrystallized from hot hexanes to afford 159 g (62% yield) of product. A second crop of product was obtained from the reaction solution by reducing the $PCl_3$ volume to one fourth and cooling overnight. Recrystallization gave an additional 40 g (16% yield) of product. 31P{1H} NMR (282.5 MHz, $C_6D_6$) δ/ppm: 157.04 (s).

Example 3

Preparation of Bis(difluorophosphine)-3,5-xylidene (dfpx)

Solid $SbF_3$ (76.1 g, 0.426 mol) and dcpx (50.4 g, 0.156 mol) were loaded into a 500-mL flask equipped with stir bar, reflux condenser and nitrogen inlet. Pentane (250 mL) was added and the vessel was purged for 5 minutes with $N_2$. The mixture was then heated to reflux for 3 hr. Upon cooling back down to room temperature, the pentane solution was decanted and the solid antimony residue washed with a 100-mL aliquot of pentane. The washings were added to the original reaction solution and the solvent was removed on a rotary evaporator to afford 35 g (87% yield) of crude product. White crystalline material is readily obtained by sublimation at 40–50° C. (0.1 torr). 1H NMR (300 MHz, $C_6D_6$) δ/ppm: 1.94 (s, 6H), 6.60 (s, 1H), 6.68 (s, 2H). 31P NMR (121.4 Hz, $C_6D_6$) δ/ppm: 133.22 (|1JPF+2JPF|=1514 Hz). $^{19}$F NMR (282.4 Hz, $C_6D_6$) δ/ppm: −68.46 (|1JPF+2JPF|=1514 Hz).

Example 4

Preparation of Bis(bis(trifluoroethyl)phosphite)-3,5-xylidene (tfepx)

Pyridine (20 g, 253 mmol) and dcpx (19.8 g, 61.3 mmol) were added under $N_2$ to 500 mL of ether in a 1 L flask. The solution was cooled in a dry ice/acetone bath. 2,2,2-Trifluoroethanol (25 g, 247 mmol) was added slowly with a syringe to the rapidly stirred solution, resulting in an exothermic reaction and formation of a white solid. After the addition, the mixture was warmed slowly and stirred at room temperature overnight. The white solid was removed by filtration, and the ether stripped from the mother liquor by a rotary evaporator, leaving a yellow solid. Recrystallization from pentane at −80° C. afforded the product as a white solid (17.41 g, 49% yield). Concentration of the pentane mother liquor to 50 mL followed by cooling to −80° C. provided a second crop of product (10.23 g, 29% yield). 1H NMR (300 MHz, $C_6D_6$) δ/ppm: 2.09 (s, 6H), 3.62 (dm, 33 Hz, 8H), 6.64 (s, 1H), 6.86 (s, 2H). 31P NMR (121.4 Hz, $C_6D_6$) δ/ppm: 141.11 (s). 19F NMR (282.4 Hz, $C_6D_6$) δ/ppm: −74.86 (m).

Example 5

Preparation of $Rh_2^{0,II}(dfpma)3X\ 2L$ (1-L, 2-L) and $Rh_2^{0,II}(dfpx)_3X2L$ (22)

In a typical experiment, $[XRh(cod)]_2$ is dissolved in 10 mL of benzene giving a pale orange solution. Successive additions of three equivalents of dfpma or dfpx and one equivalent of L (L=CNR, P(OR)$_3$, PR$_3$) results in rapid color changes finally giving a dark red solution. Stirring overnight precipitates an orange to red powder depending on L. Precipitation is completed by the addition of an equal volume of pentane. The product is collected by filtration and washed three times with 1:1 benzene/pentane and dried in vacuo. Typical yields are 80–90% based on $[ClRh(cod)]_2$. NMR spectroscopy is useful for fingerprinting the compound: 1H NMR shows two peaks in the 2.6–3.2 ppm region integrating in a 2:1 ratio for the methyl groups of the bridging dfpma ligands plus any signature resonances for the axial L ligand; $^{19}$F NMR shows a complex spectrum that simplifies to a six line pattern upon 31P decoupling. See Results and Discussion.

Example 5

Preparation of $Rh_20,0(dfpma)_3L_2$ (3-L)

In a typical reaction, $[ClRh(cod)]_2$ is stirred with three equivalents of dfpma, two equivalents of cobaltocene and two equivalents of L (L=CNR, P(OR)$_3$, PR$_3$) in diethyl ether or THF. $[CoCp_2]Cl$ precipitates as a yellow powder and is removed by filtration. The solvent is stripped and the residue taken up in a minimal amount of $CH_2Cl_2$, filtered and diluted with pentane. Cooling to −80° C. affords the product as yellow to orange micro crystals in 40–80% yield depending on L. 1H and 19F NMR spectroscopy are useful for product characterization: a single methyl resonance is observed in the 1H NMR spectrum in the 2.3–2.7 ppm region for the bridging dfpma ligands in addition to any signature resonances for L; the 19F NMR shows a simple doublet near −40 ppm displaying a 1JFP=1100–1300 Hz.

Example 6

Preparation of $Rh_2^{II,II}(dfpma)3X4$ (4 and 5)

In a typical experiment, $[XRh(cod)]_2$ is treated with three equiv of dfpma or dfpx in $CH_2Cl_2$. Excess oxidant is added in excess of 5 equiv (as either $PhICl_2$ or $Br_2$), resulting in an exothermic reaction. The reaction mixture is stirred for a few hours and the solvent volume reduced to 3 mL. Pentane addition precipitates the product as a yellow powder for X=Cl or orange-red powder for X=Br in 90–95% yield after washing with pentane and drying in vacuo. NMR spectroscopy can be used to fingerprint the complexes: 1H NMR shows a multiplet at ca. 3.2 ppm for the bridging dfpma ligands; the 19F NMR spectrum is complex, but simplifies upon 31P decoupling to a five line pattern. See Results and Discussion section.

Example 7

Preparation of $Rh_2(dmpma)_2Cl_2(\mu\text{-CO})(CO)$ (6)

An 8-mL THF solution of $[ClRh(CO)_2]_2$ (203 mg, 0.522 mmol) was treated dropwise with dmpma (238 mg, 1.11 mmol) dissolved in 2 mL of THF. The solution turned red with gas evolution as ligand was added. The solution was stirred at room temperature for 15 minutes, then a 10 mL aliquot of hexanes was added. Cooling the solution to −35° C. overnight caused 338 mg (85% yield) of orange powder to be deposited. Anal. Calcd for $C_{12}H_{30}Cl_2N_2O10P_4Rh_2$: C, 18.89; H, 3.96; N, 3.67. Found C, 19.01; H, 3.67; N, 3.50. 1H NMR (300 MHz, $C_6D_6$) δ/ppm: 2.51 (p, 3.6 Hz, 3H), 3.817 (dp, 60.0 Hz, 3.6 Hz, 12H). 31P NMR (121.4 Hz, $C_6D_6$) δ/ppm: 132.81 (|1JPRh+nJPRh|=142 Hz). IR (CHCl$_3$) νCO/cm−1: 1989 (vs), 1808 (s).

Example 8

Preparation of $Rh_2(dppma)_2Cl_2(CO)_2$ (7)

An 8-mL THF solution of $[ClRh(CO)_2]_2$ (212 mg, 0.545 mmol) and a 2-mL THF solution of dppma (508 mg, 1.10 mmol) were frozen in a liquid $N_2$ cold well. The solutions were removed from cold well and the solution of the ligand was added dropwise to the rapidly stirred solution of the rhodium carbonyl dimer immediately after thawing. The solution turned purple with gas evolution as ligand was added. After addition, the purple solution was added to 150 mL of cold pentane, prompting a fine purple powder to precipitate. The solid was washed with cold pentane and dried in vacuo to yield 412 mg (60% yield) of product. Anal. Calcd for $C_{52}H_{46}Cl_2N_2O_{10}P_4Rh_2$: C, 49.59; H, 3.68; N, 2.22. Found: C, 49.23; H, 3.72; N, 2.56. IR (KBr) νCO/cm−1: 2009 (vs). Recrystallization of this compound results in isomerization to $Rh_2(dppma)_2Cl_2(\mu\text{-CO})_2$ in quantitative yield. 1H NMR (300 MHz, $C_6D_6$) δ/ppm: 2.860 (t, 3.6 Hz, 3H), 6.8–7.5 (m, 20H), 31P NMR (121.4 Hz, $C_6D_6$) δ/ppm: 122.61 (|1JPRh+nJPRh|=170 Hz IR (KBr) νCO/cm−1: 1828 (vs).

Example 9

Preparation of [ClRh(dppma)]$_2$ (11)

Rh$_2$(dppma)$_2$Cl$_2$(CO)$_2$ (137 mg, 0.109 mmol) was dissolved in 12 mL of benzene in a Schlenk tube. The purple solution was heated to reflux under N$_2$ prompting a color change to orange. The solution was cooled to room temperature and 10 mL of pentane was added to precipitate 92 mg (70% yield) of yellow product. Anal. Calcd for C$_{50}$H$_{46}$Cl$_2$N$_2$O$_8$P$_4$Rh$_2$: C, 49.90; H, 3.85; N, 2.33. Found: C, 50.01; H, 3.84; N, 2.16. 1H NMR (300 MHz, C$_6$D$_6$) δ/ppm: 2.394 (t, 12.0 Hz, 3H), 6.82 (t, 7.5 Hz, 4 H), 6.96 (tt, 7.5 Hz, 2.1 Hz, 8), 7.43 (d, 8.1 Hz, 8H). 31P NMR (121.4 Hz, C$_6$D$_6$)δ/ppm 91.13 (d, 280 Hz).

Example 10

Preparation of Rh$_2$(tfepma)$_2$Cl$_2$(CO)$_2$ (14)

A scintillation vial containing [ClRh(CO)$_2$]$_2$ (99 mg, 0.255 mmol) in 5 mL of CH$_2$Cl$_2$ was treated with tfepma (255 mg, 0.523 mmol) resulting in gas evolution and the solution to turn dark red. The solution was stirred at room temperature for 5 minutes after gas evolution ceased. The volume was reduced to 1 mL by vacuum distillation and 10 mL of pentane was added to cause an orange powder to precipitate. The solid was collected by filtration and washed with 4×2 mL of pentane. The yield of the bright orange-yellow product was 206 mg (62% yield). Anal. Calcd for C$_{20}$H$_{22}$Cl$_2$F$_{24}$N$_2$O$_{10}$P$_4$Rh$_2$: C, 18.38; H, 1.70; N, 2.14. Found: C, 18.42; H, 1.65; N, 2.25. 1H NMR (500 MHz, CDCl$_3$) δ/ppm: 2.94 (t, 3.5 Hz, 3H), 4.45–4.77 (m, 8H). 31P NMR (202.5 Hz, CDCl3) δ/ppm: 131.16 (|1JPRh+nJPRh|= 149 Hz). IR (CHCl$_3$) vCO/cm-1: 2007 (vs), 1820 (m).

Example 11

Preparation of Rh$_2$(tfepma)$_2$Cl$_2$(μ-CO)$_2$ (15)

A Schlenk tube was charged with [ClRh(CO)$_2$]$_2$ (92 mg, 0.235 mmol) and tfepma (238 mg, 0.489 mmol) in 15 mL of toluene. The orange solution was heated to reflux under N$_2$ overnight. Cooling to room temperature followed by the addition of 30 mL of pentane caused 290 mg (95% yield) of a salmon colored powder to precipitate.

Anal. Calcd for C$_{20}$H$_{22}$Cl$_2$F$_{24}$N$_2$O$_{10}$P$_4$Rh$_2$: C, 18.38; H, 1.70; N, 2.14Found: C, 18.35; H, 1.43; N, 2.26. 1H NMR (500 MHz, C$_6$D$_6$) δ/ppm: 2.52 (p, 4.0 Hz, 3H), 4.22 (dm, 83 Hz, 4H), 4.523 (m, 4H). 31P NMR (121.4 Hz, C$_6$D$_6$) δ/ppm: 128.40 (|1JPRh+nJPRh|=164 Hz). IR (CHCl$_3$) vCO/cm-1: 1824 (vs).

Example 12

Preparation of Rh$_2$(tfepma)$_3$Cl$_2$(CO) (16)

An 8-mL THF solution of [ClRh(CO)$_2$]$_2$ (203 mg, 0.522 mmol) was treated by the dropwise addition of with dmpma (238 mg, 1.11 mmol) dissolved in 2 mL of THF. The solution turned red with gas evolution as ligand was added. The solution was stirred at room temperature for 15 minutes, then a 10 mL aliquot of hexanes was added. The mixture was cooled to −35° C. overnight, depositing 338 mg (85% yield) of orange powder. 1H and 31P NMR spectra indicate immediate formation of [ClRh(tfepma)]$_2$ upon dissolution in CDCl$_3$. Anal. Calcd for C$_{28}$H$_{33}$Cl$_2$F$_{36}$N$_3$O$_{13}$P$_6$Rh$_2$: C, 19.04; H, 1.88; N, 2.38. Found: C, 19.14; H, 1.94; N, 2.09. IR (KBr) vCO cm-1: 2020 (vs).

Example 13

Preparation of [ClRh(tfepma)]$_2$ (17)

Tfepma (200 mg, 0.410 mmol) was added to BrRh(PPh$_3$)$_3$ (151 mg, 0.156 mmol) in CH$_2$Cl$_2$ giving a bright yellow solution. The solution was stirred for 6 hr then concentrated to 2 mL by vacuum distillation. Pentane (6 mL) was added and the solution was cooled to −35° C.; yellow crystals (60 mg, 50% yield) were deposited overnight. Anal. Calcd for C$_{18}$H$_{22}$Cl$_2$F$_{24}$N$_2$O$_8$P$_4$Rh$_2$: C, 17.28; H, 1.77; N, 2.24. Found: C 18.76; H, 1.92; N, 2.36. 1H NMR (300 MHz, C$_6$D$_6$) δ/ppm: 1.99 (p, 5.7 Hz, 3H), 4.34 (m, 4H), 4.64 (m, 4H). 31P NMR (202.5 Hz, C$_6$D$_6$) δ/ppm: 109.9 (d, 179.6 Hz).

Example 14

Preparation of Rh$_2$(tfepma)$_3$(CNtBU)$_2$ (18)

A mixture of [ClRh(CO)$_2$]$_2$ (82.5 mg, 0.212 mmol), tfepma (326 mg, 0.669 mmol), cobaltocene (88 mg, 0.466 mmol) and tert-butylisonitrile (42 mg, 0.506 mmol) in Et$_2$O was stirred at room temperature for 3 hr. Solid [CoCp$_2$]Cl was removed by filtration leaving an orange solution. The solvent was stripped and the residue taken up in pentane. Cooling to −35° C. overnight afforded 349 mg (90% yield) of an orange powder. 1H NMR (500 MHz, CDCl$_3$) δ/ppm: 1.41 (s, 18H), 2.70 (s, 9H), 4.12 (dp, 51 Hz, 8 Hz, 24H). 31P NMR (121.4 Hz, C$_6$H$_6$) δ/ppm: 142.1 (|1JPRh+nJPRh|=216 Hz).

Example 15

Preparation of syn-Rh$_2$(tfepma)$_3$Cl$_4$ (19)

A 10-mL CH$_2$Cl$_2$ solution of [ClRh(CO)$_2$]$_2$ (104 mg, 0.270 mmol) was treated successively with tfepma (393 mg, 0.810 mmol) dissolved in 2 mL of CH$_2$Cl$_2$ and solid dichloroiodobenzene (182 mg, 0.660 mmol). The orange solution was stirred at room temperature for 15 min, and then concentrated to a few milliliters. Pentane addition prompted precipitation of 260 mg (53% yield) of product as a yellow powder.

Anal. Calcd for C$_{27}$H$_{33}$Cl$_4$F$_{36}$N$_3$O$_{12}$P$_6$Rh$_2$: C, 17.93; H, 1.84; N, 2.32Found: C, 18.12; H, 1.95; N, 2.34. 1H NMR (500 MHz, CDCl$_3$) δ/ppm: 2.89 (7, 7.7 Hz, 6H), 2.99 (t, 22 Hz, 3H), 4.32–4.55 (m, 8H), 4.63 (m, 2H), 4.78 (m, 4H), 5.07 (m, 2H), 5.15 (m, 4H), 5.41 (m, 2H), 5.58 (m, 2H). 31P NMR (202.5 Hz, CDCl$_3$) δ/ppm: 105.62 (m), 109.79 (m).

Example 16

Preparation of anti-Rh$_2$(tfepma)$_3$Cl4 (20)

A Schlenk tube was charged with [ClRh(cod)]$_2$ (514 mg, 1.04 mmol), tfepma (1.58 g, 3.24 mmol) and dichloroiodobenzene (420 mg, 1.5 mmol) in 35 mL of toluene. The solution was refluxed under N$_2$ for 60 min to give a red solution. Cooling to 0° C. followed by pentane addition caused 1.27 g (68% yield) of orange product to precipitate. The solid was washed with pentane and dried. Anal. Calcd for C$_{27}$H$_{33}$Cl$_4$F$_{36}$N$_3$O$_{12}$P$_6$Rh$_2$: C, 17.93; H, 1.84; N, 2.32. Found: C, 18.09; H, 2.02; N, 2.14. 1H NMR (500 MHz, CDCl$_3$) δ/ppm: 2.88 (m, 9H), 4.26 (m, 2H), 4.30–4.52 (m, 8H) 4.61 (m, 4H), 4.80 (m, 2H), 5.12–5.30 (m, 8H). 31P NMR (202.5 Hz, CDCl$_3$) δ/ppm: 100.2 (m), 105.4 (m), 109.9.(m), 112.4 (m), 114.8 (m).

Example 17

Preparation of Rh$_2^{0,II}$(tfepma)$_3$Cl$_2$ (21)

In the glove box, [ClRh(cod)]$_2$ (0.518 g, 1.05 mmol) and tfepma (1.58 g, 3.24 mmol) were combined with 25 mL of CH$_2$Cl$_2$ in a 50 mL flask. The solution color progressed from orange to green and finally red. The red solution was set aside for two days, during which time a green microcrystalline solid was deposited (680 mg, 37% yield). This solid was collected and the mother liquor concentrated to 10 mL. After several days a second crop of product was collected (150 mg, 8% yield).

Example 18

Preparation of [ClRh(tfepx)]$_2$($\mu$-tfepx) (33)

Three equivalents of tfepx (740 mg, 1.28 mmol) was added to a 10-mL CH$_2$Cl$_2$ solution of [ClRh(cod)]$_2$ (203 mg, 0.412 mmol). The solution color immediately changed from yellow-orange to olive green. A bright yellow solid began to precipitate after an hour, concentration of the solvent volume to a few milliliters afforded 230 mg (48% yield) of product, which was washed with pentane and dried. The 1H NMR spectrum of analytically pure samples of 43 suggests the presence of multiple species in solution, yet the 31P NMR shows only two phosphorus resonances. 1H NMR (500 MHz, CD$_3$CN) $\delta$/ppm: 2.21 (s), 2.23 (s), 2.29 (s), 4.69 (m), 4.79 (m), 4.97 (m), 6.74 (s), 6.85 (s), 6.89 (s), 6.95 (s), 7.05 (s), 7.23 (s), 7.86 (s). 31P NMR (121.5 Hz, CD$_3$CN) $\delta$/ppm : 108.8 (d, 2JRhP=181 Hz), 111.1 (d, 2JRhP=252 Hz).

Example 19

Preparation of Ir$_2$I,II(dfpma)$_2$Cl4(cod) (31)

A 20-mL scintillation vial containing 202 mg of [ClIr(cod)]$_2$ (0.301 mmol) in 10 mL of CH$_2$Cl$_2$ was successively treated with 155 mg of dfpma (0.928 mmol) and 455 mg of PhICl$_2$ (1.66 mmol). The solution was stirred at ambient, glove-box temperature for a few hours and then the volume was reduced to ~3 mL. Addition of a 10 mL aliquot of pentane precipitated a sticky yellow-orange solid, which was collected and repeatedly washed with pentane to afford 154 mg of a yellow-orange powder (53% yield). 1H NMR (300 MHz, C$_6$D$_6$) $\delta$/ppm: 2.506 (td, 3.898 Hz, 0.600 Hz, 3H), 3.55 (dp, 17.12 Hz, 4.4 Hz, 8H). 31P{1H} NMR (121.4 MHz, C$_6$D$_6$) $\delta$/ppm: 148.614 (s). 19F NMR (282 MHz, C$_6$D$_6$) $\delta$/ppm: −76.90 (m).

Example 20

Preparation of Ir$_2$I,III(dppma)$_2$\{MeN[P(OPh)$_2$][P(OPh)(OC$_6$H4)]\}HCl$_2$ (32)

In a glove box, 137 mg of [ClIr(cod)]$_2$ (0.204 mmol) and 282 mg of dppma (0.608 mmol) were combined in 20 mL of benzene in a three-neck round-bottomed flask. The flask was fitted with a reflux condenser and nitrogen inlet, removed from the box and heated to reflux for 12 h under a N$_2$ atmosphere provided by a Schlenk line. The solvent volume was reduced to 5 mL by vacuum distillation and 15 mL of pentane was added to precipitate a fluffy yellow solid, which was collected and washed with 3×15 mL of pentane to yield 299 mg of product (80% yield). Anal. Calcd For C$_{75}$H$_{69}$Cl$_2$Ir$_2$N$_3$O$_{12}$P$_6$: C, 48.81; H, 3.77; N, 2.28. Found: C, 48.61; H, 3.73; N, 2.42. 1H NMR (300 MHz, CD$_3$CN) $\delta$/ppm: −17.08 (dtd, 213 Hz, 16.5 Hz, 12.3 Hz, 1H), 2.1–3.2 (m, 9H), 6.0–7.9 (m, 59H).

Example 21

Preparation of Ir$_2$$^{0,II}$(tfepma)$_3$Cl$_2$ (33)

In a nitrogen atmosphere, 734 mg (0.493 mmol) of dfpma was added to a solution of 331 mg (0.493 mmol) of [ClIr(cod)]$_2$ dissolved in 15 mL of CH$_2$Cl$_2$. The mixture was stirred at room temperature for 24 h during which a dark precipitate formed. A green powder precipitated from solution over several days. The solid was collected by filtration, washed with 5 mL of benzene and three 5-mL aliquots of pentane and then dried in vacuo to yield 590 mg (62%) of the analytically pure product. Anal. Calcd for C$_{27}$H$_{33}$Cl$_2$F$_{36}$Ir$_2$N$_3$O$_{12}$P$_6$: C, 16.92; H, 1.74; N, 2.19; P, 9.70. Found. 17.06; H, 1.65; N, 2.29; P, 9.63. 1H NMR (CD$_3$CN, 300 MHz) $\delta$/ppm: 2.576 (t, 10.5 Hz, 3H), 2.763 (s, 6H), 4.0–5.5 (m, 24H). 31P NMR (CD$_3$CN, 121 MHz) $\delta$/ppm: 32.710 (s), 47.665 (dd, 299 Hz, 292 Hz), 64.702 (m), 70.509 (m), 94.002 (m).

Dark green crystals of 33 are obtained by dissolving microcrystalline samples of the compound in a minimal amount of MeCN, diluting the resulting solution with CH$_2$Cl$_2$, filtering and layering the filtrate with an alkane solvent. Occasionally, a small crop of large yellow crystals (34) would co-precipitate from solution. The 31P NMR spectra of the green-brown crystals of 33 and the yellow crystals of 4 dissolved in CD$_3$CN are identical; however, the 1H NMR spectrum of 34 shows an additional peak at 1.963 ppm, attributed to approximately one equivalent of uncoordinated proteo MeCN.

Example 22

Reaction of 3 with Donor Ligands (35-L)

For illustrative purposes, the preparation of Ir$_2$$^{0,II}$(tfepma)$_3$Cl$_2$(PEt$_3$) (35-PEt$_3$) is described; the preparation of other L derivatives follow similar methodology. In an N$_2$ atmosphere, PEt$_3$ (19 mg, 0.160 mmol) was added to 33 (102 mg, 0.053 mmol) suspended in 10 mL of CH$_2$Cl$_2$ at room temperature. The solution immediately turned yellow and all solids dissolved. The solution was concentrated and 10 mL of pentane was added. Cooling to −35° C. overnight caused a yellow microcrystalline solid to precipitate from solution. Yield, 87 mg (81%). Anal. Calcd for C$_{33}$H$_{48}$Cl$_2$F$_{36}$Ir$_2$N$_3$O$_{12}$P$_7$: C, 19.22; H, 2.12; N, 2.80. Found: C, 19.58; H, 2.55; N, 2.12. 1H NMR (CD$_3$CN, 300 MHz) $\delta$/ppm: 1.230 (dt, 13.2 Hz, 7.6 Hz, 9H), 2.114 (dq, 7.4 Hz, 7.5 Hz, 6H), 2.559 (dd, 11.7 Hz, 8.7 Hz, 3H), 2.648 (m, 6H), 4.040 (m, 2H), 4.29–4.87 (m, 18H), 5.010 (m, 4 H). 31P NMR (CD$_3$CN, 121 MHz) $\delta$/ppm: −18.189 (dd, 205 Hz, 18.8 Hz), 44.238 (t, 288 Hz), 53.340 (d, 208 Hz), 65.967 (t, 71.4 Hz), 97.496 (dm, 291 Hz).

NMR data for Ir$_2$$^{0,II}$(tfepma)$_3$Cl$_2$(CNtBu) (5-CNtBu). 1H NMR (CD$_3$CN, 300 MHz) □/ppm: 1.510 (s, 9H), 2.494 (dd, 12.3 Hz, 9.0 Hz, 3H), 2.730 (dt, 9.0 Hz, 3.6 Hz, 6H), 4.15–4.95 (m, 24H). 31P NMR (CD$_3$CN, 121 MHz) □/ppm: 46.056 (t, 290 Hz), 52.509 (s), 72.530 (t, 75.4 Hz), 93.960 (dm, 290 Hz).

NMR data for [Bu4N][Ir$_2$$^{0,II}$(tfepma)$_3$Cl$_2$(Br)] (5-Br—). 1H NMR (CD$_3$CN, 202.5 MHz) $\delta$/ppm: 0.961 (t, 7.39 Hz, 12H), 1.352 (dq, 15.0 Hz, 7.38 Hz, 8H), 1.604 (m, 8H), 3.109 (m, 9H), 4.2–6.0 (m, 24H). 31P{1H} NMR (CD$_3$CN) $\delta$/ppm: 35.015 (s, 1P) 41.074 (t, 303 Hz, 1P), 70.748 (t, 70.6 Hz, 2P), 98.240 (dm, 308 Hz, 2P).

Example 23

Halide Removal from 33

Thallium hexafluorophosphate (40 mg, 0.11 mmol) was added to 33 (100 mg, 0.052 mmol) dissolved in 4 mL of MeCN. A rapid color change was accompanied by the formation of a white precipitate. The mixture was stirred at ambient temperature for 3 h, then concentrated to 1 mL and filtered. The remaining MeCN was removed and the residue washed with 10 mL of a 1:5 mixture of $CH_2Cl_2$ and pentane. Drying gave 102 mg (87% yield) of 6 as a yellow powder that slowly turns reddish under prolonged drying. 1H NMR ($CD_3CN$, 300 MHz) δ/ppm: 2.70 (t, 12 Hz, 3H), 2.83 (s, 6H), 4.1–4.7 (m, 24H). 31P NMR ($CD_3CN$, 121.5 MHz) δ/ppm: −143 (sept, 730 Hz), 28 (s, 1P), 50 (t, 273 Hz, 1P), 57 (t, 60 Hz, 2P), 89 (dm, 300 Hz, 2P)

Example 24

Preparation of $Ir_2I,III$ (tfepma)$_3$Cl4 (37)

$PhICl_2$ (20 mg, 0.073 mmol, 1.3 equiv) in 2 mL of $CH_2Cl_2$ was added to an 8-mL $CH_2Cl_2$ suspension of 33 (105 mg, 0.055 mmol, 1 equiv). As 33 reacts, the suspension is brought into solution, which turns bright yellow and a yellow solid subsequently forms; to ensure complete reaction, stirring was continued at room temperature for 2 h after the onset of precipitation. Addition of pentane followed by filtration gave 54 mg (37% yield) of a bright yellow powder. Single crystals of 37 were grown from saturated solutions of the complex in $CH_2Cl_2$, layered with heptane. Anal. Calcd for $C_{27}H_{33}Cl_4F_{36}Ir_2N_3O_{12}P_6$: C, 16.32; H, 1.67; N, 2.11; P, 9.35. Found: C, 16.37: H, 1.78; N, 2.09; P, 9.40. 1H NMR ($CD_3CN$) δ/ppm: 2.71 (t, 8.40 Hz, 3H), 2.87 (t, 9.38 Hz, 3H), 2.93 (t, 7.78 Hz, 3H), 4.3–4.6 (m, 6H), 4.7–5.1 (m, 12H), 5.40 (ddqd 179.6 Hz, 12.14 Hz, 8.80 Hz, 2.93 Hz, 2H), 5.91 (ddq, 151.1 Hz, 12.20 Hz, 8.81 Hz, 2H). 31P{1H} NMR ($CD_3CN$) δ/ppm: 9.24 (dt, 80.50 Hz, 25.86 Hz, 1P), 13.14 (ddd, 900.7 Hz, 79.93 Hz, 31.16 Hz, 1P), 54.98 (dt, 136.2 Hz, 29.08 Hz, 1P), 57.11 (dt, 125.6 Hz, 28.48 Hz, 1P), 66.46 (dt, 124.5 Hz, 30.50 Hz, 1P), 74.31 (ddd, 900.8 Hz, 136.6 Hz, 30.89 Hz, 1P).

Example 25

Preparation of $Ir_2^{II,II}$(tfepma)$_2$Cl$_4$(MeCN)$_2$ (38

A solution of 33 (150 mg, 0.078 mmol, 1 equiv) and $PhICl_2$ (150 mg, 0.50 mmol, 6 equiv of $Cl_2$) in 10 mL $CH_3CN$ was heated to reflux for 48 h. The solvent was removed under reduced pressure and the residue was taken up in 5 mL of $CH_2Cl_2$. The solution was filtered and then concentrated to 2 mL by vacuum distillation. Addition of a 10-mL aliquot of pentane caused 100 mg (81% yield) of 38 to precipitate as a yellow powder, which was collected and dried in vacuo. Layering saturated $CH_2Cl_2$ solutions of the complex with heptane gave single crystals of 8. Anal. Calcd for $C_{22}H_{28}Cl_4F_{24}Ir_2N_4O_8P_4$: C, 16.70; H, 1.78; N, 3.54. Found: C, 16.58: H, 1.88; N, 3.52. 1H NMR ($CD_3CN$) δ/ppm: 2.80 (t, 8.13 Hz, 6H), 4.48 (q, 2.93 Hz, 4H), 4.6–4.8 (m, 4H), 4.95–5.15 (m, 6H), 5.46 (dqd, 12.31 Hz, 8.93 Hz, 3.62 Hz, 2H). 31P{1H} NMR δ/ppm: 54.97 (dd, 121.4 Hz, 42.41 Hz, 2P), 57.87 (dd, 121.4 Hz, 41.64 Hz, 2P).

Example 26

Reaction of 33 with HCl

A suspension of 33 (120 mg, 0.063 mmol) in 10 mL of $CH_2Cl_2$ was purged with HCl gas. Within 5 min, all solid had dissolved to give a yellow solution. Immediate solvent removal gave 131 mg (97% yield) of 39 with an empirical formula $Ir_2$(tfepma)$_3$HCl$_3$. Anal. Calcd. for $C_{27}H_{34}Cl_3F_{36}Ir_2N_3O_{12}P_6$: C, 16.60; H, 1.75; N, 2.15; P, 9.52. Found: C,16.57: H, 1.84; N, 2.08; P, 9.68. 1H NMR ($CD_3CN$) δ/ppm: −12.985 (m, 1H), 2.757 (t, 11.2 Hz, 3H), 2.916 (s, 6H), 4.0–5.9 (m, 24H). 31P{1H} NMR ($CD_3CN$) δ/ppm: 35.712 (ddd, 795 Hz, 44 Hz, 18.9 Hz, 1P), 47.878 (dd, 752 Hz, 49 Hz, 1P), 63.794 (dd, 147 Hz, 34 Hz, 1P), 66.339 (dd, 146 Hz, 35 Hz, 1P), 80.880 (ddd 795 Hz, 146 Hz, 54 Hz, 29 Hz, 1P), 88.657 (dddd, 751 Hz, 147 Hz, 44 Hz, 29 Hz, 1P). IR (KBr) vIr—H/cm−1: 203

When solvent was not immediately removed, and the solution was stirred for 24 h at room temperature, a very pale yellow solid precipitated from solution. NMR analysis of this solid in $CD_3CN$ revealed the formation of an isomer of $Ir_2$(tfepma)$_3$HCl$_3$, 40, in 68% isolated yield. The preparation of 10 on a larger scale proceeds smoothly by treating a suspension of 33 (1.153 g, 0.6016 mmol) in 150 mL of $CH_2Cl_2$ with HCl gas for 10 min. The flask headspace was purged with $N_2$ and the solution was stirred for 24 h. The volume of the mixture was reduced to ca. 40 mL by distillation under reduced pressure. Addition of 60 mL of pentane facilitated the precipitation of 640 mg (54%) of analytically pure 40, which was washed with pentane and dried in vacuo. Single crystals of this complex are readily obtained by layering a $CH_2Cl_2$ solution of 40 with heptane. Anal. Calcd. for $C_{27}H_{34}Cl_3F_{36}Ir_2N_3O_{12}P_6$: C, 16.60; H, 1.75; N, 2.15; P, 9.52. Found: C, 16.47: H, 1.74; N, 2.15; P, 9.58. 1H NMR ($CD_3CN$) δ/ppm: −10.261 (ddt, 178 Hz, 18.2 Hz, 12.2 Hz, 1H), 2.65 (t, 10.84 Hz, 3H), 2.77 (t, 7.49 Hz, 3H), 2.89 (t, 7.74 Hz, 3H), 4.1–5.1 (m, 21H), 5.3–5.5 (m, 1H), 5.7–6.1 (m, 2H). 31P{1H} NMR ($CD_3CN$) δ/ppm: 21.64 (tp, 34.17 Hz, 21.68 Hz, 1P), 26.61 (dtd, 761.5 Hz, 33.05 Hz, 10.27 Hz, 1P), 64.38 (dddd, 130.6 Hz, 35.66 Hz, 21.52 Hz, 10.06 Hz, 1P), 67.79 (ddd, 162.2 Hz, 36.45 Hz, 19.99 Hz, 1P), 82.15 (dddd, 760.1 Hz, 130.8 Hz, 22.02 Hz, 13.08 Hz, 1P), 86.40 (dm, 162.6 Hz, 1P). IR (KBr) vIr—H/cm−1: 2115.

Example 27

Reaction of 33 with Triflic Acid

An NMR tube was charged with 33 (74 mg, 0.039 mmol, 1 equiv) in 0.7 mL of $CD_3CN$. The solution was treated with 34 μL of HOTf (OTf =$OSO_2CF_3$) (0.39 mmol of HOTf, 10 equiv), delivered via auto pipette. Upon mixing, the solution turned pale yellow. [HIr$_2$(tfepma)$_3$Cl$_2$(MeCN)]OTf (41) was obtained quantitatively. Alternatively, treatment of a suspension of 33 (192 mg, 0.100 mmol, 1 equiv) in 9 mL of $CH_2Cl_2$ with HOTf (20 mg, 0.13 mmol, 1.3 equiv) in 1 mL of MeCN caused all solid to dissolve, giving a very pale yellow solution. Precipitation of an eggshell solid was aided by the addition of 10 mL of pentane, affording 163 mg (77%) of 41. 1H NMR ($CD_3CN$) δ/ppm: −12.669 (m, 1H), 1.964 (s, see text), 2.586 (d, 1 Hz, see text), 2.728 (t, 11.5 Hz, 3H), 2.865 (dd, 8.84 Hz, 7.53 Hz, 3H), 3.092 (t, 7.86 Hz, 3H), 4.1–5.3 (m, 24H) 31P{1H} NMR ($CD_3CN$) δ/ppm: 43.007 (dd, 744 Hz, 35.3 Hz, 1P), 48.383 (ddt, 716 Hz, 45.6 Hz, 17.9 Hz, 1P), 53.628 (dd, 147 Hz, 38.0 Hz, 1P), 66.898 (dd, 150 Hz, 39.3 Hz, 1P), 75.931 (ddt, 739 Hz, 148 Hz, 39.7 Hz, 1P), 84.947 (ddt, 722 Hz, 146 Hz, 34.9 Hz 1P). IR (Fluorolube) vIr—H/cm−1: 2042.

Example 28

Addition of $H_2$ to 33

Dihydrogen was bubbled slowly into a 10-mL $CH_2Cl_2$ suspension of 33 (76 mg, 0.040 mmol). The solid dissolved immediately to give a yellow solution, which returned to brown with concomitant formation of solid upon purging with $N_2$. Treating with $H_2$ regenerated the yellow solution.

The solution could be cycled reversibly between yellow and brown with treatment of $H_2$ and $N_2$, respectively. The reaction proceeds with equal facility in $CD_3CN$. Integration of the 1H NMR spectra obtained on solutions before and after $H_2$ addition indicates a quantitative reaction. A pale yellow solid is isolated when $CH_2Cl_2$ solutions were concentrated under a stream of $H_2$ to a few mL, followed by pentane addition and cooling to $-80°$ C. Meaningful yields and elemental analyses of the compound could not be determined because the complex loses $H_2$ in an atmosphere devoid of dihydrogen. The reaction is so prevalent that it occurs even in the solid state thus requiring us to grow X-ray quality single crystals of the complex from a $CH_2Cl_2$ solution of 12 layered with octane under a dihydrogen atmosphere. 1H NMR ($CD_3CN$) δ/ppm: -11.626 (dq, 188 Hz, 16.0 Hz, 1H), -8.174 (d, 278 Hz, 1H), 2.81 (t, 6.72 Hz, 3H), 2.82 (t, 7.37 Hz, 6H), 4.2–5.7 (m, 24H). 31P{1H} NMR ($CD_3CN$) δ/ppm: 17.85 (s, 1P), 45.26 (d, 746 Hz, 1P), 71.34 (d, 159 Hz, 1P), 86.84 (d, 155 Hz, 1P), 95.50 (dd, 752 Hz, 218 Hz, 1P), 99.40 (d, 222 Hz, 1P). IR (KBr) $vIr—H$/ cm-1: 2053, 2071.

Example 29

Thermolysis of 42

An NMR tube equipped with a Teflon valve was charged with 20 mg of 33 (0.01 mmol). d8-THF was distilled in under vacuum and the tube was pressurized with $H_2$ to 1 atm at $20°$ C. After acquiring an initial 1H NMR spectrum, the solution was heated overnight to $80°$ C. After cooling to room temperature, 1H NMR revealed the formation of equal quantities of 43a and 43b, accounting for 90% of the starting iridium complex. 1H NMR (d8-THF, 500 MHz) δ/ppm: -14.07 (q, 12 Hz, 1H), -13.71 (dm, 181 Hz, 1H), -12.63 (dt, 177 Hz, 18 Hz, 1H)–11.23 (dq, 184 Hz, 16 Hz, 1H), 2.7–3.1 (m, 9H), 3.82 (dq, 28 Hz, 5 Hz, 2H), 4.2–5.9 (m, 24H). 31P{1H} NMR (d8-THF, 202.5 MHz δ/ppm: 41.73 (d, 692 Hz), 59.00 (s), 63.65 (dd, 118 Hz, 30 Hz), 67.04 (ddd, 167 Hz, 38 Hz, 14 Hz), 70.28 (dt, 162 Hz, 32 Hz), 72.54 (dt, 132 Hz, 35 Hz), 82.44 (dt, 117 Hz, 30 Hz), 84.15 (dq, 142 Hz, 35 Hz), 85.77 (dm, 117 Hz), 90.34 (d, 165 Hz), 94.60 (d, 130 Hz), 99.90 (dd, 698 Hz, 130 Hz).

Example 30

Preparation of $Ir_2^{0,II}(tfepma)_3(Me)Cl(MeCN)$ (44)

An 8-mL THF solution of 33 (117 mg, 0.061 mmol) and a 2-mL THF solution containing 21 μL of 3.0 M MeMgBr (0.063 mmol) were frozen in the liquid nitrogen cold well of a glove box. The solutions were removed from the cold well and mixed immediately upon thawing prompting a color change from dark brown to yellow. As the yellow solution warmed to room temperature the color darkened to brown. After 1 h, the solvent was stripped and the residue triturated three times and washed once with $CH_2Cl_2$ before drying to yield the product as a green powder. 1H NMR ($CD_3CN$) δ/ppm: 1.11 (dd, 8 Hz, 3 Hz, 3H), 2.61 (t, 6 Hz, 3H), 2.70 (m, 3H), 2.80 (m, 3 H), 4.1–5.4 (m, 24H). 31P NMR ($CD_3CN$) δ/ppm: 29.5 (s, 1P), 44.8 (t, 303 Hz, 1P), 72.5 (134 Hz, 1P), 93.8 (dm, 298 Hz, 1P), 95.5 (dm, 310 Hz, 1P), 109.3 (dm, 152 Hz, 1P).

Example 31

$Rh_2^{0,II}(dfpma)_3Cl_2(PPh_3)$ photochemistry in d8-THF

An NMR tube with a resealable Teflon valve was charged with 15 mg of $Rh_2^{0,II}(dfpma)_3Cl_2(PPh_3)$ (0.014 mmol) in the glove box. The NMR tube was brought out of the glove box and connected to the vacuum line. d8-THF (ca. 0.7 mL) was distilled into the NMR tube. HCl was generated from the reaction of $H_2SO4$ with NaCl and collected in a 25 mL flask, then freeze-pump-thaw degassed once. The pressure was adjusted to 129 mm of Hg (0.18 mmol HCl), and the HCl was transferred into the NMR tube. The solution was thawed and an initial 1H NMR spectrum recorded. Irradiation was carried out at $20°$ C. with $\lambda \geq 338$ nm excitation light, after three hours, irradiation was halted and another NMR spectrum was recorded. A singlet at 4.53 ppm signaled the formation of $H_2$. Irradiation was continued for a total of 18 h after which a final 1H NMR spectrum was recorded. An increased intensity for the $H_2$ resonance was accompanied by a 1:1:1 triplet at 4.50 ppm (1JHD 43 Hz) for HD gas. All non-condensable gas was collected by Toepler pumping. Hydrogen formation (0.096 mmol) was confirmed by complete combustion over hot CuO.

Example 32

Reaction of dfpma with $HRh(PPh_3)4$

A 100-mL flask was charged with 190 mg (0.165 mmol) of $HRh(PPh_3)_4$ in the glove box and fitted with a Teflon valve. The vessel was removed from the glove box, attached to a vacuum line and evacuated. Benzene (20 mL), stored under vacuum over Na/benzophenone-ketyl, was then condensed into the reaction flask. Due to its high volatility, dfpma was added to the flask by standard gas transfer techniques. A flask with a nominal volume of 36 mL was filled with dfpma to a pressure of 134 mm of Hg (0.27 mmol dfpma). The ligand was freeze-pump-thaw degassed once prior to its condensation into the reaction flask containing the frozen benzene solution. Thawing of the solution prompted immediate reaction as evidenced by a slight color change and gas evolution. After stirring overnight, a bright orange solid precipitated from solution. The solvent was frozen and 0.059 mmol of hydrogen was collected via Toepler pumping (72% yield based on rhodium starting material). The reaction solution was then thawed and brought into the glove box. After reducing the solvent volume to ~10 mL, a 10 mL-aliquot of pentane was added. The orange solid was collected by filtration and washed with 3×5 mL of pentane to yield 86 mg (85%) of dirhodium product. The 1H and 19F NMR data for the product match the data presented for $Rh_20,0(dfpma)_3(PPh_3)_2$ (3-$PPh_3$) in Table 1.3.

Example 33

Preparation of $Rh_2^{0,II}(dfpma)_3Cl_2(CO)$ and $Rh_2^{0,II}(dfpma)_3Cl_2$

A 20-mL scintillation vial was charged with 255 mg (0.656 mmol) of $[ClRh(CO)_2]_2$ and 10 mL of $CH_2Cl_2$. Dfpma was then added dropwise (336 mg, 2.01 mmol) under rapid stirring, prompting gas evolution and a concurrent color change from orange to dark blue and finally deep red. The solvent was removed to afford a sticky red solid that was treated with 5 mL of benzene and 10 mL of pentane to give 400 mg of orange powder analyzing as $Rh_2^{0,II}(dfpma)_3Cl_2(CO)$ (76%). This product was characterized by a strong carbonyl stretch in the IR at 2057 cm-1. A portion of this material was exposed to high vacuum (10-5 torr) for several days resulting in a color change to green. The infrared spectrum of a KBr pellet showed no absorption corresponding to a carbonyl ligand. For $Rh_2^{0,II}(dfpma)_3Cl_2$: 1H NMR (d8-THF) δ/ppm: 3.05 (m). 19F NMR (d8-THF) δ/ppm:

−15.4 (d, 1186 Hz), −38.2 (d 1180, Hz), −42.4 (d, 1271 Hz), −49.5 (d, 1101 Hz), −53.8 (d, 1073 Hz), −80.8 (d, 1158 Hz).

Example 34

Preparation of $Rh_2 0,0(dfpma)_3(CO)(PPh_3)$

In the glove box, $Rh_2^{0,II}(dfpma)3Cl_2(CO)$ (185 mg, 0.230 mmol) was dissolved in 8 mL of THF and treated successively with cobaltocene (91 mg, 0.48 mmol) and triphenylphosphine (63 mg, 0.24 mmol). The solution turned red with concomitant precipitation of yellow $[CoCp_2]Cl$. The mixture was filtered and the solvent removed. The residue was re-dissolved in $CH_2Cl_2$ and filtered through a plug of Florisil. The volume was reduced to 5 mL and pentane was added. Cooling to −80° C. overnight afforded 189 mg of the product as a yellow-orange microcrystalline solid (83% yield). 1H NMR ($CDCl_3$) δ/ppm: 2.74 (s, 9H), 7.36 (m, 15H). 19F NMR ($CDCl_3$) δ/ppm: −41.75 (d, 1125 Hz, 6F), −43.56 (d, 1115 Hz, 6F).

Example 35

Addition of [PPN]Cl to $Rh_2^{0,II}(dfpma)_3Cl_2$

Dissolution of $Rh_2^{0,II}(dfpma)_3Cl_2$ (295 mg, 0.379 mmol) in 10 mL of THF afforded a deep red solution. Solid bis(triphenylphosphine)iminium chloride ([PPN]Cl) was then sifted into the solution prompting a color change to orange. The solution volume was reduced to 3 mL and ether was added to precipitate the product as an orange microcrystalline solid in 70% yield (360 mg). 1H NMR (d8-THF) δ/ppm: 2.79 (t, 3 Hz, 3H), 2.86 (s, 6H), 7.48–7.70 (m, 30H). $^{19}$F NMR (d8-THF) δ/ppm: 7.36 (d, 1260 Hz, 2F), −43.93 (d, 1084 Hz, 2F), −46.75 (d, 1109 Hz, 2F), −52.64 (d, 1160 Hz, 2F), −54.69 (d, 1109 Hz, 2F), −80.90 (d, 1135 Hz, 2F).

Example 36

Oxidation of $Rh_2^{0,II}(dfpma)_3Cl_2$ with $Br_2$

A dark red THF solution of $Rh_2^{0,II}(dfpma)_3Cl_2$ (97 mg, 0.125 mmol) was reacted with 12 μL (37 mg, 0.23 mmol) of bromine delivered with an auto pipette. The solution immediately turned transparent red. The solvent was removed by vacuum distillation and the resulting residue was taken up in a minimal volume of $CH_2Cl_2$. Pentane addition caused the precipitation of 80 mg of the product as a bright orange-red powder (68% yield). 1H NMR (d8-THF) δ/ppm: 3.38 (m). 19F NMR (d8-THF) δ/ppm: −47.5 (d, 930 Hz), −49.9 (d, 1186 Hz), −50.6 (d, 1214 Hz), −51.3 (d, 1017 Hz), −62.6 (d, 1101 Hz), −63.9 (d, 1186 Hz), −76.4 (d, 1214 Hz), −77.8 (d, 1130 Hz).

Example 37

$Rh_2^{II,II}(dfpma)_3Br4$ and $Rh_2^{0,II}(dfpma)_3Br_2(\eta 1\text{-}dfpma)$ Dark Reactions The thermal reactivity of $Rh_2^{II,II}(dfpma)_3Br4$ and $Rh_2^{0,II}(dfpma)_3Br_2(\eta 1\text{-}dfpma)$ in THF was evaluated under the conditions employed for photochemical experiments. Thus, a cuvette of a photolysis cell was charged with either a small amount of the $Rh_2^{II,II}$ or $Rh_2^{0,II}$ complex. THF was distilled into the solvent reservoir of the cell under vacuum and subjected to three freeze-pump-thaw cycles. The solvent was then mixed with the rhodium complex under photographic darkroom lights and an initial absorption spectrum was recorded. The cell was wrapped in foil and maintained at 0° C. overnight. After twelve hours, another UV-Vis spectrum of the sample showed only negligible changes in the absorption profile.

Example 38

Identification of the $Rh_2 0,0$ Product from $Rh_2^{II,II}(dfpma)_3Br4$ Photochemistry A 200-mL quartz photolysis tube was charged with 45 mg (44,mol) of $Rh_2^{II,II}(dfpma)_3Br4$ in 20 mL of THF under nitrogen. The solution was degassed by three freeze-pump-thaw cycles and 0.178 mmol of dfpma was added to the cell by vacuum distillation. The solution was irradiated at 0° C. with 395-nm longpass filtered light for 46 h. After solvent removal, the residue was extracted with pentane and removing solvent in vacuo to afford the orange photoproduct. 19F NMR ($C_6D_6$), δ/ppm: −29.72 (d, 1252 Hz, 4F), −40.96 (d, 1117 Hz, 12F), −76.29 (d, 1252 Hz, 4F).

Example 39

Identification of the Bromine Product from $Rh_2$-dfpma Photochemistry

In the environment of a nitrogen-filled glove box, 21 mg (20 μmol) of $Rh_2^{II,II}(dfpma)_3Br4$ was dissolved in 150 mL of THF contained within a quartz photolysis tube. The solution was cooled to −78° C. and 13 mg (50 μmol) of triphenylphosphine was added, followed by the addition of 10 μl (9.2 mg, 86 μmol) of 2,6-lutidine. The sealed tube was removed from the glove box and the solution was irradiated at λ≧335 nm for 17 h at 0° C. Solvent was distilled from the photolyzed solution and the entire residue was dissolved in $CDCl_3$. 1H NMR ($CDCl_3$), δ/ppm: 2.60 (bs, 0.96H), 2.70 (bs, 0.27H), 2.83 (bs, 0.59H), 2.91 (bs, 1.18H), 3.23 (s, 0.09H), 16.77 (bs, 3.00H).

What is claimed is:

1. A process, comprising:

providing a reaction medium comprising:
   a protic solution;
   a photocatalyst capable of a two electron reduction of hydrogen ions; and
   a coproduct trap;

exposing the reaction medium to radiation capable of photoexciting the photocatalyst to produce hydrogen.

2. The process of claim 1, wherein the protic solution comprises at least one of hydrohalic acid, a silane, and water.

3. The process of claim 2, wherein the hydrohalic acid is selected from hydrochloric acid, hydrogen bromide, hydrogen fluoride and hydrogen iodide.

4. The process of claim 1, wherein the coproduct trap comprises at least one of tetrahydrofuran, silane, isopropanal, dihydroanthracene and 2,3-dimethylbutadiene.

5. The process of claim 1, wherein the photocatalyst capable of a two electron reduction of hydrogen ions comprises a multinuclear transition metal core.

6. The process of claim 5, wherein the multinuclear transition metal core comprises at least one of rhodium, irridium, platinum and paladium.

7. The process of claim 6, wherein the photocatalyst capable of a two electron reduction of hydrogen ions further comprises at least one of triphenyl phosphine, carbon monoxide, bis(difluorophosphino)methyl amine, MeCN, a phosphazene based ligand and a two electron donor ligand.

8. The process of claim 1, wherein the photocatalyst capable of a two electron reduction of hydrogen ions comprises:
a binuclear transition metal core; and
ligands capable of stabilizing a two electron mixed valence state of the binuclear transition metal core.

9. The process of claim 8, wherein the ligands comprise:
at least two π-acid groups capable of coordinating with the binuclear transition metal core; and
at least one Lewis basic atom or group.

10. The process of claim 9, wherein the ligands comprise a phosphazane group.

11. The process of claim 10, wherein the ligands comprise a group capable of giving at least one phosphorous atom of the phosphazane group strong π-acid characteristics.

12. The process of claim 11, wherein the group capable of giving one phosphorous atom strong π-acid characteristics comprises at least one of halogen, fluorine, chlorine, halogenated alkanes, halogenated alkenes, aryl substituted with electron withdrawing groups, and alcohols.

13. The process of claim 10, wherein the ligands comprise a group attached to a nitrogen atom of the phosphazane group which allows participation of a lone pair of electrons to participate in π-bonding.

14. The process of claim 13, wherein the group attached to a nitrogen atom comprises at least one of substituted or unsubstituted $C_1$–$C_{10}$ alkyl groups, methyl, ethyl, propyl, butyl, pentyl, hydrogen and a substituted phenyl, wherein the alkyl group is selected from branched and unbranched alkyl groups.

15. The process of claim 8, wherein the ligands comprise:
at least two π-donating groups capable of coordinating with the binuclear transition metal core; and
at least one Lewis acidic atom or group.

16. The process of claim 15, wherein the ligand comprises a boron bonded to two nitrogen atoms.

17. A process, comprising:
providing a reaction medium comprising:
a protic solution;
a photocatalyst comprising a binuclear transition metal complex and a ligand capable of supporting the photocatalyst in a two electron mixed valence state; and
a coproduct trap; and
photoexciting the photocatalyst to produce hydrogen and eliminate halogen atoms.

18. The process of claim 17, wherein the ligand is a diphosphazane ligand.

19. The process of claim 18, wherein the ligand has strongly π-acidic phosphine group.

20. The process of claim 17, wherein the binuclear transition metal complex comprises at least one of rhodium and iridium.

21. A process, comprising:
irradiating to photoexcite a transition metal complex comprising:
two rhodium atoms,
three bis(difluorophosphine) methyl amine ligands, and triphenyl phosphine;
in a solution comprising hydrohalic acid and a halogen trap.

22. The process of claim 21, wherein hydrogen is produced.

23. The process of claim 22, wherein the halogen trap comprises at least one of tetrahydrofuran, dihydroanthracene, silane and 2,3-dimethylbutadiene.

24. A process, comprising:
providing a reaction medium comprising:
a protic solution;
a photocatalyst capable of a two electron reduction of hydrogen ions, wherein the photocatalyst comprises:
a binuclear transition metal care; and
at least one chelating ligand coordinated to one transition metal of the binuclear transition metal core; and
a coproduct trap;
exposing the reaction medium to radiation capable of photoexciting the photocatalyst to produce hydrogen.

25. The process of claim 24, wherein the protic solution comprises at least one of hydrohalic acid, a silane, and water.

26. The process of claim 25, wherein the hydrohalic acid is selected from hydrochloric acid, hydrogen bromide, hydrogen fluoride and hydrogen iodide.

27. A process of claim 24, wherein the coproduct trap comprises at least one of tetrahydrofuran, silane, isopropanal, dihydroanthracene and 2,3-dimethylbutadiene.

28. A process of claim 24, wherein the binuclear transition metal core comprises at least one of rhodium, iriidium, platinum and palladium.

29. The process of claim 28, wherein the photocatalyst capable of a two electron reduction of hydrogen ions further comprises at least one of triphenyl phosphine carbon monoxide, bis(difluorophosphino)methyl amine, MeCN, a phosphazene based ligand and a two electron donor ligand.

30. The process of claim 24, wherein the photocatalyst capable of a two electron reduction of hydrogen ions comprises:
the binuclear transition metal core; and
the at least one chelating ligands is capable of stabilizing a two electron mixed valence state of the binuclear transition metal core.

31. The process of claim 30, wherein the at least one chelating ligands comprises:
at least two π-acid groups capable of coordinating with the binuclear transition metal core; and
at least one Lewis basic atom or group.

32. The process of claim 31, wherein the at least one chelating ligands comprises a phosphazane group.

33. The process of claim 32, wherein the ligands comprise a group capable of giving at least one phosphorous atom of the phosphazane group strong π-acid characteristics.

34. The process of claim 33, wherein the group capable of giving one phosphorous atom strong π-acid characteristics comprises at least one of halogen, fluorine, chlorine, halogenated alkanes, halogenated alkenes, aryl substituted with electron withdrawing groups, and alcohols.

35. The process of claim 32, wherein the at least one chelating ligand comprises a group attached to a nitrogen atom of the phosphazane group which allows participation of a lone pair of electrons to participate in π-bonding.

36. The process of claim 35, wherein the group attached to a nitrogen atom comprises at least one of substituted or unsubstituted $C_1$–$C_{10}$ alkyl groups methyl, ethyl, propyl, butyl, pentyl, hydrogen and a substituted phenyl, wherein the alkyl group is selected from branched and unbranched alkyl groups.

37. The process of claim 30, wherein the at least one chelating ligands comprises:
at least two π-donating groups capable of of coordinating with the binuclear transition metal core; and
at least one Lewis acidic atom or group.

38. The process of claim 37, wherein the at lease one chelating ligand comprises a boron bonded to two nitrogen atoms.

39. The process of claim 24, wherein the photocatalyst is in two electron mixed valence state and the at least one chelating ligand comprises:

two charged ligands coordinated to the transition metal in a higher oxidation state.

40. The process of claim 39, wherein at least one chelating ligand is coordinated to the transition metal in a lower oxidation state.

41. The process of claim 39, further comprising:

forming of the photocatalyst to a valence-symmetric state; and rearranging the chelating ligand to coordinate with both transition metals of the binuclear core.

42. The process of claim 41, wherein the protic solution is a hydrohalic acid and the photocatalyst in a valence-symmetric state comprises four halogen atoms.

43. The process of claim 42, further comprising:

photoexciting the photocatalyst in a valence-symmetric state to eliminate two of the halogen atoms and regenerate the photocatalyst capable of a two electron reduction of hydrogen ions.

* * * * *

UNITED STATES PATENT AND TRADEMARK OFFICE
CERTIFICATE OF CORRECTION

| | |
|---|---|
| PATENT NO. | : 6,863,781 B2 |
| APPLICATION NO. | : 10/083200 |
| DATED | : March 8, 2005 |
| INVENTOR(S) | : Daniel G. Nocera et al. |

Page 1 of 1

It is certified that error appears in the above-identified patent and that said Letters Patent is hereby corrected as shown below:

Col. 39, line 44, delete "HID" and substitute --H/D--

Col. 54, line 63, delete "do" and substitute --dσ--

Col. 57, line 6, insert the word --this-- after the word "Despite"

Col. 90, Claim 6, delete "irridium" and substitute --iridium--

Col. 90, Claim 6, delete "paladium" and substitute --palladium--

Col. 92, Claim 24, line 6, delete "care" and substitute --core--

Col. 92, Claim 28, line 21, delete "irridium" and substitute --iridium--

Col. 92, Claim 29, delete "phosphine" and substitute --phosphine,--

Col. 92, Claim 30, delete "ligands" and substitute --ligand--

Col. 92, Claim 31, delete "ligands" and substitute --ligand--

Col. 92, Claim 32, delete "ligands" and substitute --ligand--

Col. 92, Claim 37, delete "ligands" and substitute --ligand--

Signed and Sealed this

Fourth Day of November, 2008

JON W. DUDAS
*Director of the United States Patent and Trademark Office*